US012808872B2

(12) United States Patent
Coverley

(10) Patent No.: US 12,808,872 B2
(45) Date of Patent: Nov. 24, 2026

(54) USE OF A FIBRINOGEN CAPTURE AGENT TO DETECT A Ciz1 b-VARIANT

(71) Applicant: Cizzle Biotechnology Limited, Yorkshire (GB)

(72) Inventor: Dawn Alison Coverley, Yorkshire (GB)

(73) Assignee: Cizzle Biotechnology Limited, Yorkshire (GB)

( * ) Notice: Subject to any disclaimer, the term of this patent is extended or adjusted under 35 U.S.C. 154(b) by 280 days.

(21) Appl. No.: 18/188,958

(22) Filed: Mar. 23, 2023

(65) Prior Publication Data

US 2023/0266327 A1 Aug. 24, 2023

Related U.S. Application Data

(62) Division of application No. 15/768,946, filed as application No. PCT/GB2016/053203 on Oct. 14, 2016, now abandoned.

(30) Foreign Application Priority Data

Oct. 19, 2015 (GB) .................................... 1518466

(51) Int. Cl.

| | |
|---|---|
| ***G01N 33/5752*** | (2026.01) |
| ***A21D 8/04*** | (2006.01) |
| ***A61K 38/36*** | (2006.01) |
| ***C07K 14/75*** | (2006.01) |
| ***C12N 9/26*** | (2006.01) |
| ***G01N 33/50*** | (2006.01) |
| ***G01N 33/575*** | (2026.01) |

(52) U.S. Cl.

CPC ........... *G01N 33/5752* (2026.01); *A21D 8/04* (2013.01); *A61K 38/363* (2013.01); *C07K 14/75* (2013.01); *C12N 9/2414* (2013.01); *C12Y 302/01133* (2013.01); *G01N 33/5076* (2013.01); *G01N 33/575* (2026.01)

(58) Field of Classification Search

None

See application file for complete search history.

(56) References Cited

U.S. PATENT DOCUMENTS

| | | | |
|---|---|---|---|
| 4,275,149 | A | 6/1981 | Litman et al. |
| 2007/0117164 | A1 | 5/2007 | Raskov et al. |
| 2010/0092579 | A1 | 4/2010 | Noguchi et al. |
| 2012/0164628 | A1 | 6/2012 | Duffin et al. |
| 2013/0210663 | A1 | 8/2013 | Coverley |
| 2013/0287772 | A1 | 10/2013 | Halbert et al. |
| 2014/0113310 | A9 | 4/2014 | Skolnick et al. |
| 2017/0059572 | A1 | 3/2017 | Kalluri et al. |
| 2018/0306795 | A1 | 10/2018 | Coverley |

FOREIGN PATENT DOCUMENTS

| | | | |
|---|---|---|---|
| CN | 102405413 | A | 4/2012 |
| CN | 103328500 | A | 9/2013 |
| CN | 103421886 | A | 12/2013 |
| JP | 2011510309 | A | 3/2011 |
| JP | 2013539534 | A | 10/2013 |
| WO | WO-2004051269 | A2 | 6/2004 |
| WO | WO-2010089559 | A1 | 8/2010 |
| WO | WO-2012017208 | A1 | 2/2012 |
| WO | WO-2012078208 | A1 | 6/2012 |
| WO | WO-2017068330 | A1 | 4/2017 |

OTHER PUBLICATIONS

Ahn et al., "Current Serum Lung Cancer Biomarkers," (2013) Current Serum Lung Cancer Biomarkers. J Mol Biomark Diagn, 7 pages.

Ainscough et al., "C-terminal domains deliver the DNA replication factor Ciz1 to the nuclear matrix", Journal of Cell Science, 120:115-124 (2007).

Allin et al., "inflammatory biomarkers and risk of cancer in 84,000 individuals from the general population", International Journal of Cancer, 139:1493-1500 (2016).

Baxevanis, C.N., "Antibody-based Cancer Therapy", Expert Opinion: Drug Discovery, 2008, vol. 3 (4), pp. 441-452.

Bendig, M. M., "Humanization of Rodent Monoclonal Antibodies by CDR Grafting", Methods: A Companion to Methods: A Companion to Methods in Enzymology (1995); 8: 83-93.

Brawer, M.K., et al., "Measurement of Complexed Psa Improves Specificity for Early Detection of Prostate Cancer", Elsevier, 1998, pp. 372-378.

Budman, L.I., et al., "Biomarkers for Detection and Surveillance of Bladder Cancer", Bladder Cancer Biomarkers, 2008, vol. 2 (3), pp. 212-221.

Cheruvanky et al., "Rapid isolation of urinary exosomal biomarkers using a nanomembrane ultrafiltration concentrator", American Journal of Physiology—Renal Physiology, 292: F1657-F1661 (2007).

Coverley et al., "A quantitative immunoassay for lung cancer biomarker CIZ1b in patient plasma", Clin Biochem. Apr. 2017; 50(6): 336-343. Epub Nov. 17, 2016.

Den Hollander et al., "Ciz1, a Novel DNA-Binding Coactivator of the Estrogen Receptor a, Confers Hypersensitivity to Estrogen Action", Cancer Research, 66: 11021-11029 (2006).

Higgins et al., "Variant Ciz1 is a circulating biomarker for early-stage lung cancer", Proceedings of the National Academy of Sciences, 109: E3128-E3135 (2012).

International Preliminary Report on Patentability and Written Opinion issued in corresponding International Patent Application No. PCT/GB2016/053203 dated Apr. 24, 2018, 8 pages.

International Search Report issued in corresponding International Patent Application No. PCT/GB2016/053203 dated Mar. 16, 2017, 9 pages.

(Continued)

*Primary Examiner* — Anne M. Gussow

(74) *Attorney, Agent, or Firm* — COOLEY LLP

(57) ABSTRACT

The present application provides methods of detecting lung cancer in a subject comprising detecting a fibrinogen/Ciz1 b-variant peptide complex in the subject, wherein the presence of the Ciz1 b-variant peptide indicates that the subject has lung cancer. The present application further provides methods of enriching a fibrinogen/Ciz1 b-variant complex in a blood or plasma sample.

2 Claims, 32 Drawing Sheets

Specification includes a Sequence Listing.

(56) References Cited

OTHER PUBLICATIONS

Invitrogen Total Exosome Isolation Kit (Catalog No. 4484450) (2016), 2 pages.
Lamparski et al., "Production and characterization of clinical grade exosomes derived from dendritic cells", Journal of Immunological Methods, 270: 211-226 (2002).
Ludwig, J.A., et al., "Biomarkers in Cancer Staging, prognosis and Treatment Selection", Nature Reviews, 2005, vol. 5, pp. 845-856.
Mantovani, L.T., et al., "Folate Binding Protein Distribution in Normal Tissues and Biological Fluids From Ovarian Carcinoma Patients as Detected by the Monoclonal Antibodies MOv18 and MOv19", European Journal of Cancer, 1994, vol. 30 (3), pp. 363-369.
Mathivanan et al., "Exosomes: extracellular organelles important in intercellular communication", Journal of Proteomics, 73: 1907-1920 (2010).
Mettlin, C., et al., "Relative Sensitivity and Specificity of Serum Prostate Specific Antigen (PSA)Level Compared with Age-Referenced PSA, PSA Density, and PSA Change", Cancer, 1994, vol. 74 (5), pp. 1615-1620.
Mosesson, "Fibrinogen and fibrin structure and functions," Journal of Thrombosis and Haemostasis, 3: 1894-1940 (2005).
NCBI Reference Sequence: NM_001131016.1 *Homo sapiens* CDKN1A interacting zinc finger protein 1 (CIZ1). Transcript variant 5, mRNA (2018), 5 pages.
NCBI Reference Sequence: NM_012127.2 *Homo sapiens* CDKN1A interacting zinc finger protein 1 (CIZ1). Transcript variant 1, mRNA (2019), 5 pages.
Paul, W.E., "Fundamental Immunology", Laboratory of Immunology National Institute of Allergy and Infectious Diseases National Institutes of Health Bethesda, Maryland, 1993, 6 pages.
Pepe, M.S., et al., "Phases of Biomarker Development for Early Detection of Cancer", Journal of the National Cancer Institute, 2001, vol. 93 (14), pp. 1054-1106.
Pisitkun et al., "Identification and proteomic profiling of exosomes in human urine", Proc Natl Acad Sci U S A. Sep. 7, 2004; 101(36): 13368-73. Epub Aug. 23, 2004.
Rahman et al., "Differential detection of alternatively spliced variants of Ciz1 in normal and cancer cells using a custom exon-junction microarray", BMC Cancer. Sep. 10, 2010; 10: 482, 12 pages.
Rudikoff, S. et al. "Single amino acid substitution altering antigen-binding specificity", Proc Natl Acad Sci, (Mar. 1982); 79:1979-1983.
Simpson et al., "Proteomic profiling of exosomes: current perspectives", Proteomics, 8: 4083-4099 (2008).
Taylor et al., "Tumour-derived exosomes and their role in cancer-associated T-cell signaling defects", British Journal of Cancer, 92: 305-311 (2005).
UniProtKB accession No. P02671 FIBA_HUMAN (1986) (updated 2019), 22 pages.
UniProtKB accession No. P02675 FIBB_HUMAN (1986) (updated 2019), 21 pages.
UniProtKB accession No. P02679 FIBG_HUMAN (1986) (updated 2019), 16 pages.
Van Der Pol et al., "Classification, functions, and clinical relevance of extracellular vesicles", Pharmacological Reviews, 4: 676-705 (2012).
Van Niel et al., "Exosomes: a common pathway for a specialized function", Journal of Biochemistry, 140: 13-21 (2006).
Brawer, M.K., et al., "Measurement of complexed PSA improves specificity for early detection of prostate cancer", Elsevier Science Inc., Urology, 1998, 52(3):372-378.
Budman, L.I., et al., "Biomarkers for detection and surveillance of bladder cancer", Can Urol Assoc J. Jun. 2008; 2(3):212-221.
Coverley et al., "Ciz1 promotes mammalian DNA replication", J Cell Sci. Jan. 1, 2005;118(Pt 1):101-112. Epub Dec. 7, 2004.
Emelie Fransson, "Establishment and characterization of antibodies against Ciz1b for detection of early-stage lung cancer", Master of Science Thesis, Department of Chemical and Biological Engineering, Chalmers University of Technology, 2013, 52 pages.
Pepe, M.S., et al., "Phases of biomarker development for early detection of cancer", J Natl Cancer Inst. Jul. 18, 2001; 93(14):1054-1061.

FIG. 2A

SEQ ID NO: 1 (Full Ciz1 b-variant sequence, specified by exclusion of VEEELCKQ (SEQ ID NO: 10) from NCBI Reference Sequence: NM_001131016.1)

MFSQQQQQLQQQQQLQQLQQQLQQQLQQQLLQLQQLLQQSPPQAPLPMAVSRGLPPQQPQQPL
LNLQGTNSASLLNGSMLQRALLLQQLQGLDQFAMPPATYDTAGLTMPTATLGNLRGYGMASPGLAAPS
LTPPQLATPNLQQFFPQATRQSLLGPPPVGVPMNPSQFNLSGRNPQKQARTSSSTTPNRKDSSSQTMP
VEDKSDPPEGSEEAAEPRMDTPEDQDLPPCPEDIAKEKRTPAPEPEPCEASELPAKRLRSSEEPTEKE
PPGQLQVKAQPQARMTVPKQTQTPDLLPEALEAQVLPRFQPRVLQVQAQVQSQTQPRIPSTDTQVQPK
LQKQAQTQTSPEHLVLQQKQVQPQLQQEAEPQKQVQPQVQPQAHSQGPRQVQLQQEAEPLKQVQPQVQ
PQAHSQPPRQVQLQLQKQVQTQTYPQVHTQAQPSVQPQEHPPAQVSVQPPEQTHEQPHTQPQVSLLAP
EQTPVVVHVCGLEMPPDAVEAGGGMEKTLPEPVGTQVSMEEIQNESACGLDVGECENRAREMPGVWGA
GGSLKVTILQSSDSRAFSTVPLTPVPRPSDSVSSTPAATSTPSKQALQFFCYICKASCSSQQEFQDHM
SEPQHQQRLGEIQHMSQACLLSLLPVPRDVLETEDEEPPPRRWCNTCQLYYMGDLIQHRRTQDHKIAK
QSLRPFCTVCNRYFKTPRKFVEHVKSQGHKDKAKELKSLEKEIAGQDEDHFITVDAVGCFEGDEEEEE
DDEDEEEIEVRSRDISREEWKGSETYSPNTAYGVDFLVPVMGYICRICHKFYHSNSGAQLSHCKSLGH
FENLQKYKAAKNPSPTTRPVSRRCAINARNALTALFTSSGRPPSQPNTQDKTPSKVTARPSQPPLPRR
STRLKT

SEQ ID NO: 2 (Example of a sequence comprising the exon 14b/exon 15 amino acid junction sequence, other sequences comprising the exon 14b/Exon 15 amino acid junction sequences are given in Table 1)

DEEEIEVRSRDIS

SEQ ID NO: 3 (Exon 14b nucleotide sequence)

CUGAAGUCGCUUGAGAAAGAAAUUGCUGGCCAAGAUGAGGAGCACUUCAUUACAGUGGACGCUGUGGG
UUGCUUCGAGGGUGAUGAAGAAGAGGAAGAGGAUGAUGAGGAUGAAGAAGAGAUCGAG

SEQ ID NO: 4 (Exon 14a nucleotide sequence)

CUGAAGUCGCUUGAGAAAGAAAUUGCUGGCCAAGAUGAGGAGCACUUCAUUACAGUGGACGCUGUGGG
UUGCUUCGAGGGUGAUGAAGAAGAGGAAGAGGAUGAUGAGGAUGAAGAAGAGAUCGAGGUUGAGGAGG
AACUCUGCAAGCAG

SEQ ID NO: 5 (Exon 14b amino acid sequence)

LKSLEKEIAGQDEDHFITVDAVGCFEGDEEEEEDDEDEEEIE

SEQ ID NO: 6 (Exon 14a amino acid sequence)

LKSLEKEIAGQDEDHFITVDAVGCFEGDEEEEEDDEDEEEIEVEEELCKQ

SEQ ID NO: 7 (Exon 15 amino acid sequence)

VRSRDISREEWKGSETYSPNTAY

SEQ ID NO: 8 (Full Ciz1 sequence)

MFSQQQQQLQQQQQLQQLQQQLQQQLQQQLLQLQQLLQQSPPQAPLPMAVSRGLPPQQPQQPL
LNLQGTNSASLLNGSMLQRALLLQQLQGLDQFAMPPATYDTAGLTMPTATLGNLRGYGMASPGLAAPS
LTPPQLATPNLQQFFPQATRQSLLGPPPVGVPMNPSQFNLSGRNPQKQARTSSSTTPNRKDSSSQTMP
VEDKSDPPEGSEEAAEPRMDTPEDQDLPPCPEDIAKEKRTPAPEPEPCEASELPAKRLRSSEEPTEKE

FIG. 2B

PPGQLQVKAQPQARMTVPKQTQTPDLLPEALEAQVLPRFQPRVLQVQAQVQSQTQPRIPSTDTQVQPK
LQKQAQTQTSPEHLVLQQKQVQPQLQQEAEPQKQVQPQVQPQAHSQGPRQVQLQQEAEPLKQVQPQVQ
PQAHSQPPRQVQLQLQKQVQTQTYPQVHTQAQPSVQPQEHPPAQVSVQPPEQTHEQPHTQPQVSLLAP
EQTPVVVHVCGLEMPPDAVEAGGGMEKTLPEPVGTQVSMEEIQNESACGLDVGECENRAREMPGVWGA
GGSLKVTILQSSDSRAFSTVPLTPVPRPSDSVSSTPAATSTPSKQALQFFCYICKASCSSQQEFQDHM
SEPQHQQRLGEIQHMSQACLLSLLPVPRDVLETEDEEPPPRRWCNTCQLYYMGDLIQHRRTQDHKIAK
QSLRPFCTVCNRYFKTPRKFVEHVKSQGHKDKAKELKSLEKEIAGQDEDHFITVDAVGCFEGDEEEEE
DDEDEEEIEVEEELCKQVRSRDISREEWKGSETYSPNTAYGVDFLVPVMGYICRICHKFYHSNSGAQL
SHCKSLGHFENLQKYKAAKNPSPTTRPVSRRCAINARNALTALFTSSGRPPSQPNTQDKTPSKVTARP
SQPPLPRRSTRLKT

SEQ ID NO: 9 (example of sequence comprising the exon 14a/exon 15 splice junction)

DEEEIEVEEELCKQVRSRDIS

SEQ ID NO: 10 (excluded sequence from Ciz1 exon 14/exon 15 junction which specifies a Ciz1 b-variant)

VEEELCKQ

Cancer
Non cancer
65-70 kDa species (b-variant)
Control band kDa
77
55
28
11 kDa
70
55
40
35
25
15
10
M 1 2 3 4 5 - M

Plasma (0.5 µl) - N C C C C C C N
Peptide (nmol) 1 0 0 .5 1 2 4 0 0
Normal

MATRIX SCIENCE Mascot Search Results

FIG. 4D

| | |
|---|---|
| User | : ps |
| Email | : |
| Search title | : Ultraflex_ProteinID |
| MS data file | : 13229323905433938.mgf |
| Database | : UniProt_human_SP human_reviewed_20140609 (20259 sequences; 11329622 residues) |
| Timestamp | : 16 Apr 2015 at 10:31:51 GMT |
| Enzyme | : Trypsin |
| Fixed modifications | : Carbamidomethyl (C) |
| Variable modifications | : Deamidated (NQ),Oxidation (M) |
| Mass values | : Monoisotopic |
| Protein Mass | : Unrestricted |
| Peptide Mass Tolerance | : ± 100 ppm |
| Fragment Mass Tolerance | : ± 0.5 Da |
| Max Missed Cleavages | : 1 |
| Instrument type | : MALDI-TOF-TOF |
| Number of queries | : 10 |
| Protein hits | : P02671 Fibrinogen alpha chain OS=Homo sapiens GN=FGA PE=1 SV=2 |

Select Summary Report

Format As | Select Summary (protein hits) | Help

Significance threshold p< 0.05 | Max. number of hits AUTO

Standard scoring ⦿ MudPIT scoring ○ | Ions score or expect cut-off 0.0001 | Show sub-sets 0

Show pop-ups ⦿ Suppress pop-ups ○ | Require bold red ☑

Preferred taxonomy All entries

Re-Search ⦿ All queries ○ Unassigned ○ Below homology threshold ○ Below identity threshold 1. P02671 Mass: 95656 Score: 165 Matches: 2(2) Sequences: 2(2)

Fibrinogen alpha chain OS=Homo sapiens GN=FGA PE=1 SV=2

| Query | Observed | Mr(expt) | Mr(calc) | ppm | Miss | Score | Expect | Rank | Unique | Peptide | |
|---|---|---|---|---|---|---|---|---|---|---|---|
| 9 | 1520.7372 | 1519.7299 | 1519.7267 | 2.12 | 0 | 70 | 8.8e-06 | 1 | U | K.GLIDEVNQDFTNR.I | SEQ ID NO: 1064 |
| 10 | 1637.7706 | 1636.7634 | 1636.7594 | 2.43 | 0 | 95 | 3.7e-08 | 1 | U | K.ESSSHHPGIAEFPSR.G | SEQ ID NO: 1065 |

FIG. 6A

Table 1

Ciz1 b-variant peptides specified by exclusion of VEEELCKQ (SEQ ID NO:10) (comprising an exon 14b/exon 15 junction) from NCBI Reference Sequence: NM_001131016.1

EIAGQDEDHFITVDAVGCFEGDEEEEEDDEDEEEIEVR (SEQ ID NO:24)
IAGQDEDHFITVDAVGCFEGDEEEEEDDEDEEEIEVR (SEQ ID NO:25)
AGQDEDHFITVDAVGCFEGDEEEEEDDEDEEEIEVR (SEQ ID NO:26)
GQDEDHFITVDAVGCFEGDEEEEEDDEDEEEIEVR (SEQ ID NO:27)
QDEDHFITVDAVGCFEGDEEEEEDDEDEEEIEVR (SEQ ID NO:28)
DEDHFITVDAVGCFEGDEEEEEDDEDEEEIEVR (SEQ ID NO:29)
EDHFITVDAVGCFEGDEEEEEDDEDEEEIEVR (SEQ ID NO:30)
DHFITVDAVGCFEGDEEEEEDDEDEEEIEVR (SEQ ID NO:31)
HFITVDAVGCFEGDEEEEEDDEDEEEIEVR (SEQ ID NO:32)
FITVDAVGCFEGDEEEEEDDEDEEEIEVR (SEQ ID NO:33)
ITVDAVGCFEGDEEEEEDDEDEEEIEVR (SEQ ID NO:34)
TVDAVGCFEGDEEEEEDDEDEEEIEVR (SEQ ID NO:35)
VDAVGCFEGDEEEEEDDEDEEEIEVR (SEQ ID NO:36)
DAVGCFEGDEEEEEDDEDEEEIEVR (SEQ ID NO:37)
AVGCFEGDEEEEEDDEDEEEIEVR (SEQ ID NO:38)
VGCFEGDEEEEEDDEDEEEIEVR (SEQ ID NO:39)
GCFEGDEEEEEDDEDEEEIEVR (SEQ ID NO:40)
CFEGDEEEEEDDEDEEEIEVR (SEQ ID NO:41)
FEGDEEEEEDDEDEEEIEVR (SEQ ID NO:42)
EGDEEEEEDDEDEEEIEVR (SEQ ID NO:43)
GDEEEEEDDEDEEEIEVR (SEQ ID NO:44)
DEEEEEDDEDEEEIEVR (SEQ ID NO:45)
EEEEEDDEDEEEIEVR (SEQ ID NO:46)
EEEEDDEDEEEIEVR (SEQ ID NO:47)
EEEDDEDEEEIEVR (SEQ ID NO:48)
EEDDEDEEEIEVR (SEQ ID NO:49)
EDDEDEEEIEVR (SEQ ID NO:50)
DDEDEEEIEVR (SEQ ID NO:51)
DEDEEEIEVR (SEQ ID NO:52)
EDEEEIEVR (SEQ ID NO:53)
DEEEIEVR (SEQ ID NO:54)
EEEIEVR (SEQ ID NO:55)
EEIEVR (SEQ ID NO:56)
EIEVR (SEQ ID NO:57)
IEVR (SEQ ID NO:58)
EVR

EIAGQDEDHFITVDAVGCFEGDEEEEEDDEDEEEIEVRS (SEQ ID NO:59)
IAGQDEDHFITVDAVGCFEGDEEEEEDDEDEEEIEVRS (SEQ ID NO:60)
AGQDEDHFITVDAVGCFEGDEEEEEDDEDEEEIEVRS (SEQ ID NO:61)
GQDEDHFITVDAVGCFEGDEEEEEDDEDEEEIEVRS (SEQ ID NO:62)
QDEDHFITVDAVGCFEGDEEEEEDDEDEEEIEVRS (SEQ ID NO:63)
DEDHFITVDAVGCFEGDEEEEEDDEDEEEIEVRS (SEQ ID NO:64)
EDHFITVDAVGCFEGDEEEEEDDEDEEEIEVRS (SEQ ID NO:65)
DHFITVDAVGCFEGDEEEEEDDEDEEEIEVRS (SEQ ID NO:66)
HFITVDAVGCFEGDEEEEEDDEDEEEIEVRS (SEQ ID NO:67)
FITVDAVGCFEGDEEEEEDDEDEEEIEVRS (SEQ ID NO:68)
ITVDAVGCFEGDEEEEEDDEDEEEIEVRS (SEQ ID NO:69)
TVDAVGCFEGDEEEEEDDEDEEEIEVRS (SEQ ID NO:70)
VDAVGCFEGDEEEEEDDEDEEEIEVRS (SEQ ID NO:71)
DAVGCFEGDEEEEEDDEDEEEIEVRS (SEQ ID NO:72)
AVGCFEGDEEEEEDDEDEEEIEVRS (SEQ ID NO:73)

FIG. 6B

VGCFEGDEEEEEEDDEDEEEIEVRS (SEQ ID NO:74)
GCFEGDEEEEEEDDEDEEEIEVRS (SEQ ID NO:75)
CFEGDEEEEEEDDEDEEEIEVRS (SEQ ID NO:76)
FEGDEEEEEEDDEDEEEIEVRS (SEQ ID NO:77)
EGDEEEEEEDDEDEEEIEVRS (SEQ ID NO:78)
GDEEEEEEDDEDEEEIEVRS (SEQ ID NO:79)
DEEEEEEDDEDEEEIEVRS (SEQ ID NO:80)
EEEEEDDEDEEEIEVRS (SEQ ID NO:81)
EEEEDDEDEEEIEVRS (SEQ ID NO:82)
EEEDDEDEEEIEVRS (SEQ ID NO:83)
EEDDEDEEEIEVRS (SEQ ID NO:84)
EDDEDEEEIEVRS (SEQ ID NO:85)
DDEDEEEIEVRS (SEQ ID NO:86)
DEDEEEIEVRS (SEQ ID NO:87)
EDEEEIEVRS (SEQ ID NO:88)
DEEEIEVRS (SEQ ID NO:89)
EEEIEVRS (SEQ ID NO:90)
EEIEVRS (SEQ ID NO:91)
EIEVRS (SEQ ID NO:92)
IEVRS (SEQ ID NO:93)
EVRS (SEQ ID NO:94)

EIAGQDEDHFITVDAVGCFEGDEEEEEEDDEDEEEIEVRSR (SEQ ID NO:95)
IAGQDEDHFITVDAVGCFEGDEEEEEEDDEDEEEIEVRSR (SEQ ID NO:96)
AGQDEDHFITVDAVGCFEGDEEEEEEDDEDEEEIEVRSR (SEQ ID NO:97)
GQDEDHFITVDAVGCFEGDEEEEEEDDEDEEEIEVRSR (SEQ ID NO:98)
QDEDHFITVDAVGCFEGDEEEEEEDDEDEEEIEVRSR (SEQ ID NO:99)
DEDHFITVDAVGCFEGDEEEEEEDDEDEEEIEVRSR (SEQ ID NO:100)
EDHFITVDAVGCFEGDEEEEEEDDEDEEEIEVRSR (SEQ ID NO:101)
DHFITVDAVGCFEGDEEEEEEDDEDEEEIEVRSR (SEQ ID NO:102)
HFITVDAVGCFEGDEEEEEEDDEDEEEIEVRSR (SEQ ID NO:103)
FITVDAVGCFEGDEEEEEEDDEDEEEIEVRSR (SEQ ID NO:104)
ITVDAVGCFEGDEEEEEEDDEDEEEIEVRSR (SEQ ID NO:105)
TVDAVGCFEGDEEEEEEDDEDEEEIEVRSR (SEQ ID NO:106)
VDAVGCFEGDEEEEEEDDEDEEEIEVRSR (SEQ ID NO:107)
DAVGCFEGDEEEEEEDDEDEEEIEVRSR (SEQ ID NO:108)
AVGCFEGDEEEEEEDDEDEEEIEVRSR (SEQ ID NO:109)
VGCFEGDEEEEEEDDEDEEEIEVRSR (SEQ ID NO:110)
GCFEGDEEEEEEDDEDEEEIEVRSR (SEQ ID NO:111)
CFEGDEEEEEEDDEDEEEIEVRSR (SEQ ID NO:112)
FEGDEEEEEEDDEDEEEIEVRSR (SEQ ID NO:113)
EGDEEEEEEDDEDEEEIEVRSR (SEQ ID NO:114)
GDEEEEEEDDEDEEEIEVRSR (SEQ ID NO:115)
DEEEEEEDDEDEEEIEVRSR (SEQ ID NO:116)
EEEEEDDEDEEEIEVRSR (SEQ ID NO:117)
EEEEDDEDEEEIEVRSR (SEQ ID NO:118)
EEEDDEDEEEIEVRSR (SEQ ID NO:119)
EEDDEDEEEIEVRSR (SEQ ID NO:120)
EDDEDEEEIEVRSR (SEQ ID NO:121)
DDEDEEEIEVRSR (SEQ ID NO:122)
DEDEEEIEVRSR (SEQ ID NO:123)
EDEEEIEVRSR (SEQ ID NO:124)
DEEEIEVRSR (SEQ ID NO:16)
EEEIEVRSR (SEQ ID NO:125)
EEIEVRSR (SEQ ID NO:126)
EIEVRSR (SEQ ID NO:127)
IEVRSR (SEQ ID NO:128)
EVRSR (SEQ ID NO:129)

EIAGQDEDHFITVDAVGCFEGDEEEEEEDDEDEEEIEVRSRD (SEQ ID NO:130)

FIG. 6C

IAGQDEDHFITVDAVGCFEGDEEEEEDDEDEEEIEVRSRD (SEQ ID NO:131)
AGQDEDHFITVDAVGCFEGDEEEEEDDEDEEEIEVRSRD (SEQ ID NO:132)
GQDEDHFITVDAVGCFEGDEEEEEDDEDEEEIEVRSRD (SEQ ID NO:133)
QDEDHFITVDAVGCFEGDEEEEEDDEDEEEIEVRSRD (SEQ ID NO:134)
DEDHFITVDAVGCFEGDEEEEEDDEDEEEIEVRSRD (SEQ ID NO:135)
EDHFITVDAVGCFEGDEEEEEDDEDEEEIEVRSRD (SEQ ID NO:136)
DHFITVDAVGCFEGDEEEEEDDEDEEEIEVRSRD (SEQ ID NO:137)
HFITVDAVGCFEGDEEEEEDDEDEEEIEVRSRD (SEQ ID NO:138)
FITVDAVGCFEGDEEEEEDDEDEEEIEVRSRD (SEQ ID NO:139)
ITVDAVGCFEGDEEEEEDDEDEEEIEVRSRD (SEQ ID NO:140)
TVDAVGCFEGDEEEEEDDEDEEEIEVRSRD (SEQ ID NO:141)
VDAVGCFEGDEEEEEDDEDEEEIEVRSRD (SEQ ID NO:142)
DAVGCFEGDEEEEEDDEDEEEIEVRSRD (SEQ ID NO:143)
AVGCFEGDEEEEEDDEDEEEIEVRSRD (SEQ ID NO:144)
VGCFEGDEEEEEDDEDEEEIEVRSRD (SEQ ID NO:145)
GCFEGDEEEEEDDEDEEEIEVRSRD (SEQ ID NO:146)
CFEGDEEEEEDDEDEEEIEVRSRD (SEQ ID NO:147)
FEGDEEEEEDDEDEEEIEVRSRD (SEQ ID NO:148)
EGDEEEEEDDEDEEEIEVRSRD (SEQ ID NO:149)
GDEEEEEDDEDEEEIEVRSRD (SEQ ID NO:150)
DEEEEEDDEDEEEIEVRSRD (SEQ ID NO:151)
EEEEEDDEDEEEIEVRSRD (SEQ ID NO:152)
EEEEDDEDEEEIEVRSRD (SEQ ID NO:153)
EEEDDEDEEEIEVRSRD (SEQ ID NO:154)
EEDDEDEEEIEVRSRD (SEQ ID NO:155)
EDDEDEEEIEVRSRD (SEQ ID NO:156)
DDEDEEEIEVRSRD (SEQ ID NO:157)
DEDEEEIEVRSRD (SEQ ID NO:158)
EDEEEIEVRSRD (SEQ ID NO:159)
DEEEIEVRSRD (SEQ ID NO:160)
EEEIEVRSRD (SEQ ID NO:161)
EEIEVRSRD (SEQ ID NO:162)
EIEVRSRD (SEQ ID NO:163)
IEVRSRD (SEQ ID NO:164)
EVRSRD (SEQ ID NO:165)

EIAGQDEDHFITVDAVGCFEGDEEEEEDDEDEEEIEVRSRDI (SEQ ID NO:166)
IAGQDEDHFITVDAVGCFEGDEEEEEDDEDEEEIEVRSRDI (SEQ ID NO:167)
AGQDEDHFITVDAVGCFEGDEEEEEDDEDEEEIEVRSRDI (SEQ ID NO:168)
GQDEDHFITVDAVGCFEGDEEEEEDDEDEEEIEVRSRDI (SEQ ID NO:169)
QDEDHFITVDAVGCFEGDEEEEEDDEDEEEIEVRSRDI (SEQ ID NO:170)
DEDHFITVDAVGCFEGDEEEEEDDEDEEEIEVRSRDI (SEQ ID NO:171)
EDHFITVDAVGCFEGDEEEEEDDEDEEEIEVRSRDI (SEQ ID NO:172)
DHFITVDAVGCFEGDEEEEEDDEDEEEIEVRSRDI (SEQ ID NO:173)
HFITVDAVGCFEGDEEEEEDDEDEEEIEVRSRDI (SEQ ID NO:174)
FITVDAVGCFEGDEEEEEDDEDEEEIEVRSRDI (SEQ ID NO:175)
ITVDAVGCFEGDEEEEEDDEDEEEIEVRSRDI (SEQ ID NO:176)
TVDAVGCFEGDEEEEEDDEDEEEIEVRSRDI (SEQ ID NO:177)
VDAVGCFEGDEEEEEDDEDEEEIEVRSRDI (SEQ ID NO:178)
DAVGCFEGDEEEEEDDEDEEEIEVRSRDI (SEQ ID NO:179)
AVGCFEGDEEEEEDDEDEEEIEVRSRDI (SEQ ID NO:180)
VGCFEGDEEEEEDDEDEEEIEVRSRDI (SEQ ID NO:181)
GCFEGDEEEEEDDEDEEEIEVRSRDI (SEQ ID NO:182)
CFEGDEEEEEDDEDEEEIEVRSRDI (SEQ ID NO:183)
FEGDEEEEEDDEDEEEIEVRSRDI (SEQ ID NO:184)
EGDEEEEEDDEDEEEIEVRSRDI (SEQ ID NO:185)
GDEEEEEDDEDEEEIEVRSRDI (SEQ ID NO:186)
DEEEEEDDEDEEEIEVRSRDI (SEQ ID NO:187)
EEEEEDDEDEEEIEVRSRDI (SEQ ID NO:188)
EEEEDDEDEEEIEVRSRDI (SEQ ID NO:189)

FIG. 6D

EEEDDEDEEEIEVRSRDI (SEQ ID NO:190)
EEDDEDEEEIEVRSRDI (SEQ ID NO:191)
EDDEDEEEIEVRSRDI (SEQ ID NO:192)
DDEDEEEIEVRSRDI (SEQ ID NO:193)
DEDEEEIEVRSRDI (SEQ ID NO:194)
EDEEEIEVRSRDI (SEQ ID NO:195)
DEEEIEVRSRDI (SEQ ID NO:196)
EEEIEVRSRDI (SEQ ID NO:197)
EEIEVRSRDI (SEQ ID NO:198)
EIEVRSRDI (SEQ ID NO:199)
IEVRSRDI (SEQ ID NO:200)
EVRSRDI (SEQ ID NO:201)

EIAGQDEDHFITVDAVGCFEGDEEEEEDDEDEEEIEVRSRDIS (SEQ ID NO:202)
IAGQDEDHFITVDAVGCFEGDEEEEEDDEDEEEIEVRSRDIS (SEQ ID NO:203)
AGQDEDHFITVDAVGCFEGDEEEEEDDEDEEEIEVRSRDIS (SEQ ID NO:204)
GQDEDHFITVDAVGCFEGDEEEEEDDEDEEEIEVRSRDIS (SEQ ID NO:205)
QDEDHFITVDAVGCFEGDEEEEEDDEDEEEIEVRSRDIS (SEQ ID NO:206)
DEDHFITVDAVGCFEGDEEEEEDDEDEEEIEVRSRDIS (SEQ ID NO:207)
EDHFITVDAVGCFEGDEEEEEDDEDEEEIEVRSRDIS (SEQ ID NO:208)
DHFITVDAVGCFEGDEEEEEDDEDEEEIEVRSRDIS (SEQ ID NO:209)
HFITVDAVGCFEGDEEEEEDDEDEEEIEVRSRDIS (SEQ ID NO:210)
FITVDAVGCFEGDEEEEEDDEDEEEIEVRSRDIS (SEQ ID NO:211)
ITVDAVGCFEGDEEEEEDDEDEEEIEVRSRDIS (SEQ ID NO:212)
TVDAVGCFEGDEEEEEDDEDEEEIEVRSRDIS (SEQ ID NO:213)
VDAVGCFEGDEEEEEDDEDEEEIEVRSRDIS (SEQ ID NO:214)
DAVGCFEGDEEEEEDDEDEEEIEVRSRDIS (SEQ ID NO:215)
AVGCFEGDEEEEEDDEDEEEIEVRSRDIS (SEQ ID NO:216)
VGCFEGDEEEEEDDEDEEEIEVRSRDIS (SEQ ID NO:217)
GCFEGDEEEEEDDEDEEEIEVRSRDIS (SEQ ID NO:218)
CFEGDEEEEEDDEDEEEIEVRSRDIS (SEQ ID NO:219)
FEGDEEEEEDDEDEEEIEVRSRDIS (SEQ ID NO:220)
EGDEEEEEDDEDEEEIEVRSRDIS (SEQ ID NO:221)
GDEEEEEDDEDEEEIEVRSRDIS (SEQ ID NO:222)
DEEEEEDDEDEEEIEVRSRDIS (SEQ ID NO:223)
EEEEEDDEDEEEIEVRSRDIS (SEQ ID NO:224)
EEEEDDEDEEEIEVRSRDIS (SEQ ID NO:225)
EEEDDEDEEEIEVRSRDIS (SEQ ID NO:226)
EEDDEDEEEIEVRSRDIS (SEQ ID NO:227)
EDDEDEEEIEVRSRDIS (SEQ ID NO:228)
DDEDEEEIEVRSRDIS (SEQ ID NO:229)
DEDEEEIEVRSRDIS (SEQ ID NO:230)
EDEEEIEVRSRDIS (SEQ ID NO:231)
DEEEIEVRSRDIS (SEQ ID NO:2)
EEEIEVRSRDIS (SEQ ID NO:232)
EEIEVRSRDIS (SEQ ID NO:233)
EIEVRSRDIS (SEQ ID NO:234)
IEVRSRDIS (SEQ ID NO:235)
EVRSRDIS (SEQ ID NO:236)

EIAGQDEDHFITVDAVGCFEGDEEEEEDDEDEEEIEVRSRDISR (SEQ ID NO:237)
IAGQDEDHFITVDAVGCFEGDEEEEEDDEDEEEIEVRSRDISR (SEQ ID NO:238)
AGQDEDHFITVDAVGCFEGDEEEEEDDEDEEEIEVRSRDISR (SEQ ID NO:239)
GQDEDHFITVDAVGCFEGDEEEEEDDEDEEEIEVRSRDISR (SEQ ID NO:240)
QDEDHFITVDAVGCFEGDEEEEEDDEDEEEIEVRSRDISR (SEQ ID NO:241)
DEDHFITVDAVGCFEGDEEEEEDDEDEEEIEVRSRDISR (SEQ ID NO:242)
EDHFITVDAVGCFEGDEEEEEDDEDEEEIEVRSRDISR (SEQ ID NO:243)
DHFITVDAVGCFEGDEEEEEDDEDEEEIEVRSRDISR (SEQ ID NO:244)
HFITVDAVGCFEGDEEEEEDDEDEEEIEVRSRDISR (SEQ ID NO:245)
FITVDAVGCFEGDEEEEEDDEDEEEIEVRSRDISR (SEQ ID NO:246)

FIG. 6E

ITVDAVGCFEGDEEEEEDDEDEEEIEVRSRDISR (SEQ ID NO:247)
TVDAVGCFEGDEEEEEDDEDEEEIEVRSRDISR (SEQ ID NO:248)
VDAVGCFEGDEEEEEDDEDEEEIEVRSRDISR (SEQ ID NO:249)
DAVGCFEGDEEEEEDDEDEEEIEVRSRDISR (SEQ ID NO:250)
AVGCFEGDEEEEEDDEDEEEIEVRSRDISR (SEQ ID NO:251)
VGCFEGDEEEEEDDEDEEEIEVRSRDISR (SEQ ID NO:252)
GCFEGDEEEEEDDEDEEEIEVRSRDISR (SEQ ID NO:253)
CFEGDEEEEEDDEDEEEIEVRSRDISR (SEQ ID NO:254)
FEGDEEEEEDDEDEEEIEVRSRDISR (SEQ ID NO:255)
EGDEEEEEDDEDEEEIEVRSRDISR (SEQ ID NO:256)
GDEEEEEDDEDEEEIEVRSRDISR (SEQ ID NO:257)
DEEEEEDDEDEEEIEVRSRDISR (SEQ ID NO:258)
EEEEEDDEDEEEIEVRSRDISR (SEQ ID NO:259)
EEEEDDEDEEEIEVRSRDISR (SEQ ID NO:260)
EEEDDEDEEEIEVRSRDISR (SEQ ID NO:261)
EEDDEDEEEIEVRSRDISR (SEQ ID NO:262)
EDDEDEEEIEVRSRDISR (SEQ ID NO:263)
DDEDEEEIEVRSRDISR (SEQ ID NO:264)
DEDEEEIEVRSRDISR (SEQ ID NO:265)
EDEEEIEVRSRDISR (SEQ ID NO:266)
DEEEIEVRSRDISR (SEQ ID NO:267)
EEEIEVRSRDISR (SEQ ID NO:268)
EEIEVRSRDISR (SEQ ID NO:269)
EIEVRSRDISR (SEQ ID NO:270)
IEVRSRDISR (SEQ ID NO:271)
EVRSRDISR (SEQ ID NO:272)

EIAGQDEDHFITVDAVGCFEGDEEEEEDDEDEEEIEVRSRDISRE (SEQ ID NO:273)
IAGQDEDHFITVDAVGCFEGDEEEEEDDEDEEEIEVRSRDISRE (SEQ ID NO:274)
AGQDEDHFITVDAVGCFEGDEEEEEDDEDEEEIEVRSRDISRE (SEQ ID NO:275)
GQDEDHFITVDAVGCFEGDEEEEEDDEDEEEIEVRSRDISRE (SEQ ID NO:276)
QDEDHFITVDAVGCFEGDEEEEEDDEDEEEIEVRSRDISRE (SEQ ID NO:277)
DEDHFITVDAVGCFEGDEEEEEDDEDEEEIEVRSRDISRE (SEQ ID NO:278)
EDHFITVDAVGCFEGDEEEEEDDEDEEEIEVRSRDISRE (SEQ ID NO:279)
DHFITVDAVGCFEGDEEEEEDDEDEEEIEVRSRDISRE (SEQ ID NO:280)
HFITVDAVGCFEGDEEEEEDDEDEEEIEVRSRDISRE (SEQ ID NO:281)
FITVDAVGCFEGDEEEEEDDEDEEEIEVRSRDISRE (SEQ ID NO:282)
ITVDAVGCFEGDEEEEEDDEDEEEIEVRSRDISRE (SEQ ID NO:283)
TVDAVGCFEGDEEEEEDDEDEEEIEVRSRDISRE (SEQ ID NO:284)
VDAVGCFEGDEEEEEDDEDEEEIEVRSRDISRE (SEQ ID NO:285)
DAVGCFEGDEEEEEDDEDEEEIEVRSRDISRE (SEQ ID NO:286)
AVGCFEGDEEEEEDDEDEEEIEVRSRDISRE (SEQ ID NO:287)
VGCFEGDEEEEEDDEDEEEIEVRSRDISRE (SEQ ID NO:288)
GCFEGDEEEEEDDEDEEEIEVRSRDISRE (SEQ ID NO:289)
CFEGDEEEEEDDEDEEEIEVRSRDISRE (SEQ ID NO:290)
FEGDEEEEEDDEDEEEIEVRSRDISRE (SEQ ID NO:291)
EGDEEEEEDDEDEEEIEVRSRDISRE (SEQ ID NO:292)
GDEEEEEDDEDEEEIEVRSRDISRE (SEQ ID NO:293)
DEEEEEDDEDEEEIEVRSRDISRE (SEQ ID NO:294)
EEEEEDDEDEEEIEVRSRDISRE (SEQ ID NO:295)
EEEEDDEDEEEIEVRSRDISRE (SEQ ID NO:296)
EEEDDEDEEEIEVRSRDISRE (SEQ ID NO:297)
EEDDEDEEEIEVRSRDISRE (SEQ ID NO:298)
EDDEDEEEIEVRSRDISRE (SEQ ID NO:299)
DDEDEEEIEVRSRDISRE (SEQ ID NO:300)
DEDEEEIEVRSRDISRE (SEQ ID NO:301)
EDEEEIEVRSRDISRE (SEQ ID NO:302)
DEEEIEVRSRDISRE (SEQ ID NO:303)
EEEIEVRSRDISRE (SEQ ID NO:304)
EEIEVRSRDISRE (SEQ ID NO:305)

FIG. 6F

EIEVRSRDISRE (SEQ ID NO:306)
IEVRSRDISRE (SEQ ID NO:307)
EVRSRDISRE (SEQ ID NO:308)

EIAGQDEDHFITVDAVGCFEGDEEEEEDDEDEEEIEVRSRDISREE (SEQ ID NO:309)
IAGQDEDHFITVDAVGCFEGDEEEEEDDEDEEEIEVRSRDISREE (SEQ ID NO:310)
AGQDEDHFITVDAVGCFEGDEEEEEDDEDEEEIEVRSRDISREE (SEQ ID NO:311)
GQDEDHFITVDAVGCFEGDEEEEEDDEDEEEIEVRSRDISREE (SEQ ID NO:312)
QDEDHFITVDAVGCFEGDEEEEEDDEDEEEIEVRSRDISREE (SEQ ID NO:313)
DEDHFITVDAVGCFEGDEEEEEDDEDEEEIEVRSRDISREE (SEQ ID NO:314)
EDHFITVDAVGCFEGDEEEEEDDEDEEEIEVRSRDISREE (SEQ ID NO:315)
DHFITVDAVGCFEGDEEEEEDDEDEEEIEVRSRDISREE (SEQ ID NO:316)
HFITVDAVGCFEGDEEEEEDDEDEEEIEVRSRDISREE (SEQ ID NO:317)
FITVDAVGCFEGDEEEEEDDEDEEEIEVRSRDISREE (SEQ ID NO:318)
ITVDAVGCFEGDEEEEEDDEDEEEIEVRSRDISREE (SEQ ID NO:319)
TVDAVGCFEGDEEEEEDDEDEEEIEVRSRDISREE (SEQ ID NO:320)
VDAVGCFEGDEEEEEDDEDEEEIEVRSRDISREE (SEQ ID NO:321)
DAVGCFEGDEEEEEDDEDEEEIEVRSRDISREE (SEQ ID NO:322)
AVGCFEGDEEEEEDDEDEEEIEVRSRDISREE (SEQ ID NO:323)
VGCFEGDEEEEEDDEDEEEIEVRSRDISREE (SEQ ID NO:324)
GCFEGDEEEEEDDEDEEEIEVRSRDISREE (SEQ ID NO:325)
CFEGDEEEEEDDEDEEEIEVRSRDISREE (SEQ ID NO:326)
FEGDEEEEEDDEDEEEIEVRSRDISREE (SEQ ID NO:327)
EGDEEEEEDDEDEEEIEVRSRDISREE (SEQ ID NO:328)
GDEEEEEDDEDEEEIEVRSRDISREE (SEQ ID NO:329)
DEEEEEDDEDEEEIEVRSRDISREE (SEQ ID NO:330)
EEEEEDDEDEEEIEVRSRDISREE (SEQ ID NO:331)
EEEEDDEDEEEIEVRSRDISREE (SEQ ID NO:332)
EEEDDEDEEEIEVRSRDISREE (SEQ ID NO:333)
EEDDEDEEEIEVRSRDISREE (SEQ ID NO:334)
EDDEDEEEIEVRSRDISREE (SEQ ID NO:335)
DDEDEEEIEVRSRDISREE (SEQ ID NO:336)
DEDEEEIEVRSRDISREE (SEQ ID NO:337)
EDEEEIEVRSRDISREE (SEQ ID NO:338)
DEEEIEVRSRDISREE (SEQ ID NO:339)
EEEIEVRSRDISREE (SEQ ID NO:340)
EEIEVRSRDISREE (SEQ ID NO:341)
EIEVRSRDISREE (SEQ ID NO:342)
IEVRSRDISREE (SEQ ID NO:343)
EVRSRDISREE (SEQ ID NO:344)

EIAGQDEDHFITVDAVGCFEGDEEEEEDDEDEEEIEVRSRDISREEW (SEQ ID NO:345)
IAGQDEDHFITVDAVGCFEGDEEEEEDDEDEEEIEVRSRDISREEW (SEQ ID NO:346)
AGQDEDHFITVDAVGCFEGDEEEEEDDEDEEEIEVRSRDISREEW (SEQ ID NO:347)
GQDEDHFITVDAVGCFEGDEEEEEDDEDEEEIEVRSRDISREEW (SEQ ID NO:348)
QDEDHFITVDAVGCFEGDEEEEEDDEDEEEIEVRSRDISREEW (SEQ ID NO:349)
DEDHFITVDAVGCFEGDEEEEEDDEDEEEIEVRSRDISREEW (SEQ ID NO:350)
EDHFITVDAVGCFEGDEEEEEDDEDEEEIEVRSRDISREEW (SEQ ID NO:351)
DHFITVDAVGCFEGDEEEEEDDEDEEEIEVRSRDISREEW (SEQ ID NO:352)
HFITVDAVGCFEGDEEEEEDDEDEEEIEVRSRDISREEW (SEQ ID NO:353)
FITVDAVGCFEGDEEEEEDDEDEEEIEVRSRDISREEW (SEQ ID NO:354)
ITVDAVGCFEGDEEEEEDDEDEEEIEVRSRDISREEW (SEQ ID NO:355)
TVDAVGCFEGDEEEEEDDEDEEEIEVRSRDISREEW (SEQ ID NO:356)
VDAVGCFEGDEEEEEDDEDEEEIEVRSRDISREEW (SEQ ID NO:357)
DAVGCFEGDEEEEEDDEDEEEIEVRSRDISREEW (SEQ ID NO:358)
AVGCFEGDEEEEEDDEDEEEIEVRSRDISREEW (SEQ ID NO:359)
VGCFEGDEEEEEDDEDEEEIEVRSRDISREEW (SEQ ID NO:360)
GCFEGDEEEEEDDEDEEEIEVRSRDISREEW (SEQ ID NO:361)
CFEGDEEEEEDDEDEEEIEVRSRDISREEW (SEQ ID NO:362)
FEGDEEEEEDDEDEEEIEVRSRDISREEW (SEQ ID NO:363)

FIG. 6G

EGDEEEEEEDDEDEEEIEVRSRDISREEW (SEQ ID NO:364)
GDEEEEEEDDEDEEEIEVRSRDISREEW (SEQ ID NO:365)
DEEEEEEDDEDEEEIEVRSRDISREEW (SEQ ID NO:366)
EEEEEDDEDEEEIEVRSRDISREEW (SEQ ID NO:367)
EEEEDDEDEEEIEVRSRDISREEW (SEQ ID NO:368)
EEEDDEDEEEIEVRSRDISREEW (SEQ ID NO:369)
EEDDEDEEEIEVRSRDISREEW (SEQ ID NO:370)
EDDEDEEEIEVRSRDISREEW (SEQ ID NO:371)
DDEDEEEIEVRSRDISREEW (SEQ ID NO:372)
DEDEEEIEVRSRDISREEW (SEQ ID NO:373)
EDEEEIEVRSRDISREEW (SEQ ID NO:374)
DEEEIEVRSRDISREEW (SEQ ID NO:375)
EEEIEVRSRDISREEW (SEQ ID NO:376)
EEIEVRSRDISREEW (SEQ ID NO:377)
EIEVRSRDISREEW (SEQ ID NO:378)
IEVRSRDISREEW (SEQ ID NO:379)
EVRSRDISREEW (SEQ ID NO:380)

EIAGQDEDHFITVDAVGCFEGDEEEEEEDDEDEEEIEVRSRDISREEWK (SEQ ID NO:381)
IAGQDEDHFITVDAVGCFEGDEEEEEEDDEDEEEIEVRSRDISREEWK (SEQ ID NO:382)
AGQDEDHFITVDAVGCFEGDEEEEEEDDEDEEEIEVRSRDISREEWK (SEQ ID NO:383)
GQDEDHFITVDAVGCFEGDEEEEEEDDEDEEEIEVRSRDISREEWK (SEQ ID NO:384)
QDEDHFITVDAVGCFEGDEEEEEEDDEDEEEIEVRSRDISREEWK (SEQ ID NO:385)
DEDHFITVDAVGCFEGDEEEEEEDDEDEEEIEVRSRDISREEWK (SEQ ID NO:386)
EDHFITVDAVGCFEGDEEEEEEDDEDEEEIEVRSRDISREEWK (SEQ ID NO:387)
DHFITVDAVGCFEGDEEEEEEDDEDEEEIEVRSRDISREEWK (SEQ ID NO:388)
HFITVDAVGCFEGDEEEEEEDDEDEEEIEVRSRDISREEWK (SEQ ID NO:389)
FITVDAVGCFEGDEEEEEEDDEDEEEIEVRSRDISREEWK (SEQ ID NO:390)
ITVDAVGCFEGDEEEEEEDDEDEEEIEVRSRDISREEWK (SEQ ID NO:391)
TVDAVGCFEGDEEEEEEDDEDEEEIEVRSRDISREEWK (SEQ ID NO:392)
VDAVGCFEGDEEEEEEDDEDEEEIEVRSRDISREEWK (SEQ ID NO:393)
DAVGCFEGDEEEEEEDDEDEEEIEVRSRDISREEWK (SEQ ID NO:394)
AVGCFEGDEEEEEEDDEDEEEIEVRSRDISREEWK (SEQ ID NO:395)
VGCFEGDEEEEEEDDEDEEEIEVRSRDISREEWK (SEQ ID NO:396)
GCFEGDEEEEEEDDEDEEEIEVRSRDISREEWK (SEQ ID NO:397)
CFEGDEEEEEEDDEDEEEIEVRSRDISREEWK (SEQ ID NO:398)
FEGDEEEEEEDDEDEEEIEVRSRDISREEWK (SEQ ID NO:399)
EGDEEEEEEDDEDEEEIEVRSRDISREEWK (SEQ ID NO:400)
GDEEEEEEDDEDEEEIEVRSRDISREEWK (SEQ ID NO:401)
DEEEEEEDDEDEEEIEVRSRDISREEWK (SEQ ID NO:402)
EEEEEDDEDEEEIEVRSRDISREEWK (SEQ ID NO:403)
EEEEDDEDEEEIEVRSRDISREEWK (SEQ ID NO:404)
EEEDDEDEEEIEVRSRDISREEWK (SEQ ID NO:405)
EEDDEDEEEIEVRSRDISREEWK (SEQ ID NO:406)
EDDEDEEEIEVRSRDISREEWK (SEQ ID NO:407)
DDEDEEEIEVRSRDISREEWK (SEQ ID NO:408)
DEDEEEIEVRSRDISREEWK (SEQ ID NO:409)
EDEEEIEVRSRDISREEWK (SEQ ID NO:410)
DEEEIEVRSRDISREEWK (SEQ ID NO:411)
EEEIEVRSRDISREEWK (SEQ ID NO:412)
EEIEVRSRDISREEWK (SEQ ID NO:413)
EIEVRSRDISREEWK (SEQ ID NO:414)
IEVRSRDISREEWK (SEQ ID NO:415)
EVRSRDISREEWK (SEQ ID NO:416)

EIAGQDEDHFITVDAVGCFEGDEEEEEEDDEDEEEIEVRSRDISREEWKG (SEQ ID NO:417)
IAGQDEDHFITVDAVGCFEGDEEEEEEDDEDEEEIEVRSRDISREEWKG (SEQ ID NO:418)
AGQDEDHFITVDAVGCFEGDEEEEEEDDEDEEEIEVRSRDISREEWKG (SEQ ID NO:419)
GQDEDHFITVDAVGCFEGDEEEEEEDDEDEEEIEVRSRDISREEWKG (SEQ ID NO:420)
QDEDHFITVDAVGCFEGDEEEEEEDDEDEEEIEVRSRDISREEWKG (SEQ ID NO:421)

FIG. 6H

DEDHFITVDAVGCFEGDEEEEEDDEDEEEIEVRSRDISREEWKG (SEQ ID NO:422)
EDHFITVDAVGCFEGDEEEEEDDEDEEEIEVRSRDISREEWKG (SEQ ID NO:423)
DHFITVDAVGCFEGDEEEEEDDEDEEEIEVRSRDISREEWKG (SEQ ID NO:424)
HFITVDAVGCFEGDEEEEEDDEDEEEIEVRSRDISREEWKG (SEQ ID NO:425)
FITVDAVGCFEGDEEEEEDDEDEEEIEVRSRDISREEWKG (SEQ ID NO:426)
ITVDAVGCFEGDEEEEEDDEDEEEIEVRSRDISREEWKG (SEQ ID NO:427)
TVDAVGCFEGDEEEEEDDEDEEEIEVRSRDISREEWKG (SEQ ID NO:428)
VDAVGCFEGDEEEEEDDEDEEEIEVRSRDISREEWKG (SEQ ID NO:429)
DAVGCFEGDEEEEEDDEDEEEIEVRSRDISREEWKG (SEQ ID NO:430)
AVGCFEGDEEEEEDDEDEEEIEVRSRDISREEWKG (SEQ ID NO:431)
VGCFEGDEEEEEDDEDEEEIEVRSRDISREEWKG (SEQ ID NO:432)
GCFEGDEEEEEDDEDEEEIEVRSRDISREEWKG (SEQ ID NO:433)
CFEGDEEEEEDDEDEEEIEVRSRDISREEWKG (SEQ ID NO:434)
FEGDEEEEEDDEDEEEIEVRSRDISREEWKG (SEQ ID NO:435)
EGDEEEEEDDEDEEEIEVRSRDISREEWKG (SEQ ID NO:436)
GDEEEEEDDEDEEEIEVRSRDISREEWKG (SEQ ID NO:437)
DEEEEEDDEDEEEIEVRSRDISREEWKG (SEQ ID NO:438)
EEEEEDDEDEEEIEVRSRDISREEWKG (SEQ ID NO:439)
EEEEDDEDEEEIEVRSRDISREEWKG (SEQ ID NO:440)
EEEDDEDEEEIEVRSRDISREEWKG (SEQ ID NO:441)
EEDDEDEEEIEVRSRDISREEWKG (SEQ ID NO:442)
EDDEDEEEIEVRSRDISREEWKG (SEQ ID NO:443)
DDEDEEEIEVRSRDISREEWKG (SEQ ID NO:444)
DEDEEEIEVRSRDISREEWKG (SEQ ID NO:445)
EDEEEIEVRSRDISREEWKG (SEQ ID NO:446)
DEEEIEVRSRDISREEWKG (SEQ ID NO:447)
EEEIEVRSRDISREEWKG (SEQ ID NO:448)
EEIEVRSRDISREEWKG (SEQ ID NO:449)
EIEVRSRDISREEWKG (SEQ ID NO:450)
IEVRSRDISREEWKG (SEQ ID NO:451)
EVRSRDISREEWKG (SEQ ID NO:452)

EIAGQDEDHFITVDAVGCFEGDEEEEEDDEDEEEIEVRSRDISREEWKGS (SEQ ID NO:453)
IAGQDEDHFITVDAVGCFEGDEEEEEDDEDEEEIEVRSRDISREEWKGS (SEQ ID NO:454)
AGQDEDHFITVDAVGCFEGDEEEEEDDEDEEEIEVRSRDISREEWKGS (SEQ ID NO:455)
GQDEDHFITVDAVGCFEGDEEEEEDDEDEEEIEVRSRDISREEWKGS (SEQ ID NO:456)
QDEDHFITVDAVGCFEGDEEEEEDDEDEEEIEVRSRDISREEWKGS (SEQ ID NO:457)
DEDHFITVDAVGCFEGDEEEEEDDEDEEEIEVRSRDISREEWKGS (SEQ ID NO:458)
EDHFITVDAVGCFEGDEEEEEDDEDEEEIEVRSRDISREEWKGS (SEQ ID NO:459)
DHFITVDAVGCFEGDEEEEEDDEDEEEIEVRSRDISREEWKGS (SEQ ID NO:460)
HFITVDAVGCFEGDEEEEEDDEDEEEIEVRSRDISREEWKGS (SEQ ID NO:461)
FITVDAVGCFEGDEEEEEDDEDEEEIEVRSRDISREEWKGS (SEQ ID NO:462)
ITVDAVGCFEGDEEEEEDDEDEEEIEVRSRDISREEWKGS (SEQ ID NO:463)
TVDAVGCFEGDEEEEEDDEDEEEIEVRSRDISREEWKGS (SEQ ID NO:464)
VDAVGCFEGDEEEEEDDEDEEEIEVRSRDISREEWKGS (SEQ ID NO:465)
DAVGCFEGDEEEEEDDEDEEEIEVRSRDISREEWKGS (SEQ ID NO:466)
AVGCFEGDEEEEEDDEDEEEIEVRSRDISREEWKGS (SEQ ID NO:467)
VGCFEGDEEEEEDDEDEEEIEVRSRDISREEWKGS (SEQ ID NO:468)
GCFEGDEEEEEDDEDEEEIEVRSRDISREEWKGS (SEQ ID NO:469)
CFEGDEEEEEDDEDEEEIEVRSRDISREEWKGS (SEQ ID NO:470)
FEGDEEEEEDDEDEEEIEVRSRDISREEWKGS (SEQ ID NO:471)
EGDEEEEEDDEDEEEIEVRSRDISREEWKGS (SEQ ID NO:472)
GDEEEEEDDEDEEEIEVRSRDISREEWKGS (SEQ ID NO:473)
DEEEEEDDEDEEEIEVRSRDISREEWKGS (SEQ ID NO:474)
EEEEEDDEDEEEIEVRSRDISREEWKGS (SEQ ID NO:475)
EEEEDDEDEEEIEVRSRDISREEWKGS (SEQ ID NO:476)
EEEDDEDEEEIEVRSRDISREEWKGS (SEQ ID NO:477)
EEDDEDEEEIEVRSRDISREEWKGS (SEQ ID NO:478)
EDDEDEEEIEVRSRDISREEWKGS (SEQ ID NO:479)
DDEDEEEIEVRSRDISREEWKGS (SEQ ID NO:480)

FIG. 6I

DEDEEEIEVRSRDISREEWKGS (SEQ ID NO:481)
EDEEEIEVRSRDISREEWKGS (SEQ ID NO:482)
DEEEIEVRSRDISREEWKGS (SEQ ID NO:483)
EEEIEVRSRDISREEWKGS (SEQ ID NO:484)
EEIEVRSRDISREEWKGS (SEQ ID NO:485)
EIEVRSRDISREEWKGS (SEQ ID NO:486)
IEVRSRDISREEWKGS (SEQ ID NO:487)
EVRSRDISREEWKGS (SEQ ID NO:488)

EIAGQDEDHFITVDAVGCFEGDEEEEEDDEDEEEIEVRSRDISREEWKGSE (SEQ ID NO:489)
IAGQDEDHFITVDAVGCFEGDEEEEEDDEDEEEIEVRSRDISREEWKGSE (SEQ ID NO:490)
AGQDEDHFITVDAVGCFEGDEEEEEDDEDEEEIEVRSRDISREEWKGSE (SEQ ID NO:491)
GQDEDHFITVDAVGCFEGDEEEEEDDEDEEEIEVRSRDISREEWKGSE (SEQ ID NO:492)
QDEDHFITVDAVGCFEGDEEEEEDDEDEEEIEVRSRDISREEWKGSE (SEQ ID NO:493)
DEDHFITVDAVGCFEGDEEEEEDDEDEEEIEVRSRDISREEWKGSE (SEQ ID NO:494)
EDHFITVDAVGCFEGDEEEEEDDEDEEEIEVRSRDISREEWKGSE (SEQ ID NO:495)
DHFITVDAVGCFEGDEEEEEDDEDEEEIEVRSRDISREEWKGSE (SEQ ID NO:496)
HFITVDAVGCFEGDEEEEEDDEDEEEIEVRSRDISREEWKGSE (SEQ ID NO:497)
FITVDAVGCFEGDEEEEEDDEDEEEIEVRSRDISREEWKGSE (SEQ ID NO:498)
ITVDAVGCFEGDEEEEEDDEDEEEIEVRSRDISREEWKGSE (SEQ ID NO:499)
TVDAVGCFEGDEEEEEDDEDEEEIEVRSRDISREEWKGSE (SEQ ID NO:500)
VDAVGCFEGDEEEEEDDEDEEEIEVRSRDISREEWKGSE (SEQ ID NO:501)
DAVGCFEGDEEEEEDDEDEEEIEVRSRDISREEWKGSE (SEQ ID NO:502)
AVGCFEGDEEEEEDDEDEEEIEVRSRDISREEWKGSE (SEQ ID NO:503)
VGCFEGDEEEEEDDEDEEEIEVRSRDISREEWKGSE (SEQ ID NO:504)
GCFEGDEEEEEDDEDEEEIEVRSRDISREEWKGSE (SEQ ID NO:505)
CFEGDEEEEEDDEDEEEIEVRSRDISREEWKGSE (SEQ ID NO:506)
FEGDEEEEEDDEDEEEIEVRSRDISREEWKGSE (SEQ ID NO:507)
EGDEEEEEDDEDEEEIEVRSRDISREEWKGSE (SEQ ID NO:508)
GDEEEEEDDEDEEEIEVRSRDISREEWKGSE (SEQ ID NO:509)
DEEEEEDDEDEEEIEVRSRDISREEWKGSE (SEQ ID NO:510)
EEEEEDDEDEEEIEVRSRDISREEWKGSE (SEQ ID NO:511)
EEEEDDEDEEEIEVRSRDISREEWKGSE (SEQ ID NO:512)
EEEDDEDEEEIEVRSRDISREEWKGSE (SEQ ID NO:513)
EEDDEDEEEIEVRSRDISREEWKGSE (SEQ ID NO:514)
EDDEDEEEIEVRSRDISREEWKGSE (SEQ ID NO:515)
DDEDEEEIEVRSRDISREEWKGSE (SEQ ID NO:516)
DEDEEEIEVRSRDISREEWKGSE (SEQ ID NO:517)
EDEEEIEVRSRDISREEWKGSE (SEQ ID NO:518)
DEEEIEVRSRDISREEWKGSE (SEQ ID NO:519)
EEEIEVRSRDISREEWKGSE (SEQ ID NO:520)
EEIEVRSRDISREEWKGSE (SEQ ID NO:521)
EIEVRSRDISREEWKGSE (SEQ ID NO:522)
IEVRSRDISREEWKGSE (SEQ ID NO:523)
EVRSRDISREEWKGSE (SEQ ID NO:524)

EIAGQDEDHFITVDAVGCFEGDEEEEEDDEDEEEIEVRSRDISREEWKGSET (SEQ ID NO:525)
IAGQDEDHFITVDAVGCFEGDEEEEEDDEDEEEIEVRSRDISREEWKGSET (SEQ ID NO:526)
AGQDEDHFITVDAVGCFEGDEEEEEDDEDEEEIEVRSRDISREEWKGSET (SEQ ID NO:527)
GQDEDHFITVDAVGCFEGDEEEEEDDEDEEEIEVRSRDISREEWKGSET (SEQ ID NO:528)
QDEDHFITVDAVGCFEGDEEEEEDDEDEEEIEVRSRDISREEWKGSET (SEQ ID NO:529)
DEDHFITVDAVGCFEGDEEEEEDDEDEEEIEVRSRDISREEWKGSET (SEQ ID NO:530)
EDHFITVDAVGCFEGDEEEEEDDEDEEEIEVRSRDISREEWKGSET (SEQ ID NO:531)
DHFITVDAVGCFEGDEEEEEDDEDEEEIEVRSRDISREEWKGSET (SEQ ID NO:532)
HFITVDAVGCFEGDEEEEEDDEDEEEIEVRSRDISREEWKGSET (SEQ ID NO:533)
FITVDAVGCFEGDEEEEEDDEDEEEIEVRSRDISREEWKGSET (SEQ ID NO:534)
ITVDAVGCFEGDEEEEEDDEDEEEIEVRSRDISREEWKGSET (SEQ ID NO:535)
TVDAVGCFEGDEEEEEDDEDEEEIEVRSRDISREEWKGSET (SEQ ID NO:536)
VDAVGCFEGDEEEEEDDEDEEEIEVRSRDISREEWKGSET (SEQ ID NO:537)
DAVGCFEGDEEEEEDDEDEEEIEVRSRDISREEWKGSET (SEQ ID NO:538)

FIG. 6J

AVGCFEGDEEEEEDDEDEEEIEVRSRDISREEWKGSET (SEQ ID NO:539)
VGCFEGDEEEEEDDEDEEEIEVRSRDISREEWKGSET (SEQ ID NO:540)
GCFEGDEEEEEDDEDEEEIEVRSRDISREEWKGSET (SEQ ID NO:541)
CFEGDEEEEEDDEDEEEIEVRSRDISREEWKGSET (SEQ ID NO:542)
FEGDEEEEEDDEDEEEIEVRSRDISREEWKGSET (SEQ ID NO:543)
EGDEEEEEDDEDEEEIEVRSRDISREEWKGSET (SEQ ID NO:544)
GDEEEEEDDEDEEEIEVRSRDISREEWKGSET (SEQ ID NO:545)
DEEEEEDDEDEEEIEVRSRDISREEWKGSET (SEQ ID NO:546)
EEEEEDDEDEEEIEVRSRDISREEWKGSET (SEQ ID NO:547)
EEEEDDEDEEEIEVRSRDISREEWKGSET (SEQ ID NO:548)
EEEDDEDEEEIEVRSRDISREEWKGSET (SEQ ID NO:549)
EEDDEDEEEIEVRSRDISREEWKGSET (SEQ ID NO:550)
EDDEDEEEIEVRSRDISREEWKGSET (SEQ ID NO:551)
DDEDEEEIEVRSRDISREEWKGSET (SEQ ID NO:552)
DEDEEEIEVRSRDISREEWKGSET (SEQ ID NO:553)
EDEEEIEVRSRDISREEWKGSET (SEQ ID NO:554)
DEEEIEVRSRDISREEWKGSET (SEQ ID NO:555)
EEEIEVRSRDISREEWKGSET (SEQ ID NO:556)
EEIEVRSRDISREEWKGSET (SEQ ID NO:557)
EIEVRSRDISREEWKGSET (SEQ ID NO:558)
IEVRSRDISREEWKGSET (SEQ ID NO:559)
EVRSRDISREEWKGSET (SEQ ID NO:560)

EIAGQDEDHFITVDAVGCFEGDEEEEEDDEDEEEIEVRSRDISREEWKGSETY (SEQ ID NO:561)
IAGQDEDHFITVDAVGCFEGDEEEEEDDEDEEEIEVRSRDISREEWKGSETY (SEQ ID NO:562)
AGQDEDHFITVDAVGCFEGDEEEEEDDEDEEEIEVRSRDISREEWKGSETY (SEQ ID NO:563)
GQDEDHFITVDAVGCFEGDEEEEEDDEDEEEIEVRSRDISREEWKGSETY (SEQ ID NO:564)
QDEDHFITVDAVGCFEGDEEEEEDDEDEEEIEVRSRDISREEWKGSETY (SEQ ID NO:565)
DEDHFITVDAVGCFEGDEEEEEDDEDEEEIEVRSRDISREEWKGSETY (SEQ ID NO:566)
EDHFITVDAVGCFEGDEEEEEDDEDEEEIEVRSRDISREEWKGSETY (SEQ ID NO:567)
DHFITVDAVGCFEGDEEEEEDDEDEEEIEVRSRDISREEWKGSETY (SEQ ID NO:568)
HFITVDAVGCFEGDEEEEEDDEDEEEIEVRSRDISREEWKGSETY (SEQ ID NO:569)
FITVDAVGCFEGDEEEEEDDEDEEEIEVRSRDISREEWKGSETY (SEQ ID NO:570)
ITVDAVGCFEGDEEEEEDDEDEEEIEVRSRDISREEWKGSETY (SEQ ID NO:571)
TVDAVGCFEGDEEEEEDDEDEEEIEVRSRDISREEWKGSETY (SEQ ID NO:572)
VDAVGCFEGDEEEEEDDEDEEEIEVRSRDISREEWKGSETY (SEQ ID NO:573)
DAVGCFEGDEEEEEDDEDEEEIEVRSRDISREEWKGSETY (SEQ ID NO:574)
AVGCFEGDEEEEEDDEDEEEIEVRSRDISREEWKGSETY (SEQ ID NO:575)
VGCFEGDEEEEEDDEDEEEIEVRSRDISREEWKGSETY (SEQ ID NO:576)
GCFEGDEEEEEDDEDEEEIEVRSRDISREEWKGSETY (SEQ ID NO:577)
CFEGDEEEEEDDEDEEEIEVRSRDISREEWKGSETY (SEQ ID NO:578)
FEGDEEEEEDDEDEEEIEVRSRDISREEWKGSETY (SEQ ID NO:579)
EGDEEEEEDDEDEEEIEVRSRDISREEWKGSETY (SEQ ID NO:580)
GDEEEEEDDEDEEEIEVRSRDISREEWKGSETY (SEQ ID NO:581)
DEEEEEDDEDEEEIEVRSRDISREEWKGSETY (SEQ ID NO:582)
EEEEEDDEDEEEIEVRSRDISREEWKGSETY (SEQ ID NO:583)
EEEEDDEDEEEIEVRSRDISREEWKGSETY (SEQ ID NO:584)
EEEDDEDEEEIEVRSRDISREEWKGSETY (SEQ ID NO:585)
EEDDEDEEEIEVRSRDISREEWKGSETY (SEQ ID NO:586)
EDDEDEEEIEVRSRDISREEWKGSETY (SEQ ID NO:587)
DDEDEEEIEVRSRDISREEWKGSETY (SEQ ID NO:588)
DEDEEEIEVRSRDISREEWKGSETY (SEQ ID NO:589)
EDEEEIEVRSRDISREEWKGSETY (SEQ ID NO:590)
DEEEIEVRSRDISREEWKGSETY (SEQ ID NO:591)
EEEIEVRSRDISREEWKGSETY (SEQ ID NO:592)
EEIEVRSRDISREEWKGSETY (SEQ ID NO:593)
EIEVRSRDISREEWKGSETY (SEQ ID NO:594)
IEVRSRDISREEWKGSETY (SEQ ID NO:595)
EVRSRDISREEWKGSETY (SEQ ID NO:596)

FIG. 6K

EIAGQDEDHFITVDAVGCFEGDEEEEEDDEDEEEIEVRSRDISREEWKGSETYS (SEQ ID NO:597)
IAGQDEDHFITVDAVGCFEGDEEEEEDDEDEEEIEVRSRDISREEWKGSETYS (SEQ ID NO:598)
AGQDEDHFITVDAVGCFEGDEEEEEDDEDEEEIEVRSRDISREEWKGSETYS (SEQ ID NO:599)
GQDEDHFITVDAVGCFEGDEEEEEDDEDEEEIEVRSRDISREEWKGSETYS (SEQ ID NO:600)
QDEDHFITVDAVGCFEGDEEEEEDDEDEEEIEVRSRDISREEWKGSETYS (SEQ ID NO:601)
DEDHFITVDAVGCFEGDEEEEEDDEDEEEIEVRSRDISREEWKGSETYS (SEQ ID NO:602)
EDHFITVDAVGCFEGDEEEEEDDEDEEEIEVRSRDISREEWKGSETYS (SEQ ID NO:603)
DHFITVDAVGCFEGDEEEEEDDEDEEEIEVRSRDISREEWKGSETYS (SEQ ID NO:604)
HFITVDAVGCFEGDEEEEEDDEDEEEIEVRSRDISREEWKGSETYS (SEQ ID NO:605)
FITVDAVGCFEGDEEEEEDDEDEEEIEVRSRDISREEWKGSETYS (SEQ ID NO:606)
ITVDAVGCFEGDEEEEEDDEDEEEIEVRSRDISREEWKGSETYS (SEQ ID NO:607)
TVDAVGCFEGDEEEEEDDEDEEEIEVRSRDISREEWKGSETYS (SEQ ID NO:608)
VDAVGCFEGDEEEEEDDEDEEEIEVRSRDISREEWKGSETYS (SEQ ID NO:609)
DAVGCFEGDEEEEEDDEDEEEIEVRSRDISREEWKGSETYS (SEQ ID NO:610)
AVGCFEGDEEEEEDDEDEEEIEVRSRDISREEWKGSETYS (SEQ ID NO:611)
VGCFEGDEEEEEDDEDEEEIEVRSRDISREEWKGSETYS (SEQ ID NO:612)
GCFEGDEEEEEDDEDEEEIEVRSRDISREEWKGSETYS (SEQ ID NO:613)
CFEGDEEEEEDDEDEEEIEVRSRDISREEWKGSETYS (SEQ ID NO:614)
FEGDEEEEEDDEDEEEIEVRSRDISREEWKGSETYS (SEQ ID NO:615)
EGDEEEEEDDEDEEEIEVRSRDISREEWKGSETYS (SEQ ID NO:616)
GDEEEEEDDEDEEEIEVRSRDISREEWKGSETYS (SEQ ID NO:617)
DEEEEEDDEDEEEIEVRSRDISREEWKGSETYS (SEQ ID NO:618)
EEEEEDDEDEEEIEVRSRDISREEWKGSETYS (SEQ ID NO:619)
EEEEDDEDEEEIEVRSRDISREEWKGSETYS (SEQ ID NO:620)
EEEDDEDEEEIEVRSRDISREEWKGSETYS (SEQ ID NO:621)
EEDDEDEEEIEVRSRDISREEWKGSETYS (SEQ ID NO:622)
EDDEDEEEIEVRSRDISREEWKGSETYS (SEQ ID NO:623)
DDEDEEEIEVRSRDISREEWKGSETYS (SEQ ID NO:624)
DEDEEEIEVRSRDISREEWKGSETYS (SEQ ID NO:625)
EDEEEIEVRSRDISREEWKGSETYS (SEQ ID NO:626)
DEEEIEVRSRDISREEWKGSETYS (SEQ ID NO:627)
EEEIEVRSRDISREEWKGSETYS (SEQ ID NO:628)
EEIEVRSRDISREEWKGSETYS (SEQ ID NO:629)
EIEVRSRDISREEWKGSETYS (SEQ ID NO:630)
IEVRSRDISREEWKGSETYS (SEQ ID NO:631)
EVRSRDISREEWKGSETYS (SEQ ID NO:632)

EIAGQDEDHFITVDAVGCFEGDEEEEEDDEDEEEIEVRSRDISREEWKGSETYSP (SEQ ID NO:633)
IAGQDEDHFITVDAVGCFEGDEEEEEDDEDEEEIEVRSRDISREEWKGSETYSP (SEQ ID NO:634)
AGQDEDHFITVDAVGCFEGDEEEEEDDEDEEEIEVRSRDISREEWKGSETYSP (SEQ ID NO:635)
GQDEDHFITVDAVGCFEGDEEEEEDDEDEEEIEVRSRDISREEWKGSETYSP (SEQ ID NO:636)
QDEDHFITVDAVGCFEGDEEEEEDDEDEEEIEVRSRDISREEWKGSETYSP (SEQ ID NO:637)
DEDHFITVDAVGCFEGDEEEEEDDEDEEEIEVRSRDISREEWKGSETYSP (SEQ ID NO:638)
EDHFITVDAVGCFEGDEEEEEDDEDEEEIEVRSRDISREEWKGSETYSP (SEQ ID NO:639)
DHFITVDAVGCFEGDEEEEEDDEDEEEIEVRSRDISREEWKGSETYSP (SEQ ID NO:640)
HFITVDAVGCFEGDEEEEEDDEDEEEIEVRSRDISREEWKGSETYSP (SEQ ID NO:641)
FITVDAVGCFEGDEEEEEDDEDEEEIEVRSRDISREEWKGSETYSP (SEQ ID NO:642)
ITVDAVGCFEGDEEEEEDDEDEEEIEVRSRDISREEWKGSETYSP (SEQ ID NO:643)
TVDAVGCFEGDEEEEEDDEDEEEIEVRSRDISREEWKGSETYSP (SEQ ID NO:644)
VDAVGCFEGDEEEEEDDEDEEEIEVRSRDISREEWKGSETYSP (SEQ ID NO:645)
DAVGCFEGDEEEEEDDEDEEEIEVRSRDISREEWKGSETYSP (SEQ ID NO:646)
AVGCFEGDEEEEEDDEDEEEIEVRSRDISREEWKGSETYSP (SEQ ID NO:647)
VGCFEGDEEEEEDDEDEEEIEVRSRDISREEWKGSETYSP (SEQ ID NO:648)
GCFEGDEEEEEDDEDEEEIEVRSRDISREEWKGSETYSP (SEQ ID NO:649)
CFEGDEEEEEDDEDEEEIEVRSRDISREEWKGSETYSP (SEQ ID NO:650)
FEGDEEEEEDDEDEEEIEVRSRDISREEWKGSETYSP (SEQ ID NO:651)
EGDEEEEEDDEDEEEIEVRSRDISREEWKGSETYSP (SEQ ID NO:652)
GDEEEEEDDEDEEEIEVRSRDISREEWKGSETYSP (SEQ ID NO:653)
DEEEEEDDEDEEEIEVRSRDISREEWKGSETYSP (SEQ ID NO:654)
EEEEEDDEDEEEIEVRSRDISREEWKGSETYSP (SEQ ID NO:655)

FIG. 6L

EEEEDDEDEEEIEVRSRDISREEWKGSETYSP (SEQ ID NO:656)
EEEDDEDEEEIEVRSRDISREEWKGSETYSP (SEQ ID NO:657)
EEDDEDEEEIEVRSRDISREEWKGSETYSP (SEQ ID NO:658)
EDDEDEEEIEVRSRDISREEWKGSETYSP (SEQ ID NO:659)
DDEDEEEIEVRSRDISREEWKGSETYSP (SEQ ID NO:660)
DEDEEEIEVRSRDISREEWKGSETYSP (SEQ ID NO:661)
EDEEEIEVRSRDISREEWKGSETYSP (SEQ ID NO:662)
DEEEIEVRSRDISREEWKGSETYSP (SEQ ID NO:663)
EEEIEVRSRDISREEWKGSETYSP (SEQ ID NO:664)
EEIEVRSRDISREEWKGSETYSP (SEQ ID NO:665)
EIEVRSRDISREEWKGSETYSP (SEQ ID NO:666)
IEVRSRDISREEWKGSETYSP (SEQ ID NO:667)
EVRSRDISREEWKGSETYSP (SEQ ID NO:668)

EIAGQDEDHFITVDAVGCFEGDEEEEEDDEDEEEIEVRSRDISREEWKGSETYSPN (SEQ ID NO:669)
IAGQDEDHFITVDAVGCFEGDEEEEEDDEDEEEIEVRSRDISREEWKGSETYSPN (SEQ ID NO:670)
AGQDEDHFITVDAVGCFEGDEEEEEDDEDEEEIEVRSRDISREEWKGSETYSPN (SEQ ID NO:671)
GQDEDHFITVDAVGCFEGDEEEEEDDEDEEEIEVRSRDISREEWKGSETYSPN (SEQ ID NO:672)
QDEDHFITVDAVGCFEGDEEEEEDDEDEEEIEVRSRDISREEWKGSETYSPN (SEQ ID NO:673)
DEDHFITVDAVGCFEGDEEEEEDDEDEEEIEVRSRDISREEWKGSETYSPN (SEQ ID NO:674)
EDHFITVDAVGCFEGDEEEEEDDEDEEEIEVRSRDISREEWKGSETYSPN (SEQ ID NO:675)
DHFITVDAVGCFEGDEEEEEDDEDEEEIEVRSRDISREEWKGSETYSPN (SEQ ID NO:676)
HFITVDAVGCFEGDEEEEEDDEDEEEIEVRSRDISREEWKGSETYSPN (SEQ ID NO:677)
FITVDAVGCFEGDEEEEEDDEDEEEIEVRSRDISREEWKGSETYSPN (SEQ ID NO:678)
ITVDAVGCFEGDEEEEEDDEDEEEIEVRSRDISREEWKGSETYSPN (SEQ ID NO:679)
TVDAVGCFEGDEEEEEDDEDEEEIEVRSRDISREEWKGSETYSPN (SEQ ID NO:680)
VDAVGCFEGDEEEEEDDEDEEEIEVRSRDISREEWKGSETYSPN (SEQ ID NO:681)
DAVGCFEGDEEEEEDDEDEEEIEVRSRDISREEWKGSETYSPN (SEQ ID NO:682)
AVGCFEGDEEEEEDDEDEEEIEVRSRDISREEWKGSETYSPN (SEQ ID NO:683)
VGCFEGDEEEEEDDEDEEEIEVRSRDISREEWKGSETYSPN (SEQ ID NO:684)
GCFEGDEEEEEDDEDEEEIEVRSRDISREEWKGSETYSPN (SEQ ID NO:685)
CFEGDEEEEEDDEDEEEIEVRSRDISREEWKGSETYSPN (SEQ ID NO:686)
FEGDEEEEEDDEDEEEIEVRSRDISREEWKGSETYSPN (SEQ ID NO:687)
EGDEEEEEDDEDEEEIEVRSRDISREEWKGSETYSPN (SEQ ID NO:688)
GDEEEEEDDEDEEEIEVRSRDISREEWKGSETYSPN (SEQ ID NO:689)
DEEEEEDDEDEEEIEVRSRDISREEWKGSETYSPN (SEQ ID NO:690)
EEEEEDDEDEEEIEVRSRDISREEWKGSETYSPN (SEQ ID NO:691)
EEEEDDEDEEEIEVRSRDISREEWKGSETYSPN (SEQ ID NO:692)
EEEDDEDEEEIEVRSRDISREEWKGSETYSPN (SEQ ID NO:693)
EEDDEDEEEIEVRSRDISREEWKGSETYSPN (SEQ ID NO:694)
EDDEDEEEIEVRSRDISREEWKGSETYSPN (SEQ ID NO:695)
DDEDEEEIEVRSRDISREEWKGSETYSPN (SEQ ID NO:696)
DEDEEEIEVRSRDISREEWKGSETYSPN (SEQ ID NO:697)
EDEEEIEVRSRDISREEWKGSETYSPN (SEQ ID NO:698)
DEEEIEVRSRDISREEWKGSETYSPN (SEQ ID NO:699)
EEEIEVRSRDISREEWKGSETYSPN (SEQ ID NO:700)
EEIEVRSRDISREEWKGSETYSPN (SEQ ID NO:701)
EIEVRSRDISREEWKGSETYSPN (SEQ ID NO:702)
IEVRSRDISREEWKGSETYSPN (SEQ ID NO:703)
EVRSRDISREEWKGSETYSPN (SEQ ID NO:704)

EIAGQDEDHFITVDAVGCFEGDEEEEEDDEDEEEIEVRSRDISREEWKGSETYSPNT
(SEQ ID NO:705)
IAGQDEDHFITVDAVGCFEGDEEEEEDDEDEEEIEVRSRDISREEWKGSETYSPNT
(SEQ ID NO:706)
AGQDEDHFITVDAVGCFEGDEEEEEDDEDEEEIEVRSRDISREEWKGSETYSPNT (SEQ ID NO:707)
GQDEDHFITVDAVGCFEGDEEEEEDDEDEEEIEVRSRDISREEWKGSETYSPNT (SEQ ID NO:708)
QDEDHFITVDAVGCFEGDEEEEEDDEDEEEIEVRSRDISREEWKGSETYSPNT (SEQ ID NO:709)
DEDHFITVDAVGCFEGDEEEEEDDEDEEEIEVRSRDISREEWKGSETYSPNT (SEQ ID NO:710)
EDHFITVDAVGCFEGDEEEEEDDEDEEEIEVRSRDISREEWKGSETYSPNT (SEQ ID NO:711)

FIG. 6M

DHFITVDAVGCFEGDEEEEEDDEDEEEIEVRSRDISREEWKGSETYSPNT (SEQ ID NO:712)
HFITVDAVGCFEGDEEEEEDDEDEEEIEVRSRDISREEWKGSETYSPNT (SEQ ID NO:713)
FITVDAVGCFEGDEEEEEDDEDEEEIEVRSRDISREEWKGSETYSPNT (SEQ ID NO:714)
ITVDAVGCFEGDEEEEEDDEDEEEIEVRSRDISREEWKGSETYSPNT (SEQ ID NO:715)
TVDAVGCFEGDEEEEEDDEDEEEIEVRSRDISREEWKGSETYSPNT (SEQ ID NO:716)
VDAVGCFEGDEEEEEDDEDEEEIEVRSRDISREEWKGSETYSPNT (SEQ ID NO:717)
DAVGCFEGDEEEEEDDEDEEEIEVRSRDISREEWKGSETYSPNT (SEQ ID NO:718)
AVGCFEGDEEEEEDDEDEEEIEVRSRDISREEWKGSETYSPNT (SEQ ID NO:719)
VGCFEGDEEEEEDDEDEEEIEVRSRDISREEWKGSETYSPNT (SEQ ID NO:720)
GCFEGDEEEEEDDEDEEEIEVRSRDISREEWKGSETYSPNT (SEQ ID NO:721)
CFEGDEEEEEDDEDEEEIEVRSRDISREEWKGSETYSPNT (SEQ ID NO:722)
FEGDEEEEEDDEDEEEIEVRSRDISREEWKGSETYSPNT (SEQ ID NO:723)
EGDEEEEEDDEDEEEIEVRSRDISREEWKGSETYSPNT (SEQ ID NO:724)
GDEEEEEDDEDEEEIEVRSRDISREEWKGSETYSPNT (SEQ ID NO:725)
DEEEEEDDEDEEEIEVRSRDISREEWKGSETYSPNT (SEQ ID NO:726)
EEEEEDDEDEEEIEVRSRDISREEWKGSETYSPNT (SEQ ID NO:727)
EEEEDDEDEEEIEVRSRDISREEWKGSETYSPNT (SEQ ID NO:728)
EEEDDEDEEEIEVRSRDISREEWKGSETYSPNT (SEQ ID NO:729)
EEDDEDEEEIEVRSRDISREEWKGSETYSPNT (SEQ ID NO:730)
EDDEDEEEIEVRSRDISREEWKGSETYSPNT (SEQ ID NO:731)
DDEDEEEIEVRSRDISREEWKGSETYSPNT (SEQ ID NO:732)
DEDEEEIEVRSRDISREEWKGSETYSPNT (SEQ ID NO:733)
EDEEEIEVRSRDISREEWKGSETYSPNT (SEQ ID NO:734)
DEEEIEVRSRDISREEWKGSETYSPNT (SEQ ID NO:735)
EEEIEVRSRDISREEWKGSETYSPNT (SEQ ID NO:736)
EEIEVRSRDISREEWKGSETYSPNT (SEQ ID NO:737)
EIEVRSRDISREEWKGSETYSPNT (SEQ ID NO:738)
IEVRSRDISREEWKGSETYSPNT (SEQ ID NO:739)
EVRSRDISREEWKGSETYSPNT (SEQ ID NO:740)

EIAGQDEDHFITVDAVGCFEGDEEEEEDDEDEEEIEVRSRDISREEWKGSETYSPNTA
(SEQ ID NO:741)
IAGQDEDHFITVDAVGCFEGDEEEEEDDEDEEEIEVRSRDISREEWKGSETYSPNTA
(SEQ ID NO:742)
AGQDEDHFITVDAVGCFEGDEEEEEDDEDEEEIEVRSRDISREEWKGSETYSPNTA
(SEQ ID NO:743)
GQDEDHFITVDAVGCFEGDEEEEEDDEDEEEIEVRSRDISREEWKGSETYSPNTA (SEQ ID NO:744)
QDEDHFITVDAVGCFEGDEEEEEDDEDEEEIEVRSRDISREEWKGSETYSPNTA (SEQ ID NO:745)
DEDHFITVDAVGCFEGDEEEEEDDEDEEEIEVRSRDISREEWKGSETYSPNTA (SEQ ID NO:746)
EDHFITVDAVGCFEGDEEEEEDDEDEEEIEVRSRDISREEWKGSETYSPNTA (SEQ ID NO:747)
DHFITVDAVGCFEGDEEEEEDDEDEEEIEVRSRDISREEWKGSETYSPNTA (SEQ ID NO:748)
HFITVDAVGCFEGDEEEEEDDEDEEEIEVRSRDISREEWKGSETYSPNTA (SEQ ID NO:749)
FITVDAVGCFEGDEEEEEDDEDEEEIEVRSRDISREEWKGSETYSPNTA (SEQ ID NO:750)
ITVDAVGCFEGDEEEEEDDEDEEEIEVRSRDISREEWKGSETYSPNTA (SEQ ID NO:751)
TVDAVGCFEGDEEEEEDDEDEEEIEVRSRDISREEWKGSETYSPNTA (SEQ ID NO:752)
VDAVGCFEGDEEEEEDDEDEEEIEVRSRDISREEWKGSETYSPNTA (SEQ ID NO:753)
DAVGCFEGDEEEEEDDEDEEEIEVRSRDISREEWKGSETYSPNTA (SEQ ID NO:754)
AVGCFEGDEEEEEDDEDEEEIEVRSRDISREEWKGSETYSPNTA (SEQ ID NO:755)
VGCFEGDEEEEEDDEDEEEIEVRSRDISREEWKGSETYSPNTA (SEQ ID NO:756)
GCFEGDEEEEEDDEDEEEIEVRSRDISREEWKGSETYSPNTA (SEQ ID NO:757)
CFEGDEEEEEDDEDEEEIEVRSRDISREEWKGSETYSPNTA (SEQ ID NO:758)
FEGDEEEEEDDEDEEEIEVRSRDISREEWKGSETYSPNTA (SEQ ID NO:759)
EGDEEEEEDDEDEEEIEVRSRDISREEWKGSETYSPNTA (SEQ ID NO:760)
GDEEEEEDDEDEEEIEVRSRDISREEWKGSETYSPNTA (SEQ ID NO:761)
DEEEEEDDEDEEEIEVRSRDISREEWKGSETYSPNTA (SEQ ID NO:762)
EEEEEDDEDEEEIEVRSRDISREEWKGSETYSPNTA (SEQ ID NO:763)
EEEEDDEDEEEIEVRSRDISREEWKGSETYSPNTA (SEQ ID NO:764)
EEEDDEDEEEIEVRSRDISREEWKGSETYSPNTA (SEQ ID NO:765)
EEDDEDEEEIEVRSRDISREEWKGSETYSPNTA (SEQ ID NO:766)
EDDEDEEEIEVRSRDISREEWKGSETYSPNTA (SEQ ID NO:767)

FIG. 6N

DDEDEEEIEVRSRDISREEWKGSETYSPNTA (SEQ ID NO:768)
DEDEEEIEVRSRDISREEWKGSETYSPNTA (SEQ ID NO:769)
EDEEEIEVRSRDISREEWKGSETYSPNTA (SEQ ID NO:770)
DEEEIEVRSRDISREEWKGSETYSPNTA (SEQ ID NO:771)
EEEIEVRSRDISREEWKGSETYSPNTA (SEQ ID NO:772)
EEIEVRSRDISREEWKGSETYSPNTA (SEQ ID NO:773)
EIEVRSRDISREEWKGSETYSPNTA (SEQ ID NO:774)
IEVRSRDISREEWKGSETYSPNTA (SEQ ID NO:775)
EVRSRDISREEWKGSETYSPNTA (SEQ ID NO:776)

EIAGQDEDHFITVDAVGCFEGDEEEEEDDEDEEEIEVRSRDISREEWKGSETYSPNTAY
(SEQ ID NO:777)
IAGQDEDHFITVDAVGCFEGDEEEEEDDEDEEEIEVRSRDISREEWKGSETYSPNTAY
(SEQ ID NO:778)
AGQDEDHFITVDAVGCFEGDEEEEEDDEDEEEIEVRSRDISREEWKGSETYSPNTAY
(SEQ ID NO:779)
GQDEDHFITVDAVGCFEGDEEEEEDDEDEEEIEVRSRDISREEWKGSETYSPNTAY
(SEQ ID NO:780)
QDEDHFITVDAVGCFEGDEEEEEDDEDEEEIEVRSRDISREEWKGSETYSPNTAY (SEQ ID NO:781)
DEDHFITVDAVGCFEGDEEEEEDDEDEEEIEVRSRDISREEWKGSETYSPNTAY (SEQ ID NO:782)
EDHFITVDAVGCFEGDEEEEEDDEDEEEIEVRSRDISREEWKGSETYSPNTAY (SEQ ID NO:783)
DHFITVDAVGCFEGDEEEEEDDEDEEEIEVRSRDISREEWKGSETYSPNTAY (SEQ ID NO:784)
HFITVDAVGCFEGDEEEEEDDEDEEEIEVRSRDISREEWKGSETYSPNTAY (SEQ ID NO:785)
FITVDAVGCFEGDEEEEEDDEDEEEIEVRSRDISREEWKGSETYSPNTAY (SEQ ID NO:786)
ITVDAVGCFEGDEEEEEDDEDEEEIEVRSRDISREEWKGSETYSPNTAY (SEQ ID NO:787)
TVDAVGCFEGDEEEEEDDEDEEEIEVRSRDISREEWKGSETYSPNTAY (SEQ ID NO:788)
VDAVGCFEGDEEEEEDDEDEEEIEVRSRDISREEWKGSETYSPNTAY (SEQ ID NO:789)
DAVGCFEGDEEEEEDDEDEEEIEVRSRDISREEWKGSETYSPNTAY (SEQ ID NO:790)
AVGCFEGDEEEEEDDEDEEEIEVRSRDISREEWKGSETYSPNTAY (SEQ ID NO:791)
VGCFEGDEEEEEDDEDEEEIEVRSRDISREEWKGSETYSPNTAY (SEQ ID NO:792)
GCFEGDEEEEEDDEDEEEIEVRSRDISREEWKGSETYSPNTAY (SEQ ID NO:793)
CFEGDEEEEEDDEDEEEIEVRSRDISREEWKGSETYSPNTAY (SEQ ID NO:794)
FEGDEEEEEDDEDEEEIEVRSRDISREEWKGSETYSPNTAY (SEQ ID NO:795)
EGDEEEEEDDEDEEEIEVRSRDISREEWKGSETYSPNTAY (SEQ ID NO:796)
GDEEEEEDDEDEEEIEVRSRDISREEWKGSETYSPNTAY (SEQ ID NO:797)
DEEEEEDDEDEEEIEVRSRDISREEWKGSETYSPNTAY (SEQ ID NO:798)
EEEEEDDEDEEEIEVRSRDISREEWKGSETYSPNTAY (SEQ ID NO:799)
EEEEDDEDEEEIEVRSRDISREEWKGSETYSPNTAY (SEQ ID NO:800)
EEEDDEDEEEIEVRSRDISREEWKGSETYSPNTAY (SEQ ID NO:801)
EEDDEDEEEIEVRSRDISREEWKGSETYSPNTAY (SEQ ID NO:802)
EDDEDEEEIEVRSRDISREEWKGSETYSPNTAY (SEQ ID NO:803)
DDEDEEEIEVRSRDISREEWKGSETYSPNTAY (SEQ ID NO:804)
DEDEEEIEVRSRDISREEWKGSETYSPNTAY (SEQ ID NO:805)
EDEEEIEVRSRDISREEWKGSETYSPNTAY (SEQ ID NO:806)
DEEEIEVRSRDISREEWKGSETYSPNTAY (SEQ ID NO:807)
EEEIEVRSRDISREEWKGSETYSPNTAY (SEQ ID NO:808)
EEIEVRSRDISREEWKGSETYSPNTAY (SEQ ID NO:809)
EIEVRSRDISREEWKGSETYSPNTAY (SEQ ID NO:810)
IEVRSRDISREEWKGSETYSPNTAY (SEQ ID NO:811)
EVRSRDISREEWKGSETYSPNTAY (SEQ ID NO:812)

EIAGQDEDHFITVDAVGCFEGDEEEEEDDEDEEEIEVRSRDISREEWKGSETYSPNTAYG
(SEQ ID NO:813)
IAGQDEDHFITVDAVGCFEGDEEEEEDDEDEEEIEVRSRDISREEWKGSETYSPNTAYG
(SEQ ID NO:814)
AGQDEDHFITVDAVGCFEGDEEEEEDDEDEEEIEVRSRDISREEWKGSETYSPNTAYG
(SEQ ID NO:815)
GQDEDHFITVDAVGCFEGDEEEEEDDEDEEEIEVRSRDISREEWKGSETYSPNTAYG
(SEQ ID NO:816)
QDEDHFITVDAVGCFEGDEEEEEDDEDEEEIEVRSRDISREEWKGSETYSPNTAYG

FIG. 6O (SEQ ID NO:817)
DEDHFITVDAVGCFEGDEEEEEDDEDEEEIEVRSRDISREEWKGSETYSPNTAYG (SEQ ID NO:818)
EDHFITVDAVGCFEGDEEEEEDDEDEEEIEVRSRDISREEWKGSETYSPNTAYG (SEQ ID NO:819)
DHFITVDAVGCFEGDEEEEEDDEDEEEIEVRSRDISREEWKGSETYSPNTAYG (SEQ ID NO:820)
HFITVDAVGCFEGDEEEEEDDEDEEEIEVRSRDISREEWKGSETYSPNTAYG (SEQ ID NO:821)
FITVDAVGCFEGDEEEEEDDEDEEEIEVRSRDISREEWKGSETYSPNTAYG (SEQ ID NO:822)
ITVDAVGCFEGDEEEEEDDEDEEEIEVRSRDISREEWKGSETYSPNTAYG (SEQ ID NO:823)
TVDAVGCFEGDEEEEEDDEDEEEIEVRSRDISREEWKGSETYSPNTAYG (SEQ ID NO:824)
VDAVGCFEGDEEEEEDDEDEEEIEVRSRDISREEWKGSETYSPNTAYG (SEQ ID NO:825)
DAVGCFEGDEEEEEDDEDEEEIEVRSRDISREEWKGSETYSPNTAYG (SEQ ID NO:826)
AVGCFEGDEEEEEDDEDEEEIEVRSRDISREEWKGSETYSPNTAYG (SEQ ID NO:827)
VGCFEGDEEEEEDDEDEEEIEVRSRDISREEWKGSETYSPNTAYG (SEQ ID NO:828)
GCFEGDEEEEEDDEDEEEIEVRSRDISREEWKGSETYSPNTAYG (SEQ ID NO:829)
CFEGDEEEEEDDEDEEEIEVRSRDISREEWKGSETYSPNTAYG (SEQ ID NO:830)
FEGDEEEEEDDEDEEEIEVRSRDISREEWKGSETYSPNTAYG (SEQ ID NO:831)
EGDEEEEEDDEDEEEIEVRSRDISREEWKGSETYSPNTAYG (SEQ ID NO:832)
GDEEEEEDDEDEEEIEVRSRDISREEWKGSETYSPNTAYG (SEQ ID NO:833)
DEEEEEDDEDEEEIEVRSRDISREEWKGSETYSPNTAYG (SEQ ID NO:834)
EEEEEDDEDEEEIEVRSRDISREEWKGSETYSPNTAYG (SEQ ID NO:835)
EEEEDDEDEEEIEVRSRDISREEWKGSETYSPNTAYG (SEQ ID NO:836)
EEEDDEDEEEIEVRSRDISREEWKGSETYSPNTAYG (SEQ ID NO:837)
EEDDEDEEEIEVRSRDISREEWKGSETYSPNTAYG (SEQ ID NO:838)
EDDEDEEEIEVRSRDISREEWKGSETYSPNTAYG (SEQ ID NO:839)
DDEDEEEIEVRSRDISREEWKGSETYSPNTAYG (SEQ ID NO:840)
DEDEEEIEVRSRDISREEWKGSETYSPNTAYG (SEQ ID NO:841)
EDEEEIEVRSRDISREEWKGSETYSPNTAYG (SEQ ID NO:842)
DEEEIEVRSRDISREEWKGSETYSPNTAYG (SEQ ID NO:843)
EEEIEVRSRDISREEWKGSETYSPNTAYG (SEQ ID NO:844)
EEIEVRSRDISREEWKGSETYSPNTAYG (SEQ ID NO:845)
EIEVRSRDISREEWKGSETYSPNTAYG (SEQ ID NO:846)
IEVRSRDISREEWKGSETYSPNTAYG (SEQ ID NO:847)
EVRSRDISREEWKGSETYSPNTAYG (SEQ ID NO:848)

EIAGQDEDHFITVDAVGCFEGDEEEEEDDEDEEEIEVRSRDISREEWKGSETYSPNTAYGV
(SEQ ID NO:849)
IAGQDEDHFITVDAVGCFEGDEEEEEDDEDEEEIEVRSRDISREEWKGSETYSPNTAYGV
(SEQ ID NO:850)
AGQDEDHFITVDAVGCFEGDEEEEEDDEDEEEIEVRSRDISREEWKGSETYSPNTAYGV
(SEQ ID NO:851)
GQDEDHFITVDAVGCFEGDEEEEEDDEDEEEIEVRSRDISREEWKGSETYSPNTAYGV
(SEQ ID NO:852)
QDEDHFITVDAVGCFEGDEEEEEDDEDEEEIEVRSRDISREEWKGSETYSPNTAYGV
(SEQ ID NO:853)
DEDHFITVDAVGCFEGDEEEEEDDEDEEEIEVRSRDISREEWKGSETYSPNTAYGV
(SEQ ID NO:854)
EDHFITVDAVGCFEGDEEEEEDDEDEEEIEVRSRDISREEWKGSETYSPNTAYGV (SEQ ID NO:855)
DHFITVDAVGCFEGDEEEEEDDEDEEEIEVRSRDISREEWKGSETYSPNTAYGV (SEQ ID NO:856)
HFITVDAVGCFEGDEEEEEDDEDEEEIEVRSRDISREEWKGSETYSPNTAYGV (SEQ ID NO:857)
FITVDAVGCFEGDEEEEEDDEDEEEIEVRSRDISREEWKGSETYSPNTAYGV (SEQ ID NO:858)
ITVDAVGCFEGDEEEEEDDEDEEEIEVRSRDISREEWKGSETYSPNTAYGV (SEQ ID NO:859)
TVDAVGCFEGDEEEEEDDEDEEEIEVRSRDISREEWKGSETYSPNTAYGV (SEQ ID NO:860)
VDAVGCFEGDEEEEEDDEDEEEIEVRSRDISREEWKGSETYSPNTAYGV (SEQ ID NO:861)
DAVGCFEGDEEEEEDDEDEEEIEVRSRDISREEWKGSETYSPNTAYGV (SEQ ID NO:862)
AVGCFEGDEEEEEDDEDEEEIEVRSRDISREEWKGSETYSPNTAYGV (SEQ ID NO:863)
VGCFEGDEEEEEDDEDEEEIEVRSRDISREEWKGSETYSPNTAYGV (SEQ ID NO:864)
GCFEGDEEEEEDDEDEEEIEVRSRDISREEWKGSETYSPNTAYGV (SEQ ID NO:865)
CFEGDEEEEEDDEDEEEIEVRSRDISREEWKGSETYSPNTAYGV (SEQ ID NO:866)
FEGDEEEEEDDEDEEEIEVRSRDISREEWKGSETYSPNTAYGV (SEQ ID NO:867)
EGDEEEEEDDEDEEEIEVRSRDISREEWKGSETYSPNTAYGV (SEQ ID NO:868)
GDEEEEEDDEDEEEIEVRSRDISREEWKGSETYSPNTAYGV (SEQ ID NO:869)

FIG. 6P

DEEEEEDDEDEEEIEVRSRDISREEWKGSETYSPNTAYGV (SEQ ID NO:870)
EEEEEDDEDEEEIEVRSRDISREEWKGSETYSPNTAYGV (SEQ ID NO:871)
EEEEDDEDEEEIEVRSRDISREEWKGSETYSPNTAYGV (SEQ ID NO:872)
EEEDDEDEEEIEVRSRDISREEWKGSETYSPNTAYGV (SEQ ID NO:873)
EEDDEDEEEIEVRSRDISREEWKGSETYSPNTAYGV (SEQ ID NO:874)
EDDEDEEEIEVRSRDISREEWKGSETYSPNTAYGV (SEQ ID NO:875)
DDEDEEEIEVRSRDISREEWKGSETYSPNTAYGV (SEQ ID NO:876)
DEDEEEIEVRSRDISREEWKGSETYSPNTAYGV (SEQ ID NO:877)
EDEEEIEVRSRDISREEWKGSETYSPNTAYGV (SEQ ID NO:878)
DEEEIEVRSRDISREEWKGSETYSPNTAYGV (SEQ ID NO:879)
EEEIEVRSRDISREEWKGSETYSPNTAYGV (SEQ ID NO:880)
EEIEVRSRDISREEWKGSETYSPNTAYGV (SEQ ID NO:881)
EIEVRSRDISREEWKGSETYSPNTAYGV (SEQ ID NO:882)
IEVRSRDISREEWKGSETYSPNTAYGV (SEQ ID NO:883)
EVRSRDISREEWKGSETYSPNTAYGV (SEQ ID NO:884)

EIAGQDEDHFITVDAVGCFEGDEEEEEDDEDEEEIEVRSRDISREEWKGSETYSPNTAYGVD (SEQ ID NO:885)
IAGQDEDHFITVDAVGCFEGDEEEEEDDEDEEEIEVRSRDISREEWKGSETYSPNTAYGVD (SEQ ID NO:886)
AGQDEDHFITVDAVGCFEGDEEEEEDDEDEEEIEVRSRDISREEWKGSETYSPNTAYGVD (SEQ ID NO:887)
GQDEDHFITVDAVGCFEGDEEEEEDDEDEEEIEVRSRDISREEWKGSETYSPNTAYGVD (SEQ ID NO:888)
QDEDHFITVDAVGCFEGDEEEEEDDEDEEEIEVRSRDISREEWKGSETYSPNTAYGVD (SEQ ID NO:889)
DEDHFITVDAVGCFEGDEEEEEDDEDEEEIEVRSRDISREEWKGSETYSPNTAYGVD (SEQ ID NO:890)
EDHFITVDAVGCFEGDEEEEEDDEDEEEIEVRSRDISREEWKGSETYSPNTAYGVD (SEQ ID NO:891)
DHFITVDAVGCFEGDEEEEEDDEDEEEIEVRSRDISREEWKGSETYSPNTAYGVD (SEQ ID NO:892)
HFITVDAVGCFEGDEEEEEDDEDEEEIEVRSRDISREEWKGSETYSPNTAYGVD (SEQ ID NO:893)
FITVDAVGCFEGDEEEEEDDEDEEEIEVRSRDISREEWKGSETYSPNTAYGVD (SEQ ID NO:894)
ITVDAVGCFEGDEEEEEDDEDEEEIEVRSRDISREEWKGSETYSPNTAYGVD (SEQ ID NO:895)
TVDAVGCFEGDEEEEEDDEDEEEIEVRSRDISREEWKGSETYSPNTAYGVD (SEQ ID NO:896)
VDAVGCFEGDEEEEEDDEDEEEIEVRSRDISREEWKGSETYSPNTAYGVD (SEQ ID NO:897)
DAVGCFEGDEEEEEDDEDEEEIEVRSRDISREEWKGSETYSPNTAYGVD (SEQ ID NO:898)
AVGCFEGDEEEEEDDEDEEEIEVRSRDISREEWKGSETYSPNTAYGVD (SEQ ID NO:899)
VGCFEGDEEEEEDDEDEEEIEVRSRDISREEWKGSETYSPNTAYGVD (SEQ ID NO:900)
GCFEGDEEEEEDDEDEEEIEVRSRDISREEWKGSETYSPNTAYGVD (SEQ ID NO:901)
CFEGDEEEEEDDEDEEEIEVRSRDISREEWKGSETYSPNTAYGVD (SEQ ID NO:902)
FEGDEEEEEDDEDEEEIEVRSRDISREEWKGSETYSPNTAYGVD (SEQ ID NO:903)
EGDEEEEEDDEDEEEIEVRSRDISREEWKGSETYSPNTAYGVD (SEQ ID NO:904)
GDEEEEEDDEDEEEIEVRSRDISREEWKGSETYSPNTAYGVD (SEQ ID NO:905)
DEEEEEDDEDEEEIEVRSRDISREEWKGSETYSPNTAYGVD (SEQ ID NO:906)
EEEEEDDEDEEEIEVRSRDISREEWKGSETYSPNTAYGVD (SEQ ID NO:907)
EEEEDDEDEEEIEVRSRDISREEWKGSETYSPNTAYGVD (SEQ ID NO:908)
EEEDDEDEEEIEVRSRDISREEWKGSETYSPNTAYGVD (SEQ ID NO:909)
EEDDEDEEEIEVRSRDISREEWKGSETYSPNTAYGVD (SEQ ID NO:910)
EDDEDEEEIEVRSRDISREEWKGSETYSPNTAYGVD (SEQ ID NO:911)
DDEDEEEIEVRSRDISREEWKGSETYSPNTAYGVD (SEQ ID NO:912)
DEDEEEIEVRSRDISREEWKGSETYSPNTAYGVD (SEQ ID NO:913)
EDEEEIEVRSRDISREEWKGSETYSPNTAYGVD (SEQ ID NO:914)
DEEEIEVRSRDISREEWKGSETYSPNTAYGVD (SEQ ID NO:915)
EEEIEVRSRDISREEWKGSETYSPNTAYGVD (SEQ ID NO:916)
EEIEVRSRDISREEWKGSETYSPNTAYGVD (SEQ ID NO:917)
EIEVRSRDISREEWKGSETYSPNTAYGVD (SEQ ID NO:918)
IEVRSRDISREEWKGSETYSPNTAYGVD (SEQ ID NO:919)
EVRSRDISREEWKGSETYSPNTAYGVD (SEQ ID NO:920)

FIG. 6Q

EIAGQDEDHFITVDAVGCFEGDEEEEEDDEDEEEIEVRSRDISREEWKGSETYSPNTAYGVDF
(SEQ ID NO:921)
IAGQDEDHFITVDAVGCFEGDEEEEEDDEDEEEIEVRSRDISREEWKGSETYSPNTAYGVDF
(SEQ ID NO:922)
AGQDEDHFITVDAVGCFEGDEEEEEDDEDEEEIEVRSRDISREEWKGSETYSPNTAYGVDF
(SEQ ID NO:923)
GQDEDHFITVDAVGCFEGDEEEEEDDEDEEEIEVRSRDISREEWKGSETYSPNTAYGVDF
(SEQ ID NO:924)
QDEDHFITVDAVGCFEGDEEEEEDDEDEEEIEVRSRDISREEWKGSETYSPNTAYGVDF
(SEQ ID NO:925)
DEDHFITVDAVGCFEGDEEEEEDDEDEEEIEVRSRDISREEWKGSETYSPNTAYGVDF
(SEQ ID NO:926)
EDHFITVDAVGCFEGDEEEEEDDEDEEEIEVRSRDISREEWKGSETYSPNTAYGVDF
(SEQ ID NO:927)
DHFITVDAVGCFEGDEEEEEDDEDEEEIEVRSRDISREEWKGSETYSPNTAYGVDF
(SEQ ID NO:928)
HFITVDAVGCFEGDEEEEEDDEDEEEIEVRSRDISREEWKGSETYSPNTAYGVDF (SEQ ID NO:929)
FITVDAVGCFEGDEEEEEDDEDEEEIEVRSRDISREEWKGSETYSPNTAYGVDF (SEQ ID NO:930)
ITVDAVGCFEGDEEEEEDDEDEEEIEVRSRDISREEWKGSETYSPNTAYGVDF (SEQ ID NO:931)
TVDAVGCFEGDEEEEEDDEDEEEIEVRSRDISREEWKGSETYSPNTAYGVDF (SEQ ID NO:932)
VDAVGCFEGDEEEEEDDEDEEEIEVRSRDISREEWKGSETYSPNTAYGVDF (SEQ ID NO:933)
DAVGCFEGDEEEEEDDEDEEEIEVRSRDISREEWKGSETYSPNTAYGVDF (SEQ ID NO:934)
AVGCFEGDEEEEEDDEDEEEIEVRSRDISREEWKGSETYSPNTAYGVDF (SEQ ID NO:935)
VGCFEGDEEEEEDDEDEEEIEVRSRDISREEWKGSETYSPNTAYGVDF (SEQ ID NO:936)
GCFEGDEEEEEDDEDEEEIEVRSRDISREEWKGSETYSPNTAYGVDF (SEQ ID NO:937)
CFEGDEEEEEDDEDEEEIEVRSRDISREEWKGSETYSPNTAYGVDF (SEQ ID NO:938)
FEGDEEEEEDDEDEEEIEVRSRDISREEWKGSETYSPNTAYGVDF (SEQ ID NO:939)
EGDEEEEEDDEDEEEIEVRSRDISREEWKGSETYSPNTAYGVDF (SEQ ID NO:940)
GDEEEEEDDEDEEEIEVRSRDISREEWKGSETYSPNTAYGVDF (SEQ ID NO:941)
DEEEEEDDEDEEEIEVRSRDISREEWKGSETYSPNTAYGVDF (SEQ ID NO:942)
EEEEEDDEDEEEIEVRSRDISREEWKGSETYSPNTAYGVDF (SEQ ID NO:943)
EEEEDDEDEEEIEVRSRDISREEWKGSETYSPNTAYGVDF (SEQ ID NO:944)
EEEDDEDEEEIEVRSRDISREEWKGSETYSPNTAYGVDF (SEQ ID NO:945)
EEDDEDEEEIEVRSRDISREEWKGSETYSPNTAYGVDF (SEQ ID NO:946)
EDDEDEEEIEVRSRDISREEWKGSETYSPNTAYGVDF (SEQ ID NO:947)
DDEDEEEIEVRSRDISREEWKGSETYSPNTAYGVDF (SEQ ID NO:948)
DEDEEEIEVRSRDISREEWKGSETYSPNTAYGVDF (SEQ ID NO:949)
EDEEEIEVRSRDISREEWKGSETYSPNTAYGVDF (SEQ ID NO:950)
DEEEIEVRSRDISREEWKGSETYSPNTAYGVDF (SEQ ID NO:951)
EEEIEVRSRDISREEWKGSETYSPNTAYGVDF (SEQ ID NO:952)
EEIEVRSRDISREEWKGSETYSPNTAYGVDF (SEQ ID NO:953)
EIEVRSRDISREEWKGSETYSPNTAYGVDF (SEQ ID NO:954)
IEVRSRDISREEWKGSETYSPNTAYGVDF (SEQ ID NO:955)
EVRSRDISREEWKGSETYSPNTAYGVDF (SEQ ID NO:956)

EIAGQDEDHFITVDAVGCFEGDEEEEEDDEDEEEIEVRSRDISREEWKGSETYSPNTAYGVDFL
(SEQ ID NO:957)
IAGQDEDHFITVDAVGCFEGDEEEEEDDEDEEEIEVRSRDISREEWKGSETYSPNTAYGVDFL
(SEQ ID NO:958)
AGQDEDHFITVDAVGCFEGDEEEEEDDEDEEEIEVRSRDISREEWKGSETYSPNTAYGVDFL
(SEQ ID NO:959)
GQDEDHFITVDAVGCFEGDEEEEEDDEDEEEIEVRSRDISREEWKGSETYSPNTAYGVDFL
(SEQ ID NO:960)
QDEDHFITVDAVGCFEGDEEEEEDDEDEEEIEVRSRDISREEWKGSETYSPNTAYGVDFL
(SEQ ID NO:961)
DEDHFITVDAVGCFEGDEEEEEDDEDEEEIEVRSRDISREEWKGSETYSPNTAYGVDFL
(SEQ ID NO:962)
EDHFITVDAVGCFEGDEEEEEDDEDEEEIEVRSRDISREEWKGSETYSPNTAYGVDFL
(SEQ ID NO:963)
DHFITVDAVGCFEGDEEEEEDDEDEEEIEVRSRDISREEWKGSETYSPNTAYGVDFL

FIG. 6R (SEQ ID NO:964)
HFITVDAVGCFEGDEEEEEDDEDEEEIEVRSRDISREEWKGSETYSPNTAYGVDFL
(SEQ ID NO:965)
FITVDAVGCFEGDEEEEEDDEDEEEIEVRSRDISREEWKGSETYSPNTAYGVDFL (SEQ ID NO:966)
ITVDAVGCFEGDEEEEEDDEDEEEIEVRSRDISREEWKGSETYSPNTAYGVDFL (SEQ ID NO:967)
TVDAVGCFEGDEEEEEDDEDEEEIEVRSRDISREEWKGSETYSPNTAYGVDFL (SEQ ID NO:968)
VDAVGCFEGDEEEEEDDEDEEEIEVRSRDISREEWKGSETYSPNTAYGVDFL (SEQ ID NO:969)
DAVGCFEGDEEEEEDDEDEEEIEVRSRDISREEWKGSETYSPNTAYGVDFL (SEQ ID NO:970)
AVGCFEGDEEEEEDDEDEEEIEVRSRDISREEWKGSETYSPNTAYGVDFL (SEQ ID NO:971)
VGCFEGDEEEEEDDEDEEEIEVRSRDISREEWKGSETYSPNTAYGVDFL (SEQ ID NO:972)
GCFEGDEEEEEDDEDEEEIEVRSRDISREEWKGSETYSPNTAYGVDFL (SEQ ID NO:973)
CFEGDEEEEEDDEDEEEIEVRSRDISREEWKGSETYSPNTAYGVDFL (SEQ ID NO:974)
FEGDEEEEEDDEDEEEIEVRSRDISREEWKGSETYSPNTAYGVDFL (SEQ ID NO:975)
EGDEEEEEDDEDEEEIEVRSRDISREEWKGSETYSPNTAYGVDFL (SEQ ID NO:976)
GDEEEEEDDEDEEEIEVRSRDISREEWKGSETYSPNTAYGVDFL (SEQ ID NO:977)
DEEEEEDDEDEEEIEVRSRDISREEWKGSETYSPNTAYGVDFL (SEQ ID NO:978)
EEEEEDDEDEEEIEVRSRDISREEWKGSETYSPNTAYGVDFL (SEQ ID NO:979)
EEEEDDEDEEEIEVRSRDISREEWKGSETYSPNTAYGVDFL (SEQ ID NO:980)
EEEDDEDEEEIEVRSRDISREEWKGSETYSPNTAYGVDFL (SEQ ID NO:981)
EEDDEDEEEIEVRSRDISREEWKGSETYSPNTAYGVDFL (SEQ ID NO:982)
EDDEDEEEIEVRSRDISREEWKGSETYSPNTAYGVDFL (SEQ ID NO:983)
DDEDEEEIEVRSRDISREEWKGSETYSPNTAYGVDFL (SEQ ID NO:984)
DEDEEEIEVRSRDISREEWKGSETYSPNTAYGVDFL (SEQ ID NO:985)
EDEEEIEVRSRDISREEWKGSETYSPNTAYGVDFL (SEQ ID NO:986)
DEEEIEVRSRDISREEWKGSETYSPNTAYGVDFL (SEQ ID NO:987)
EEEIEVRSRDISREEWKGSETYSPNTAYGVDFL (SEQ ID NO:988)
EEIEVRSRDISREEWKGSETYSPNTAYGVDFL (SEQ ID NO:989)
EIEVRSRDISREEWKGSETYSPNTAYGVDFL (SEQ ID NO:990)
IEVRSRDISREEWKGSETYSPNTAYGVDFL (SEQ ID NO:991)
EVRSRDISREEWKGSETYSPNTAYGVDFL (SEQ ID NO:992)

EIAGQDEDHFITVDAVGCFEGDEEEEEDDEDEEEIEVRSRDISREEWKGSETYSPNTAYGVDFLV
(SEQ ID NO:993)
IAGQDEDHFITVDAVGCFEGDEEEEEDDEDEEEIEVRSRDISREEWKGSETYSPNTAYGVDFLV
(SEQ ID NO:994)
AGQDEDHFITVDAVGCFEGDEEEEEDDEDEEEIEVRSRDISREEWKGSETYSPNTAYGVDFLV
(SEQ ID NO:995)
GQDEDHFITVDAVGCFEGDEEEEEDDEDEEEIEVRSRDISREEWKGSETYSPNTAYGVDFLV
(SEQ ID NO:996)
QDEDHFITVDAVGCFEGDEEEEEDDEDEEEIEVRSRDISREEWKGSETYSPNTAYGVDFLV
(SEQ ID NO:997)
DEDHFITVDAVGCFEGDEEEEEDDEDEEEIEVRSRDISREEWKGSETYSPNTAYGVDFLV
(SEQ ID NO:998)
EDHFITVDAVGCFEGDEEEEEDDEDEEEIEVRSRDISREEWKGSETYSPNTAYGVDFLV
(SEQ ID NO:999)
DHFITVDAVGCFEGDEEEEEDDEDEEEIEVRSRDISREEWKGSETYSPNTAYGVDFLV
(SEQ ID NO:1000)
HFITVDAVGCFEGDEEEEEDDEDEEEIEVRSRDISREEWKGSETYSPNTAYGVDFLV
(SEQ ID NO:1001)
FITVDAVGCFEGDEEEEEDDEDEEEIEVRSRDISREEWKGSETYSPNTAYGVDFLV
(SEQ ID NO:1002)
ITVDAVGCFEGDEEEEEDDEDEEEIEVRSRDISREEWKGSETYSPNTAYGVDFLV (SEQ ID NO:1003)
TVDAVGCFEGDEEEEEDDEDEEEIEVRSRDISREEWKGSETYSPNTAYGVDFLV (SEQ ID NO:1004)
VDAVGCFEGDEEEEEDDEDEEEIEVRSRDISREEWKGSETYSPNTAYGVDFLV (SEQ ID NO:1005)
DAVGCFEGDEEEEEDDEDEEEIEVRSRDISREEWKGSETYSPNTAYGVDFLV (SEQ ID NO:1006)
AVGCFEGDEEEEEDDEDEEEIEVRSRDISREEWKGSETYSPNTAYGVDFLV (SEQ ID NO:1007)
VGCFEGDEEEEEDDEDEEEIEVRSRDISREEWKGSETYSPNTAYGVDFLV (SEQ ID NO:1008)
GCFEGDEEEEEDDEDEEEIEVRSRDISREEWKGSETYSPNTAYGVDFLV (SEQ ID NO:1009)
CFEGDEEEEEDDEDEEEIEVRSRDISREEWKGSETYSPNTAYGVDFLV (SEQ ID NO:1010)
FEGDEEEEEDDEDEEEIEVRSRDISREEWKGSETYSPNTAYGVDFLV (SEQ ID NO:1011)

FIG. 6S

EGDEEEEEEDDEDEEEIEVRSRDISREEWKGSETYSPNTAYGVDFLV (SEQ ID NO:1012)
GDEEEEEEDDEDEEEIEVRSRDISREEWKGSETYSPNTAYGVDFLV (SEQ ID NO:1013)
DEEEEEEDDEDEEEIEVRSRDISREEWKGSETYSPNTAYGVDFLV (SEQ ID NO:1014)
EEEEEDDEDEEEIEVRSRDISREEWKGSETYSPNTAYGVDFLV (SEQ ID NO:1015)
EEEEDDEDEEEIEVRSRDISREEWKGSETYSPNTAYGVDFLV (SEQ ID NO:1016)
EEEDDEDEEEIEVRSRDISREEWKGSETYSPNTAYGVDFLV (SEQ ID NO:1017)
EEDDEDEEEIEVRSRDISREEWKGSETYSPNTAYGVDFLV (SEQ ID NO:1018)
EDDEDEEEIEVRSRDISREEWKGSETYSPNTAYGVDFLV (SEQ ID NO:1019)
DDEDEEEIEVRSRDISREEWKGSETYSPNTAYGVDFLV (SEQ ID NO:1020)
DEDEEEIEVRSRDISREEWKGSETYSPNTAYGVDFLV (SEQ ID NO:1021)
EDEEEIEVRSRDISREEWKGSETYSPNTAYGVDFLV (SEQ ID NO:1022)
DEEEIEVRSRDISREEWKGSETYSPNTAYGVDFLV (SEQ ID NO:1023)
EEEIEVRSRDISREEWKGSETYSPNTAYGVDFLV (SEQ ID NO:1024)
EEIEVRSRDISREEWKGSETYSPNTAYGVDFLV (SEQ ID NO:1025)
EIEVRSRDISREEWKGSETYSPNTAYGVDFLV (SEQ ID NO:1026)
IEVRSRDISREEWKGSETYSPNTAYGVDFLV (SEQ ID NO:1027)
EVRSRDISREEWKGSETYSPNTAYGVDFLV (SEQ ID NO:1028)

EIAGQDEDHFITVDAVGCFEGDEEEEEEDDEDEEEIEVRSRDISREEWKGSETYSPNTAYGVDFLVP (SEQ ID NO: 11)
IAGQDEDHFITVDAVGCFEGDEEEEEEDDEDEEEIEVRSRDISREEWKGSETYSPNTAYGVDFLVP (SEQ ID NO:1029)
AGQDEDHFITVDAVGCFEGDEEEEEEDDEDEEEIEVRSRDISREEWKGSETYSPNTAYGVDFLVP (SEQ ID NO:1030)
GQDEDHFITVDAVGCFEGDEEEEEEDDEDEEEIEVRSRDISREEWKGSETYSPNTAYGVDFLVP (SEQ ID NO:1031)
QDEDHFITVDAVGCFEGDEEEEEEDDEDEEEIEVRSRDISREEWKGSETYSPNTAYGVDFLVP (SEQ ID NO:1032)
DEDHFITVDAVGCFEGDEEEEEEDDEDEEEIEVRSRDISREEWKGSETYSPNTAYGVDFLVP (SEQ ID NO:1033)
EDHFITVDAVGCFEGDEEEEEEDDEDEEEIEVRSRDISREEWKGSETYSPNTAYGVDFLVP (SEQ ID NO:1034)
DHFITVDAVGCFEGDEEEEEEDDEDEEEIEVRSRDISREEWKGSETYSPNTAYGVDFLVP (SEQ ID NO:1035)
HFITVDAVGCFEGDEEEEEEDDEDEEEIEVRSRDISREEWKGSETYSPNTAYGVDFLVP (SEQ ID NO:1036)
FITVDAVGCFEGDEEEEEEDDEDEEEIEVRSRDISREEWKGSETYSPNTAYGVDFLVP (SEQ ID NO:1037)
ITVDAVGCFEGDEEEEEEDDEDEEEIEVRSRDISREEWKGSETYSPNTAYGVDFLVP (SEQ ID NO:1038)
TVDAVGCFEGDEEEEEEDDEDEEEIEVRSRDISREEWKGSETYSPNTAYGVDFLVP (SEQ ID NO:1039)
VDAVGCFEGDEEEEEEDDEDEEEIEVRSRDISREEWKGSETYSPNTAYGVDFLVP (SEQ ID NO:1040)
DAVGCFEGDEEEEEEDDEDEEEIEVRSRDISREEWKGSETYSPNTAYGVDFLVP (SEQ ID NO:1041)
AVGCFEGDEEEEEEDDEDEEEIEVRSRDISREEWKGSETYSPNTAYGVDFLVP (SEQ ID NO:1042)
VGCFEGDEEEEEEDDEDEEEIEVRSRDISREEWKGSETYSPNTAYGVDFLVP (SEQ ID NO:1043)
GCFEGDEEEEEEDDEDEEEIEVRSRDISREEWKGSETYSPNTAYGVDFLVP (SEQ ID NO:1044)
CFEGDEEEEEEDDEDEEEIEVRSRDISREEWKGSETYSPNTAYGVDFLVP (SEQ ID NO:1045)
FEGDEEEEEEDDEDEEEIEVRSRDISREEWKGSETYSPNTAYGVDFLVP (SEQ ID NO:1046)
EGDEEEEEEDDEDEEEIEVRSRDISREEWKGSETYSPNTAYGVDFLVP (SEQ ID NO:1047)
GDEEEEEEDDEDEEEIEVRSRDISREEWKGSETYSPNTAYGVDFLVP (SEQ ID NO:1048)
DEEEEEEDDEDEEEIEVRSRDISREEWKGSETYSPNTAYGVDFLVP (SEQ ID NO:1049)
EEEEEDDEDEEEIEVRSRDISREEWKGSETYSPNTAYGVDFLVP (SEQ ID NO:1050)
EEEEDDEDEEEIEVRSRDISREEWKGSETYSPNTAYGVDFLVP (SEQ ID NO:1051)
EEEDDEDEEEIEVRSRDISREEWKGSETYSPNTAYGVDFLVP (SEQ ID NO:1052)
EEDDEDEEEIEVRSRDISREEWKGSETYSPNTAYGVDFLVP (SEQ ID NO:1053)
EDDEDEEEIEVRSRDISREEWKGSETYSPNTAYGVDFLVP (SEQ ID NO:1054)
DDEDEEEIEVRSRDISREEWKGSETYSPNTAYGVDFLVP (SEQ ID NO:1055)
DEDEEEIEVRSRDISREEWKGSETYSPNTAYGVDFLVP (SEQ ID NO:1056)
EDEEEIEVRSRDISREEWKGSETYSPNTAYGVDFLVP (SEQ ID NO:1057)

FIG. 6T

DEEEIEVRSRDISREEWKGSETYSPNTAYGVDFLVP (SEQ ID NO:1058)
EEEIEVRSRDISREEWKGSETYSPNTAYGVDFLVP (SEQ ID NO:1059)
EEIEVRSRDISREEWKGSETYSPNTAYGVDFLVP (SEQ ID NO:1060)
EIEVRSRDISREEWKGSETYSPNTAYGVDFLVP (SEQ ID NO:1061)
IEVRSRDISREEWKGSETYSPNTAYGVDFLVP (SEQ ID NO:1062)
EVRSRDISREEWKGSETYSPNTAYGVDFLVP (SEQ ID NO:1063)

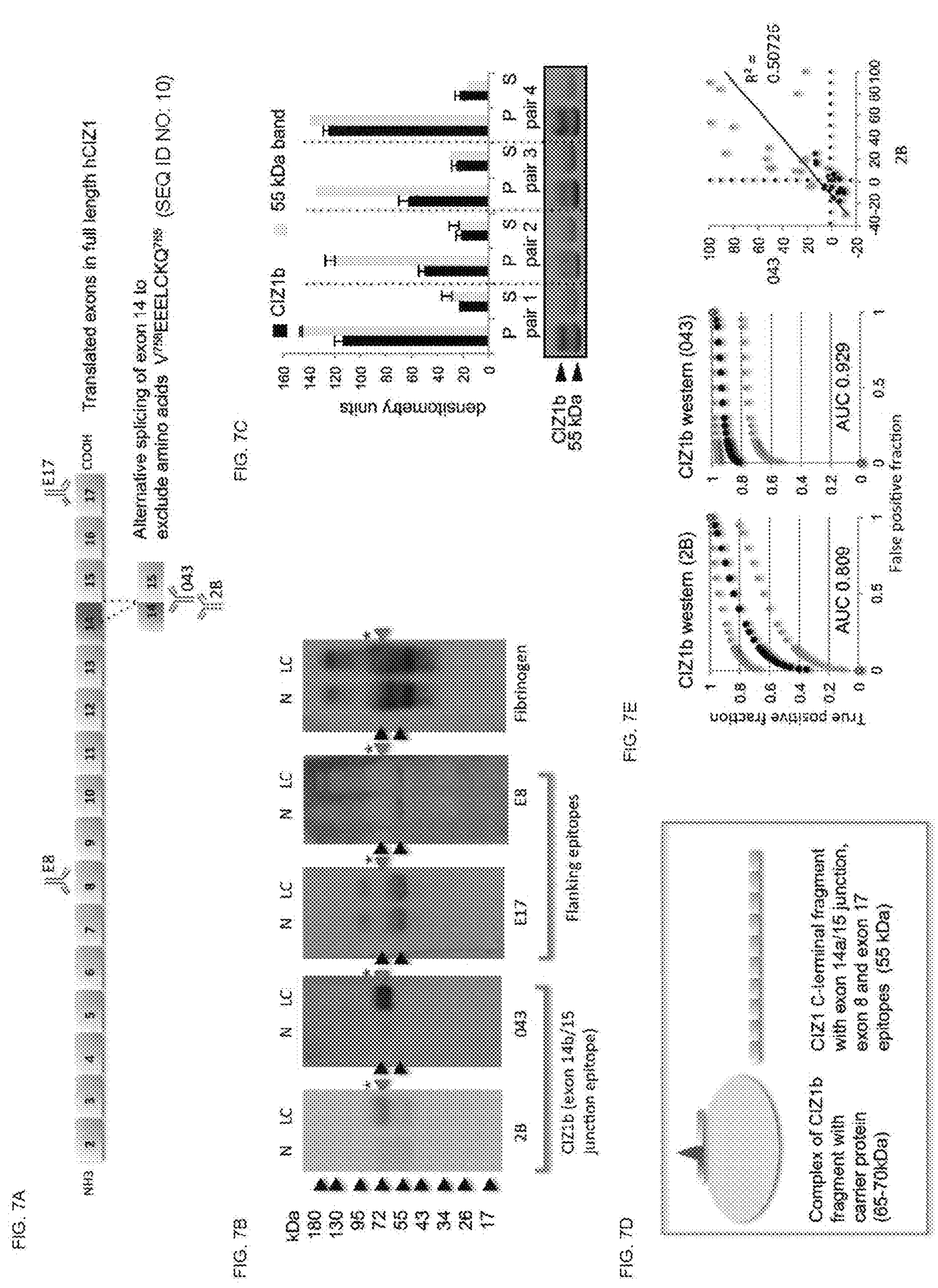
FIG. 7A
NH3
COOH
E8
E17
043
2B
Translated exons in full length hCIZ1
Alternative splicing of exon 14 to exclude amino acids V779EEELCKQ789 (SEQ ID NO: 10)
FIG. 7B
kDa
180
130
95
72
55
43
34
26
17
N LC
2B
043
E17
E8
Fibrinogen
CIZ1b (exon 14b/15 junction epitope)
Flanking epitopes
FIG. 7C
CIZ1b
55 kDa band
densitometry units
P S
pair 1
pair 2
pair 3
pair 4
CIZ1b
55 kDa
FIG. 7D
Complex of CIZ1b fragment with carrier protein (65-70kDa)
CIZ1 C-terminal fragment with exon 14a/15 junction, exon 8 and exon 17 epitopes (55 kDa)
FIG. 7E
CIZ1b western (2B)
CIZ1b western (043)
AUC 0.809
AUC 0.929
True positive fraction
False positive fraction
R² = 0.50725
043
2B kDa
1048
720
480
242
146
66
m C m N
m C N
m C N
043
Lung cancer
Non cancer
70 kDa
55 kDa
2B
043
Denaturing gel Cancer plasma lane from native gel
Normal plasma lane from native gel
top
Second dimension
SDS-PAGE
130
100
70
55
2B
native
70kDa
55kDa kDa
350
250
130
95
72
55
43
34
26
17
10
+ reducing agent
- reducing agent
37 °C 50°C 80 °C 90°C
C N C N C N C N
CIZ1b (043)

mM DTT
0 1 10 100 500 10xβME
350 kDa
70 kDa
CIZ1b (043)
Fibrinogen
Reducing agent concentration (plus 1% SDS, 37°C)

βME
0 1x 10x
043
Fib

CIZ1b 043 Western blot
AUC 0.823
P=0.0002

CIZ1b 043/Fibrinogen ELISA
AUC 0.830
P=0.0007

Fibrinogen/Fibrinogen ELISA
AUC 0.628
P=0.225

CIZ1b 043/IgG ELISA
AUC 0.504
P=0.827

Direct IgG ELISA
AUC 0.421
P=0.187

CIZ1b 043/Fibrinogen ELISA (normalized to IgG)
AUC 0.847
P=0.0002
True positive fraction
False positive fraction
Non-cancer
Lung cancer

USE OF A FIBRINOGEN CAPTURE AGENT TO DETECT A Ciz1 b-VARIANT

CROSS-REFERENCE TO RELATED APPLICATIONS

This application is a divisional of U.S. patent application Ser. No. 15/768,946, filed Apr. 17, 2018, which is a U.S. National Phase Application, filed under 35 U.S.C. § 371, of International Application No. PCT/GB2016/053203, filed on Oct. 14, 2016, which claims the benefit of priority to GB1518466.6, filed on Oct. 19, 2015, the contents of each of which are incorporated by reference herein in their entireties.

INCORPORATION OF SEQUENCE LISTING

The contents of the electronic sequence listing (CIZL_001_02US_SubSeqList_ST26.xml; Size: 1,405,601 bytes; and Date of Creation: Jul. 16, 2025) are herein incorporated by reference in its entirety.

FIELD OF THE INVENTION

The present invention relates to assays and methods useful for the detection of Cip1-interacting zinc finger protein (Ciz1) in a sample. In particular, the present invention relates to the use of such assays and methods for the diagnosis of cancer.

BACKGROUND OF THE INVENTION

Cip1-interacting zinc finger protein 1 (Ciz1) (as exemplified by NCBI Reference Sequence: NM_001131016.1) is required for cell proliferation. Ciz1 localises to nuclear matrix bound foci that form sites of DNA replication during early S phase and promotes the initiation of DNA replication in association with cell cycle regulators including cyclin A/cyclin dependent kinase (CDK)2, cyclin E/CDK2 and p21cip1. In the context of transcription, CIZ1 is an oestrogen responsive gene that is itself a positive cofactor of the oestrogen receptor (ER), capable of enhancing the recruitment of ER to target chromatin. Ciz1 is alternatively spliced to produce conserved isoforms in mouse and man. Normal Ciz1 protein comprises at least two defined functional domains, a 'replication' domain and an 'immobilisation' domain.

Alternative splicing of Ciz1 exon 14 to generate a Ciz1 b-variant has been determined in various cancers, including small cell lung cancer (SCLC), non-small cell lung cancer (NSCLC), lymphomas, thyroid, kidney and liver cancer. Excess expression of either the replication or immobilisation domain of Ciz1 has also been demonstrated in cancers, for example in NSCLC, breast, colon, kidney, liver, bladder and thyroid cancers. A correlation of domain expression with the stage of the cancer has also been determined (see WO 2012/078208).

The present invention addresses the continued need to develop diagnostic tests and treatments that improve the survival rates of patients suffering from cancers such as lung cancer through novel biomarkers and targets.

SUMMARY OF THE INVENTION

The present inventors have determined that Ciz1 b-variant exists in a complex with fibrinogen. This has allowed the inventors to develop a novel assay for detecting the presence of Ciz1 b-variant in a subject.

Furthermore, the present inventors have determined that Ciz1 b-variant may exist as peptide fragments. Furthermore, the present inventors have determined that Ciz1 b-variant and/or fibrinogen/Ciz1 b-variant complexes may exist in the exosomal compartment of a blood sample.

These findings instruct the design of assays for the detection of Ciz1 b-variant peptides, either when alone or when in complex with fibrinogen.

In particular, the finding that Ciz1 b-variant is complexed with fibrinogen has enabled the provision of a detection assay, in particular a diagnostic assay, which utilises the capture of fibrinogen or Ciz1 b-variant as an initial step in order to isolate the fibrinogen/Ciz1 b-variant complex. The assay may involve the use a fibrinogen capture agent to isolate the fibrinogen/Ciz1 b-variant complex followed by the use of Ciz1 b-variant detection agent to detect the Ciz1 b-variant which may be within said isolated complex. Alternatively, the assay may involve the use a Ciz1 b-variant capture agent to isolate the fibrinogen/Ciz1 b-variant complex followed by the use of fibrinogen detection agent to detect the fibrinogen which may be within said isolated complex.

Thus, in a first aspect the present invention relates to the use of a fibrinogen capture agent or a fibrinogen detection agent in an assay to detect a Ciz1 b-variant.

As used herein, a capture agent refers to an agent which is used to isolate (i.e. enrich) the fibrinogen/Ciz1 b-variant complex from a sample. For example, the sample may be a sample which has been isolated from a subject. In particular, the sample may be a blood sample (e.g. a plasma sample) which has been isolated from a subject.

As used herein, a detection agent refers to an agent which is used to bind the fibrinogen/Ciz1 b-variant complex after it has been isolated (i.e. enriched) from a sample using a capture agent. As such, the detection agent is typically used after a capture step to determine the presence of the isolated (i.e. enriched) fibrinogen/Ciz1 b-variant complex.

Suitably, the assay may be an enzyme-linked immunosorbent assay.

The fibrinogen capture agent or fibrinogen detection agent may be an antibody or a fragment thereof, non-protein scaffold, aptamer or Ciz1 b-variant peptide which specifically binds fibrinogen.

In a preferred embodiment, the fibrinogen capture agent or fibrinogen detection agent is an antibody or a fragment thereof which specifically binds fibrinogen. In another preferred embodiment, the fibrinogen capture agent is a Ciz1 b-variant peptide which specifically binds fibrinogen.

The fibrinogen may be fibrinogen alpha chain.

The Ciz1 b-variant may be detected in a sample from a subject, for example a blood, urine, saliva or bronchoalveolar lavage sample.

In a preferred embodiment the sample is a blood sample from a subject. In a particularly preferred embodiment the sample is a plasma sample.

The Ciz1 b-variant may be detected by a method which comprises the following steps: a) capturing a fibrinogen/Ciz1 b-variant complex using a fibrinogen capture agent; and b) detecting Ciz1 b-variant using a Ciz1 b-variant detection agent; or a) capturing a fibrinogen/Ciz1 b-variant complex using a Ciz1 b-variant capture agent; and b) detecting fibrinogen using a fibrinogen detection agent.

The Ciz1 b-variant capture agent may be an antibody or a fragment thereof, or a non-protein scaffold which specifically binds Ciz1 b-variant.

The Ciz1 b-variant capture agent may be an antibody or a fragment thereof which specifically binds Ciz1 b-variant.

In a further aspect the present invention relates to a method of diagnosing cancer in a subject which comprises detecting a Ciz1 b-variant peptide in a sample from the subject, wherein the presence of Ciz1 b-variant peptide in the sample indicates that the subject has cancer and wherein the method comprises the step of capturing a fibrinogen/Ciz1 b-variant peptide complex from the sample.

In a further aspect the present invention relates to a method of diagnosing cancer in a subject which comprises detecting a Ciz1 b-variant peptide in a sample from the subject, wherein the presence of Ciz1 b-variant peptide in the sample indicates that the subject has cancer and wherein the Ciz1 b-variant peptide is the sequence shown as SEQ ID NO: 11 or a fragment thereof which comprises EVR as shown in positions 36 to 38 of SEQ ID NO: 11.

In another aspect the present invention relates to method of detecting a Ciz1 b-variant peptide in a sample, for example detecting a Ciz1 b-variant peptide in a sample from a subject, wherein the method comprises the step of capturing a fibrinogen/Ciz1 b-variant peptide complex from the sample.

The method may comprise the steps of capturing a fibrinogen/Ciz1 b-variant complex using a fibrinogen capture agent; and detecting Ciz1 b-variant using a Ciz1 b-variant detection agent; or capturing a fibrinogen/Ciz1 b-variant complex using a Ciz1 b-variant capture agent; and detecting fibrinogen using a fibrinogen detection agent.

Suitably, the step of detecting the Ciz1 b-variant peptide or fibrinogen may employ antibody-based arrays, enzyme linked immunosorbent assays (ELISA), non-antibody protein scaffolds, radioimmuno-assay (RIA), western blotting, aptamers or mass spectrometry.

The method may further comprise the step of releasing a Ciz1 b-variant peptide and/or a fibrinogen/Ciz1 b-variant peptide complex from an exosomal component of the sample.

The Ciz1 b-variant peptide and/or fibrinogen/Ciz1 b-variant peptide complex may be released from the exosomal component by detergent treatment, such as SDS treatment.

The method may further comprise the step of enriching the exosomal fraction from the sample.

For example, the step of enriching the exosomal fraction may comprise ultracentrifugation, ultrafiltration, continuous flow electrophoresis, chromatography or cross-flow ultrafiltration.

The cancer may be selected from lung, lymphoma, kidney, breast, liver, bladder, ovarian or thyroid cancer.

In particular, the cancer may be lung cancer.

The present invention further relates to a method for treating a subject with cancer comprising administering to the subject a cancer therapeutic; wherein the subject has been identified as having cancer by the method of the invention.

The present invention also provides an anticancer drug for use in treating cancer wherein the subject has been identified as having cancer by the method of the invention.

The present invention further provides an anticancer lung cancer drug for use in treating lung cancer wherein the subject has been identified as having lung cancer by the method of the invention.

In a further aspect the present invention provides the use of a detergent to release a Ciz1 b-variant and/or a fibrinogen/Ciz1 b-variant complex from an exosomal compartment of a sample.

In another aspect the present invention relates to a method for detecting a Ciz1 b-variant in a sample which comprises the step of releasing the Ciz1 b-variant and/or a fibrinogen/Ciz1 b-variant complex from an exosomal compartment of the sample by treating the sample with detergent and detecting if the Ciz1 b-variant is present in the sample. The method may further comprise the step of enriching the exosomal fraction from the sample prior to releasing the Ciz1 b-variant.

The step of enriching the exosomal fraction may comprise ultracentrifugation, ultrafiltration, continuous flow electrophoresis, chromatography or cross-flow ultrafiltration.

In a further aspect the present invention provides a kit comprising an agent which specifically binds fibrinogen and an agent which specifically binds Ciz1 b-variant.

The fibrinogen may fibrinogen alpha chain.

The agent which specifically binds fibrinogen and/or the agent which specifically binds Ciz1 b-variant may be an antibody or a fragment thereof, a non-protein scaffold or an aptamer.

The agent which specifically binds to fibrinogen may be a Ciz1 b-variant peptide.

According to any of the above aspects of the present invention, the Ciz1 b-variant may be a Ciz1 b-variant peptide shown as SEQ ID NO: 11 or a fragment thereof which comprises EVR as shown in positions 36 to 38 of SEQ ID NO: 11.

DESCRIPTION OF THE DRAWINGS

FIGS. 1A-1F—FIG. 1A shows Ciz1 b-variant epitope-containing species, detected with splice junction-selective anti-Ciz1 rabbit polyclonal antibody 043. 043 was generated and validated as described for antibody 2B (Higgins et al.; (2012); PNAS; Nov 6; 109(45):E3128-35) and is capable of detection of Ciz1 b-variant by western blot in plasma from lung cancer patients. Western blots were performed and show Ciz1 b-variant in 0.5 ul of representative samples from 5 patients with lung carcinomas (various stages) and five from individuals with no disease. FIG. 1B shows separation of plasma from lung cancer patients into the exosomal compartment and soluble compartment illustrated here using Invitrogen Total Exosome Isolation Kit (Catalog Number 4484450) used as recommended by the manufacturer. Fractions were separated by SDS-PAGE, and probed with 043 to reveal Ciz1 b-variant, or with 'generic' Ciz1 antibodies that recognizes an epitope elsewhere in the protein (data shown here is generated with NB100-74624 (Nov4), Novus Biologicals that detects the C-terminus of Ciz1). Lane 1, untreated plasma (0.5 ul), lane 2 after low speed clearing spin (0.5 ul), lane 3 after high speed clearing spin (0.5 ul), lane 4 after addition of exosome reagent (0.5 ul equivalent), lane 5 high speed spin supernatant (SN, 0.5 ul equivalent), lane 6 high speed spin pellet (0.5 ul equivalent), lane 7 high speed spin pellet (P, 1 ul equivalent), lane 8 high speed spin pellet (2 ul equivalent). Red arrows indicate key lanes, showing different partitioning of Ciz1 epitopes. M, molecular weight marker. FIG. 1C shows a comparison of type 1 plasma samples in which Ciz1 b-variant is exclusively in the exosome fraction, and rare patients who display a type 2 pattern in which a fraction of Ciz1 b-variant is in the soluble fraction. FIG. 1D shows quantitative immuno-analysis generated using a prototype sandwich ELISA (without treating samples with detergent) showing increased signal in the type 2 plasma sample illustrated in c. FIG. 1E shows partitioning of Ciz1 b-variant in naïve type 1 plasma, and after treatment with 3% SDS (tested in the presence of protease inhibitor, PI, or 10 mM EDTA), revealing a shift of epitope into the soluble fraction. Blue arrows indicate soluble fraction after application of exosome isolation protocol. MW markers are shown to the right. SN=supernatant, P=pellet (exosome). FIG. 1F shows enhanced cancer-specific signal in SDS-treated type 1 plasma in ELISA immunoassay.

FIG. 2A and FIG. 2B show—Ciz1 Sequences.

FIG. 3A shows a western blot illustrating cancer-selective epitope recognised by anti-Ciz1 b-variant antibody 2B, as described previously (Higgins et al; as above). FIG. 3B shows reconstitution of a Ciz1 b-variant epitope from synthetic b-variant peptide (50 nmols of EIAGQDEDHFITV-DAVGCFEGDEEEEEDDEDEEEIEVRSRDISREEWKG-SETYSPNTAYGV DFLV—SEQ ID NO: 12) mixed with 0.5 ul of non-cancer plasma. Free peptide migrates with mobility indicative of a MW 3-4× greater than predicted (~30 kDa instead of 7.6 kDa), indicated by blue arrow. When incubated in plasma mobility decreases, antigenicity increases, and a new species is created at ~80 kDa, indicated by red arrow. FIG. 3C shows similar results were generated with a separate anti-Ciz1 b-variant monoclonal antibody. FIG. 3D shows for reference, a duplicate blot is probed with a monoclonal antibody that is selective for the exon 14a version of the peptide (EIAGQDEDHFITV-DAVGCFEGDEEEEEDDEDEEEIEVEEELCKQRSRDIS-REEWKGSETYS PNTAYGVDFLV—SEQ ID NO: 13), showing detection of the peptide in lanes 1 and 3. Key: Lane 1, WT peptide only. Lane 2, B-var peptide only. Lane 3, WT peptide+normal plasma. Lane 4, B-var peptide+normal plasma. Lane 5, normal plasma only. Results show that normal plasma acquires Ciz1 b-variant signal at ~80 kDa upon addition of b-var peptide, but not a-var peptide. FIG. 3E shows similar results were obtained using short b-variant peptide (DEEEIEVRSRDIS—SEQ ID NO: 2), when combined with either cancer or non-cancer plasma. Western blot shows results with anti-Ciz1 b-variant monoclonal antibody (left) or anti-Ciz1 b-variant polyclonal antibody 043 (right). Key: Lane 1, B-var peptide only. Lane 2, B-var peptide+normal plasma. Lane 3, B-var peptide+lung cancer plasma. Lane 4, Normal plasma alone. Lane 5, Lung cancer plasma alone. Note that mobility of new signal is similar to endogenous signal in cancer patient plasma. FIG. 3F shows a western blot showing titration of short peptide (DEEE-IEVRSRDIS—SEQ ID NO: 2) into cancer patient plasma, detected with anti-Ciz1 b-variant monoclonal antibody (upper) or anti-Ciz1 b-variant polyclonal antibody 043 (lower). Graph shows quantification of results by densitometry, with signal in normal plasma (N) set at 1. Results show that carrier protein is not limiting up to 4 nmol peptide/0.5 ul plasma. Overall, results show that endogenous b-var65 species, detected by anti Ciz1 b-variant antibodies, is likely not one single 65 kDa Ciz1 b-variant species, but a stable composite of Ciz1 b-variant fragment and carrier protein with MW close to 65 kDa.

FIGS. 4A-4D—Isolation using a two-dimensional gel approach shows that the carrier protein is Fibrinogen. FIG. 4A shows a western blot of cancer (C) and non-cancer (N) plasma samples after incubation in 2% SDS sample buffer with and without 200 mM b-mercaptoethanol. In the presence of reducing agent, a cancer-specific signal at ~65 kDa is produced with anti-b variant antibodies, while in the absence of reducing agent cancer-specific signal is retarded to ~340 kDa. FIG. 4B shows a first dimension gel (without reducing agent) used to isolate Ciz1 b-variant epitope-containing ~340 kDa band. FIG. 4C shows the band is further resolved after incubation in reducing agent to reveal constitutive polypeptides and migration of Ciz1 b-variant epitope with a ~70 kDa component. The band was excised for mass spectrometry. FIG. 4D shows a MASCOT assigned one significant identity based on two separate peptide masses after trypsin digest. Identity: Fibrinogen alpha chain.

FIG. 5A shows a silver stained gel (left) showing 6 nmols of purified fibrinogen complex (Sigma Cat. F3879), after electrophoresis in the absence of reducing agent (in 2% SDS loading buffer). Peptides are included in the experiment (100 pmols/lane) but do not stain well with silver due to their amino-acid content. Western blots of parallel gels are shown on the right, probed with two anti-b variant antibodies. L, Long Ciz1 b-variant peptide EIAGQDEDHFITV-DAVGCFEGDEEEEEDDEDEEEIEVRSRDISREEWKG-SETYSPNTAYGV DFLV (SEQ ID NO: 12). S, Short Ciz1 b-variant peptide DEEEIEVRSRDIS (SEQ ID NO: 2). FIG. 5B shows a similar experiment comparing a range of Ciz1 b-variant and a-variant peptides for their ability to form epitope that is reactive to the same antibodies, when in complex with fibrinogen. Key: 1, no additions. 2, Long Ciz1 b-variant peptide EIAGQDEDHFITV-DAVGCFEGDEEEEEDDEDEEEIEVRSRDISREEWKG-SETYSPNTAYGV DFLV (SEQ ID NO: 12). 3, WT long peptide EIAGQDEDHFITVDAVGCFEGDEEEEED-DEDEEEIEVEEELCKQRSRDISREEWKGSETYS PNTAYGVDFLV (SEQ ID NO: 13). 4, no additions. 5, Short Ciz1 b-variant DEEEIEVRSRDIS (SEQ ID NO: 2). 6, C-DEEyEVRSRDIS-coNH2 (SEQ ID NO: 14). 7, C-DEyEIEVRSRDIS-coNH2 (SEQ ID NO: 23). 8, C-Dyyy-lyVRSRDIS-coNH2 (SEQ ID NO: 15).

FIG. 6A, FIG. 6B, FIG. 6C, FIG. 6D, FIG. 6E, FIG. 6F, FIG. 6G, FIG. 6H, FIG. 6I, FIG. 6J, FIG. 6K, FIG. 6L, FIG. 6M, FIG. 6N, FIG. 6O, FIG. 6P, FIG. 6Q, FIG. 6R, FIG. 6S, and FIG. 6T collectively show—Table 1:Ciz1 b-variant peptides comprising an exon 14b/exon 15 junction (specified by exclusion of VEEELCKQ—SEQ ID NO: 10) from NCBI Reference Sequence: NM_001131016.1.

FIGS. 7A-7E—Exon junction specific antibodies detect CIZ1b in lung cancer patient plasma. FIG. 7A shows a map of CIZ1 translated exons showing alternative splicing of exon 14 to yield 14b (CIZ1b) by exclusion of the indicated 8 amino-acids (positions refer to NCBI Reference Sequence: NM_012127.2). Also shown are the location of epitopes detected with antibodies used in B. FIG. 7B shows a western blot of representative plasma samples from a patient with NSCLC (LC) and normal control (N) after denaturation for SDS-PAGE, showing CIZ1b band at 65-70 kDa in LC (red arrow, marked "*") detected by CIZ1b antibodies 2B and 043, and a 'generic' CIZ1 antibody-reactive band at 55 kDa in both N and LC, detected via epitopes in exon 8 and exon 17. Also indicated is fibrinogen alpha chain. FIG. 7C shows a comparison of CIZ1b levels in paired plasma (P) and serum (S) samples from four individuals analysed with CIZ1b antibody 2B. Histogram shows quantified band intensities for the 65-70 kDa and 55 kDa entities, derived from triplicate samples, with standard deviation. Note that serum lacks the 65-70 kDa CIZ1b band. FIG. 7D shows a model showing the simplest interpretation of the data in B, though extensive alternative splicing and likely secondary modification mean that the exact identity of the 55 kDa entity in plasma is unverified. FIG. 7E shows receiver operating characteristic (ROC) curves showing area under the curve (AUC) values for 2B and 043 western blot results on lung cancer test set A. Dot plot shows correlation between the two date sets (LC samples are orange). Thresholds (black dotted lines) are set at the mean of non-cancer samples in the set, plus one SD. These yield sensitivity/specificity estimates for this set of 20 lung cancer and 20 non-cancer samples of: 2B, 85/67.5; 043, 90/77.5. Using an arbitrary threshold specified by both antibodies these are 90/87.5.

FIG. 8A left shows Coomassie blue stained gel of a representative lung cancer (C) and normal (N) plasma sample (2 ul), separated under fully native conditions (in the absence of SDS or reducing agent). m indicates marker lanes. Middle, parallel gel after transfer to nitrocellulose stained with Ponceau S. FIG. 8A right shows the same membrane probed with CIZ1b antibody 043. Lower panel shows the same two samples (red arrows) separated by denaturing SDS-PAGE, also probed with 043. FIG. 8B shows a native gel first dimension soaked in 4× SDS-PAGE loading buffer for 30 minutes without heating, and further separated by size (second dimension). Western blot reveals one band at 55 kDa that is reactive with antibody 2B in the non-cancer sample, and two bands (55 and 70 kDa) in the cancer sample. Two additional cancer plasma samples, treated in the same way are shown below. FIG. 8C shows migration of 043-reactive bands in a representative cancer (C) and non-cancer (N) plasma sample through a non-denaturing gel, after prior incubation at the indicated temperatures, in the presence of 2% SDS, with and without reducing agent (200 mM β-mercaptoethanol, βME) as indicated. Note the shift of cancer-specific band (red box) from relative mobility of approximately 340 kDa in the absence of reducing agent, to ~70 kDa in the presence of reducing agent (accompanied by complete loss of the 'generic' band that was detected in all samples in the absence of reducing agent). FIG. 8D shows plasma from a lung cancer patient showing 043-reactive band after incubation with 1% SDS at 37° C. for 30 mins, with the indicated concentrations of DTT, or a 10-fold excess of βME. The reactive band is indicated as it shifts from 340 kDa to 70 kDa, and is then lost under maximally reducing conditions. The behaviour of fibrinogen in the same samples is shown for comparison, detected with antibody F8512. FIG. 8E shows synthetic CIZ1b epitope generated by combining CIZ1b peptide (b66, Table 2) with normal (non-cancer) plasma, behaves similarly to endogenous epitope, dissociating from within a high molecular weight complex, to a ~70 kDa species, and then disappearing under maximally reducing conditions. Fibrinogen is detected with antibody AF4786. βME concentrations refer to multiples of the standard concentration used in SDS-PAGE of 200 mM.

FIG. 9A shows a schematic of results shown in FIGS. 8A-8E, illustrating the complexity of the native complex in which CIZ1b epitope (red bar, marked "*") resides in plasma, and the disrupting effect of detergent and reducing agents. Under native conditions CIZ1b is part of a complex in excess of 720 kDa, most likely encompassed within lipid vesicles. SDS shifts the epitope to 340 kDa, and reducing agents shift it further to the mobility typically observed in standard SDS-PAGE gels (65-70 kDa). In the presence of excess reducing agent the western blot epitope is lost for both 2B and 043 CIZ1b antibodies. FIG. 9B shows a schematic of sandwich ELISA format based on information summarised in FIG. 9A.

FIG. 10A shows two independent lung cancer patient plasmas were separated after incubation with 1% SDS (no reducing agent), in order to isolate the 340 kDa band from stained gels (left). Band identity was verified by ponceau S stain followed by Western blot with anti-CIZ1b antibody 043 of a parallel gel (right). FIG. 10B shows gel slices were soaked in 2% SDS-PAGE loading buffer (with 200 mM βME) and separated through a denaturing gel to recover the 043-reactive species at 70 kDa. Note that sample loaded as a gel slice is slightly retardation compared to markers which are loaded in solution. Coomassie blue staining revealed 5 dominant bands including one at 70 kDa, which was isolated and digested with either trypsin (cancer plasma 1, C1) or AspN (cancer plasma 2, C2). FIG. 10C shows a western blot of normal human plasma (non-cancer, N) showing reconstitution of CIZ1b epitope via complex formation between a carrier protein in plasma and synthetic CIZ1b peptides of the indicated lengths, but not equivalent CIZ1a peptide (Table 2). Note that free peptides migrate in reducing SDS-PAGE with a relative mobility 3 times expected (~21 kDa instead of 7.6 kDa for b66, ~5 kDa instead of 1.6 for b13). None are recognized by CIZ1b antibodies in western blot unless complexed with carrier protein. For CIZ1b66 peptide a new reactive species is created at ~80 kDa, while CIZ1b13 peptide increases antigenicity at the same mobility as the endogenous epitope in lung cancer plasmas (C, lane 1). FIG. 10D shows a western blot of non-reducing SDS-PAGE gel showing purified fibrinogen (6 nmols) in all lanes (upper), with and without prior incubation with 100 pmols of the indicated peptides (Table 2), probed with CIZ1b antibodies as indicated. Under non-reducing conditions fibrinogen migrates with apparent molecular weight of ~340 kDa and this co-migrates with CIZ1b signal. FIG. 10E shows direct ELISA showing mean A450 nm (triplicate analysis with SEM) generated by CIZ1b antibodies 2B or 043 as indicated, using molar equivalents of preformed peptide/fibrinogen complex as analyte. **T test $p<0.05$.

FIG. 11A shows a CIZ1b western blot with antibody 043. FIG. 11B shows a sandwich ELISA format for CIZ1b antigen in plasma, using 043 capture antibody and anti-fibrinogen detector antibody. FIG. 11C shows quantitative detection of fibrinogen in the same samples using paired fibrinogen antibodies. FIG. 11D shows a substitution of anti-human IgG for anti-fibrinogen in a sandwich format similar to that shown in B. FIG. 11E shows detection of IgG in plasma by direct ELISA. FIG. 11F shows normalization of the data in FIG. 11B against the data of total IqG levels in FIG. 11E. In all cases, receiver operating characteristic curves (ROC) indicate the relationship between true positive and false positive fraction (black points) and 95% confidence interval of the fitted ROC curve (grey points), and area under the curve (AUC) values in bold. Box and whisker plots display minimum and maximum, lower, median, and upper quartile, and outliers.

DETAILED DESCRIPTION OF THE INVENTION

Ciz1

Figure 1C:
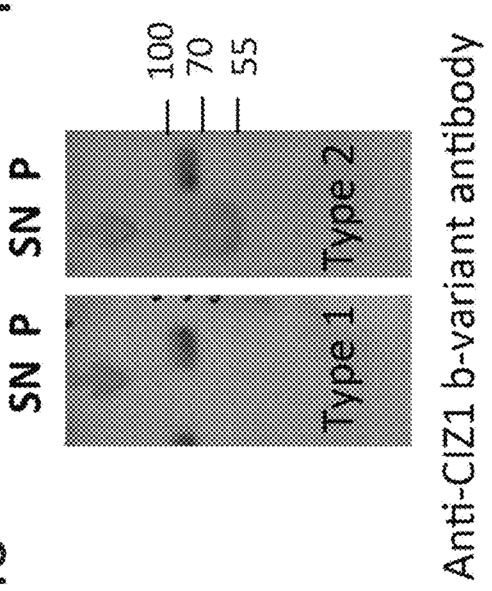
Figure 1D:
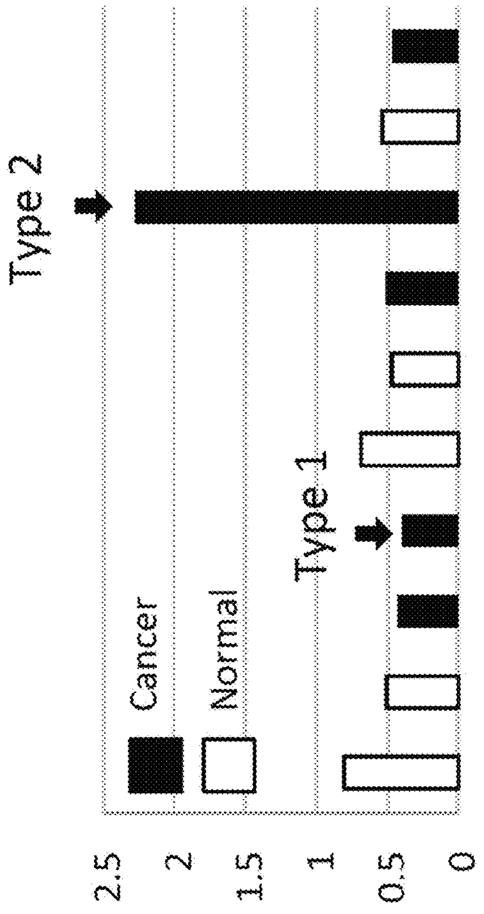

Cip1-interacting zinc finger protein (Ciz1) is a protein that in humans is encoded by the CIZ1 gene.

Ciz1 promotes initiation of mammalian DNA replication, where it helps coordinate the sequential functions of cyclin E- and A-dependent protein kinases (Coverley et al; J Cell Sci. 2005; 118(Pt 1):101-112). It interacts directly with cyclins E and A, CDK2, and cyclin-dependent kinase inhibitor p21 and also plays an indirect role in DNA replication by modulating the expression of genes, including cyclin D, that influence cell proliferation (den Hollander et al; Cancer Res. 2006; 66(22):11021-11029). Ciz1 is often attached to the salt- and nuclease-resistant protein component of the nucleus referred to as the "nuclear matrix" and resides within foci that partially colocalize with sites of DNA replication (Ainscough; J Cell Sci. 2007; 120(Pt 1):115-124), implicating Ciz1 in the spatial organization of DNA replication.

Various splice variants of Ciz1 are known in the art. For example, as described in WO 2004/051269 and Rahman et al. (BMC Cancer; 2010; 10:482).

The alternative splicing of Ciz1 exon 14 to generate a Ciz1 b-variant isoform has previously been demonstrated in various cancers ((WO 2012/017208) and (Higgins et al.; PNAS; Nov 6; 109(45):E3128-35)).

As described herein, a Ciz1 b-variant isoform is derived from a Ciz1 mRNA transcript which comprises a variant of exon 14 referred to herein as exon 14b (SEQ ID NO: 3). Ciz1 exon 14b lacks 24 nucleotides at the 3' end as compared to full length exon 14, referred to as exon 14a (SEQ ID NO: 4). Ciz1 transcripts expressing exon 14b rather than exon 14a (a-variant) are referred to herein as Ciz1 b-variant, CIZ1b or simply b-variant. The corresponding amino acid sequences of Ciz1 exon 14b and 14a are shown as SEQ ID NO: 5 (LKSLEKEIAGQDEDHFITVDAVGCFEGDEEEEEDDEDEEEIE) and SEQ ID NO: 6 (LKSLEKEIAGQDEDHFITVDAVGCFEGDEEEEED-DEDEEEIEVEEELCKQ) respectively (see FIGS. 2A-2B).

The sequence spanning a splice junction of exon 14b and exon 15 is therefore different to the sequence spanning a splice junction of exon 14a and exon 15. In particular, the junction of exon 14b and exon 15 lacks the sequence VEEELCKQ (SEQ ID NO: 10) which is present at the junction between exon 14a and exon 15 in Ciz1 a-variant proteins.

The present inventors have determined that Ciz1 b-variant peptides exist in a complex with fibrinogen. In particular, it has been shown that Ciz1 b-variant peptides which span an exon 14b/exon 15 junction are able to bind to fibrinogen. In contrast, Ciz1 a-variant peptides are not able to bind to fibrinogen.

Accordingly, as described herein, a Ciz1 b-variant peptide refers to a peptide which can be derived from a Ciz1 b-variant protein but not a Ciz1 a-variant protein. In other words, a Ciz1 b-variant peptide refers to a portion of a Ciz1 b-variant protein which is derived from exons 14b and exon 15 of a Ciz1 b-variant protein and therefore lacks the sequence VEEELCKQ (SEQ ID NO: 10) at the splice junction.

In particular, a Ciz1 b-variant peptide comprises an exon 14b/exon 15 splice junction. In other words, a ciz1 b-variant peptide comprises amino acid sequences derived from Ciz1 exon 14b (SEQ ID NO: 5) and Ciz1 exon 15 (SEQ ID NO: 7) and comprises the sequence EVR as shown in positions 36 to 38 of SEQ ID NO: 11.

```
                                   SEQ ID NO: 11
EIAGQDEDHFITVDAVGCFEGDEEEEEDDEDEEEIEVRSRDISREEWKG

SETYSPNTAYGVDFLVP
```

Notably, Ciz1 b-variant peptides do not contain amino acids which are specific to Ciz1 a-variant proteins and therefore do not comprise the sequence VEEELCKQ (SEQ ID NO: 10).

As such, a Ciz1 b-variant peptide may be the Ciz1 b-variant peptide shown as SEQ ID NO: 11 or a fragment thereof which comprises EVR as shown in positions 36 to 38 of SEQ ID NO: 11.

Suitably, the Ciz1 b-variant peptide may comprise at least 3, at least 5, at least 10, at least 20, at least 30, at least 40, at least 50 or at least 60 contiguous amino acids of SEQ ID NO: 11 and comprise EVR as shown in positions 36 to 38 of SEQ ID NO: 11.

Suitably, the Ciz1 b-variant peptide may comprise or consist of from 3 to 60, 5 to 60, 5 to 50, 10 to 50, 10 to 40, 10 to 30, 15 to 30 or 10 to 20 contiguous amino acids of SEQ ID NO: 11 and comprise EVR as shown in positions 36 to 38 of SEQ ID NO: 11.

Suitably, the Ciz1 b-variant peptide may comprise or consist of 10 to 20 contiguous amino acids of SEQ ID NO: 11 and comprise EVR as shown in positions 36 to 38 of SEQ ID NO: 11.

Suitably, a Ciz1 b-variant peptide may be a peptide shown in Table 1 (see FIGS. 6A-6T).

Fibrinogen

In one aspect, the present invention relates to the use of a fibrinogen capture agent or a fibrinogen detection agent in an assay to detect Ciz1 b-variant.

In one aspect, the present invention relates to the use of a fibrinogen binding agent in an assay to detect Ciz1 b-variant.

The fibrinogen binding agent may be an antibody or a fragment thereof, non-protein scaffold or aptamer which specifically binds fibrinogen.

In particular, the present invention provides the use of an antibody or a fragment thereof, which binds fibrinogen in an assay to detect Ciz1 b-variant.

Fibrinogen is involved in blood clotting, fibrinolysis, cellular and matrix interactions, the inflammatory response, wound healing and neoplasia.

Fibrinogen molecules are elongated 45 nm structures that consist of two outer D domains, each connected by a coiled-coil segment to a central E domain. The molecule is comprised of two sets of three polypeptide chains termed α, β, and γ, which are joined together in the N-terminal E domain by five symmetrical disulfide bridges. Non-symmetrical disulfide bridges form a 'disulfide ring' in this region (Mosesson; 2005; Journal of Thrombosis and Haemostasis; 3(8); 1894-1940).

Polymerisation of fibrinogen molecules results in the formation of an insoluble fibrin matrix. Conversion of fibrinogen to fibrin is triggered by thrombin, which cleaves fibrinopeptides A and B from a and p chains, and thus exposes the N-terminal polymerization sites responsible for the formation of the soft clot. The soft clot is converted into the hard clot by factor XIIIA which catalyzes the epsilon-(gamma-glutamyl)lysine cross-linking between γ chains (stronger) and between a chains (weaker) of different monomers.

The α-chain consists of 610, the β-chain 461, and the major γ-chain form, γA, 411 residues. Each fibrinogen α-chain contains an N-terminal fibrinopeptide A (FPA) sequence, cleavage of which by thrombin initiates fibrin assembly by exposing a polymerization site termed EA. One portion of EA is at the N-terminus of the fibrin α-chain comprising residues 17-20 gly-pro-arg-val (GPRV), and another portion is located in the fibrin β-chain between residues 15 and 42. Each EA-site combines with a constitutive complementary-binding pocket (Da) in the D domain of neighbouring molecules that is located between γ337 and γ379. The initial EA:Da associations cause fibrin molecules to align in a staggered overlapping end-to-middle domain arrangement to form double-stranded twisting fibrils. Fibrils also undergo lateral associations to create multi-stranded fibres (Mosesson; as above).

An example fibrinogen α protein is the human fibrinogen α protein having the UniProtKB accession number P02671. This exemplified sequence is 866 amino acids in length of which amino acids 1 to 19 form a signal peptide.

An example fibrinogen β protein is the human fibrinogen β protein having the UniProtKB accession number P02675. This exemplified sequence is 491 amino acids in length of which amino acids 1 to 30 form a signal peptide.

An example fibrinogen γ protein is the human fibrinogen γ protein having the UniProtKB accession number P02679. This exemplified sequence is 453 amino acids in length of which amino acids 1 to 26 form a signal peptide.

The term 'fibrinogen' may refer to a complex comprising two a chains, two p chains and two γ chains or a sub-complex thereof (e.g. which does not include all the chains of the full fibrinogen complex).

The present inventors have determined that Ciz1 b-variant peptides are capable of binding to the fibrinogen α chain. As such, in particular embodiments the present assays and methods may involve the capture or detection of the fibrinogen α chain. For example the present assays and methods may involve the detection of fibrinogen (e.g. fibrinogen α chain) following the capture of Ciz1 b-variant in the fibrinogen/Ciz1 b-variant complex.

A 'fibrinogen/Ciz1 b-variant complex' as referred to herein may comprise other peptides and/or proteins aside from the fibrinogen and/or Ciz1 b-variant peptide.

As used herein, a capture agent refers to an agent which is used to isolate (i.e. enrich) the fibrinogen/Ciz1 b-variant complex from a sample. For example, the sample may be a sample which has been isolated from a subject. In particular, the sample may be a blood sample (e.g. a plasma sample) which has been isolated from a subject.

A 'fibrinogen capture agent' refers to an entity which is capable of binding to a fibrinogen/Ciz1 b-variant complex. Preferably, a 'fibrinogen capture agent' is an entity which is capable of specifically binding to fibrinogen and is used to isolate (i.e. enrich) the fibrinogen/Ciz1 b-variant complex from a sample. Such specific binding may enable the isolation/enrichment of fibrinogen from a sample. In particular embodiments, the fibrinogen capture agent may be capable of specifically binding to a fibrinogen α chain.

The fibrinogen capture agent may be an antibody or a fragment thereof, non-protein scaffold, aptamer or Ciz1 b-variant peptide which specifically binds fibrinogen.

As used herein, a detection agent refers to an agent which is used to bind the fibrinogen/Ciz1 b-variant complex after it has been isolated (i.e. enriched) from a sample using a capture agent. As such, the detection agent is typically used after a capture step to determine the presence of the isolated (i.e. enriched) fibrinogen/Ciz1 b-variant complex.

A 'fibrinogen detection agent' refers to an entity which is capable of binding to a fibrinogen. Preferably, a 'fibrinogen detection agent' is an entity which is capable of specifically binding to fibrinogen. Such specific binding enables the detection of fibrinogen following the capture of Ciz1 b-variant in the fibrinogen/Ciz1 b-variant complex. In particular embodiments, the fibrinogen capture agent or fibrinogen detection agent may be capable of specifically binding to a fibrinogen α chain.

The fibrinogen detection agent may be an antibody or a fragment thereof, non-protein scaffold, or aptamer which specifically binds fibrinogen.

The fibrinogen detection agent may be labelled with an entity which enables it to be detected in an assay as described herein. For example, the fibrinogen detection agent may be labelled with a fluorescent entity or an enzyme-substrate label as described herein.

Antibody

An antibody or a fragment thereof, refers to any portion of an antibody which retains the ability to bind to the same antigen target as the parental antibody—e.g. a fibrinogen antibody or a fragment thereof is able to bind to fibrinogen.

Fibrinogen antibodies are known in the art. For example, sheep anti-fibrinogen pAb (AF4786 R&D systems), ab58207 (Abcam); Anti-Fibrinogen, clone 85D4 (Cat. No. F9902; Sigma Aldrich); and Fibrinogen Antibody (MFB-HB) (Cat. No. MA1-35371; Life Technologies).

Fibrinogen α chain antibodies are also known in the art. For example, EPR2918 (ab108616; Abcam); Fibrinogen Antibody (5C5) (LF-MA0108; Pierce); and EPR2919 (TA307697; Origene).

The present invention also encompasses methods which comprise the step of detecting Ciz1 b-variant or capturing Ciz1 b-variant/fibrinogen complex by contacting the Ciz1 b-variant with an antibody or fragment thereof that binds to the Ciz1 b-variant. An antibody which specifically binds a Ciz1 b-variant peptide may be generated as previously described for antibody 2B (Higgins et al; 2012; PNAS; Nov 6; 109(45):E3128-35).

The antibody may be a chimeric antibody. Chimeric antibodies may be produced by transplanting antibody variable domains from one species (for example, a mouse) onto antibody constant domains from another species (for example a human).

The antibody may be a full-length, classical antibody. For example the antibody may be an IgG, IgM or IgA molecule.

The antibody may be a functional antibody fragment. Specific antibody fragments include, but are not limited to, (i) the Fab fragment consisting of VL, VH, CL and CH1 domains, (ii) the Fd fragment consisting of the VH and CH1 domains, (iii) the Fv fragment consisting of the VL and VH domains of a single antibody, (iv) the dAb fragment, which consists of a single variable domain, (v) isolated CDR regions, (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site, (viii) bispecific single chain Fv dimers, and (ix) "diabodies" or "triabodies", multivalent or multispecific fragments constructed by gene fusion. The antibody fragments may be modified. For example, the molecules may be stabilized by the incorporation of disulphide bridges linking the VH and VL domains.

The antibody described herein may be a multispecific antibody, and notably a bispecific antibody, also sometimes referred to as "diabodies". These are antibodies that bind to two (or more) different antigens. Diabodies can be manufactured in a variety of ways known in the art, e.g., prepared chemically or from hybrid hybridomas. The antibody may be a minibody. Minibodies are minimized antibody-like proteins comprising a scFv joined to a CH3 domain. In some cases, the scFv can be joined to the Fc region, and may include some or all of the hinge region.

The antibody may be a domain antibody (also referred to as a single-domain antibody or nanobody). This is an antibody fragment containing a single monomeric single variable antibody domain. Examples of single-domain antibodies include, but are not limited to, VHH fragments originally found in camelids and VNAR fragments originally found in cartilaginous fishes. Single-domain antibodies may also be generated by splitting the dimeric variable domains from common IgG molecules into monomers.

The antibody may be a synthetic antibody (also referred to as an antibody mimetic). Antibody mimetics include, but are not limited to, AFFIBODIES® (small affinity proteins derived from the Z domain of Protein A), DARPINs® (designed ankyrin repeat protein), ANTICALINs® (small proteins derived from human lipocalins), AVIMERs™ (avidity multimer of two or more peptide sequences derived from A domains of membrane receptors), VERSABODIES™ (microprotein-based small antibody mimetic proteins) and DUOCALINs® (dual targeting proteins derived from human lipocalins).

Aptamers

Aptamers that specifically recognize fibrinogen or Ciz1 b-variant may be synthesized using standard nucleic acid synthesis techniques or selected from a large random sequence pool, for example using the Systematic Evolution of Ligands by Exponential Enrichment (SELEX) technique.

Aptamers can be single strand DNA or RNA sequences that fold in a unique 3D structure having a combination of stems, loops, quadruplexes, pseudoknots, bulges, or hairpins. The molecular recognition of aptamers results from intermolecular interactions such as the stacking of aromatic rings, electrostatic and van der Waals interactions, or hydrogen bonding with a target compound. In addition, the specific interaction between an aptamer and its target is complemented through an induced fit mechanism, which requires the aptamer to adopt a unique folded structure to its target. Aptamers can be modified to be linked with labeling molecules such as dyes, or immobilized on the surface of beads or substrates for different applications.

Aptamers may be paired with nanotechnology, microarray, microfluidics, mass spectrometry and other technologies for quantification in a given sample.

Typically, a fibrinogen capture agent or a Ciz1 b-variant capture agent will be immobilised on a support, such as an array, or be captured on a solid support, such as beads. A sample to be tested is then incubated with the support comprising the capture agent such that Ciz1 b-variant/fibrinogen complex can be isolated/enriched from the sample. Supports (eg. solid supports) can be made of a variety of materials—such as glass, silica, plastic, nylon or nitrocellulose. When attached to a solid support it is preferably rigid and have a planar surface.

The fibrinogen capture agent or Ciz1 b-variant capture agent may comprise a moiety that can be captured on a solid surface, such as a biotin moiety which can be captured by streptavidin beads. In such embodiments, capture to a support can occur follow incubation of the capture agent with a sample.

Detecting Ciz1 b-Variant or Capturing a Ciz1 b-Variant

Suitably, the Ciz1 b-variant may be a Ciz1 b-variant peptide as described herein.

A Ciz1 b-variant may be detected using a variety of suitable methods and techniques known in the art.

The method may comprise the following steps: a) capturing a fibrinogen/Ciz1 b-variant complex using a fibrinogen capture agent; and b) detecting Ciz1 b-variant using a Ciz1 b-variant detection agent.

The method may comprise the following steps: a) capturing a fibrinogen/Ciz1 b-variant complex using a Ciz1 b-variant capture agent; and b) detecting fibrinogen using a fibrinogen detection agent.

As used herein, a 'Ciz1 b-variant capture agent' refers to an entity which is capable of binding to a Ciz1 b-variant and is used to isolate (i.e. enrich) the fibrinogen/Ciz1 b-variant complex from a sample. Preferably, a 'Ciz1 b-variant capture agent' is an entity which is capable of specifically binding to Ciz1 b-variant. Such specific binding enables the isolation/enrichment of the fibrinogen/Ciz1 b-variant complex from a sample.

The Ciz1 b-variant capture agent may be an antibody or a fragment thereof, non-protein scaffold, aptamer or Ciz1 b-variant peptide which specifically binds fibrinogen.

In particular embodiments, a Ciz1 b-variant/fibrinogen complex may be captured using an antibody or fragment thereof that binds to the Ciz1 b-variant peptide. An antibody which specifically binds a Ciz1 b-variant peptide may be generated as previously described for antibody 2B (Higgins et al; 2012; PNAS; Nov 6; 109(45):E3128-35).

A 'Ciz1 b-variant detection agent' refers to an entity which is capable of binding to a Ciz1 b-variant and is used to bind the fibrinogen/Ciz1 b-variant complex after it has been isolated (i.e. enriched) from a sample using a capture agent. Preferably, a 'Ciz1 b-variant detection agent' is an entity which is capable of specifically binding to Ciz1 b-variant. Such specific binding enables the detection of Ciz1 b-variant following the capture of the fibrinogen/Ciz1 b-variant complex.

The Ciz1 b-variant detection agent may be an antibody or a fragment thereof, non-protein scaffold, or aptamer which specifically binds Ciz1 b-variant.

The Ciz1 b-variant detection agent may be labelled with an entity which enables it to be detected in an assay as described herein. For example, the Ciz1 b-variant detection agent may be labelled with a fluorescent entity or an enzyme-substrate label as described herein.

For example, methods for detecting Ciz1 b-variant may employ antibody-based arrays, enzyme linked immunosorbent assays (ELISA), non-antibody protein scaffolds, radioimmuno-assay (RIA), western blotting, aptamers or mass spectrometry.

An ELISA may be performed according to general methods which are known in the art. For example, the ELISA may be a sandwich or competitive ELISA.

A sandwich ELISA may comprise the following steps:

a surface (i.e. a microtitre plate well) is prepared to which a known quantity of capture agent is bound (e.g. a Ciz1 b-variant capture agent or a fibrinogen capture agent);

any nonspecific binding sites on the surface are blocked;

the sample comprising the Ciz1 b-variant is applied to the plate;

the plate is washed to remove unbound antigen;

a primary antibody which is capable of specifically binding the fibrinogen or Ciz1 b-variant is added, and binds to antigen;

an enzyme-linked secondary antibody is applied as a detection antibody that bind specifically to the antibody Fc region;

the plate is washed to remove the unbound antibody-enzyme conjugates, before a chemical is added to be converted by the enzyme into a colour or fluorescent or electrochemical signal;

the absorbency or fluorescence or electrochemical signal of the plate wells is measured to determine the presence and quantity of antigen.

In particular embodiments, the present methods comprise the step of capturing a fibrinogen/Ciz1 b-variant complex using a fibrinogen capture agent or a Ciz1 b-variant capture agent as described herein.

In one embodiment the present methods comprise a sandwich ELISA which comprises the steps of capturing a fibrinogen/Ciz1 b-variant complex using a Ciz1 b-variant capture agent as described herein and detecting the fibrinogen/Ciz1 b-variant complex using a fibrinogen detection agent as described herein.

A competitive ELISA may comprise the following steps:

a labelled antibody which specifically binds the Ciz1 b-variant is incubated in the presence of a sample comprising the Ciz1 b-variant;

the bound antibody/antigen complexes are then added to an antigen-coated well;

the plate is washed, so unbound antibody is removed;

a secondary antibody, specific to the primary antibody, and coupled to an enzyme is added;

a substrate for the enzyme is added, and the reaction of the enzyme with its substrate elicits a chromogenic or fluorescent signal;

the reaction is stopped to prevent eventual saturation of the signal.

Various enzyme-substrate labels are available, e.g. as disclosed in U.S. Pat. No. 4,275,149. The enzyme generally catalyses a chemical alteration of the chromogenic substrate that can be detected. For example, the enzyme may catalyse a colour change in a substrate, or may alter the fluorescence or chemiluminescence of the substrate. Examples of enzymatic labels include peroxidase such as horseradish peroxidase (HRPO), alkaline phosphatase, beta-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are well known.

Detecting a Ciz1 b-variant peptide may comprise contacting said Ciz1 b-variant peptide with an antibody or fragment thereof that binds to the Ciz1 b-variant peptide. An antibody which specifically binds a Ciz1 b-variant peptide may be generated as previously described for antibody 2B (Higgins et al; 2012; PNAS; Nov 6; 109(45):E3128-35).

In some embodiments the b-variant specific antibody may bind to an epitope comprising the EVR sequence shown in positions 36 to 38 of SEQ ID NO: 11.

In some embodiments, the antibody specifically binds to an amino acid sequence comprising DEEEIEVRSRDIS (SEQ ID NO: 2) but does not specifically bind to an amino acid sequence comprising DEEEIEVEEELCKQVRSRDIS (SEQ ID NO: 9).

However, in some embodiments, the sequence bound by a b-variant specific antibody may be present in both Ciz1 exon 14a (SEQ ID NO: 6) and Ciz1 exon 14b (SEQ ID NO: 5). In such embodiments, the b-variant specific antibody may be unable to bind to Ciz1 a-variant because the presence of the VEEELCKQ sequence (SEQ ID NO: 10) prevents the antibody binding. In other embodiments, the antibodies may bind to sequences present in both Ciz1 exon 14a and Ciz1 exon 14b, because the sequences are presented in a b-variant specific conformation or structure.

In some embodiments, the b-variant specific antibody may bind to an epitope formed by a Ciz1 b-variant peptide/fibrinogen complex.

Without being bound by theory, the binding of Ciz1 b-variant to fibrinogen may expose epitopes which comprise amino acid sequences which are common between Ciz1 exon 14a (SEQ ID NO: 6) and Ciz1 exon 14b (SEQ ID NO: 5) in a conformation which is unique to the fibrinogen/Ciz1 b-variant. Such conformational epitopes will therefore not be present in Ciz1 a-variant.

Sample

In certain embodiments, the present invention utilises a sample isolated from a subject. This sample may be referred to as a 'test sample'. Thus the present methods are typically practiced outside of the human or animal body, e.g. on a sample that was previously obtained from the subject to be tested.

The sample may be a blood, urine, saliva or bronchoalveolar lavage sample.

In a preferred embodiment the sample is a blood sample. Suitably, the blood sample may be a whole blood sample. Suitably, the blood sample may be a blood fraction, for example a plasma sample.

Techniques for collecting blood samples and separating blood fractions are well known in the art. For instance, vena blood samples can be collected from patients using a needle and deposited into plastic tubes. The collection tubes may, for example, contain anticoagulants, spray-coated silica, or a polymer gel for separation. Plasma can be separated by centrifugation at 1300 RCF for 10 min at room temperature and stored in small plastic tubes at −80° C.

In a preferred embodiment the sample is a blood sample, in particular a plasma sample. In a preferred embodiment the blood sample is treated with anticoagulants (e.g. heparin) following collection.

Detergent

In one embodiment, the present methods may comprise treating the sample with a detergent in order to release the Ciz1 b-variant and/or a fibrinogen/Ciz1 b-variant complex.

Examples of detergent include, but are not limited to, sodium dodecyl sulfate (SDS) and polysorbate 20. For example, the sample may be treated with about 1 to 5%, preferably 1 to 2% SDS.

Suitably, the present methods may further comprise treating the sample with a reducing agent in order to further purify the Ciz1 b-variant and/or a fibrinogen/Ciz1 b-variant complex. Examples of suitable reducing agents include, but are not limited to, Dithiothreitol (DTT)-which may be used at a concentration of about 10 mM DTT, for example.

Exosomes

The present methods may comprise the step of releasing Ciz1 b-variant and/or a fibrinogen/Ciz1 b-variant complex from the exosomal compartment of a sample. Suitably, the present methods may comprise the step of releasing Ciz1 b-variant peptides from the exosomal compartment of a sample.

Exosomes are nanometer-sized (30-100 nm) vesicles found in many biological fluids, such as urine, blood (in both plasma and serum), ascites, and cerebrospinal fluid. They originate as internal vesicles of multi-vesicular bodies (MVBs) in cells and were first described as products of circulating blood cells, such as erythrocytes and lymphocytes.

Exosomes are surrounded by a phospholipid membrane containing relatively high levels of cholesterol, sphingomyelin, and ceramide and containing detergent-resistant membrane domains (lipid rafts) (Mathivanan et al., 2010; J Proteomics 73:1907-1920).

Exosomes are characterized by the presence of proteins involved in membrane transport and fusion, such as Rab, GTPases, annexins, and flotillin, components of the endosomal sorting complex required for transport (ESCRT) complex such as Alix, tumor susceptibility gene 101 (TSG101), heat shock proteins (HSPs), integrins, and tetraspanins, including CD63, CD81, and CD82 (van der Pol et al.; 2012; 64(3); 676-705).

Releasing Ciz1 b-variant and/or a fibrinogen/Ciz1 b-variant complex from an exosomal compartment refers to disrupting the structural integrity of the exosome such that Ciz1 b-variant epitopes which were previously concealed within the internal structure of the exosomes are exposed for binding.

Suitably, releasing Ciz1 b-variant and/or a fibrinogen/Ciz1 b-variant complex from an exosomal compartment may refer to treating a sample with a detergent. Examples of detergent include, but are not limited to, sodium dodecyl sulfate (SDS) and polysorbate 20.

In one embodiment, the sample may be treated with a detergent at a concentration which is suitable to release Ciz1 b-variant and/or a fibrinogen/Ciz1 b-variant complex from an exosomal compartment. For example, the sample may be treated with about 1 to 5%, preferably 1 to 2% SDS.

Exosome Enrichment

The present methods may involve enriching an exosomal fraction from a sample.

As used herein, enriching an exosomal fraction is synonymous to purifying or isolating an exosomal fraction.

Exosomes may be purified by methods known in the art such as ultracentrifugation (Pisitkun et al (2004) PNAS 101:13368-13373) or ultrafiltration (Cheruvanky et al (2007) Am. J. Physiol. Renal Physiol. 292:F1657-F1661). Methods are also known involving continuous flow electrophoresis and chromatography procedures which may precede centrifugation (Taylor and Gercel-Taylor (2005) Br J Cancer 92:305-311). Cross-flow ultrafiltration may also be used as part of the exosome purification method (Lamparski et al (2002) J Immunol. Methods 270:211-226).

Commercial kits for the isolation of exosomes are also available, for example the Total Exosome Isolation Kit provided by Invitrogen.

Exosomes can be isolated from a multitude of cell line and body fluids by combining differential centrifugation, membrane filtration, concentration, rate zonal centrifugation and immunocapture, exosomes (Simpson et al.; Proteomics, 8 (2008), pp. 4083-4099).

Exosomes can be detected and/or purified on the basis of their expression of exosomal markers such as tumour susceptibility gene (TSG101), aqua-porin-2 (AQP2), neuron-specific enolase (NES), annexin V, podocalyxin (PODXL) and CD9. For example, exosomes may be captured on to a microplate, for example by immunoaffinity capture.

Characterization of isolated exosomes is typically performed using electron microscopy, FACS, LC-MS/MS, Western blotting or ELISA (Simpson et al.; as above) and (van Niel et al; J Biochem (Tokyo), 140 (2006), pp. 13-21).

Cancer

In one aspect, the present invention relates to a method of diagnosing cancer in a subject.

As used herein, the term "cancer" or "cancerous" refers to cells having the capacity for autonomous growth, i.e., an abnormal state or condition characterized by rapidly proliferating cell growth. The term is meant to include all types of cancerous growths or oncogenic processes, metastatic tissues or malignantly transformed cells, tissues, or organs, irrespective of histopathologic type or stage of invasiveness. The term "cancer" includes malignancies of the various organ systems, such as those affecting, for example, lung, breast, thyroid, lymphoid, gastrointestinal, reproductive and genito-urinary tract, as well as adenocarcinomas which include malignancies such as most colon cancers, renal-cell carcinoma, prostate cancer and/or testicular tumours, non-small cell carcinoma of the lung, cancer of the small intestine and cancer of the esophagus.

Suitably, the cancer may be lung cancer, lymphoma, kidney cancer, breast cancer, liver cancer, bladder cancer, ovarian or thyroid cancer.

In one embodiment, the cancer is lung cancer. The lung cancer may be small cell lung cancer. The lung cancer may be non-small cell lung cancer.

Subject

The subject may be a human or animal subject. Preferably, the subject is a human.

The subject may have or be at risk of cancer, as described herein. 'At risk of cancer' refers to a subject who is not showing any symptoms of the disease. The subject may have a predisposition for, or be thought to be at risk of developing, cancer.

Treating

In one aspect the present invention relates to a method for treating a subject with cancer comprising administering to the subject a cancer therapeutic; wherein the subject has been identified as having cancer by a method of the present invention.

In another aspect the present invention provides an anti-cancer drug for use in treating cancer wherein the subject has been identified as having cancer by a method of the present invention. In a further aspect, the present invention relates to an anticancer lung cancer drug for use in treating lung cancer wherein the subject has been identified as having lung cancer by a method of the present invention. 'Treating' or 'to treat' refers to the therapeutic use of a cancer therapeutic or anticancer agent. Herein the cancer therapeutic or anticancer agent may be administered to a subject having an existing disease or condition in order to lessen, reduce or improve at least one symptom associated with the disease and/or to slow down, reduce or block the progression of the disease.

Anticancer Drug

An 'anticancer drug' is synonymous with a cancer therapeutic and refers to an entity which may be used to treat cancer.

The anti-cancer drug may be a cytokine or haematopoietic factor including, but not limited to, IL-1, IL-2, IL-4, IL-5, IL-13, IL-6, CSF-1, M-CSF, GM-CSF, IFNα, IFNβ, IFNγ, IL-10, IL-12, VEGF, bone morphogenic proteins, FGFs, TNF and TGFβ.

The anticancer drug may be a chemotherapeutic agent, which may be a cytotoxic drug. A chemotherapeutic agent contemplated includes, without limitation, alkylating agents, nitrosoureas, ethylenimines/methylmelamine, alkyl sulfonates, antimetabolites, pyrimidine analogs, epipodophylotoxins, enzymes such as L-asparaginase; biological response modifiers such as IFNα, IL-2, G-CSF and GM-CSF; platinum coordination complexes such as cisplatin and carboplatin, anthracenediones, substituted urea such as hydroxyurea, methylhydrazine derivatives including N-methylhydrazine (MIH) and procarbazine, adrenocortical suppressants such as mitotane (o,p'-DDD) and aminoglutethimide; hormones and antagonists including adrenocorticosteroid antagonists such as prednisone and equivalents, dexamethasone and aminoglutethimide; progestin such as hydroxyprogesterone caproate, medroxyprogesterone acetate and megestrol acetate; estrogen such as diethylstilbestrol and ethinyl estradiol equivalents; antiestrogen such as tamoxifen; androgens including testosterone propionate and fluoxymesterone/equivalents; antiandrogens such as flutamide, gonadotropin-releasing hormone analogs and leuprolide; and non-steroidal antiandrogens such as flutamide.

The anticancer drug may be a siRNA or shRNA.

Suitably, the anticancer drug may be an anticancer lung cancer drug. An anticancer lung cancer drug refers to an entity which may be used to treat lung cancer.

Kit

In one aspect, the present invention provides a kit comprising an agent which specifically binds fibrinogen and an agent which specifically binds Ciz1 b-variant.

The agent which specifically binds fibrinogen may be a fibrinogen capture agent as described herein.

The agent which specifically binds Ciz1 b-variant may be a Ciz1 b-variant detection agent as described herein.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" also include the term "consisting of".

The invention will now be further described by way of Examples, which are meant to serve to assist one of ordinary skill in the art in carrying out the invention and are not intended in any way to limit the scope of the invention.

EXAMPLES

Example 1—Enrichment of Ciz1 b-Variant in an Exosomal Fraction from a Blood Sample The antibody 043 was generated and validated as described previously for antibody 2B (Higgins et al; PNAS 2012; Nov 6; 109(45):E3128-35)). The antibody was capable of detecting of Ciz-1 b-variant polypeptide by western blot in plasma from lung cancer patients (see FIG. 1A).

Plasma from lung cancer patients was separated into the exosomal compartment and soluble compartment using Invitrogen Total Exosome Isolation Kit (Catalog Number 4484450) used as recommended by the manufacturer. Fractions were separated by SDS-PAGE and probed with 043 antibody or with 'generic' CIZ1 antibodies that recognize an epitope elsewhere in the protein (data shown in FIG. 1B is generated with NB100-74624 (Nov4), Novus Biologicals).

Figure 1E:
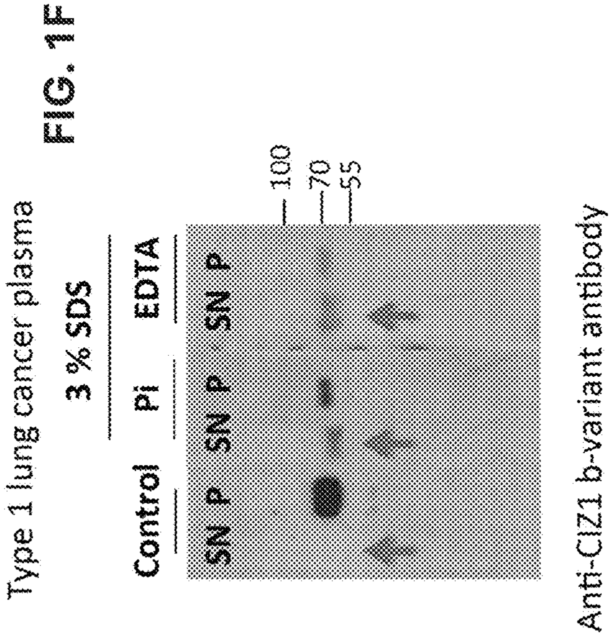
Figure 1F:
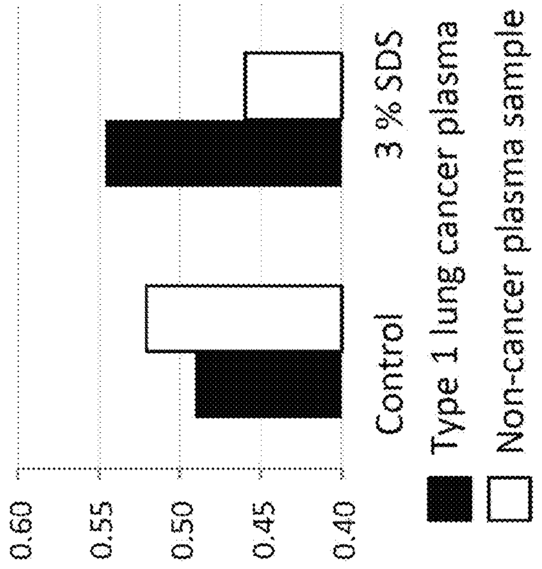

The Ciz1 b-variant epitope containing species migrated with relative mobility of ~70 kDa. The Ciz1 b-variant epitope containing species co-fractionated with the exosomal fraction in lung cancer patients (see FIG. 1B, red and blue arrows indicate lanes showing different partitioning of Ciz1 isoforms). In rare patients, the Ciz1 b-variant epitope containing species partly partitions with the non-exosomal fraction (type 2, FIG. 1C). Plasma from these patients gave a positive signal in Ciz1 b-variant sandwich ELISA without any pre-treatment to dissolve exosomes. For patients whose Ciz1 b-variant epitope containing species is wholly in the exosome fraction, the Ciz1 b-variant epitope may be accessed by treating plasma (type 1) with detergent prior to assay (FIGS. 1E-1F).

Figures 3A, 3B, 3C, 3D, 3E, 3F:
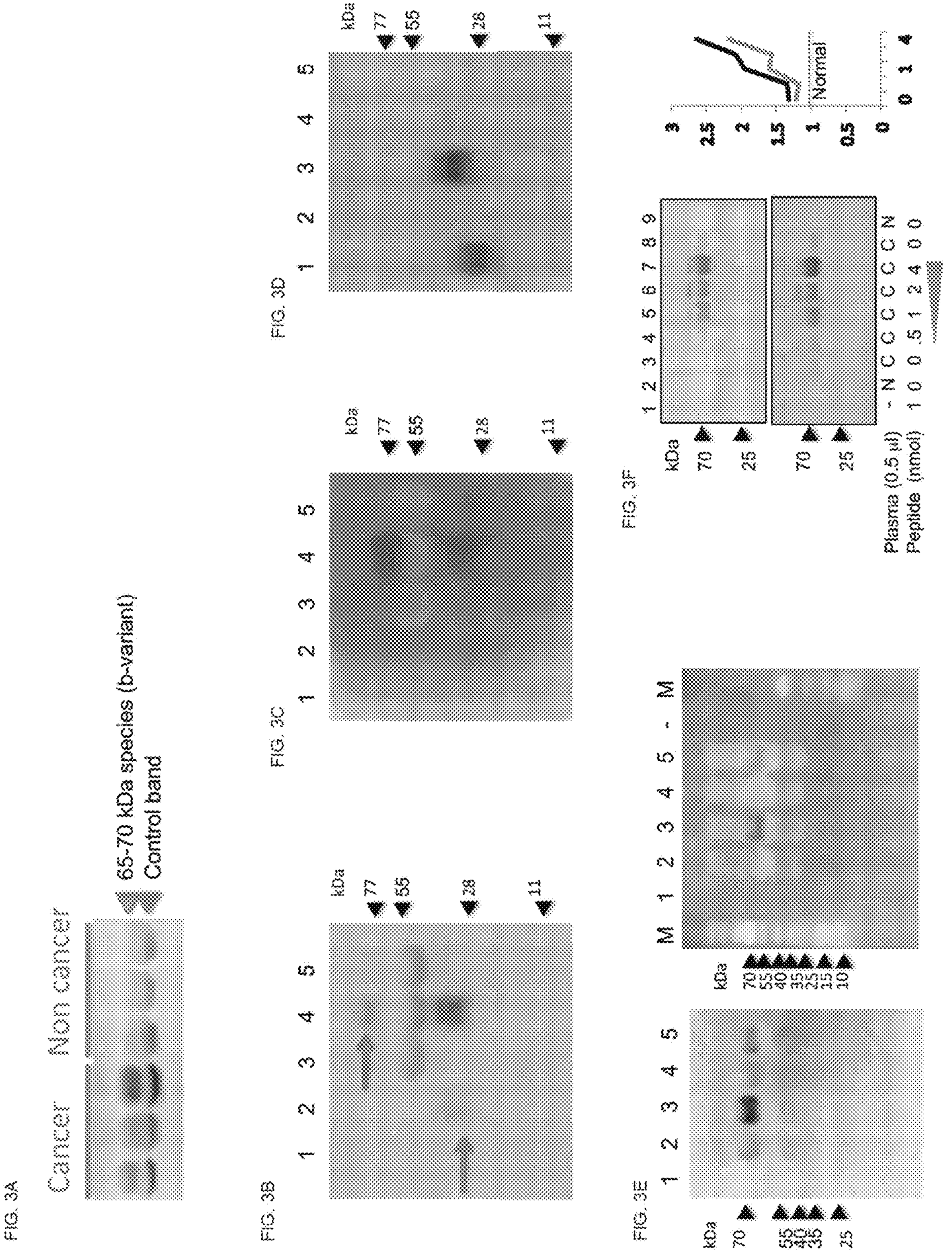
FIGS. 3A-3F—Ciz1 b-variant ~65-70 kDa species is a Ciz1 b-variant peptide stably bound to a carrier protein, which may augment antigenicity of Ciz1 b-variant peptide.

Example 2—Reconstitution of Epitope from Synthetic b-Variant Peptides and Fibrinogen The antibody 2B (FIG. 3A) and 043 (FIG. 1A) recognise Ciz1 b-variant in the region of the unique junction between exon 14b and 15. They do not react with a species with relative mobility of ~70 kDa in normal plasma (FIGS. 3B-3C), but do weakly react with synthetic b-variant peptide (FIGS. 3B-3C). However when combined, synthetic b-variant peptides and normal plasma generate a new, highly reactive species of ~80 kDa. Similar results are obtained with a synthetic b-variant peptide of a different length (FIG. 3E), quantitatively generating epitope (FIG. 3F).

Figure 4A:
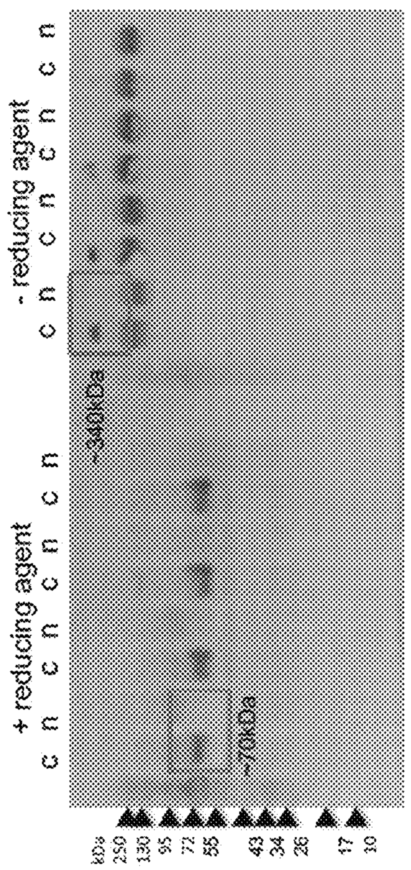
Figure 4B:
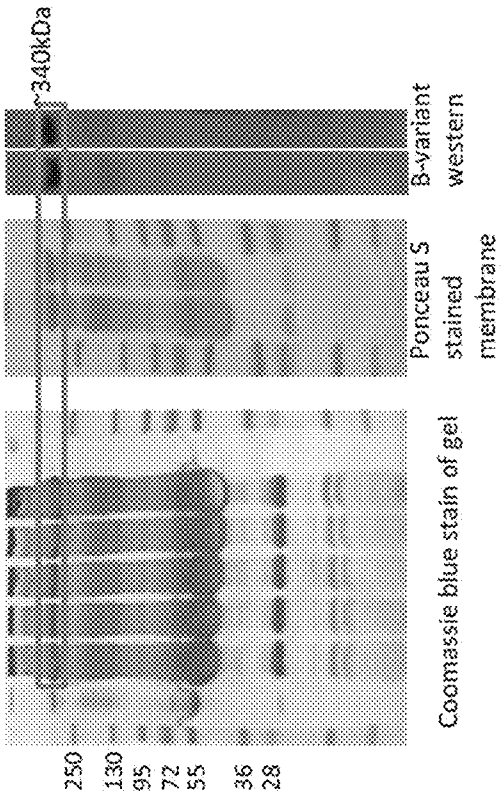
Figure 4C:
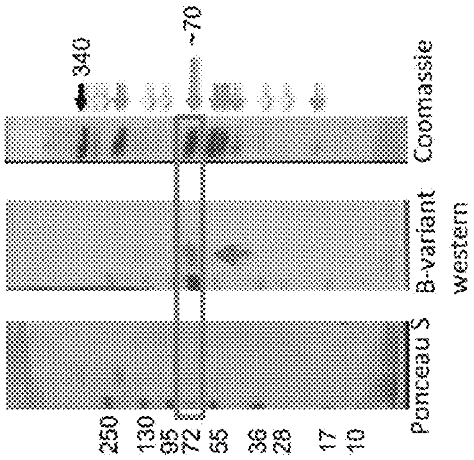

Mobility of endogenous b-variant epitope in plasma from cancer patients is sensitive to reducing agent, migrating at ~340 kDa in the absence of DTT and at ~70 kDa in the presence of DTT (FIG. 4A). Excision of the 340 kDa complex (FIG. 4B), followed by further separation into constituent polypeptides upon reduction shifts the epitope to ~70 kDa (FIG. 4C). Excision and elution of this band identified fibrinogen alpha chain by mass spectrometry (FIG. 4D).

Figure 5B:
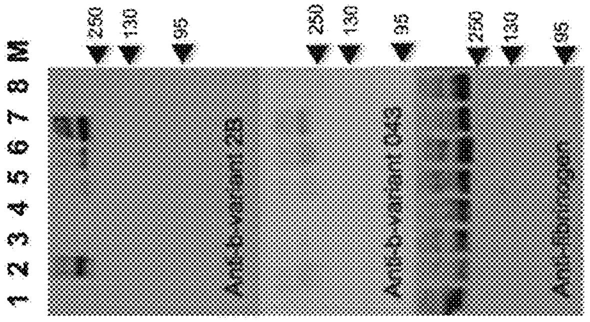
FIGS. 5A-5B—Reconstitution of Ciz1 b-variant epitope from purified fibrinogen and synthetic peptides.
Figure 5A:
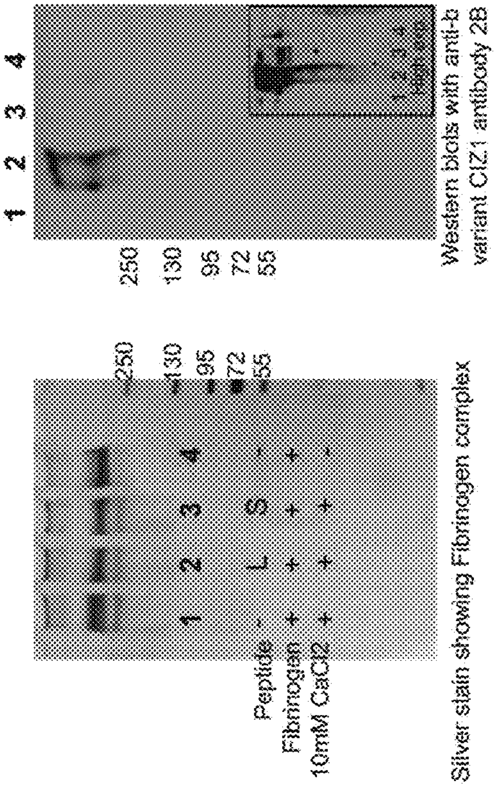

Incubation of purified fibrinogen complex (FIG. 5A) with synthetic b-variant peptides generates a b-variant epitope with mobility similar to the fibrinogen complex (FIG. 5A). Comparison with a-variant peptides, or carboxylated derivatives of b-variant peptides, or with different lengths of b-variant peptides showed that i) reconstitution of epitope is specific to b-variant containing peptides, ii) carboxylation of certain E residues near the splice junction affects reconstitution of epitope, iii) b-variant junction containing peptides of different lengths may constitute the epitope that naturally exists in human plasma.

Example 3—Characterisation of Ciz-1 b-Variant as a Biomarker

Analysis of CIZ1b was carried out with anti-peptide rabbit polyclonal antibody 2B, which was raised against a short unique peptide spanning the alternatively spliced 14b-15 junction (FIG. 7A), with sequence DEEEIEVRSRDIS (SEQ ID NO: 2—junction indicated by underlined valine). The strategy for generation, validation and purification was described previously (Higgins et al., as above). The western blot reactivity profile for 2B includes a 65-70 kDa entity in SDS-PAGE of plasma from lung cancer patients, plus a 55 kDa entity in plasma from all people (FIG. 7B). The cancer-specific 65-70 kDa species is the CIZ1b biomarker that is referred to here and by Higgins et al. In contrast to plasma, this protein could not be detected in serum samples from the same lung cancer patients (FIG. 7C), suggesting that CIZ1b biomarker is sequestered in coagulated blood. Notably the 55 kDa generic band co-migrates with CIZ1 spec7), identifying the 55 kDa species as a variant or proteolytic fragment of full-length hCIZ1 (which has a predicted full length MW of 99 kDa, NCBI Reference Sequence: NM_012127.2). The width of the bands detected via exon 8 and exon 17 is different, possibly because the exon 8 epitope lies within an alternatively spiced region, while detection via exon 17 would reveal species with or without alternative splicing at exon 8. Thus at least one form of the CIZ1 protein is present in the circulatory system in cancer and non-cancer plasma samples alike, suggesting it to be part of normal physiology.

Exon 17 and exon 8 epitopes are not present in the 65-70 kDa species recognised by CIZ1b antibody 2B in cancer patients, which means that sequences both upstream and downstream of the CIZ1b epitope are missing from this protein. The data suggest that the 65-70 kDa species is either a complicated CIZ1 splice variant, or an SDS-stable complex between a CIZ1b fragment of CIZ1 and a carrier protein (FIG. 7D).

A further set of rabbit antibodies was generated using the same immunisation protocol as for 2B (see Higgins et al., as above). This yielded antibody 043, which cleanly and uniquely reacts with the 65-70 kDa band in cancer patients (FIG. 7B). Thus 043 provides a detection tool with applications in other assay formats, including ELISA. The lack of recognition of the 55 kDa species suggests less contribution of junction flanking sequences to its epitope compared to 2B, and suggests that the 55 kDa species does not contain the CIZ1b junction. Direct comparison of the ability of these two antibodies to discriminate lung cancer patients by western blot shows them both to be discriminatory, with a high degree of correlation (FIG. 7E), though notably they do not share exactly the same profile across plasma test set. Thus, there is some variation in their epitopes but a common ability to discriminate patients with lung cancer from those without. There is also a small advantage in integrating their output to maximise selectivity.

Example 4—Stability of the Ciz-1 b-Variant Biomarker

The data support the assertion that CIZ1b is a potent circulating biomarker for lung cancer with significant potential for application in clinical practise. To realise this potential it must be robust enough to withstand variations in sample processing and collection regimes that occur in busy hospitals. Therefore, the stability of the 65-70 kDa cancer-selective CIZ1b species in plasma and whole blood was tested, and compared with the 55 kDa species, using antibody 2B. The data show stability in isolated plasma over at least 6 hours when incubated at 37° C., with gradual decay in both species thereafter. Similarly there was relatively little change during an hour at temperatures up to 50° C., and stability over at least 3 freeze-thaw cycles. Furthermore, when whole blood was left on the bench for up to 24 hours prior to fractionation there was no loss of signal, all of which indicate it to be a robust biomarker suitable for application in a range of clinical settings.

Example 5—Dissociation of the Ciz-1 b-Variant Biomarker Complex

Figures 8A, 8B, 8C, 8D, 8E:
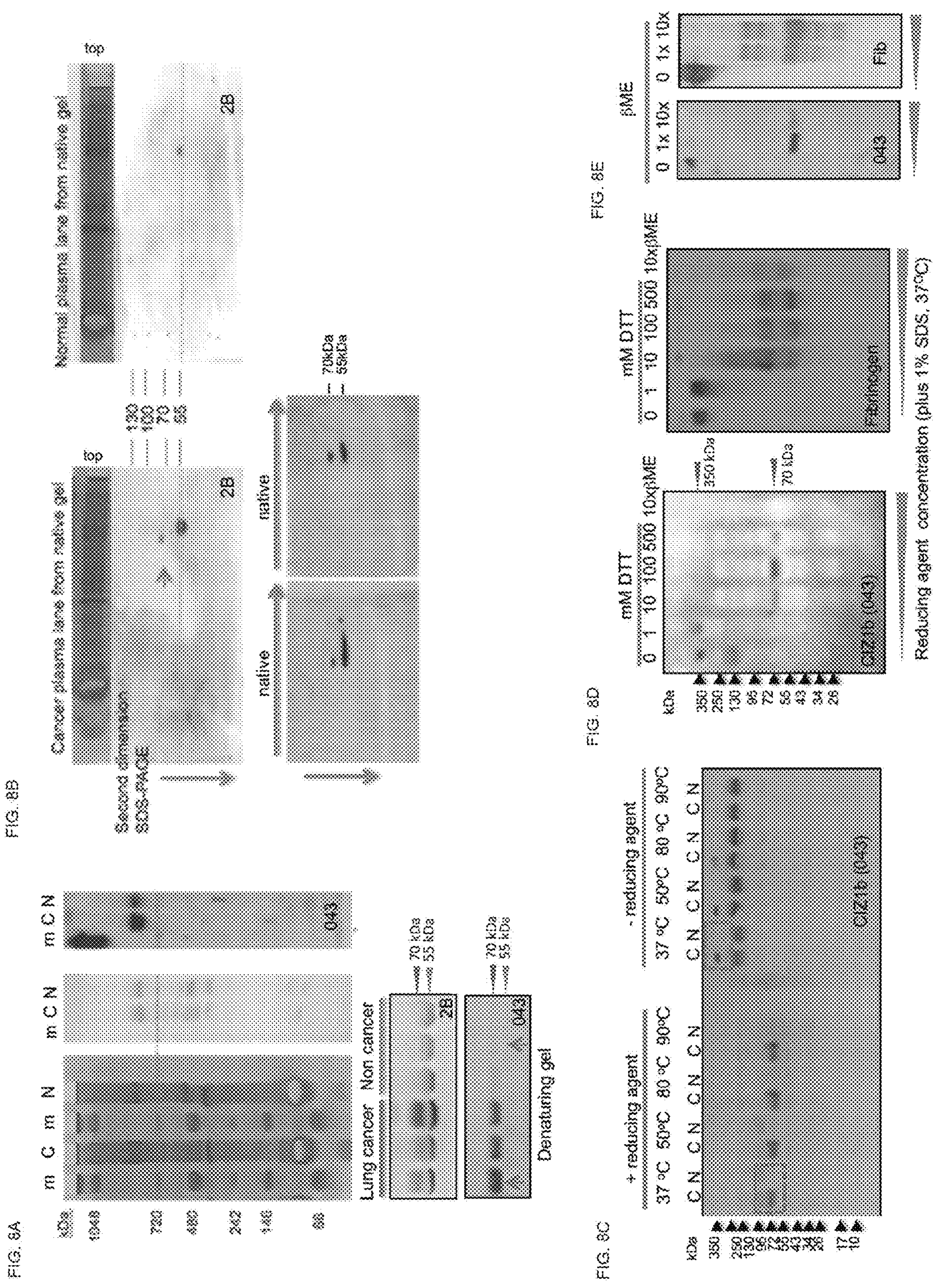
FIGS. 8A-8E—Effect of denaturation on CIZ1b epitope.
Figure 9A:
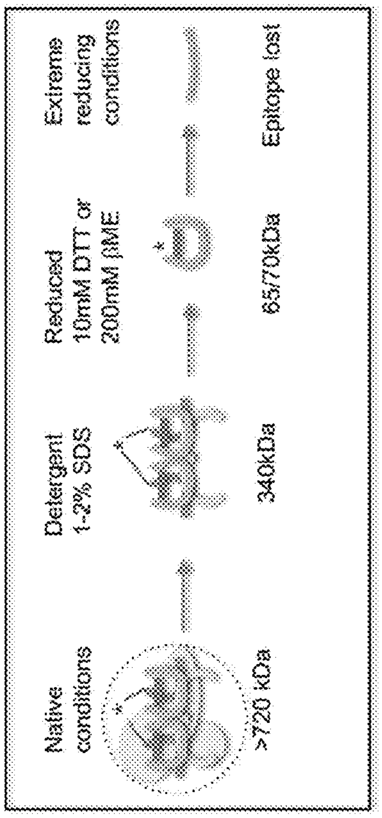
FIGS. 9A-9B—Deconstruction of CIZ1b biomarker and immunoassay design.
Figure 9B:
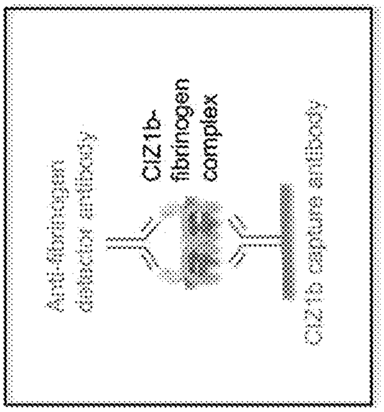

Under native conditions both 2B and 043 detect a complex in excess of 720 kDa that co-migrates with an abundant protein in plasma (FIG. 8A), but there is very little discrimination between cancer and non-cancer plasmas. Upon further separation through a second dimension under denaturing conditions the cancer-specific 65-70 kDa species is revealed and (for 2B) separated from the 55 kDa generic band (FIG. 8B). Thus cancer-specific detection of CIZ1b in a completely native immunoassay format is unlikely even with 043. The three major denaturing influences (heat, SDS, reducing agent) that reveal cancer-specific signal and were evaluated for their effect on the mobility and discrimination of CIZ1b by 043. This showed that 1% SDS shifts the major reactive species from >720 kDa in native gel, to approximately 340 kDa (FIG. 8C, right), revealing cancer-specific signal, as well as an unspecific band at ~200 kDa in both cancer and non-cancer samples. Increasing the incubation temperature has a detrimental effect on the cancer-specific species, with maximum differential achieved at 37° C. Inclusion of reducing agent further shifted the mobility of the cancer specific signal to the expected position of 65-70 kDa (FIG. 8C, left). Notably, higher concentrations of reducing agent resulted in loss of CIZ1b signal (FIGS. 8D-8E). Taken together these data suggest that the 65-70 kDa entity is itself a complex that is resistant to standard SDSPAGE denaturing conditions (10 mM DTT) but not more aggressive treatments (500 mM DTT), and that it is normally present within a higher order complex of 340 kDa, which is itself released by SDS from a still bigger complex in excess of 720 kDa (illustrated in FIG. 9A). In fact, fractionation of plasma to enrich for the exosomal compartment differentially partitioned the 55 kDa species (detected via exon 17) and 65-70 kDa species (detected via 043), with the 65-70 kDa species detected exclusively in the pellet, which is a complex fraction that includes exosomes.

Example 6—Identification of the Ciz-1 b-Variant Biomarker Complex

Figures 10A, 10B, 10C, 10D, 10E:
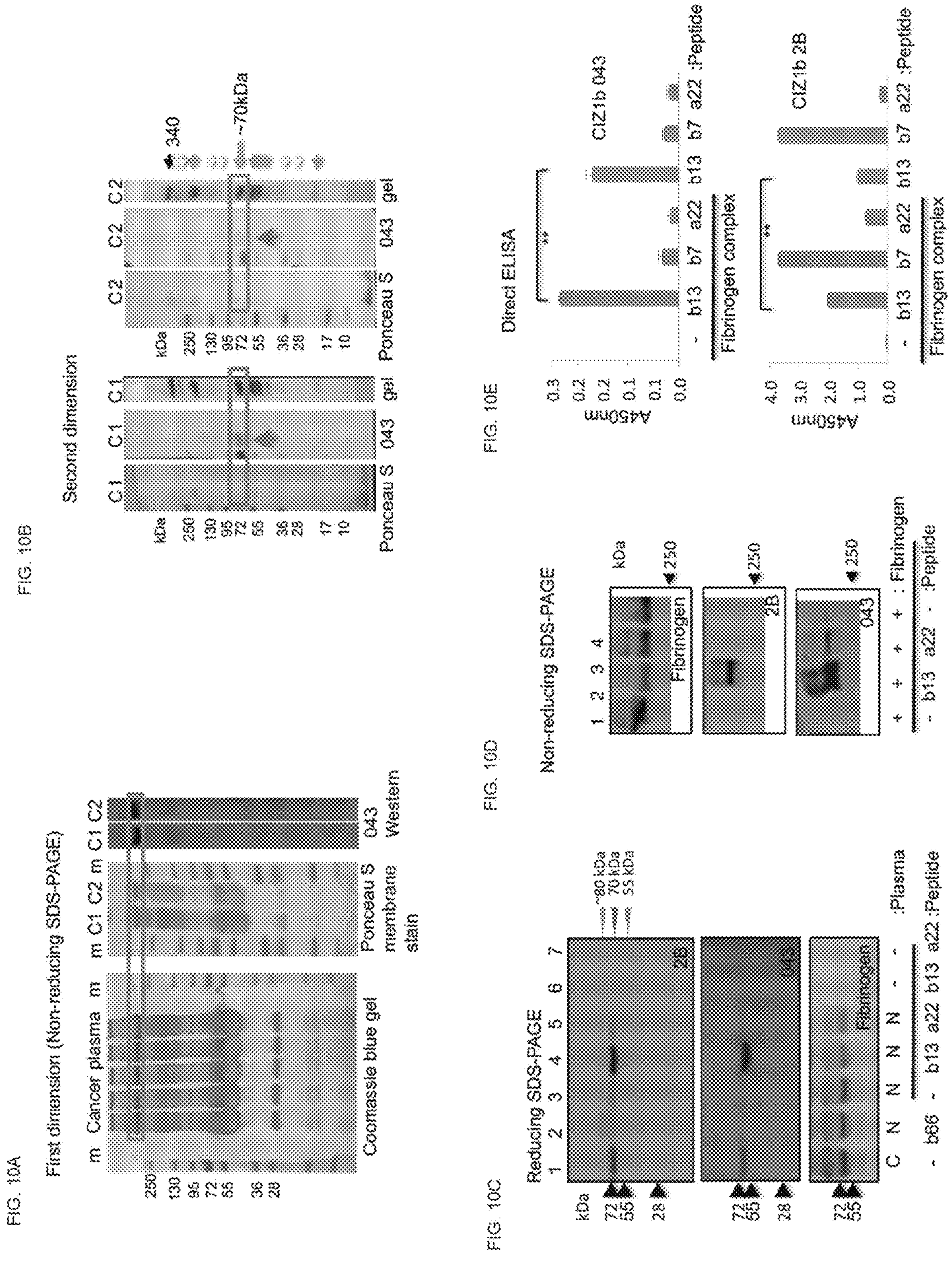
FIGS. 10A-10E—Reconstitution of CIZ1b biomarker from purified components.

These observations enable a two-step gel-purification strategy for the 65-70 kDa CIZ1b band. First, the 340 kDa species was isolated from two independent lung cancer patient plasmas (FIG. 10A), followed by further separation in the presence of reducing agent (FIG. 10B). The 65-70 kDa band corresponding to the cancer-specific western blot signal was excised and digested with either trypsin or Asp-N endoprotease, for identification by mass spectrometry (MS). For both enzymatic digestions and two patients, Mascot database searching returned a single significant identification ($P<0.05$), corresponding to Uniprot P02671; human fibrinogen alpha chain. The endogenous fibrinogen molecule is a hexameric glycoprotein with a pre-cleavage formula mass of 326 kDa and relative mobility of ~340 kDa, comprised of two sets of three different chains (α, β, and γ) of 67, 51 and 45 kDa respectively.

Notably, CIZ1b was not identified in the 65-70 kDa band after digestion with either enzyme. To determine whether a diagnostic CIZ1b fragment could be observed by MS if present, a short synthetic CIZ1b peptide (b13) and long CIZ1b peptide (b66, Table 2) were digested with Asp-N, which generates the diagnostic fragment DEEEIEVRSR (SEQ ID NO: 16) by cutting either side of the CIZ1b exon junction. The peptide was positively identified post digestion of b13 and b66 by MALDI-MS/MS, though at low intensity relative to other peptides in the digest. Further analysis was performed by LC-MS/MS using both data dependent acquisition (DDA) and targeted selection reaction monitoring (SRM), which focused the analysis to cycle through fragmentation of the expected 2+ and 3+ ions of DEEEIEVRSR (SEQ ID NO: 16), excluding all other precursors, to maximize specificity and sensitivity for this analyte. DEEEIEVRSR (SEQ ID NO: 16) was identified in both the DDA and SRM analyses, indicating that the diagnostic peptide is observable by MS when excised from chemically synthesized peptide (SRM chromatogram).

However, when the same peptide was spiked into normal human plasma to reconstitute CIZ1b, the diagnostic DEEEIEVRSR (SEQ ID NO: 16) peptide was not detected in the excised 65-70 kDa band. Lack of identification could reflect: i) secondary modifications that alter the expected mass of the CIZ1b diagnostic peptide or impair enzymatic digestion, ii) the more abundant proteins in the sample, primarily fibrinogen alpha chain, causing ion suppression or iii) absolute abundance falling below the limit of detection for the instrumentation after the losses incurred from the PAGE and digestion steps. It should be noted that the peptide is highly acidic, which is likely to reduce ionization efficiency in positive-mode MS, so that even with SRM a small drop in abundance could fall below the limit of detection. It was concluded if the spiked peptide could not be reliably detected at physiologically relevant levels it was unlikely to be possible to detect endogenous CIZ1b, and so followed alternative approaches were followed.

TABLE 2

| Designation | Sequence |
|---|---|
| Short CIZ1b (b13) | CDEEEIEVRSRDIS-NH2 (SEQ ID NO: 22) |
| Super short CIZ1b (b7) | CELEVRSR-NH2 (SEQ ID NO: 17) |
| Short CIZ1a (a22) | CDEEEIEVEEELCKQVRSRDISR-NH2 (SEQ ID NO: 18) |
| Long CIZ1b peptide (b66) | ELAGQDEDHFITVDAVGCFEGDEEEEEDDEDEEELEVR SRDISREEWKGSETYSPNTAYGVDFLVP (SEQ ID NO: 11) |
| Long CIZ1a peptide (a74) | ELAGQDEDHFITVDAVGCFEGDEEEEEDDEDEEEIEVE EELCKQVRSRDISREEWKGSETYSPNTAYGVDFLVP (SEQ ID NO: 19) |
| GLA3 | CDEEγIEVRSRDIS-NH2 (SEQ ID NO: 14) |
| GLA4 | CDEγEIEVRSRDIS-NH2 (SEQ ID NO: 23) |
| GLA6 | CDγγγLγVRSRDIS-NH2 (SEQ ID NO: 15) |
| Exon 17 | C-TSSGRPPSQPNTQDKTPSK (SEQ ID NO: 20) C-TARPSQPPLPRRSTRLKT (SEQ ID NO: 21) |

The 8 amino-acids spliced out of CIZ1b are underlined in non-alternatively spliced sequences, and the junction created by their absence is indicated in CIZ1b sequences by a V. Where indicated peptides contain an additional N-terminal cysteine residue, and amidation of the C-terminus. Carboxylated glutamic acid residues are indicated by γ.

Example 7—Epitope Reconstitution of the Ciz-1 b-Variant Biomarker Complex

In order to confirm that the 65-70 kDa cancer-specific epitope does indeed contain CIZ1b sequences, an epitope reconstitution strategy was adopted. To achieve this, a pair of synthetic peptides spanning the exon14/15 junction (CIZ1b13, and CIZ1a22 which includes the alternatively spliced intervening sequence, Table 2) were incubated with normal human plasma (FIG. 10C), and the output compared to lung cancer patient plasma. The CIZ1b peptide, but not CIZ1a, generated 043 and 2B-reactive epitope of comparable mobility to the endogenous epitope (65 70 kDa), which is far in excess of the relative molecular mass of free peptide and not present in either of the individual components of the reaction (peptide lanes 6, 7, or plasma lane 3). This suggests that CIZ1b peptide forms an SDS/DTT-resistant complex with a carrier protein in human plasma, recreating the CIZ1b biomarker recognised by 2B and 043. Since no mobility difference between endogenous (cancer plasma lane 1) and reconstituted epitope was detected, the data also imply that the CIZ1b fragment contributing to the 65-70 kDa cancer-specific species is very short, in the order of 10-20 amino acids in length. Furthermore, individual molecules may not necessarily have uniform molecular boundaries, possibly accounting for the often-diffuse nature of the band.

A molar equivalent of the much longer CIZ1b peptide (b66, Table 2) reconstituted reactive epitope less efficiently, and was detectable only by 2B (FIG. 10C lane 2, and at higher concentration). With this peptide the reconstituted signal migrated with greater relative molecular mass, at ~80 kDa, consistent with the increased size of the contributing peptide. Importantly reconstituted CIZ1b epitope, like endogenous epitope, resists standard denaturing SDS-PAGE conditions (10 mM DTT, 2% SDS, 90° C.), but is dissociated by a more aggressive reducing environment. Taken together the data suggest that, in vivo, the cancer specific epitope is composed of a relatively short fragment of CIZ1 encompassing the exon14b/15 junction, mounted on fibrinogen alpha chain, which itself makes up most of the mass of the 65-70 kDa species. To further confirm this, epitope reconstitution experiments were performed with purified human fibrinogen (FIG. 10D). For both antibodies, reactive epitope was generated at the mobility of fibrinogen complex (340 kDa in non-reducing gels) and the specificity of the signal was confirmed by lack of reactivity with equivalent CIZ1a peptide. Direct ELISA using human fibrinogen complexed with molar equivalents of CIZ1a and CIZ1b peptides (FIG. 10E), confirmed i) the specificity of epitope reconstitution with peptide b13 over a22, ii) negligible signal with fibrinogen alone, and iii) greater reactivity when peptide is mounted on fibrinogen. Moreover, inclusion of the very short CIZ1b peptide b7 (Table 2) revealed differences between 2B and 043; 2B recognises b7 while 043 does not in a manner that is unrelated to the presence of fibrinogen. The existence of CIZ1b epitope in a complex with fibrinogen is consistent with the earlier observations that the biomarker is depleted from serum samples isolated from clotted blood (FIG. 7C).

Example 8—CIZ1b Immunoassay

Based on knowledge of the composition of CIZ1b biomarker, a sandwich immunoassay format capable of quantitative detection in partially denatured plasma was designed. Antigen capture with CIZ1b antibody 043 from 5 ul of plasma and detection via fibrinogen alpha chain, generated a cancer-specific signal. Specifically, results by western blot with 043 generated ROC AUC 0.823 (P=0.0002) and by ELISA with 043/anti-fibrinogen of 0.830 (P=0.0007, FIGS. 11A-11B). Thus, the two methods generate very similar outcomes, and the data is significantly correlated.

Figures 11A, 11B, 11C, 11D, 11E, 11F:
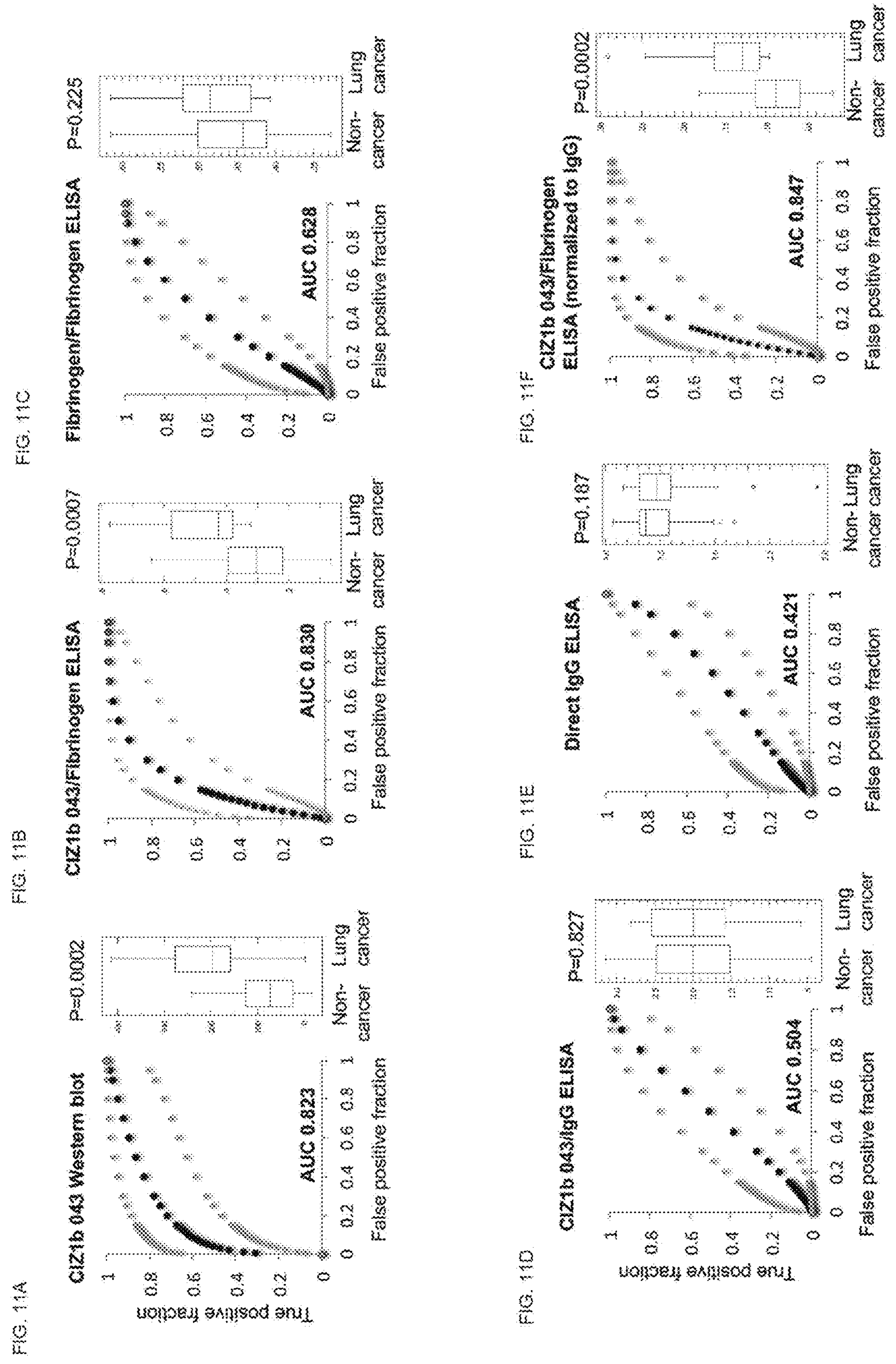
FIGS. 11A-11F—Immunoassay validation using lung cancer plasma and controls (n=39 non-cancer, 13 lung cancer).

This data set, which represents patients with a wide range of conditions presenting at York Hospital respiratory medicine clinics, was also used to evaluate the contribution of the CIZ1 b component of the assay, since fibrinogen alone has been reported to have some potential as a biomarker for lung cancer (Allin et al.; 2016; Int J Cancer 139(7):1493-1500). Quantitative detection of fibrinogen in the linear range returned some discriminatory capability across this set, though relatively poor ROC AUC of 0.628 (p=0.225). This is consistent with western blot evaluation of fibrinogen, which indicated little difference between lung cancer patients and those without malignant disease. Thus capture of CIZ1b is the element that contributes the majority of the cancer selectivity to this assay. The specificity of the configuration was further tested by analysing the sample set after capture with 043, but substituting anti-fibrinogen detector antibody with anti-human IgG (FIG. 11D). Results indicate no discrimination between patients and control plasmas, confirming that anti-fibrinogen is an informative detector reagent that specifically detects a cancer-selective complex retrieved via CIZ1b. Finally, measurement of total IgG levels across set B by direct ELISA (FIG. 11E) was used to normalize the output generated by 043/fibrinogen, leading to a marginal improvement in discrimination and ROC AUC 0.845 (p=0.0002, FIG. 11F).

The CIZ1b-fibrinogen alpha chain complex ELISA was performed as a sandwich ELISA after partial denaturation of 5 ul of plasma in 100 ul of 0.5% tween20, 1% SDS in PBS, supplemented with 0.5 mM PMSF (protease inhibitors) and incubation at 20° C. for 30 mins with repeated vortexing. Plates (Nunc Maxisorb 442404) were coated with 1 ug of 043 CIZ1b pAb protein A fraction, overnight at 4° C. in 100 ul of 50 mM carbonate pH 9.6, then blocked for two hours at room temperature with 300 ul of filtered 1% BSA in PBS. After three washes in 300 ul of 0.05% tween20 in PBS, analyte was added for 2 hours at room temperature with gentle shaking. After fives washes, captured complex was detected with sheep anti-fibrinogen pAb (AF4786 R&D systems) followed by anti-sheep HRP (Jackson ImmunoResearch 213-032-177), and results developed using 100 ul Sure Blue (KPL 520001) with detection at A450 nm using a FLUOstar OPTIMA plate reader (BMG Labtech). For measurement of fibrinogen capture antibody was chicken IgY (1 ug/well, Genway 15-288-22856), and analyte concentration was reduced five orders of magnitude by serial dilution. For measurement of human IgG in direct ELISA, 0.5 ul of plasma was coated directly onto plates in 100 ul of 50 mM carbonate buffer pH 9.6, blocked, washed and detected with anti-IgG (Jackson Immuno Research 709-035-149). For direct ELISA of synthetic analyte, 0.5 ug purified fibrinogen (Sigma F3879) complexed with 100 pmol peptide was coated onto plates in 100 ul of 50 mM carbonate pH 9.6 as above, probe with 043 or 2B and detected with anti-rabbit HRP (Jackson ImmunoResearch).

Thus, the present sandwich ELISA format is suitable for high-throughput application on hospital platforms, and can reliably quantify circulating CIZ1b biomarker, and can be used to identify patients with early stage lung cancer.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

The invention claimed is:

1. A method of detecting lung cancer in a human subject comprising detecting a fibrinogen/Ciz1 b-variant peptide complex in the subject, wherein the presence of the Ciz1 b-variant peptide comprising the sequence of SEQ ID NO: 2 indicates that the human subject has lung cancer, the method comprising the steps of:

a) obtaining a blood or plasma sample from the human subject, and b) capturing or detecting the fibrinogen/Ciz1 b-variant peptide complex from the blood or plasma sample using an anti-fibrinogen antibody or an antigen binding fragment thereof.

2. The method according to claim 1, wherein the step of detecting the fibrinogen/Ciz1 b-variant peptide complex employs antibody-based arrays, enzyme linked immunosorbent assays (ELISA), radioimmuno-assay (RIA), western blotting, aptamers, or mass spectrometry.

* * * * *

SEQUENCE LISTING

```
Sequence total quantity: 1065
SEQ ID NO: 1            moltype = AA  length = 890
FEATURE                 Location/Qualifiers
REGION                  1..890
                        note = Full Ciz1 b-variant sequence
source                  1..890
                        mol_type = protein
                        organism = synthetic construct
SEQUENCE: 1
MFSQQQQQQL QQQQQQLQQL QQQQLQQQQL QQQQLLQLQQ LLQQSPPQAP LPMAVSRGLP  60
PQQPQQPLLN LQGTNSASLL NGSMLQRALL LQQLQGLDQF AMPPATYDTA GLTMPTATLG  120
NLRGYGMASP GLAAPSLTPP QLATPNLQQF FPQATRQSLL GPPPVGVPMN PSQFNLSGRN  180
PQKQARTSSS TTPNRKDSSS QTMPVEDKSD PPEGSEEAAE PRMDTPEDQD LPPCPEDIAK  240
EKRTPAPEPE PCEASELPAK RLRSSEEPTE KEPPGQLQVK AQPQARMTVP KQTQTPDLLP  300
EALEAQVLPR FQPRVLQVQA QVQSQTQPRI PSTDTQVQPK LQKQAQTQTS PEHLVLQQKQ  360
VQPQLQQEAE PQKQVQPQVQ PQAHSQGPRQ VQLQQEAEPL KQVQPQVQPQ AHSQPPRQVQ  420
LQLQKQVQTQ TYPQVHTQAQ PSVQPQEHPP AQVSVQPPEQ THEQPHTQPQ VSLLAPEQTP  480
VVVHVCGLEM PPDAVEAGGG MEKTLPEPVG TQVSMEEIQN ESACGLDVGE CENRAREMPG  540
VWGAGGSLKV TILQSSDSRA FSTVPLTPVP RPSDSVSSTP AATSTPSKQA LQFFCYICKA  600
SCSSQQEFQD HMSEPQHQQR LGEIQHMSQA CLLSLLPVPR DVLETEDEEP PPRRWCNTCQ  660
LYYMGDLIQH RRTQDHKIAK QSLRPFCTVC NRYFKTPRKF VEHVKSQGHK DKAKELKSLE  720
KEIAGQDEDH FITVDAVGCF EGDEEEEEDD EDEEEIEVRS RDISREEWKG SETYSPNTAY  780
GVDFLVPVMG YICRICHKFY HSNSGAQLSH CKSLGHFENL QKYKAAKNPS PTTRPVSRRC  840
AINARNALTA LFTSSGRPPS QPNTQDKTPS KVTARPSQPP LPRRSTRLKT             890

SEQ ID NO: 2            moltype = AA  length = 13
FEATURE                 Location/Qualifiers
REGION                  1..13
                        note = sequence comprising the exon 14b/exon 15 amino acid
                         junction sequence
source                  1..13
                        mol_type = protein
                        organism = synthetic construct
SEQUENCE: 2
DEEEIEVRSR DIS                                                     13

SEQ ID NO: 3            moltype = RNA  length = 126
FEATURE                 Location/Qualifiers
misc_feature            1..126
                        note = exon 14b nucleotide sequence
source                  1..126
                        mol_type = other RNA
                        organism = synthetic construct
SEQUENCE: 3
ctgaagtcgc ttgagaaaga aattgctggc caagatgagg agcacttcat tacagtggac  60
gctgtgggtt gcttcgaggg tgatgaagaa gaggaagagg atgatgagga tgaagaagag  120
```

```
atcgag                                                                126

SEQ ID NO: 4          moltype = RNA  length = 150
FEATURE               Location/Qualifiers
misc_feature          1..150
                      note = exon 14a nucleotide sequence
source                1..150
                      mol_type = other RNA
                      organism = synthetic construct
SEQUENCE: 4
ctgaagtcgc ttgagaaaga aattgctggc caagatgagg agcacttcat tacagtggac  60
gctgtgggtt gcttcgaggg tgatgaagaa gaggaagagg atgatgagga tgaagaagag  120
atcgaggttg aggaggaact ctgcaagcag                                      150

SEQ ID NO: 5          moltype = AA  length = 42
FEATURE               Location/Qualifiers
REGION                1..42
                      note = exon 14b amino acid sequence
source                1..42
                      mol_type = protein
                      organism = synthetic construct
SEQUENCE: 5
LKSLEKEIAG QDEDHFITVD AVGCFEGDEE EEEDDEDEEE IE                        42

SEQ ID NO: 6          moltype = AA  length = 50
FEATURE               Location/Qualifiers
REGION                1..50
                      note = exon 14a amino acid sequence
source                1..50
                      mol_type = protein
                      organism = synthetic construct
SEQUENCE: 6
LKSLEKEIAG QDEDHFITVD AVGCFEGDEE EEEDDEDEEE IEVEEELCKQ                50

SEQ ID NO: 7          moltype = AA  length = 23
FEATURE               Location/Qualifiers
REGION                1..23
                      note = exon 15 amino acid sequence
source                1..23
                      mol_type = protein
                      organism = synthetic construct
SEQUENCE: 7
VRSRDISREE WKGSETYSPN TAY                                             23

SEQ ID NO: 8          moltype = AA  length = 898
FEATURE               Location/Qualifiers
source                1..898
                      mol_type = protein
                      organism = Homo sapiens
SEQUENCE: 8
MFSQQQQQQL QQQQQQLQQL QQQQLQQQQL QQQQLLQLQQ LLQQSPPQAP LPMAVSRGLP  60
PQQPQQPLLN LQGTNSASLL NGSMLQRALL LQQLQGLDQF AMPPATYDTA GLTMPTATLG  120
NLRGYGMASP GLAAPSLTPP QLATPNLQQF FPQATRQSLL GPPPVGVPMN PSQFNLSGRN  180
PQKQARTSSS TTPNRKDSSS QTMPVEDKSD PPEGSEEAAE PRMDTPEDQD LPPCPEDIAK  240
EKRTPAPEPE PCEASELPAK RLRSSEEPTE KEPPGQLQVK AQPQARMTVP KQTQTPDLLP  300
EALEAQVLPR FQPRVLQVQA QVQSQTQPRI PSTDTQVQPK LQKQAQTQTS PEHLVLQQKQ  360
VQPQLQQEAE PQKQVQPQVQ PQAHSQGPRQ VQLQQEAEPL KQVQPQVQPQ AHSQPPRQVQ  420
LQLQKQVQTQ TYPQVHTQAQ PSVQPQEHPP AQVSVQPPEQ THEQPHTQPQ VSLLAPEQTP  480
VVVHVCGLEM PPDAVEAGGG MEKTLPEPVG TQVSMEEIQN ESACGLDVGE CENRAREMPG  540
VWGAGGSLKV TILQSSDSRA FSTVPLTPVP RPSDSVSSTP AATSTPSKQA LQFFCYICKA  600
SCSSQQEFQD HMSEPQHQQR LGEIQHMSQA CLLSLLPVPR DVLETEDEEP PPRRWCNTCQ  660
LYYMGDLIQH RRTQDHKIAK QSLRPFCTVC NRYFKTPRKF VEHVKSQGHK DKAKELKSLE  720
KEIAGQDEDH FITVDAVGCF EGDEEEEEDD EDEEEIEVEE ELCKQVRSRD ISREEWKGSE  780
TYSPNTAYGV DFLVPVMGYI CRICHKFYHS NSGAQLSHCK SLGHFENLQK YKAAKNPSPT  840
TRPVSRRCAI NARNALTALF TSSGRPPSQP NTQDKTPSKV TARPSQPPLP RRSTRLKT    898

SEQ ID NO: 9          moltype = AA  length = 21
FEATURE               Location/Qualifiers
REGION                1..21
                      note = sequence comprising the exon 14a/exon 15 splice
                       junction
source                1..21
                      mol_type = protein
                      organism = synthetic construct
SEQUENCE: 9
DEEEIEVEEE LCKQVRSRDI S                                               21

SEQ ID NO: 10         moltype = AA  length = 8
FEATURE               Location/Qualifiers
```

-continued

```
REGION                  1..8
                        note = excluded sequence from Ciz1 exon 14/exon 15 junction
                         which specifies a Ciz1 b-variant
source                  1..8
                        mol_type = protein
                        organism = synthetic construct
SEQUENCE: 10
VEEELCKQ                                                                    8

SEQ ID NO: 11           moltype = AA  length = 66
FEATURE                 Location/Qualifiers
REGION                  1..66
                        note = Ciz1 b-variant peptide
source                  1..66
                        mol_type = protein
                        organism = synthetic construct
SEQUENCE: 11
EIAGQDEDHF ITVDAVGCFE GDEEEEEDDE DEEEIEVRSR DISREEWKGS ETYSPNTAYG  60
VDFLVP                                                             66

SEQ ID NO: 12           moltype = AA  length = 65
FEATURE                 Location/Qualifiers
REGION                  1..65
                        note = long Ciz1 b-variant peptide
source                  1..65
                        mol_type = protein
                        organism = synthetic construct
SEQUENCE: 12
EIAGQDEDHF ITVDAVGCFE GDEEEEEDDE DEEEIEVRSR DISREEWKGS ETYSPNTAYG  60
VDFLV                                                              65

SEQ ID NO: 13           moltype = AA  length = 72
FEATURE                 Location/Qualifiers
REGION                  1..72
                        note = long Ciz1 exon 14a peptide
source                  1..72
                        mol_type = protein
                        organism = synthetic construct
SEQUENCE: 13
EIAGQDEDHF ITVDAVGCFE GDEEEEEDDE DEEEIEVEEE LCKQRSRDIS REEWKGSETY  60
SPNTAYGVDF LV                                                      72

SEQ ID NO: 14           moltype = AA  length = 14
FEATURE                 Location/Qualifiers
REGION                  1..14
                        note = GLA3 sequence
MOD_RES                 5
                        note = carboxylated glutamic acid
MOD_RES                 14
                        note = AMIDATION
source                  1..14
                        mol_type = protein
                        organism = synthetic construct
SEQUENCE: 14
CDEEEIEVRS RDIS                                                    14

SEQ ID NO: 15           moltype = AA  length = 14
FEATURE                 Location/Qualifiers
REGION                  1..14
                        note = GLA6 sequence
MOD_RES                 3..5
                        note = carboxylated glutamic acid
MOD_RES                 7
                        note = carboxylated glutamic acid
MOD_RES                 14
                        note = AMIDATION
source                  1..14
                        mol_type = protein
                        organism = synthetic construct
SEQUENCE: 15
CDEEEIEVRS RDIS                                                    14

SEQ ID NO: 16           moltype = AA  length = 10
FEATURE                 Location/Qualifiers
REGION                  1..10
                        note = diagnostic fragment of CIZ1b
source                  1..10
                        mol_type = protein
                        organism = synthetic construct
```

```
SEQUENCE: 16
DEEEIEVRSR                                                  10

SEQ ID NO: 17           moltype = AA  length = 8
FEATURE                 Location/Qualifiers
REGION                  1..8
                        note = super short CIZ1b peptide (b7)
MOD_RES                 8
                        note = AMIDATION
source                  1..8
                        mol_type = protein
                        organism = synthetic construct
SEQUENCE: 17
CEIEVRSR                                                    8

SEQ ID NO: 18           moltype = AA  length = 23
FEATURE                 Location/Qualifiers
REGION                  1..23
                        note = short CIZ1a peptide (a22)
MOD_RES                 23
                        note = AMIDATION
source                  1..23
                        mol_type = protein
                        organism = synthetic construct
SEQUENCE: 18
CDEEEIEVEE ELCKQVRSRD ISR                                   23

SEQ ID NO: 19           moltype = AA  length = 74
FEATURE                 Location/Qualifiers
REGION                  1..74
                        note = long CIZ1a peptide (a74)
source                  1..74
                        mol_type = protein
                        organism = synthetic construct
SEQUENCE: 19
EIAGQDEDHF ITVDAVGCFE GDEEEEEDDE DEEEIEVEEE LCKQVRSRDI SREEWKGSET  60
YSPNTAYGVD FLVP                                             74

SEQ ID NO: 20           moltype = AA  length = 20
FEATURE                 Location/Qualifiers
REGION                  1..20
                        note = exon 17 peptide sequence
source                  1..20
                        mol_type = protein
                        organism = synthetic construct
SEQUENCE: 20
CTSSGRPPSQ PNTQDKTPSK                                       20

SEQ ID NO: 21           moltype = AA  length = 19
FEATURE                 Location/Qualifiers
REGION                  1..19
                        note = exon 17 peptide sequence
source                  1..19
                        mol_type = protein
                        organism = synthetic construct
SEQUENCE: 21
CTARPSQPPL PRRSTRLKT                                        19

SEQ ID NO: 22           moltype = AA  length = 14
FEATURE                 Location/Qualifiers
REGION                  1..14
                        note = short CIZ1b peptide (b13)
MOD_RES                 14
                        note = AMIDATION
source                  1..14
                        mol_type = protein
                        organism = synthetic construct
SEQUENCE: 22
CDEEEIEVRS RDIS                                             14

SEQ ID NO: 23           moltype = AA  length = 14
FEATURE                 Location/Qualifiers
REGION                  1..14
                        note = GLA4 peptide
MOD_RES                 4
                        note = carboxylated glutamic acid
MOD_RES                 14
                        note = AMIDATION
source                  1..14
```

```
                        mol_type = protein
                        organism = synthetic construct
SEQUENCE: 23
CDEEEIEVRS RDIS                                                14

SEQ ID NO: 24           moltype = AA  length = 38
FEATURE                 Location/Qualifiers
REGION                  1..38
                        note = Ciz1 b-variant peptide comprising an exon 14b/exon
                         15 junction
source                  1..38
                        mol_type = protein
                        organism = synthetic construct
SEQUENCE: 24
EIAGQDEDHF ITVDAVGCFE GDEEEEEDDE DEEEIEVR                      38

SEQ ID NO: 25           moltype = AA  length = 37
FEATURE                 Location/Qualifiers
REGION                  1..37
                        note = Ciz1 b-variant peptide comprising an exon 14b/exon
                         15 junction
source                  1..37
                        mol_type = protein
                        organism = synthetic construct
SEQUENCE: 25
IAGQDEDHFI TVDAVGCFEG DEEEEEDDED EEEIEVR                       37

SEQ ID NO: 26           moltype = AA  length = 36
FEATURE                 Location/Qualifiers
REGION                  1..36
                        note = Ciz1 b-variant peptide comprising an exon 14b/exon
                         15 junction
source                  1..36
                        mol_type = protein
                        organism = synthetic construct
SEQUENCE: 26
AGQDEDHFIT VDAVGCFEGD EEEEEDDEDE EEIEVR                        36

SEQ ID NO: 27           moltype = AA  length = 35
FEATURE                 Location/Qualifiers
REGION                  1..35
                        note = Ciz1 b-variant peptide comprising an exon 14b/exon
                         15 junction
source                  1..35
                        mol_type = protein
                        organism = synthetic construct
SEQUENCE: 27
GQDEDHFITV DAVGCFEGDE EEEEDDEDEE EIEVR                         35

SEQ ID NO: 28           moltype = AA  length = 34
FEATURE                 Location/Qualifiers
REGION                  1..34
                        note = Ciz1 b-variant peptide comprising an exon 14b/exon
                         15 junction
source                  1..34
                        mol_type = protein
                        organism = synthetic construct
SEQUENCE: 28
QDEDHFITVD AVGCFEGDEE EEEDDEDEEE IEVR                          34

SEQ ID NO: 29           moltype = AA  length = 33
FEATURE                 Location/Qualifiers
REGION                  1..33
                        note = Ciz1 b-variant peptide comprising an exon 14b/exon
                         15 junction
source                  1..33
                        mol_type = protein
                        organism = synthetic construct
SEQUENCE: 29
DEDHFITVDA VGCFEGDEEE EEDDEDEEEI EVR                           33

SEQ ID NO: 30           moltype = AA  length = 32
FEATURE                 Location/Qualifiers
REGION                  1..32
                        note = Ciz1 b-variant peptide comprising an exon 14b/exon
                         15 junction
source                  1..32
                        mol_type = protein
                        organism = synthetic construct
```

```
SEQUENCE: 30
EDHFITVDAV GCFEGDEEEE EDDEDEEEIE VR                              32

SEQ ID NO: 31           moltype = AA  length = 31
FEATURE                 Location/Qualifiers
REGION                  1..31
                        note = Ciz1 b-variant peptide comprising an exon 14b/exon
                         15 junction
source                  1..31
                        mol_type = protein
                        organism = synthetic construct
SEQUENCE: 31
DHFITVDAVG CFEGDEEEEE DDEDEEEIEV R                               31

SEQ ID NO: 32           moltype = AA  length = 30
FEATURE                 Location/Qualifiers
REGION                  1..30
                        note = Ciz1 b-variant peptide comprising an exon 14b/exon
                         15 junction
source                  1..30
                        mol_type = protein
                        organism = synthetic construct
SEQUENCE: 32
HFITVDAVGC FEGDEEEEED DEDEEEIEVR                                 30

SEQ ID NO: 33           moltype = AA  length = 29
FEATURE                 Location/Qualifiers
REGION                  1..29
                        note = Ciz1 b-variant peptide comprising an exon 14b/exon
                         15 junction
source                  1..29
                        mol_type = protein
                        organism = synthetic construct
SEQUENCE: 33
FITVDAVGCF EGDEEEEEDD EDEEEIEVR                                  29

SEQ ID NO: 34           moltype = AA  length = 28
FEATURE                 Location/Qualifiers
REGION                  1..28
                        note = Ciz1 b-variant peptide comprising an exon 14b/exon
                         15 junction
source                  1..28
                        mol_type = protein
                        organism = synthetic construct
SEQUENCE: 34
ITVDAVGCFE GDEEEEEDDE DEEEIEVR                                   28

SEQ ID NO: 35           moltype = AA  length = 27
FEATURE                 Location/Qualifiers
REGION                  1..27
                        note = Ciz1 b-variant peptide comprising an exon 14b/exon
                         15 junction
source                  1..27
                        mol_type = protein
                        organism = synthetic construct
SEQUENCE: 35
TVDAVGCFEG DEEEEEDDED EEEIEVR                                    27

SEQ ID NO: 36           moltype = AA  length = 26
FEATURE                 Location/Qualifiers
REGION                  1..26
                        note = Ciz1 b-variant peptide comprising an exon 14b/exon
                         15 junction
source                  1..26
                        mol_type = protein
                        organism = synthetic construct
SEQUENCE: 36
VDAVGCFEGD EEEEEDDEDE EEIEVR                                     26

SEQ ID NO: 37           moltype = AA  length = 25
FEATURE                 Location/Qualifiers
REGION                  1..25
                        note = Ciz1 b-variant peptide comprising an exon 14b/exon
                         15 junction
source                  1..25
                        mol_type = protein
                        organism = synthetic construct
SEQUENCE: 37
DAVGCFEGDE EEEEDDEDEE EIEVR                                      25
```

```
SEQ ID NO: 38          moltype = AA  length = 24
FEATURE                Location/Qualifiers
REGION                 1..24
                       note = Ciz1 b-variant peptide comprising an exon 14b/exon
                        15 junction
source                 1..24
                       mol_type = protein
                       organism = synthetic construct
SEQUENCE: 38
AVGCFEGDEE EEEDDEDEEE IEVR                                          24

SEQ ID NO: 39          moltype = AA  length = 23
FEATURE                Location/Qualifiers
REGION                 1..23
                       note = Ciz1 b-variant peptide comprising an exon 14b/exon
                        15 junction
source                 1..23
                       mol_type = protein
                       organism = synthetic construct
SEQUENCE: 39
VGCFEGDEEE EEDDEDEEEI EVR                                           23

SEQ ID NO: 40          moltype = AA  length = 22
FEATURE                Location/Qualifiers
REGION                 1..22
                       note = Ciz1 b-variant peptide comprising an exon 14b/exon
                        15 junction
source                 1..22
                       mol_type = protein
                       organism = synthetic construct
SEQUENCE: 40
GCFEGDEEEE EDDEDEEEIE VR                                            22

SEQ ID NO: 41          moltype = AA  length = 21
FEATURE                Location/Qualifiers
REGION                 1..21
                       note = Ciz1 b-variant peptide comprising an exon 14b/exon
                        15 junction
source                 1..21
                       mol_type = protein
                       organism = synthetic construct
SEQUENCE: 41
CFEGDEEEEE DDEDEEEIEV R                                             21

SEQ ID NO: 42          moltype = AA  length = 20
FEATURE                Location/Qualifiers
REGION                 1..20
                       note = Ciz1 b-variant peptide comprising an exon 14b/exon
                        15 junction
source                 1..20
                       mol_type = protein
                       organism = synthetic construct
SEQUENCE: 42
FEGDEEEEED DEDEEEIEVR                                               20

SEQ ID NO: 43          moltype = AA  length = 19
FEATURE                Location/Qualifiers
REGION                 1..19
                       note = Ciz1 b-variant peptide comprising an exon 14b/exon
                        15 junction
source                 1..19
                       mol_type = protein
                       organism = synthetic construct
SEQUENCE: 43
EGDEEEEEDD EDEEEIEVR                                                19

SEQ ID NO: 44          moltype = AA  length = 18
FEATURE                Location/Qualifiers
REGION                 1..18
                       note = Ciz1 b-variant peptide comprising an exon 14b/exon
                        15 junction
source                 1..18
                       mol_type = protein
                       organism = synthetic construct
SEQUENCE: 44
GDEEEEEDDE DEEEIEVR                                                 18

SEQ ID NO: 45          moltype = AA  length = 17
```

```
FEATURE                Location/Qualifiers
REGION                 1..17
                       note = Ciz1 b-variant peptide comprising an exon 14b/exon
                        15 junction
source                 1..17
                       mol_type = protein
                       organism = synthetic construct
SEQUENCE: 45
DEEEEEDDED EEEIEVR                                                  17

SEQ ID NO: 46          moltype = AA  length = 16
FEATURE                Location/Qualifiers
REGION                 1..16
                       note = Ciz1 b-variant peptide comprising an exon 14b/exon
                        15 junction
source                 1..16
                       mol_type = protein
                       organism = synthetic construct
SEQUENCE: 46
EEEEEDDEDE EEIEVR                                                   16

SEQ ID NO: 47          moltype = AA  length = 15
FEATURE                Location/Qualifiers
REGION                 1..15
                       note = Ciz1 b-variant peptide comprising an exon 14b/exon
                        15 junction
source                 1..15
                       mol_type = protein
                       organism = synthetic construct
SEQUENCE: 47
EEEEDDEDEE EIEVR                                                    15

SEQ ID NO: 48          moltype = AA  length = 14
FEATURE                Location/Qualifiers
REGION                 1..14
                       note = Ciz1 b-variant peptide comprising an exon 14b/exon
                        15 junction
source                 1..14
                       mol_type = protein
                       organism = synthetic construct
SEQUENCE: 48
EEEDDEDEEE IEVR                                                     14

SEQ ID NO: 49          moltype = AA  length = 13
FEATURE                Location/Qualifiers
REGION                 1..13
                       note = Ciz1 b-variant peptide comprising an exon 14b/exon
                        15 junction
source                 1..13
                       mol_type = protein
                       organism = synthetic construct
SEQUENCE: 49
EEDDEDEEEI EVR                                                      13

SEQ ID NO: 50          moltype = AA  length = 12
FEATURE                Location/Qualifiers
REGION                 1..12
                       note = Ciz1 b-variant peptide comprising an exon 14b/exon
                        15 junction
source                 1..12
                       mol_type = protein
                       organism = synthetic construct
SEQUENCE: 50
EDDEDEEEIE VR                                                       12

SEQ ID NO: 51          moltype = AA  length = 11
FEATURE                Location/Qualifiers
REGION                 1..11
                       note = Ciz1 b-variant peptide comprising an exon 14b/exon
                        15 junction
source                 1..11
                       mol_type = protein
                       organism = synthetic construct
SEQUENCE: 51
DDEDEEEIEV R                                                        11

SEQ ID NO: 52          moltype = AA  length = 10
FEATURE                Location/Qualifiers
REGION                 1..10
```

```
                        note = Ciz1 b-variant peptide comprising an exon 14b/exon
                         15 junction
source                  1..10
                        mol_type = protein
                        organism = synthetic construct
SEQUENCE: 52
DEDEEEIEVR                                                          10

SEQ ID NO: 53           moltype = AA  length = 9
FEATURE                 Location/Qualifiers
REGION                  1..9
                        note = Ciz1 b-variant peptide comprising an exon 14b/exon
                         15 junction
source                  1..9
                        mol_type = protein
                        organism = synthetic construct
SEQUENCE: 53
EDEEEIEVR                                                           9

SEQ ID NO: 54           moltype = AA  length = 8
FEATURE                 Location/Qualifiers
REGION                  1..8
                        note = Ciz1 b-variant peptide comprising an exon 14b/exon
                         15 junction
source                  1..8
                        mol_type = protein
                        organism = synthetic construct
SEQUENCE: 54
DEEEIEVR                                                            8

SEQ ID NO: 55           moltype = AA  length = 7
FEATURE                 Location/Qualifiers
REGION                  1..7
                        note = Ciz1 b-variant peptide comprising an exon 14b/exon
                         15 junction
source                  1..7
                        mol_type = protein
                        organism = synthetic construct
SEQUENCE: 55
EEEIEVR                                                             7

SEQ ID NO: 56           moltype = AA  length = 6
FEATURE                 Location/Qualifiers
REGION                  1..6
                        note = Ciz1 b-variant peptide comprising an exon 14b/exon
                         15 junction
source                  1..6
                        mol_type = protein
                        organism = synthetic construct
SEQUENCE: 56
EEIEVR                                                              6

SEQ ID NO: 57           moltype = AA  length = 5
FEATURE                 Location/Qualifiers
REGION                  1..5
                        note = Ciz1 b-variant peptide comprising an exon 14b/exon
                         15 junction
source                  1..5
                        mol_type = protein
                        organism = synthetic construct
SEQUENCE: 57
EIEVR                                                               5

SEQ ID NO: 58           moltype = AA  length = 4
FEATURE                 Location/Qualifiers
REGION                  1..4
                        note = Ciz1 b-variant peptide comprising an exon 14b/exon
                         15 junction
source                  1..4
                        mol_type = protein
                        organism = synthetic construct
SEQUENCE: 58
IEVR                                                                4

SEQ ID NO: 59           moltype = AA  length = 39
FEATURE                 Location/Qualifiers
REGION                  1..39
                        note = Ciz1 b-variant peptide comprising an exon 14b/exon
                         15 junction
```

```
source                  1..39
                        mol_type = protein
                        organism = synthetic construct
SEQUENCE: 59
EIAGQDEDHF ITVDAVGCFE GDEEEEEDDE DEEEIEVRS                          39

SEQ ID NO: 60           moltype = AA  length = 38
FEATURE                 Location/Qualifiers
REGION                  1..38
                        note = Ciz1 b-variant peptide comprising an exon 14b/exon
                         15 junction
source                  1..38
                        mol_type = protein
                        organism = synthetic construct
SEQUENCE: 60
IAGQDEDHFI TVDAVGCFEG DEEEEEDDED EEEIEVRS                           38

SEQ ID NO: 61           moltype = AA  length = 37
FEATURE                 Location/Qualifiers
REGION                  1..37
                        note = Ciz1 b-variant peptide comprising an exon 14b/exon
                         15 junction
source                  1..37
                        mol_type = protein
                        organism = synthetic construct
SEQUENCE: 61
AGQDEDHFIT VDAVGCFEGD EEEEEDDEDE EEIEVRS                            37

SEQ ID NO: 62           moltype = AA  length = 36
FEATURE                 Location/Qualifiers
REGION                  1..36
                        note = Ciz1 b-variant peptide comprising an exon 14b/exon
                         15 junction
source                  1..36
                        mol_type = protein
                        organism = synthetic construct
SEQUENCE: 62
GQDEDHFITV DAVGCFEGDE EEEEDDEDEE EIEVRS                             36

SEQ ID NO: 63           moltype = AA  length = 35
FEATURE                 Location/Qualifiers
REGION                  1..35
                        note = Ciz1 b-variant peptide comprising an exon 14b/exon
                         15 junction
source                  1..35
                        mol_type = protein
                        organism = synthetic construct
SEQUENCE: 63
QDEDHFITVD AVGCFEGDEE EEEDDEDEEE IEVRS                              35

SEQ ID NO: 64           moltype = AA  length = 34
FEATURE                 Location/Qualifiers
REGION                  1..34
                        note = Ciz1 b-variant peptide comprising an exon 14b/exon
                         15 junction
source                  1..34
                        mol_type = protein
                        organism = synthetic construct
SEQUENCE: 64
DEDHFITVDA VGCFEGDEEE EEDDEDEEEI EVRS                               34

SEQ ID NO: 65           moltype = AA  length = 33
FEATURE                 Location/Qualifiers
REGION                  1..33
                        note = Ciz1 b-variant peptide comprising an exon 14b/exon
                         15 junction
source                  1..33
                        mol_type = protein
                        organism = synthetic construct
SEQUENCE: 65
EDHFITVDAV GCFEGDEEEE EDDEDEEEIE VRS                                33

SEQ ID NO: 66           moltype = AA  length = 32
FEATURE                 Location/Qualifiers
REGION                  1..32
                        note = Ciz1 b-variant peptide comprising an exon 14b/exon
                         15 junction
source                  1..32
                        mol_type = protein
```

```
                         organism = synthetic construct
SEQUENCE: 66
DHFITVDAVG CFEGDEEEEE DDEDEEEIEV RS                            32

SEQ ID NO: 67            moltype = AA  length = 31
FEATURE                  Location/Qualifiers
REGION                   1..31
                         note = Ciz1 b-variant peptide comprising an exon 14b/exon
                          15 junction
source                   1..31
                         mol_type = protein
                         organism = synthetic construct
SEQUENCE: 67
HFITVDAVGC FEGDEEEEED DEDEEEIEVR S                             31

SEQ ID NO: 68            moltype = AA  length = 30
FEATURE                  Location/Qualifiers
REGION                   1..30
                         note = Ciz1 b-variant peptide comprising an exon 14b/exon
                          15 junction
source                   1..30
                         mol_type = protein
                         organism = synthetic construct
SEQUENCE: 68
FITVDAVGCF EGDEEEEEDD EDEEEIEVRS                               30

SEQ ID NO: 69            moltype = AA  length = 29
FEATURE                  Location/Qualifiers
REGION                   1..29
                         note = Ciz1 b-variant peptide comprising an exon 14b/exon
                          15 junction
source                   1..29
                         mol_type = protein
                         organism = synthetic construct
SEQUENCE: 69
ITVDAVGCFE GDEEEEEDDE DEEEIEVRS                                29

SEQ ID NO: 70            moltype = AA  length = 28
FEATURE                  Location/Qualifiers
REGION                   1..28
                         note = Ciz1 b-variant peptide comprising an exon 14b/exon
                          15 junction
source                   1..28
                         mol_type = protein
                         organism = synthetic construct
SEQUENCE: 70
TVDAVGCFEG DEEEEEDDED EEEIEVRS                                 28

SEQ ID NO: 71            moltype = AA  length = 27
FEATURE                  Location/Qualifiers
REGION                   1..27
                         note = Ciz1 b-variant peptide comprising an exon 14b/exon
                          15 junction
source                   1..27
                         mol_type = protein
                         organism = synthetic construct
SEQUENCE: 71
VDAVGCFEGD EEEEEDDEDE EEIEVRS                                  27

SEQ ID NO: 72            moltype = AA  length = 26
FEATURE                  Location/Qualifiers
REGION                   1..26
                         note = Ciz1 b-variant peptide comprising an exon 14b/exon
                          15 junction
source                   1..26
                         mol_type = protein
                         organism = synthetic construct
SEQUENCE: 72
DAVGCFEGDE EEEEDDEDEE EIEVRS                                   26

SEQ ID NO: 73            moltype = AA  length = 25
FEATURE                  Location/Qualifiers
REGION                   1..25
                         note = Ciz1 b-variant peptide comprising an exon 14b/exon
                          15 junction
source                   1..25
                         mol_type = protein
                         organism = synthetic construct
SEQUENCE: 73
```

```
AVGCFEGDEE EEEDDEDEEE IEVRS                                           25

SEQ ID NO: 74           moltype = AA  length = 24
FEATURE                 Location/Qualifiers
REGION                  1..24
                        note = Ciz1 b-variant peptide comprising an exon 14b/exon
                         15 junction
source                  1..24
                        mol_type = protein
                        organism = synthetic construct
SEQUENCE: 74
VGCFEGDEEE EEDDEDEEEI EVRS                                            24

SEQ ID NO: 75           moltype = AA  length = 23
FEATURE                 Location/Qualifiers
REGION                  1..23
                        note = Ciz1 b-variant peptide comprising an exon 14b/exon
                         15 junction
source                  1..23
                        mol_type = protein
                        organism = synthetic construct
SEQUENCE: 75
GCFEGDEEEE EDDEDEEEIE VRS                                             23

SEQ ID NO: 76           moltype = AA  length = 22
FEATURE                 Location/Qualifiers
REGION                  1..22
                        note = Ciz1 b-variant peptide comprising an exon 14b/exon
                         15 junction
source                  1..22
                        mol_type = protein
                        organism = synthetic construct
SEQUENCE: 76
CFEGDEEEEE DDEDEEEIEV RS                                              22

SEQ ID NO: 77           moltype = AA  length = 21
FEATURE                 Location/Qualifiers
REGION                  1..21
                        note = Ciz1 b-variant peptide comprising an exon 14b/exon
                         15 junction
source                  1..21
                        mol_type = protein
                        organism = synthetic construct
SEQUENCE: 77
FEGDEEEEED DEDEEEIEVR S                                               21

SEQ ID NO: 78           moltype = AA  length = 20
FEATURE                 Location/Qualifiers
REGION                  1..20
                        note = Ciz1 b-variant peptide comprising an exon 14b/exon
                         15 junction
source                  1..20
                        mol_type = protein
                        organism = synthetic construct
SEQUENCE: 78
EGDEEEEEDD EDEEEIEVRS                                                 20

SEQ ID NO: 79           moltype = AA  length = 19
FEATURE                 Location/Qualifiers
REGION                  1..19
                        note = Ciz1 b-variant peptide comprising an exon 14b/exon
                         15 junction
source                  1..19
                        mol_type = protein
                        organism = synthetic construct
SEQUENCE: 79
GDEEEEEDDE DEEEIEVRS                                                  19

SEQ ID NO: 80           moltype = AA  length = 18
FEATURE                 Location/Qualifiers
REGION                  1..18
                        note = Ciz1 b-variant peptide comprising an exon 14b/exon
                         15 junction
source                  1..18
                        mol_type = protein
                        organism = synthetic construct
SEQUENCE: 80
DEEEEEDDED EEEIEVRS                                                   18
```

```
SEQ ID NO: 81          moltype = AA  length = 17
FEATURE                Location/Qualifiers
REGION                 1..17
                       note = Ciz1 b-variant peptide comprising an exon 14b/exon
                        15 junction
source                 1..17
                       mol_type = protein
                       organism = synthetic construct
SEQUENCE: 81
EEEEEDDEDE EEIEVRS                                          17

SEQ ID NO: 82          moltype = AA  length = 16
FEATURE                Location/Qualifiers
REGION                 1..16
                       note = Ciz1 b-variant peptide comprising an exon 14b/exon
                        15 junction
source                 1..16
                       mol_type = protein
                       organism = synthetic construct
SEQUENCE: 82
EEEEDDEDEE EIEVRS                                           16

SEQ ID NO: 83          moltype = AA  length = 15
FEATURE                Location/Qualifiers
REGION                 1..15
                       note = Ciz1 b-variant peptide comprising an exon 14b/exon
                        15 junction
source                 1..15
                       mol_type = protein
                       organism = synthetic construct
SEQUENCE: 83
EEEDDEDEEE IEVRS                                            15

SEQ ID NO: 84          moltype = AA  length = 14
FEATURE                Location/Qualifiers
REGION                 1..14
                       note = Ciz1 b-variant peptide comprising an exon 14b/exon
                        15 junction
source                 1..14
                       mol_type = protein
                       organism = synthetic construct
SEQUENCE: 84
EEDDEDEEEI EVRS                                             14

SEQ ID NO: 85          moltype = AA  length = 13
FEATURE                Location/Qualifiers
REGION                 1..13
                       note = Ciz1 b-variant peptide comprising an exon 14b/exon
                        15 junction
source                 1..13
                       mol_type = protein
                       organism = synthetic construct
SEQUENCE: 85
EDDEDEEEIE VRS                                              13

SEQ ID NO: 86          moltype = AA  length = 12
FEATURE                Location/Qualifiers
REGION                 1..12
                       note = Ciz1 b-variant peptide comprising an exon 14b/exon
                        15 junction
source                 1..12
                       mol_type = protein
                       organism = synthetic construct
SEQUENCE: 86
DDEDEEEIEV RS                                               12

SEQ ID NO: 87          moltype = AA  length = 11
FEATURE                Location/Qualifiers
REGION                 1..11
                       note = Ciz1 b-variant peptide comprising an exon 14b/exon
                        15 junction
source                 1..11
                       mol_type = protein
                       organism = synthetic construct
SEQUENCE: 87
DEDEEEIEVR S                                                11

SEQ ID NO: 88          moltype = AA  length = 10
FEATURE                Location/Qualifiers
```

```
REGION                  1..10
                        note = Ciz1 b-variant peptide comprising an exon 14b/exon
                         15 junction
source                  1..10
                        mol_type = protein
                        organism = synthetic construct
SEQUENCE: 88
EDEEEIEVRS                                                               10

SEQ ID NO: 89           moltype = AA  length = 9
FEATURE                 Location/Qualifiers
REGION                  1..9
                        note = Ciz1 b-variant peptide comprising an exon 14b/exon
                         15 junction
source                  1..9
                        mol_type = protein
                        organism = synthetic construct
SEQUENCE: 89
DEEEIEVRS                                                                9

SEQ ID NO: 90           moltype = AA  length = 8
FEATURE                 Location/Qualifiers
REGION                  1..8
                        note = Ciz1 b-variant peptide comprising an exon 14b/exon
                         15 junction
source                  1..8
                        mol_type = protein
                        organism = synthetic construct
SEQUENCE: 90
EEEIEVRS                                                                 8

SEQ ID NO: 91           moltype = AA  length = 7
FEATURE                 Location/Qualifiers
REGION                  1..7
                        note = Ciz1 b-variant peptide comprising an exon 14b/exon
                         15 junction
source                  1..7
                        mol_type = protein
                        organism = synthetic construct
SEQUENCE: 91
EEIEVRS                                                                  7

SEQ ID NO: 92           moltype = AA  length = 6
FEATURE                 Location/Qualifiers
REGION                  1..6
                        note = Ciz1 b-variant peptide comprising an exon 14b/exon
                         15 junction
source                  1..6
                        mol_type = protein
                        organism = synthetic construct
SEQUENCE: 92
EIEVRS                                                                   6

SEQ ID NO: 93           moltype = AA  length = 5
FEATURE                 Location/Qualifiers
REGION                  1..5
                        note = Ciz1 b-variant peptide comprising an exon 14b/exon
                         15 junction
source                  1..5
                        mol_type = protein
                        organism = synthetic construct
SEQUENCE: 93
IEVRS                                                                    5

SEQ ID NO: 94           moltype = AA  length = 4
FEATURE                 Location/Qualifiers
REGION                  1..4
                        note = Ciz1 b-variant peptide comprising an exon 14b/exon
                         15 junction
source                  1..4
                        mol_type = protein
                        organism = synthetic construct
SEQUENCE: 94
EVRS                                                                     4

SEQ ID NO: 95           moltype = AA  length = 40
FEATURE                 Location/Qualifiers
REGION                  1..40
                        note = Ciz1 b-variant peptide comprising an exon 14b/exon
```

```
                        15 junction
source                  1..40
                        mol_type = protein
                        organism = synthetic construct
SEQUENCE: 95
EIAGQDEDHF ITVDAVGCFE GDEEEEEDDE DEEEIEVRSR                         40

SEQ ID NO: 96           moltype = AA  length = 39
FEATURE                 Location/Qualifiers
REGION                  1..39
                        note = Ciz1 b-variant peptide comprising an exon 14b/exon
                         15 junction
source                  1..39
                        mol_type = protein
                        organism = synthetic construct
SEQUENCE: 96
IAGQDEDHFI TVDAVGCFEG DEEEEEDDED EEEIEVRSR                          39

SEQ ID NO: 97           moltype = AA  length = 38
FEATURE                 Location/Qualifiers
REGION                  1..38
                        note = Ciz1 b-variant peptide comprising an exon 14b/exon
                         15 junction
source                  1..38
                        mol_type = protein
                        organism = synthetic construct
SEQUENCE: 97
AGQDEDHFIT VDAVGCFEGD EEEEEDDEDE EEIEVRSR                           38

SEQ ID NO: 98           moltype = AA  length = 37
FEATURE                 Location/Qualifiers
REGION                  1..37
                        note = Ciz1 b-variant peptide comprising an exon 14b/exon
                         15 junction
source                  1..37
                        mol_type = protein
                        organism = synthetic construct
SEQUENCE: 98
GQDEDHFITV DAVGCFEGDE EEEEDDEDEE EIEVRSR                            37

SEQ ID NO: 99           moltype = AA  length = 36
FEATURE                 Location/Qualifiers
REGION                  1..36
                        note = Ciz1 b-variant peptide comprising an exon 14b/exon
                         15 junction
source                  1..36
                        mol_type = protein
                        organism = synthetic construct
SEQUENCE: 99
QDEDHFITVD AVGCFEGDEE EEEDDEDEEE IEVRSR                             36

SEQ ID NO: 100          moltype = AA  length = 35
FEATURE                 Location/Qualifiers
REGION                  1..35
                        note = Ciz1 b-variant peptide comprising an exon 14b/exon
                         15 junction
source                  1..35
                        mol_type = protein
                        organism = synthetic construct
SEQUENCE: 100
DEDHFITVDA VGCFEGDEEE EEDDEDEEEI EVRSR                              35

SEQ ID NO: 101          moltype = AA  length = 34
FEATURE                 Location/Qualifiers
REGION                  1..34
                        note = Ciz1 b-variant peptide comprising an exon 14b/exon
                         15 junction
source                  1..34
                        mol_type = protein
                        organism = synthetic construct
SEQUENCE: 101
EDHFITVDAV GCFEGDEEEE EDDEDEEEIE VRSR                               34

SEQ ID NO: 102          moltype = AA  length = 33
FEATURE                 Location/Qualifiers
REGION                  1..33
                        note = Ciz1 b-variant peptide comprising an exon 14b/exon
                         15 junction
source                  1..33
```

```
                         mol_type = protein
                         organism = synthetic construct
SEQUENCE: 102
DHFITVDAVG CFEGDEEEEE DDEDEEEIEV RSR                                 33

SEQ ID NO: 103           moltype = AA  length = 32
FEATURE                  Location/Qualifiers
REGION                   1..32
                         note = Ciz1 b-variant peptide comprising an exon 14b/exon
                          15 junction
source                   1..32
                         mol_type = protein
                         organism = synthetic construct
SEQUENCE: 103
HFITVDAVGC FEGDEEEEED DEDEEEIEVR SR                                  32

SEQ ID NO: 104           moltype = AA  length = 31
FEATURE                  Location/Qualifiers
REGION                   1..31
                         note = Ciz1 b-variant peptide comprising an exon 14b/exon
                          15 junction
source                   1..31
                         mol_type = protein
                         organism = synthetic construct
SEQUENCE: 104
FITVDAVGCF EGDEEEEEDD EDEEEIEVRS R                                   31

SEQ ID NO: 105           moltype = AA  length = 30
FEATURE                  Location/Qualifiers
REGION                   1..30
                         note = Ciz1 b-variant peptide comprising an exon 14b/exon
                          15 junction
source                   1..30
                         mol_type = protein
                         organism = synthetic construct
SEQUENCE: 105
ITVDAVGCFE GDEEEEEDDE DEEEIEVRSR                                     30

SEQ ID NO: 106           moltype = AA  length = 29
FEATURE                  Location/Qualifiers
REGION                   1..29
                         note = Ciz1 b-variant peptide comprising an exon 14b/exon
                          15 junction
source                   1..29
                         mol_type = protein
                         organism = synthetic construct
SEQUENCE: 106
TVDAVGCFEG DEEEEEDDED EEEIEVRSR                                      29

SEQ ID NO: 107           moltype = AA  length = 28
FEATURE                  Location/Qualifiers
REGION                   1..28
                         note = Ciz1 b-variant peptide comprising an exon 14b/exon
                          15 junction
source                   1..28
                         mol_type = protein
                         organism = synthetic construct
SEQUENCE: 107
VDAVGCFEGD EEEEEDDEDE EEIEVRSR                                       28

SEQ ID NO: 108           moltype = AA  length = 27
FEATURE                  Location/Qualifiers
REGION                   1..27
                         note = Ciz1 b-variant peptide comprising an exon 14b/exon
                          15 junction
source                   1..27
                         mol_type = protein
                         organism = synthetic construct
SEQUENCE: 108
DAVGCFEGDE EEEEDDEDEE EIEVRSR                                        27

SEQ ID NO: 109           moltype = AA  length = 26
FEATURE                  Location/Qualifiers
REGION                   1..26
                         note = Ciz1 b-variant peptide comprising an exon 14b/exon
                          15 junction
source                   1..26
                         mol_type = protein
                         organism = synthetic construct
```

```
SEQUENCE: 109
AVGCFEGDEE EEEDDEDEEE IEVRSR                                          26

SEQ ID NO: 110          moltype = AA  length = 25
FEATURE                 Location/Qualifiers
REGION                  1..25
                        note = Ciz1 b-variant peptide comprising an exon 14b/exon
                         15 junction
source                  1..25
                        mol_type = protein
                        organism = synthetic construct
SEQUENCE: 110
VGCFEGDEEE EEDDEDEEEI EVRSR                                           25

SEQ ID NO: 111          moltype = AA  length = 24
FEATURE                 Location/Qualifiers
REGION                  1..24
                        note = Ciz1 b-variant peptide comprising an exon 14b/exon
                         15 junction
source                  1..24
                        mol_type = protein
                        organism = synthetic construct
SEQUENCE: 111
GCFEGDEEEE EDDEDEEEIE VRSR                                            24

SEQ ID NO: 112          moltype = AA  length = 23
FEATURE                 Location/Qualifiers
REGION                  1..23
                        note = Ciz1 b-variant peptide comprising an exon 14b/exon
                         15 junction
source                  1..23
                        mol_type = protein
                        organism = synthetic construct
SEQUENCE: 112
CFEGDEEEEE DDEDEEEIEV RSR                                             23

SEQ ID NO: 113          moltype = AA  length = 22
FEATURE                 Location/Qualifiers
REGION                  1..22
                        note = Ciz1 b-variant peptide comprising an exon 14b/exon
                         15 junction
source                  1..22
                        mol_type = protein
                        organism = synthetic construct
SEQUENCE: 113
FEGDEEEEED DEDEEEIEVR SR                                              22

SEQ ID NO: 114          moltype = AA  length = 21
FEATURE                 Location/Qualifiers
REGION                  1..21
                        note = Ciz1 b-variant peptide comprising an exon 14b/exon
                         15 junction
source                  1..21
                        mol_type = protein
                        organism = synthetic construct
SEQUENCE: 114
EGDEEEEEDD EDEEEIEVRS R                                               21

SEQ ID NO: 115          moltype = AA  length = 20
FEATURE                 Location/Qualifiers
REGION                  1..20
                        note = Ciz1 b-variant peptide comprising an exon 14b/exon
                         15 junction
source                  1..20
                        mol_type = protein
                        organism = synthetic construct
SEQUENCE: 115
GDEEEEEDDE DEEEIEVRSR                                                 20

SEQ ID NO: 116          moltype = AA  length = 19
FEATURE                 Location/Qualifiers
REGION                  1..19
                        note = Ciz1 b-variant peptide comprising an exon 14b/exon
                         15 junction
source                  1..19
                        mol_type = protein
                        organism = synthetic construct
SEQUENCE: 116
DEEEEEDDED EEEIEVRSR                                                  19
```

```
SEQ ID NO: 117          moltype = AA  length = 18
FEATURE                 Location/Qualifiers
REGION                  1..18
                        note = Ciz1 b-variant peptide comprising an exon 14b/exon
                         15 junction
source                  1..18
                        mol_type = protein
                        organism = synthetic construct
SEQUENCE: 117
EEEEEDDEDE EEIEVRSR                                              18

SEQ ID NO: 118          moltype = AA  length = 17
FEATURE                 Location/Qualifiers
REGION                  1..17
                        note = Ciz1 b-variant peptide comprising an exon 14b/exon
                         15 junction
source                  1..17
                        mol_type = protein
                        organism = synthetic construct
SEQUENCE: 118
EEEEDDEDEE EIEVRSR                                               17

SEQ ID NO: 119          moltype = AA  length = 16
FEATURE                 Location/Qualifiers
REGION                  1..16
                        note = Ciz1 b-variant peptide comprising an exon 14b/exon
                         15 junction
source                  1..16
                        mol_type = protein
                        organism = synthetic construct
SEQUENCE: 119
EEEDDEDEEE IEVRSR                                                16

SEQ ID NO: 120          moltype = AA  length = 15
FEATURE                 Location/Qualifiers
REGION                  1..15
                        note = Ciz1 b-variant peptide comprising an exon 14b/exon
                         15 junction
source                  1..15
                        mol_type = protein
                        organism = synthetic construct
SEQUENCE: 120
EEDDEDEEEI EVRSR                                                 15

SEQ ID NO: 121          moltype = AA  length = 14
FEATURE                 Location/Qualifiers
REGION                  1..14
                        note = Ciz1 b-variant peptide comprising an exon 14b/exon
                         15 junction
source                  1..14
                        mol_type = protein
                        organism = synthetic construct
SEQUENCE: 121
EDDEDEEEIE VRSR                                                  14

SEQ ID NO: 122          moltype = AA  length = 13
FEATURE                 Location/Qualifiers
REGION                  1..13
                        note = Ciz1 b-variant peptide comprising an exon 14b/exon
                         15 junction
source                  1..13
                        mol_type = protein
                        organism = synthetic construct
SEQUENCE: 122
DDEDEEEIEV RSR                                                   13

SEQ ID NO: 123          moltype = AA  length = 12
FEATURE                 Location/Qualifiers
REGION                  1..12
                        note = Ciz1 b-variant peptide comprising an exon 14b/exon
                         15 junction
source                  1..12
                        mol_type = protein
                        organism = synthetic construct
SEQUENCE: 123
DEDEEEIEVR SR                                                    12

SEQ ID NO: 124          moltype = AA  length = 11
```

```
FEATURE              Location/Qualifiers
REGION               1..11
                     note = Ciz1 b-variant peptide comprising an exon 14b/exon
                      15 junction
source               1..11
                     mol_type = protein
                     organism = synthetic construct
SEQUENCE: 124
EDEEEIEVRS R                                                        11

SEQ ID NO: 125       moltype = AA  length = 9
FEATURE              Location/Qualifiers
REGION               1..9
                     note = Ciz1 b-variant peptide comprising an exon 14b/exon
                      15 junction
source               1..9
                     mol_type = protein
                     organism = synthetic construct
SEQUENCE: 125
EEEIEVRSR                                                           9

SEQ ID NO: 126       moltype = AA  length = 8
FEATURE              Location/Qualifiers
REGION               1..8
                     note = Ciz1 b-variant peptide comprising an exon 14b/exon
                      15 junction
source               1..8
                     mol_type = protein
                     organism = synthetic construct
SEQUENCE: 126
EEIEVRSR                                                            8

SEQ ID NO: 127       moltype = AA  length = 7
FEATURE              Location/Qualifiers
REGION               1..7
                     note = Ciz1 b-variant peptide comprising an exon 14b/exon
                      15 junction
source               1..7
                     mol_type = protein
                     organism = synthetic construct
SEQUENCE: 127
EIEVRSR                                                             7

SEQ ID NO: 128       moltype = AA  length = 6
FEATURE              Location/Qualifiers
REGION               1..6
                     note = Ciz1 b-variant peptide comprising an exon 14b/exon
                      15 junction
source               1..6
                     mol_type = protein
                     organism = synthetic construct
SEQUENCE: 128
IEVRSR                                                              6

SEQ ID NO: 129       moltype = AA  length = 5
FEATURE              Location/Qualifiers
REGION               1..5
                     note = Ciz1 b-variant peptide comprising an exon 14b/exon
                      15 junction
source               1..5
                     mol_type = protein
                     organism = synthetic construct
SEQUENCE: 129
EVRSR                                                               5

SEQ ID NO: 130       moltype = AA  length = 41
FEATURE              Location/Qualifiers
REGION               1..41
                     note = Ciz1 b-variant peptide comprising an exon 14b/exon
                      15 junction
source               1..41
                     mol_type = protein
                     organism = synthetic construct
SEQUENCE: 130
EIAGQDEDHF ITVDAVGCFE GDEEEEEDDE DEEEIEVRSR D                       41

SEQ ID NO: 131       moltype = AA  length = 40
FEATURE              Location/Qualifiers
REGION               1..40
```

```
                        note = Ciz1 b-variant peptide comprising an exon 14b/exon
                         15 junction
source                  1..40
                        mol_type = protein
                        organism = synthetic construct
SEQUENCE: 131
IAGQDEDHFI TVDAVGCFEG DEEEEEDDED EEEIEVRSRD                        40

SEQ ID NO: 132          moltype = AA  length = 39
FEATURE                 Location/Qualifiers
REGION                  1..39
                        note = Ciz1 b-variant peptide comprising an exon 14b/exon
                         15 junction
source                  1..39
                        mol_type = protein
                        organism = synthetic construct
SEQUENCE: 132
AGQDEDHFIT VDAVGCFEGD EEEEEDDEDE EEIEVRSRD                         39

SEQ ID NO: 133          moltype = AA  length = 38
FEATURE                 Location/Qualifiers
REGION                  1..38
                        note = Ciz1 b-variant peptide comprising an exon 14b/exon
                         15 junction
source                  1..38
                        mol_type = protein
                        organism = synthetic construct
SEQUENCE: 133
GQDEDHFITV DAVGCFEGDE EEEEDDEDEE EIEVRSRD                          38

SEQ ID NO: 134          moltype = AA  length = 37
FEATURE                 Location/Qualifiers
REGION                  1..37
                        note = Ciz1 b-variant peptide comprising an exon 14b/exon
                         15 junction
source                  1..37
                        mol_type = protein
                        organism = synthetic construct
SEQUENCE: 134
QDEDHFITVD AVGCFEGDEE EEEDDEDEEE IEVRSRD                           37

SEQ ID NO: 135          moltype = AA  length = 36
FEATURE                 Location/Qualifiers
REGION                  1..36
                        note = Ciz1 b-variant peptide comprising an exon 14b/exon
                         15 junction
source                  1..36
                        mol_type = protein
                        organism = synthetic construct
SEQUENCE: 135
DEDHFITVDA VGCFEGDEEE EEDDEDEEEI EVRSRD                            36

SEQ ID NO: 136          moltype = AA  length = 35
FEATURE                 Location/Qualifiers
REGION                  1..35
                        note = Ciz1 b-variant peptide comprising an exon 14b/exon
                         15 junction
source                  1..35
                        mol_type = protein
                        organism = synthetic construct
SEQUENCE: 136
EDHFITVDAV GCFEGDEEEE EDDEDEEEIE VRSRD                             35

SEQ ID NO: 137          moltype = AA  length = 34
FEATURE                 Location/Qualifiers
REGION                  1..34
                        note = Ciz1 b-variant peptide comprising an exon 14b/exon
                         15 junction
source                  1..34
                        mol_type = protein
                        organism = synthetic construct
SEQUENCE: 137
DHFITVDAVG CFEGDEEEEE DDEDEEEIEV RSRD                              34

SEQ ID NO: 138          moltype = AA  length = 33
FEATURE                 Location/Qualifiers
REGION                  1..33
                        note = Ciz1 b-variant peptide comprising an exon 14b/exon
                         15 junction
```

```
source                  1..33
                        mol_type = protein
                        organism = synthetic construct
SEQUENCE: 138
HFITVDAVGC FEGDEEEEED DEDEEEIEVR SRD                              33

SEQ ID NO: 139          moltype = AA  length = 32
FEATURE                 Location/Qualifiers
REGION                  1..32
                        note = Ciz1 b-variant peptide comprising an exon 14b/exon
                         15 junction
source                  1..32
                        mol_type = protein
                        organism = synthetic construct
SEQUENCE: 139
FITVDAVGCF EGDEEEEEDD EDEEEIEVRS RD                               32

SEQ ID NO: 140          moltype = AA  length = 31
FEATURE                 Location/Qualifiers
REGION                  1..31
                        note = Ciz1 b-variant peptide comprising an exon 14b/exon
                         15 junction
source                  1..31
                        mol_type = protein
                        organism = synthetic construct
SEQUENCE: 140
ITVDAVGCFE GDEEEEEDDE DEEEIEVRSR D                                31

SEQ ID NO: 141          moltype = AA  length = 30
FEATURE                 Location/Qualifiers
REGION                  1..30
                        note = Ciz1 b-variant peptide comprising an exon 14b/exon
                         15 junction
source                  1..30
                        mol_type = protein
                        organism = synthetic construct
SEQUENCE: 141
TVDAVGCFEG DEEEEEDDED EEEIEVRSRD                                  30

SEQ ID NO: 142          moltype = AA  length = 29
FEATURE                 Location/Qualifiers
REGION                  1..29
                        note = Ciz1 b-variant peptide comprising an exon 14b/exon
                         15 junction
source                  1..29
                        mol_type = protein
                        organism = synthetic construct
SEQUENCE: 142
VDAVGCFEGD EEEEEDDEDE EEIEVRSRD                                   29

SEQ ID NO: 143          moltype = AA  length = 28
FEATURE                 Location/Qualifiers
REGION                  1..28
                        note = Ciz1 b-variant peptide comprising an exon 14b/exon
                         15 junction
source                  1..28
                        mol_type = protein
                        organism = synthetic construct
SEQUENCE: 143
DAVGCFEGDE EEEEDDEDEE EIEVRSRD                                    28

SEQ ID NO: 144          moltype = AA  length = 27
FEATURE                 Location/Qualifiers
REGION                  1..27
                        note = Ciz1 b-variant peptide comprising an exon 14b/exon
                         15 junction
source                  1..27
                        mol_type = protein
                        organism = synthetic construct
SEQUENCE: 144
AVGCFEGDEE EEEDDEDEEE IEVRSRD                                     27

SEQ ID NO: 145          moltype = AA  length = 26
FEATURE                 Location/Qualifiers
REGION                  1..26
                        note = Ciz1 b-variant peptide comprising an exon 14b/exon
                         15 junction
source                  1..26
                        mol_type = protein
```

```
                         organism = synthetic construct
SEQUENCE: 145
VGCFEGDEEE EEDDEDEEEI EVRSRD                                          26

SEQ ID NO: 146           moltype = AA  length = 25
FEATURE                  Location/Qualifiers
REGION                   1..25
                         note = Ciz1 b-variant peptide comprising an exon 14b/exon
                          15 junction
source                   1..25
                         mol_type = protein
                         organism = synthetic construct
SEQUENCE: 146
GCFEGDEEEE EDDEDEEEIE VRSRD                                           25

SEQ ID NO: 147           moltype = AA  length = 24
FEATURE                  Location/Qualifiers
REGION                   1..24
                         note = Ciz1 b-variant peptide comprising an exon 14b/exon
                          15 junction
source                   1..24
                         mol_type = protein
                         organism = synthetic construct
SEQUENCE: 147
CFEGDEEEEE DDEDEEEIEV RSRD                                            24

SEQ ID NO: 148           moltype = AA  length = 23
FEATURE                  Location/Qualifiers
REGION                   1..23
                         note = Ciz1 b-variant peptide comprising an exon 14b/exon
                          15 junction
source                   1..23
                         mol_type = protein
                         organism = synthetic construct
SEQUENCE: 148
FEGDEEEEED DEDEEEIEVR SRD                                             23

SEQ ID NO: 149           moltype = AA  length = 22
FEATURE                  Location/Qualifiers
REGION                   1..22
                         note = Ciz1 b-variant peptide comprising an exon 14b/exon
                          15 junction
source                   1..22
                         mol_type = protein
                         organism = synthetic construct
SEQUENCE: 149
EGDEEEEEDD EDEEEIEVRS RD                                              22

SEQ ID NO: 150           moltype = AA  length = 21
FEATURE                  Location/Qualifiers
REGION                   1..21
                         note = Ciz1 b-variant peptide comprising an exon 14b/exon
                          15 junction
source                   1..21
                         mol_type = protein
                         organism = synthetic construct
SEQUENCE: 150
GDEEEEEDDE DEEEIEVRSR D                                               21

SEQ ID NO: 151           moltype = AA  length = 20
FEATURE                  Location/Qualifiers
REGION                   1..20
                         note = Ciz1 b-variant peptide comprising an exon 14b/exon
                          15 junction
source                   1..20
                         mol_type = protein
                         organism = synthetic construct
SEQUENCE: 151
DEEEEEDDED EEEIEVRSRD                                                 20

SEQ ID NO: 152           moltype = AA  length = 19
FEATURE                  Location/Qualifiers
REGION                   1..19
                         note = Ciz1 b-variant peptide comprising an exon 14b/exon
                          15 junction
source                   1..19
                         mol_type = protein
                         organism = synthetic construct
SEQUENCE: 152
```

```
EEEEEDDEDE EEIEVRSRD                                                19

SEQ ID NO: 153          moltype = AA  length = 18
FEATURE                 Location/Qualifiers
REGION                  1..18
                        note = Ciz1 b-variant peptide comprising an exon 14b/exon
                         15 junction
source                  1..18
                        mol_type = protein
                        organism = synthetic construct
SEQUENCE: 153
EEEEDDEDEE EIEVRSRD                                                 18

SEQ ID NO: 154          moltype = AA  length = 17
FEATURE                 Location/Qualifiers
REGION                  1..17
                        note = Ciz1 b-variant peptide comprising an exon 14b/exon
                         15 junction
source                  1..17
                        mol_type = protein
                        organism = synthetic construct
SEQUENCE: 154
EEEDDEDEEE IEVRSRD                                                  17

SEQ ID NO: 155          moltype = AA  length = 16
FEATURE                 Location/Qualifiers
REGION                  1..16
                        note = Ciz1 b-variant peptide comprising an exon 14b/exon
                         15 junction
source                  1..16
                        mol_type = protein
                        organism = synthetic construct
SEQUENCE: 155
EEDDEDEEEI EVRSRD                                                   16

SEQ ID NO: 156          moltype = AA  length = 15
FEATURE                 Location/Qualifiers
REGION                  1..15
                        note = Ciz1 b-variant peptide comprising an exon 14b/exon
                         15 junction
source                  1..15
                        mol_type = protein
                        organism = synthetic construct
SEQUENCE: 156
EDDEDEEEIE VRSRD                                                    15

SEQ ID NO: 157          moltype = AA  length = 14
FEATURE                 Location/Qualifiers
REGION                  1..14
                        note = Ciz1 b-variant peptide comprising an exon 14b/exon
                         15 junction
source                  1..14
                        mol_type = protein
                        organism = synthetic construct
SEQUENCE: 157
DDEDEEEIEV RSRD                                                     14

SEQ ID NO: 158          moltype = AA  length = 13
FEATURE                 Location/Qualifiers
REGION                  1..13
                        note = Ciz1 b-variant peptide comprising an exon 14b/exon
                         15 junction
source                  1..13
                        mol_type = protein
                        organism = synthetic construct
SEQUENCE: 158
DEDEEEIEVR SRD                                                      13

SEQ ID NO: 159          moltype = AA  length = 12
FEATURE                 Location/Qualifiers
REGION                  1..12
                        note = Ciz1 b-variant peptide comprising an exon 14b/exon
                         15 junction
source                  1..12
                        mol_type = protein
                        organism = synthetic construct
SEQUENCE: 159
EDEEEIEVRS RD                                                       12
```

-continued

```
SEQ ID NO: 160          moltype = AA  length = 11
FEATURE                 Location/Qualifiers
REGION                  1..11
                        note = Ciz1 b-variant peptide comprising an exon 14b/exon
                         15 junction
source                  1..11
                        mol_type = protein
                        organism = synthetic construct
SEQUENCE: 160
DEEEIEVRSR D                                                       11

SEQ ID NO: 161          moltype = AA  length = 10
FEATURE                 Location/Qualifiers
REGION                  1..10
                        note = Ciz1 b-variant peptide comprising an exon 14b/exon
                         15 junction
source                  1..10
                        mol_type = protein
                        organism = synthetic construct
SEQUENCE: 161
EEEIEVRSRD                                                         10

SEQ ID NO: 162          moltype = AA  length = 9
FEATURE                 Location/Qualifiers
REGION                  1..9
                        note = Ciz1 b-variant peptide comprising an exon 14b/exon
                         15 junction
source                  1..9
                        mol_type = protein
                        organism = synthetic construct
SEQUENCE: 162
EEIEVRSRD                                                          9

SEQ ID NO: 163          moltype = AA  length = 8
FEATURE                 Location/Qualifiers
REGION                  1..8
                        note = Ciz1 b-variant peptide comprising an exon 14b/exon
                         15 junction
source                  1..8
                        mol_type = protein
                        organism = synthetic construct
SEQUENCE: 163
EIEVRSRD                                                           8

SEQ ID NO: 164          moltype = AA  length = 7
FEATURE                 Location/Qualifiers
REGION                  1..7
                        note = Ciz1 b-variant peptide comprising an exon 14b/exon
                         15 junction
source                  1..7
                        mol_type = protein
                        organism = synthetic construct
SEQUENCE: 164
IEVRSRD                                                            7

SEQ ID NO: 165          moltype = AA  length = 6
FEATURE                 Location/Qualifiers
REGION                  1..6
                        note = Ciz1 b-variant peptide comprising an exon 14b/exon
                         15 junction
source                  1..6
                        mol_type = protein
                        organism = synthetic construct
SEQUENCE: 165
EVRSRD                                                             6

SEQ ID NO: 166          moltype = AA  length = 42
FEATURE                 Location/Qualifiers
REGION                  1..42
                        note = Ciz1 b-variant peptide comprising an exon 14b/exon
                         15 junction
source                  1..42
                        mol_type = protein
                        organism = synthetic construct
SEQUENCE: 166
EIAGQDEDHF ITVDAVGCFE GDEEEEEDDE DEEEIEVRSR DI                     42

SEQ ID NO: 167          moltype = AA  length = 41
FEATURE                 Location/Qualifiers
```

```
REGION                  1..41
                        note = Ciz1 b-variant peptide comprising an exon 14b/exon
                         15 junction
source                  1..41
                        mol_type = protein
                        organism = synthetic construct
SEQUENCE: 167
IAGQDEDHFI TVDAVGCFEG DEEEEEDDED EEEIEVRSRD I                      41

SEQ ID NO: 168          moltype = AA  length = 40
FEATURE                 Location/Qualifiers
REGION                  1..40
                        note = Ciz1 b-variant peptide comprising an exon 14b/exon
                         15 junction
source                  1..40
                        mol_type = protein
                        organism = synthetic construct
SEQUENCE: 168
AGQDEDHFIT VDAVGCFEGD EEEEEDDEDE EEIEVRSRDI                        40

SEQ ID NO: 169          moltype = AA  length = 39
FEATURE                 Location/Qualifiers
REGION                  1..39
                        note = Ciz1 b-variant peptide comprising an exon 14b/exon
                         15 junction
source                  1..39
                        mol_type = protein
                        organism = synthetic construct
SEQUENCE: 169
GQDEDHFITV DAVGCFEGDE EEEEDDEDEE EIEVRSRDI                         39

SEQ ID NO: 170          moltype = AA  length = 38
FEATURE                 Location/Qualifiers
REGION                  1..38
                        note = Ciz1 b-variant peptide comprising an exon 14b/exon
                         15 junction
source                  1..38
                        mol_type = protein
                        organism = synthetic construct
SEQUENCE: 170
QDEDHFITVD AVGCFEGDEE EEEDDEDEEE IEVRSRDI                          38

SEQ ID NO: 171          moltype = AA  length = 37
FEATURE                 Location/Qualifiers
REGION                  1..37
                        note = Ciz1 b-variant peptide comprising an exon 14b/exon
                         15 junction
source                  1..37
                        mol_type = protein
                        organism = synthetic construct
SEQUENCE: 171
DEDHFITVDA VGCFEGDEEE EEDDEDEEEI EVRSRDI                           37

SEQ ID NO: 172          moltype = AA  length = 36
FEATURE                 Location/Qualifiers
REGION                  1..36
                        note = Ciz1 b-variant peptide comprising an exon 14b/exon
                         15 junction
source                  1..36
                        mol_type = protein
                        organism = synthetic construct
SEQUENCE: 172
EDHFITVDAV GCFEGDEEEE EDDEDEEEIE VRSRDI                            36

SEQ ID NO: 173          moltype = AA  length = 35
FEATURE                 Location/Qualifiers
REGION                  1..35
                        note = Ciz1 b-variant peptide comprising an exon 14b/exon
                         15 junction
source                  1..35
                        mol_type = protein
                        organism = synthetic construct
SEQUENCE: 173
DHFITVDAVG CFEGDEEEEE DDEDEEEIEV RSRDI                             35

SEQ ID NO: 174          moltype = AA  length = 34
FEATURE                 Location/Qualifiers
REGION                  1..34
                        note = Ciz1 b-variant peptide comprising an exon 14b/exon
```

```
                     15 junction
source               1..34
                     mol_type = protein
                     organism = synthetic construct
SEQUENCE: 174
HFITVDAVGC FEGDEEEEED DEDEEEIEVR SRDI                              34

SEQ ID NO: 175       moltype = AA  length = 33
FEATURE              Location/Qualifiers
REGION               1..33
                     note = Ciz1 b-variant peptide comprising an exon 14b/exon
                      15 junction
source               1..33
                     mol_type = protein
                     organism = synthetic construct
SEQUENCE: 175
FITVDAVGCF EGDEEEEEDD EDEEEIEVRS RDI                               33

SEQ ID NO: 176       moltype = AA  length = 32
FEATURE              Location/Qualifiers
REGION               1..32
                     note = Ciz1 b-variant peptide comprising an exon 14b/exon
                      15 junction
source               1..32
                     mol_type = protein
                     organism = synthetic construct
SEQUENCE: 176
ITVDAVGCFE GDEEEEEDDE DEEEIEVRSR DI                                32

SEQ ID NO: 177       moltype = AA  length = 31
FEATURE              Location/Qualifiers
REGION               1..31
                     note = Ciz1 b-variant peptide comprising an exon 14b/exon
                      15 junction
source               1..31
                     mol_type = protein
                     organism = synthetic construct
SEQUENCE: 177
TVDAVGCFEG DEEEEEDDED EEEIEVRSRD I                                 31

SEQ ID NO: 178       moltype = AA  length = 30
FEATURE              Location/Qualifiers
REGION               1..30
                     note = Ciz1 b-variant peptide comprising an exon 14b/exon
                      15 junction
source               1..30
                     mol_type = protein
                     organism = synthetic construct
SEQUENCE: 178
VDAVGCFEGD EEEEEDDEDE EEIEVRSRDI                                   30

SEQ ID NO: 179       moltype = AA  length = 29
FEATURE              Location/Qualifiers
REGION               1..29
                     note = Ciz1 b-variant peptide comprising an exon 14b/exon
                      15 junction
source               1..29
                     mol_type = protein
                     organism = synthetic construct
SEQUENCE: 179
DAVGCFEGDE EEEEDDEDEE EIEVRSRDI                                    29

SEQ ID NO: 180       moltype = AA  length = 28
FEATURE              Location/Qualifiers
REGION               1..28
                     note = Ciz1 b-variant peptide comprising an exon 14b/exon
                      15 junction
source               1..28
                     mol_type = protein
                     organism = synthetic construct
SEQUENCE: 180
AVGCFEGDEE EEEDDEDEEE IEVRSRDI                                     28

SEQ ID NO: 181       moltype = AA  length = 27
FEATURE              Location/Qualifiers
REGION               1..27
                     note = Ciz1 b-variant peptide comprising an exon 14b/exon
                      15 junction
source               1..27
```

```
                        mol_type = protein
                        organism = synthetic construct
SEQUENCE: 181
VGCFEGDEEE EEDDEDEEEI EVRSRDI                                        27

SEQ ID NO: 182          moltype = AA  length = 26
FEATURE                 Location/Qualifiers
REGION                  1..26
                        note = Ciz1 b-variant peptide comprising an exon 14b/exon
                         15 junction
source                  1..26
                        mol_type = protein
                        organism = synthetic construct
SEQUENCE: 182
GCFEGDEEEE EDDEDEEEIE VRSRDI                                         26

SEQ ID NO: 183          moltype = AA  length = 25
FEATURE                 Location/Qualifiers
REGION                  1..25
                        note = Ciz1 b-variant peptide comprising an exon 14b/exon
                         15 junction
source                  1..25
                        mol_type = protein
                        organism = synthetic construct
SEQUENCE: 183
CFEGDEEEEE DDEDEEEIEV RSRDI                                          25

SEQ ID NO: 184          moltype = AA  length = 24
FEATURE                 Location/Qualifiers
REGION                  1..24
                        note = Ciz1 b-variant peptide comprising an exon 14b/exon
                         15 junction
source                  1..24
                        mol_type = protein
                        organism = synthetic construct
SEQUENCE: 184
FEGDEEEEED DEDEEEIEVR SRDI                                           24

SEQ ID NO: 185          moltype = AA  length = 23
FEATURE                 Location/Qualifiers
REGION                  1..23
                        note = Ciz1 b-variant peptide comprising an exon 14b/exon
                         15 junction
source                  1..23
                        mol_type = protein
                        organism = synthetic construct
SEQUENCE: 185
EGDEEEEEDD EDEEEIEVRS RDI                                            23

SEQ ID NO: 186          moltype = AA  length = 22
FEATURE                 Location/Qualifiers
REGION                  1..22
                        note = Ciz1 b-variant peptide comprising an exon 14b/exon
                         15 junction
source                  1..22
                        mol_type = protein
                        organism = synthetic construct
SEQUENCE: 186
GDEEEEEDDE DEEEIEVRSR DI                                             22

SEQ ID NO: 187          moltype = AA  length = 21
FEATURE                 Location/Qualifiers
REGION                  1..21
                        note = Ciz1 b-variant peptide comprising an exon 14b/exon
                         15 junction
source                  1..21
                        mol_type = protein
                        organism = synthetic construct
SEQUENCE: 187
DEEEEEDDED EEEIEVRSRD I                                              21

SEQ ID NO: 188          moltype = AA  length = 20
FEATURE                 Location/Qualifiers
REGION                  1..20
                        note = Ciz1 b-variant peptide comprising an exon 14b/exon
                         15 junction
source                  1..20
                        mol_type = protein
                        organism = synthetic construct
```

```
SEQUENCE: 188
EEEEEDDEDE EEIEVRSRDI                                              20

SEQ ID NO: 189          moltype = AA  length = 19
FEATURE                 Location/Qualifiers
REGION                  1..19
                        note = Ciz1 b-variant peptide comprising an exon 14b/exon
                         15 junction
source                  1..19
                        mol_type = protein
                        organism = synthetic construct
SEQUENCE: 189
EEEEDDEDEE EIEVRSRDI                                               19

SEQ ID NO: 190          moltype = AA  length = 18
FEATURE                 Location/Qualifiers
REGION                  1..18
                        note = Ciz1 b-variant peptide comprising an exon 14b/exon
                         15 junction
source                  1..18
                        mol_type = protein
                        organism = synthetic construct
SEQUENCE: 190
EEEDDEDEEE IEVRSRDI                                                18

SEQ ID NO: 191          moltype = AA  length = 17
FEATURE                 Location/Qualifiers
REGION                  1..17
                        note = Ciz1 b-variant peptide comprising an exon 14b/exon
                         15 junction
source                  1..17
                        mol_type = protein
                        organism = synthetic construct
SEQUENCE: 191
EEDDEDEEEI EVRSRDI                                                 17

SEQ ID NO: 192          moltype = AA  length = 16
FEATURE                 Location/Qualifiers
REGION                  1..16
                        note = Ciz1 b-variant peptide comprising an exon 14b/exon
                         15 junction
source                  1..16
                        mol_type = protein
                        organism = synthetic construct
SEQUENCE: 192
EDDEDEEEIE VRSRDI                                                  16

SEQ ID NO: 193          moltype = AA  length = 15
FEATURE                 Location/Qualifiers
REGION                  1..15
                        note = Ciz1 b-variant peptide comprising an exon 14b/exon
                         15 junction
source                  1..15
                        mol_type = protein
                        organism = synthetic construct
SEQUENCE: 193
DDEDEEEIEV RSRDI                                                   15

SEQ ID NO: 194          moltype = AA  length = 14
FEATURE                 Location/Qualifiers
REGION                  1..14
                        note = Ciz1 b-variant peptide comprising an exon 14b/exon
                         15 junction
source                  1..14
                        mol_type = protein
                        organism = synthetic construct
SEQUENCE: 194
DEDEEEIEVR SRDI                                                    14

SEQ ID NO: 195          moltype = AA  length = 13
FEATURE                 Location/Qualifiers
REGION                  1..13
                        note = Ciz1 b-variant peptide comprising an exon 14b/exon
                         15 junction
source                  1..13
                        mol_type = protein
                        organism = synthetic construct
SEQUENCE: 195
EDEEEIEVRS RDI                                                     13
```

```
SEQ ID NO: 196          moltype = AA  length = 12
FEATURE                 Location/Qualifiers
REGION                  1..12
                        note = Ciz1 b-variant peptide comprising an exon 14b/exon
                         15 junction
source                  1..12
                        mol_type = protein
                        organism = synthetic construct
SEQUENCE: 196
DEEEIEVRSR DI                                                 12

SEQ ID NO: 197          moltype = AA  length = 11
FEATURE                 Location/Qualifiers
REGION                  1..11
                        note = Ciz1 b-variant peptide comprising an exon 14b/exon
                         15 junction
source                  1..11
                        mol_type = protein
                        organism = synthetic construct
SEQUENCE: 197
EEEIEVRSRD I                                                  11

SEQ ID NO: 198          moltype = AA  length = 10
FEATURE                 Location/Qualifiers
REGION                  1..10
                        note = Ciz1 b-variant peptide comprising an exon 14b/exon
                         15 junction
source                  1..10
                        mol_type = protein
                        organism = synthetic construct
SEQUENCE: 198
EEIEVRSRDI                                                    10

SEQ ID NO: 199          moltype = AA  length = 9
FEATURE                 Location/Qualifiers
REGION                  1..9
                        note = Ciz1 b-variant peptide comprising an exon 14b/exon
                         15 junction
source                  1..9
                        mol_type = protein
                        organism = synthetic construct
SEQUENCE: 199
EIEVRSRDI                                                     9

SEQ ID NO: 200          moltype = AA  length = 8
FEATURE                 Location/Qualifiers
REGION                  1..8
                        note = Ciz1 b-variant peptide comprising an exon 14b/exon
                         15 junction
source                  1..8
                        mol_type = protein
                        organism = synthetic construct
SEQUENCE: 200
IEVRSRDI                                                      8

SEQ ID NO: 201          moltype = AA  length = 7
FEATURE                 Location/Qualifiers
REGION                  1..7
                        note = Ciz1 b-variant peptide comprising an exon 14b/exon
                         15 junction
source                  1..7
                        mol_type = protein
                        organism = synthetic construct
SEQUENCE: 201
EVRSRDI                                                       7

SEQ ID NO: 202          moltype = AA  length = 43
FEATURE                 Location/Qualifiers
REGION                  1..43
                        note = Ciz1 b-variant peptide comprising an exon 14b/exon
                         15 junction
source                  1..43
                        mol_type = protein
                        organism = synthetic construct
SEQUENCE: 202
EIAGQDEDHF ITVDAVGCFE GDEEEEEDDE DEEEIEVRSR DIS               43

SEQ ID NO: 203          moltype = AA  length = 42
```

```
FEATURE               Location/Qualifiers
REGION                1..42
                      note = Ciz1 b-variant peptide comprising an exon 14b/exon
                       15 junction
source                1..42
                      mol_type = protein
                      organism = synthetic construct
SEQUENCE: 203
IAGQDEDHFI TVDAVGCFEG DEEEEEDDED EEEIEVRSRD IS                    42

SEQ ID NO: 204        moltype = AA  length = 41
FEATURE               Location/Qualifiers
REGION                1..41
                      note = Ciz1 b-variant peptide comprising an exon 14b/exon
                       15 junction
source                1..41
                      mol_type = protein
                      organism = synthetic construct
SEQUENCE: 204
AGQDEDHFIT VDAVGCFEGD EEEEEDDEDE EEIEVRSRDI S                     41

SEQ ID NO: 205        moltype = AA  length = 40
FEATURE               Location/Qualifiers
REGION                1..40
                      note = Ciz1 b-variant peptide comprising an exon 14b/exon
                       15 junction
source                1..40
                      mol_type = protein
                      organism = synthetic construct
SEQUENCE: 205
GQDEDHFITV DAVGCFEGDE EEEEDDEDEE EIEVRSRDIS                       40

SEQ ID NO: 206        moltype = AA  length = 39
FEATURE               Location/Qualifiers
REGION                1..39
                      note = Ciz1 b-variant peptide comprising an exon 14b/exon
                       15 junction
source                1..39
                      mol_type = protein
                      organism = synthetic construct
SEQUENCE: 206
QDEDHFITVD AVGCFEGDEE EEEDDEDEEE IEVRSRDIS                        39

SEQ ID NO: 207        moltype = AA  length = 38
FEATURE               Location/Qualifiers
REGION                1..38
                      note = Ciz1 b-variant peptide comprising an exon 14b/exon
                       15 junction
source                1..38
                      mol_type = protein
                      organism = synthetic construct
SEQUENCE: 207
DEDHFITVDA VGCFEGDEEE EEDDEDEEEI EVRSRDIS                         38

SEQ ID NO: 208        moltype = AA  length = 37
FEATURE               Location/Qualifiers
REGION                1..37
                      note = Ciz1 b-variant peptide comprising an exon 14b/exon
                       15 junction
source                1..37
                      mol_type = protein
                      organism = synthetic construct
SEQUENCE: 208
EDHFITVDAV GCFEGDEEEE EDDEDEEEIE VRSRDIS                          37

SEQ ID NO: 209        moltype = AA  length = 36
FEATURE               Location/Qualifiers
REGION                1..36
                      note = Ciz1 b-variant peptide comprising an exon 14b/exon
                       15 junction
source                1..36
                      mol_type = protein
                      organism = synthetic construct
SEQUENCE: 209
DHFITVDAVG CFEGDEEEEE DDEDEEEIEV RSRDIS                           36

SEQ ID NO: 210        moltype = AA  length = 35
FEATURE               Location/Qualifiers
REGION                1..35
```

```
                      note = Ciz1 b-variant peptide comprising an exon 14b/exon
                       15 junction
source                1..35
                      mol_type = protein
                      organism = synthetic construct
SEQUENCE: 210
HFITVDAVGC FEGDEEEEED DEDEEEIEVR SRDIS                        35

SEQ ID NO: 211        moltype = AA  length = 34
FEATURE               Location/Qualifiers
REGION                1..34
                      note = Ciz1 b-variant peptide comprising an exon 14b/exon
                       15 junction
source                1..34
                      mol_type = protein
                      organism = synthetic construct
SEQUENCE: 211
FITVDAVGCF EGDEEEEEDD EDEEEIEVRS RDIS                         34

SEQ ID NO: 212        moltype = AA  length = 33
FEATURE               Location/Qualifiers
REGION                1..33
                      note = Ciz1 b-variant peptide comprising an exon 14b/exon
                       15 junction
source                1..33
                      mol_type = protein
                      organism = synthetic construct
SEQUENCE: 212
ITVDAVGCFE GDEEEEEDDE DEEEIEVRSR DIS                          33

SEQ ID NO: 213        moltype = AA  length = 32
FEATURE               Location/Qualifiers
REGION                1..32
                      note = Ciz1 b-variant peptide comprising an exon 14b/exon
                       15 junction
source                1..32
                      mol_type = protein
                      organism = synthetic construct
SEQUENCE: 213
TVDAVGCFEG DEEEEEDDED EEEIEVRSRD IS                           32

SEQ ID NO: 214        moltype = AA  length = 31
FEATURE               Location/Qualifiers
REGION                1..31
                      note = Ciz1 b-variant peptide comprising an exon 14b/exon
                       15 junction
source                1..31
                      mol_type = protein
                      organism = synthetic construct
SEQUENCE: 214
VDAVGCFEGD EEEEEDDEDE EEIEVRSRDI S                            31

SEQ ID NO: 215        moltype = AA  length = 30
FEATURE               Location/Qualifiers
REGION                1..30
                      note = Ciz1 b-variant peptide comprising an exon 14b/exon
                       15 junction
source                1..30
                      mol_type = protein
                      organism = synthetic construct
SEQUENCE: 215
DAVGCFEGDE EEEEDDEDEE EIEVRSRDIS                              30

SEQ ID NO: 216        moltype = AA  length = 29
FEATURE               Location/Qualifiers
REGION                1..29
                      note = Ciz1 b-variant peptide comprising an exon 14b/exon
                       15 junction
source                1..29
                      mol_type = protein
                      organism = synthetic construct
SEQUENCE: 216
AVGCFEGDEE EEEDDEDEEE IEVRSRDIS                               29

SEQ ID NO: 217        moltype = AA  length = 28
FEATURE               Location/Qualifiers
REGION                1..28
                      note = Ciz1 b-variant peptide comprising an exon 14b/exon
                       15 junction
```

```
source                1..28
                      mol_type = protein
                      organism = synthetic construct
SEQUENCE: 217
VGCFEGDEEE EEDDEDEEEI EVRSRDIS                                    28

SEQ ID NO: 218        moltype = AA  length = 27
FEATURE               Location/Qualifiers
REGION                1..27
                      note = Ciz1 b-variant peptide comprising an exon 14b/exon
                       15 junction
source                1..27
                      mol_type = protein
                      organism = synthetic construct
SEQUENCE: 218
GCFEGDEEEE EDDEDEEEIE VRSRDIS                                     27

SEQ ID NO: 219        moltype = AA  length = 26
FEATURE               Location/Qualifiers
REGION                1..26
                      note = Ciz1 b-variant peptide comprising an exon 14b/exon
                       15 junction
source                1..26
                      mol_type = protein
                      organism = synthetic construct
SEQUENCE: 219
CFEGDEEEEE DDEDEEEIEV RSRDIS                                      26

SEQ ID NO: 220        moltype = AA  length = 25
FEATURE               Location/Qualifiers
REGION                1..25
                      note = Ciz1 b-variant peptide comprising an exon 14b/exon
                       15 junction
source                1..25
                      mol_type = protein
                      organism = synthetic construct
SEQUENCE: 220
FEGDEEEEED DEDEEEIEVR SRDIS                                       25

SEQ ID NO: 221        moltype = AA  length = 24
FEATURE               Location/Qualifiers
REGION                1..24
                      note = Ciz1 b-variant peptide comprising an exon 14b/exon
                       15 junction
source                1..24
                      mol_type = protein
                      organism = synthetic construct
SEQUENCE: 221
EGDEEEEEDD EDEEEIEVRS RDIS                                        24

SEQ ID NO: 222        moltype = AA  length = 23
FEATURE               Location/Qualifiers
REGION                1..23
                      note = Ciz1 b-variant peptide comprising an exon 14b/exon
                       15 junction
source                1..23
                      mol_type = protein
                      organism = synthetic construct
SEQUENCE: 222
GDEEEEEDDE DEEEIEVRSR DIS                                         23

SEQ ID NO: 223        moltype = AA  length = 22
FEATURE               Location/Qualifiers
REGION                1..22
                      note = Ciz1 b-variant peptide comprising an exon 14b/exon
                       15 junction
source                1..22
                      mol_type = protein
                      organism = synthetic construct
SEQUENCE: 223
DEEEEEDDED EEEIEVRSRD IS                                          22

SEQ ID NO: 224        moltype = AA  length = 21
FEATURE               Location/Qualifiers
REGION                1..21
                      note = Ciz1 b-variant peptide comprising an exon 14b/exon
                       15 junction
source                1..21
                      mol_type = protein
```

```
                        organism = synthetic construct
SEQUENCE: 224
EEEEEDDEDE EEIEVRSRDI S                                                21

SEQ ID NO: 225          moltype = AA  length = 20
FEATURE                 Location/Qualifiers
REGION                  1..20
                        note = Ciz1 b-variant peptide comprising an exon 14b/exon
                         15 junction
source                  1..20
                        mol_type = protein
                        organism = synthetic construct
SEQUENCE: 225
EEEEDDEDEE EIEVRSRDIS                                                  20

SEQ ID NO: 226          moltype = AA  length = 19
FEATURE                 Location/Qualifiers
REGION                  1..19
                        note = Ciz1 b-variant peptide comprising an exon 14b/exon
                         15 junction
source                  1..19
                        mol_type = protein
                        organism = synthetic construct
SEQUENCE: 226
EEEDDEDEEE IEVRSRDIS                                                   19

SEQ ID NO: 227          moltype = AA  length = 18
FEATURE                 Location/Qualifiers
REGION                  1..18
                        note = Ciz1 b-variant peptide comprising an exon 14b/exon
                         15 junction
source                  1..18
                        mol_type = protein
                        organism = synthetic construct
SEQUENCE: 227
EEDDEDEEEI EVRSRDIS                                                    18

SEQ ID NO: 228          moltype = AA  length = 17
FEATURE                 Location/Qualifiers
REGION                  1..17
                        note = Ciz1 b-variant peptide comprising an exon 14b/exon
                         15 junction
source                  1..17
                        mol_type = protein
                        organism = synthetic construct
SEQUENCE: 228
EDDEDEEEIE VRSRDIS                                                     17

SEQ ID NO: 229          moltype = AA  length = 16
FEATURE                 Location/Qualifiers
REGION                  1..16
                        note = Ciz1 b-variant peptide comprising an exon 14b/exon
                         15 junction
source                  1..16
                        mol_type = protein
                        organism = synthetic construct
SEQUENCE: 229
DDEDEEEIEV RSRDIS                                                      16

SEQ ID NO: 230          moltype = AA  length = 15
FEATURE                 Location/Qualifiers
REGION                  1..15
                        note = Ciz1 b-variant peptide comprising an exon 14b/exon
                         15 junction
source                  1..15
                        mol_type = protein
                        organism = synthetic construct
SEQUENCE: 230
DEDEEEIEVR SRDIS                                                       15

SEQ ID NO: 231          moltype = AA  length = 14
FEATURE                 Location/Qualifiers
REGION                  1..14
                        note = Ciz1 b-variant peptide comprising an exon 14b/exon
                         15 junction
source                  1..14
                        mol_type = protein
                        organism = synthetic construct
SEQUENCE: 231
```

```
EDEEEIEVRS RDIS                                                  14

SEQ ID NO: 232          moltype = AA  length = 12
FEATURE                 Location/Qualifiers
REGION                  1..12
                        note = Ciz1 b-variant peptide comprising an exon 14b/exon
                         15 junction
source                  1..12
                        mol_type = protein
                        organism = synthetic construct
SEQUENCE: 232
EEEIEVRSRD IS                                                    12

SEQ ID NO: 233          moltype = AA  length = 11
FEATURE                 Location/Qualifiers
REGION                  1..11
                        note = Ciz1 b-variant peptide comprising an exon 14b/exon
                         15 junction
source                  1..11
                        mol_type = protein
                        organism = synthetic construct
SEQUENCE: 233
EEIEVRSRDI S                                                     11

SEQ ID NO: 234          moltype = AA  length = 10
FEATURE                 Location/Qualifiers
REGION                  1..10
                        note = Ciz1 b-variant peptide comprising an exon 14b/exon
                         15 junction
source                  1..10
                        mol_type = protein
                        organism = synthetic construct
SEQUENCE: 234
EIEVRSRDIS                                                       10

SEQ ID NO: 235          moltype = AA  length = 9
FEATURE                 Location/Qualifiers
REGION                  1..9
                        note = Ciz1 b-variant peptide comprising an exon 14b/exon
                         15 junction
source                  1..9
                        mol_type = protein
                        organism = synthetic construct
SEQUENCE: 235
IEVRSRDIS                                                        9

SEQ ID NO: 236          moltype = AA  length = 8
FEATURE                 Location/Qualifiers
REGION                  1..8
                        note = Ciz1 b-variant peptide comprising an exon 14b/exon
                         15 junction
source                  1..8
                        mol_type = protein
                        organism = synthetic construct
SEQUENCE: 236
EVRSRDIS                                                         8

SEQ ID NO: 237          moltype = AA  length = 44
FEATURE                 Location/Qualifiers
REGION                  1..44
                        note = Ciz1 b-variant peptide comprising an exon 14b/exon
                         15 junction
source                  1..44
                        mol_type = protein
                        organism = synthetic construct
SEQUENCE: 237
EIAGQDEDHF ITVDAVGCFE GDEEEEEDDE DEEEIEVRSR DISR                 44

SEQ ID NO: 238          moltype = AA  length = 43
FEATURE                 Location/Qualifiers
REGION                  1..43
                        note = Ciz1 b-variant peptide comprising an exon 14b/exon
                         15 junction
source                  1..43
                        mol_type = protein
                        organism = synthetic construct
SEQUENCE: 238
IAGQDEDHFI TVDAVGCFEG DEEEEEDDED EEEIEVRSRD ISR                  43
```

```
SEQ ID NO: 239         moltype = AA  length = 42
FEATURE                Location/Qualifiers
REGION                 1..42
                       note = Ciz1 b-variant peptide comprising an exon 14b/exon
                        15 junction
source                 1..42
                       mol_type = protein
                       organism = synthetic construct
SEQUENCE: 239
AGQDEDHFIT VDAVGCFEGD EEEEEDDEDE EEIEVRSRDI SR                     42

SEQ ID NO: 240         moltype = AA  length = 41
FEATURE                Location/Qualifiers
REGION                 1..41
                       note = Ciz1 b-variant peptide comprising an exon 14b/exon
                        15 junction
source                 1..41
                       mol_type = protein
                       organism = synthetic construct
SEQUENCE: 240
GQDEDHFITV DAVGCFEGDE EEEEDDEDEE EIEVRSRDIS R                      41

SEQ ID NO: 241         moltype = AA  length = 40
FEATURE                Location/Qualifiers
REGION                 1..40
                       note = Ciz1 b-variant peptide comprising an exon 14b/exon
                        15 junction
source                 1..40
                       mol_type = protein
                       organism = synthetic construct
SEQUENCE: 241
QDEDHFITVD AVGCFEGDEE EEEDDEDEEE IEVRSRDISR                        40

SEQ ID NO: 242         moltype = AA  length = 39
FEATURE                Location/Qualifiers
REGION                 1..39
                       note = Ciz1 b-variant peptide comprising an exon 14b/exon
                        15 junction
source                 1..39
                       mol_type = protein
                       organism = synthetic construct
SEQUENCE: 242
DEDHFITVDA VGCFEGDEEE EEDDEDEEEI EVRSRDISR                         39

SEQ ID NO: 243         moltype = AA  length = 38
FEATURE                Location/Qualifiers
REGION                 1..38
                       note = Ciz1 b-variant peptide comprising an exon 14b/exon
                        15 junction
source                 1..38
                       mol_type = protein
                       organism = synthetic construct
SEQUENCE: 243
EDHFITVDAV GCFEGDEEEE EDDEDEEEIE VRSRDISR                          38

SEQ ID NO: 244         moltype = AA  length = 37
FEATURE                Location/Qualifiers
REGION                 1..37
                       note = Ciz1 b-variant peptide comprising an exon 14b/exon
                        15 junction
source                 1..37
                       mol_type = protein
                       organism = synthetic construct
SEQUENCE: 244
DHFITVDAVG CFEGDEEEEE DDEDEEEIEV RSRDISR                           37

SEQ ID NO: 245         moltype = AA  length = 36
FEATURE                Location/Qualifiers
REGION                 1..36
                       note = Ciz1 b-variant peptide comprising an exon 14b/exon
                        15 junction
source                 1..36
                       mol_type = protein
                       organism = synthetic construct
SEQUENCE: 245
HFITVDAVGC FEGDEEEEED DEDEEEIEVR SRDISR                            36

SEQ ID NO: 246         moltype = AA  length = 35
FEATURE                Location/Qualifiers
```

```
REGION                1..35
                      note = Ciz1 b-variant peptide comprising an exon 14b/exon
                       15 junction
source                1..35
                      mol_type = protein
                      organism = synthetic construct
SEQUENCE: 246
FITVDAVGCF EGDEEEEEDD EDEEEIEVRS RDISR                            35

SEQ ID NO: 247        moltype = AA  length = 34
FEATURE               Location/Qualifiers
REGION                1..34
                      note = Ciz1 b-variant peptide comprising an exon 14b/exon
                       15 junction
source                1..34
                      mol_type = protein
                      organism = synthetic construct
SEQUENCE: 247
ITVDAVGCFE GDEEEEEDDE DEEEIEVRSR DISR                             34

SEQ ID NO: 248        moltype = AA  length = 33
FEATURE               Location/Qualifiers
REGION                1..33
                      note = Ciz1 b-variant peptide comprising an exon 14b/exon
                       15 junction
source                1..33
                      mol_type = protein
                      organism = synthetic construct
SEQUENCE: 248
TVDAVGCFEG DEEEEEDDED EEEIEVRSRD ISR                              33

SEQ ID NO: 249        moltype = AA  length = 32
FEATURE               Location/Qualifiers
REGION                1..32
                      note = Ciz1 b-variant peptide comprising an exon 14b/exon
                       15 junction
source                1..32
                      mol_type = protein
                      organism = synthetic construct
SEQUENCE: 249
VDAVGCFEGD EEEEEDDEDE EEIEVRSRDI SR                               32

SEQ ID NO: 250        moltype = AA  length = 31
FEATURE               Location/Qualifiers
REGION                1..31
                      note = Ciz1 b-variant peptide comprising an exon 14b/exon
                       15 junction
source                1..31
                      mol_type = protein
                      organism = synthetic construct
SEQUENCE: 250
DAVGCFEGDE EEEEDDEDEE EIEVRSRDIS R                                31

SEQ ID NO: 251        moltype = AA  length = 30
FEATURE               Location/Qualifiers
REGION                1..30
                      note = Ciz1 b-variant peptide comprising an exon 14b/exon
                       15 junction
source                1..30
                      mol_type = protein
                      organism = synthetic construct
SEQUENCE: 251
AVGCFEGDEE EEEDDEDEEE IEVRSRDISR                                  30

SEQ ID NO: 252        moltype = AA  length = 29
FEATURE               Location/Qualifiers
REGION                1..29
                      note = Ciz1 b-variant peptide comprising an exon 14b/exon
                       15 junction
source                1..29
                      mol_type = protein
                      organism = synthetic construct
SEQUENCE: 252
VGCFEGDEEE EEDDEDEEEI EVRSRDISR                                   29

SEQ ID NO: 253        moltype = AA  length = 28
FEATURE               Location/Qualifiers
REGION                1..28
                      note = Ciz1 b-variant peptide comprising an exon 14b/exon
```

```
                          15 junction
source                   1..28
                         mol_type = protein
                         organism = synthetic construct
SEQUENCE: 253
GCFEGDEEEE EDDEDEEEIE VRSRDISR                                   28

SEQ ID NO: 254           moltype = AA  length = 27
FEATURE                  Location/Qualifiers
REGION                   1..27
                         note = Ciz1 b-variant peptide comprising an exon 14b/exon
                          15 junction
source                   1..27
                         mol_type = protein
                         organism = synthetic construct
SEQUENCE: 254
CFEGDEEEEE DDEDEEEIEV RSRDISR                                    27

SEQ ID NO: 255           moltype = AA  length = 26
FEATURE                  Location/Qualifiers
REGION                   1..26
                         note = Ciz1 b-variant peptide comprising an exon 14b/exon
                          15 junction
source                   1..26
                         mol_type = protein
                         organism = synthetic construct
SEQUENCE: 255
FEGDEEEEED DEDEEEIEVR SRDISR                                     26

SEQ ID NO: 256           moltype = AA  length = 25
FEATURE                  Location/Qualifiers
REGION                   1..25
                         note = Ciz1 b-variant peptide comprising an exon 14b/exon
                          15 junction
source                   1..25
                         mol_type = protein
                         organism = synthetic construct
SEQUENCE: 256
EGDEEEEEDD EDEEEIEVRS RDISR                                      25

SEQ ID NO: 257           moltype = AA  length = 24
FEATURE                  Location/Qualifiers
REGION                   1..24
                         note = Ciz1 b-variant peptide comprising an exon 14b/exon
                          15 junction
source                   1..24
                         mol_type = protein
                         organism = synthetic construct
SEQUENCE: 257
GDEEEEEDDE DEEEIEVRSR DISR                                       24

SEQ ID NO: 258           moltype = AA  length = 23
FEATURE                  Location/Qualifiers
REGION                   1..23
                         note = Ciz1 b-variant peptide comprising an exon 14b/exon
                          15 junction
source                   1..23
                         mol_type = protein
                         organism = synthetic construct
SEQUENCE: 258
DEEEEEDDED EEEIEVRSRD ISR                                        23

SEQ ID NO: 259           moltype = AA  length = 22
FEATURE                  Location/Qualifiers
REGION                   1..22
                         note = Ciz1 b-variant peptide comprising an exon 14b/exon
                          15 junction
source                   1..22
                         mol_type = protein
                         organism = synthetic construct
SEQUENCE: 259
EEEEEDDEDE EEIEVRSRDI SR                                         22

SEQ ID NO: 260           moltype = AA  length = 21
FEATURE                  Location/Qualifiers
REGION                   1..21
                         note = Ciz1 b-variant peptide comprising an exon 14b/exon
                          15 junction
source                   1..21
```

```
                        mol_type = protein
                        organism = synthetic construct
SEQUENCE: 260
EEEEDDEDEE EIEVRSRDIS R                                             21

SEQ ID NO: 261          moltype = AA  length = 20
FEATURE                 Location/Qualifiers
REGION                  1..20
                        note = Ciz1 b-variant peptide comprising an exon 14b/exon
                         15 junction
source                  1..20
                        mol_type = protein
                        organism = synthetic construct
SEQUENCE: 261
EEEDDEDEEE IEVRSRDISR                                               20

SEQ ID NO: 262          moltype = AA  length = 19
FEATURE                 Location/Qualifiers
REGION                  1..19
                        note = Ciz1 b-variant peptide comprising an exon 14b/exon
                         15 junction
source                  1..19
                        mol_type = protein
                        organism = synthetic construct
SEQUENCE: 262
EEDDEDEEEI EVRSRDISR                                                19

SEQ ID NO: 263          moltype = AA  length = 18
FEATURE                 Location/Qualifiers
REGION                  1..18
                        note = Ciz1 b-variant peptide comprising an exon 14b/exon
                         15 junction
source                  1..18
                        mol_type = protein
                        organism = synthetic construct
SEQUENCE: 263
EDDEDEEEIE VRSRDISR                                                 18

SEQ ID NO: 264          moltype = AA  length = 17
FEATURE                 Location/Qualifiers
REGION                  1..17
                        note = Ciz1 b-variant peptide comprising an exon 14b/exon
                         15 junction
source                  1..17
                        mol_type = protein
                        organism = synthetic construct
SEQUENCE: 264
DDEDEEEIEV RSRDISR                                                  17

SEQ ID NO: 265          moltype = AA  length = 16
FEATURE                 Location/Qualifiers
REGION                  1..16
                        note = Ciz1 b-variant peptide comprising an exon 14b/exon
                         15 junction
source                  1..16
                        mol_type = protein
                        organism = synthetic construct
SEQUENCE: 265
DEDEEEIEVR SRDISR                                                   16

SEQ ID NO: 266          moltype = AA  length = 15
FEATURE                 Location/Qualifiers
REGION                  1..15
                        note = Ciz1 b-variant peptide comprising an exon 14b/exon
                         15 junction
source                  1..15
                        mol_type = protein
                        organism = synthetic construct
SEQUENCE: 266
EDEEEIEVRS RDISR                                                    15

SEQ ID NO: 267          moltype = AA  length = 14
FEATURE                 Location/Qualifiers
REGION                  1..14
                        note = Ciz1 b-variant peptide comprising an exon 14b/exon
                         15 junction
source                  1..14
                        mol_type = protein
                        organism = synthetic construct
```

```
SEQUENCE: 267
DEEEIEVRSR DISR                                                   14

SEQ ID NO: 268          moltype = AA  length = 13
FEATURE                 Location/Qualifiers
REGION                  1..13
                        note = Ciz1 b-variant peptide comprising an exon 14b/exon
                         15 junction
source                  1..13
                        mol_type = protein
                        organism = synthetic construct
SEQUENCE: 268
EEEIEVRSRD ISR                                                    13

SEQ ID NO: 269          moltype = AA  length = 12
FEATURE                 Location/Qualifiers
REGION                  1..12
                        note = Ciz1 b-variant peptide comprising an exon 14b/exon
                         15 junction
source                  1..12
                        mol_type = protein
                        organism = synthetic construct
SEQUENCE: 269
EEIEVRSRDI SR                                                     12

SEQ ID NO: 270          moltype = AA  length = 11
FEATURE                 Location/Qualifiers
REGION                  1..11
                        note = Ciz1 b-variant peptide comprising an exon 14b/exon
                         15 junction
source                  1..11
                        mol_type = protein
                        organism = synthetic construct
SEQUENCE: 270
EIEVRSRDIS R                                                      11

SEQ ID NO: 271          moltype = AA  length = 10
FEATURE                 Location/Qualifiers
REGION                  1..10
                        note = Ciz1 b-variant peptide comprising an exon 14b/exon
                         15 junction
source                  1..10
                        mol_type = protein
                        organism = synthetic construct
SEQUENCE: 271
IEVRSRDISR                                                        10

SEQ ID NO: 272          moltype = AA  length = 9
FEATURE                 Location/Qualifiers
REGION                  1..9
                        note = Ciz1 b-variant peptide comprising an exon 14b/exon
                         15 junction
source                  1..9
                        mol_type = protein
                        organism = synthetic construct
SEQUENCE: 272
EVRSRDISR                                                         9

SEQ ID NO: 273          moltype = AA  length = 45
FEATURE                 Location/Qualifiers
REGION                  1..45
                        note = Ciz1 b-variant peptide comprising an exon 14b/exon
                         15 junction
source                  1..45
                        mol_type = protein
                        organism = synthetic construct
SEQUENCE: 273
EIAGQDEDHF ITVDAVGCFE GDEEEEEDDE DEEEIEVRSR DISRE                 45

SEQ ID NO: 274          moltype = AA  length = 44
FEATURE                 Location/Qualifiers
REGION                  1..44
                        note = Ciz1 b-variant peptide comprising an exon 14b/exon
                         15 junction
source                  1..44
                        mol_type = protein
                        organism = synthetic construct
SEQUENCE: 274
IAGQDEDHFI TVDAVGCFEG DEEEEEDDED EEEIEVRSRD ISRE                  44
```

```
SEQ ID NO: 275          moltype = AA  length = 43
FEATURE                 Location/Qualifiers
REGION                  1..43
                        note = Ciz1 b-variant peptide comprising an exon 14b/exon
                         15 junction
source                  1..43
                        mol_type = protein
                        organism = synthetic construct
SEQUENCE: 275
AGQDEDHFIT VDAVGCFEGD EEEEEDDEDE EEIEVRSRDI SRE                      43

SEQ ID NO: 276          moltype = AA  length = 42
FEATURE                 Location/Qualifiers
REGION                  1..42
                        note = Ciz1 b-variant peptide comprising an exon 14b/exon
                         15 junction
source                  1..42
                        mol_type = protein
                        organism = synthetic construct
SEQUENCE: 276
GQDEDHFITV DAVGCFEGDE EEEEDDEDEE EIEVRSRDIS RE                       42

SEQ ID NO: 277          moltype = AA  length = 41
FEATURE                 Location/Qualifiers
REGION                  1..41
                        note = Ciz1 b-variant peptide comprising an exon 14b/exon
                         15 junction
source                  1..41
                        mol_type = protein
                        organism = synthetic construct
SEQUENCE: 277
QDEDHFITVD AVGCFEGDEE EEEDDEDEEE IEVRSRDISR E                        41

SEQ ID NO: 278          moltype = AA  length = 40
FEATURE                 Location/Qualifiers
REGION                  1..40
                        note = Ciz1 b-variant peptide comprising an exon 14b/exon
                         15 junction
source                  1..40
                        mol_type = protein
                        organism = synthetic construct
SEQUENCE: 278
DEDHFITVDA VGCFEGDEEE EEDDEDEEEI EVRSRDISRE                          40

SEQ ID NO: 279          moltype = AA  length = 39
FEATURE                 Location/Qualifiers
REGION                  1..39
                        note = Ciz1 b-variant peptide comprising an exon 14b/exon
                         15 junction
source                  1..39
                        mol_type = protein
                        organism = synthetic construct
SEQUENCE: 279
EDHFITVDAV GCFEGDEEEE EDDEDEEEIE VRSRDISRE                           39

SEQ ID NO: 280          moltype = AA  length = 38
FEATURE                 Location/Qualifiers
REGION                  1..38
                        note = Ciz1 b-variant peptide comprising an exon 14b/exon
                         15 junction
source                  1..38
                        mol_type = protein
                        organism = synthetic construct
SEQUENCE: 280
DHFITVDAVG CFEGDEEEEE DDEDEEEIEV RSRDISRE                            38

SEQ ID NO: 281          moltype = AA  length = 37
FEATURE                 Location/Qualifiers
REGION                  1..37
                        note = Ciz1 b-variant peptide comprising an exon 14b/exon
                         15 junction
source                  1..37
                        mol_type = protein
                        organism = synthetic construct
SEQUENCE: 281
HFITVDAVGC FEGDEEEEED DEDEEEIEVR SRDISRE                             37

SEQ ID NO: 282          moltype = AA  length = 36
```

```
FEATURE                Location/Qualifiers
REGION                 1..36
                       note = Ciz1 b-variant peptide comprising an exon 14b/exon
                        15 junction
source                 1..36
                       mol_type = protein
                       organism = synthetic construct
SEQUENCE: 282
FITVDAVGCF EGDEEEEEDD EDEEEIEVRS RDISRE                            36

SEQ ID NO: 283         moltype = AA  length = 35
FEATURE                Location/Qualifiers
REGION                 1..35
                       note = Ciz1 b-variant peptide comprising an exon 14b/exon
                        15 junction
source                 1..35
                       mol_type = protein
                       organism = synthetic construct
SEQUENCE: 283
ITVDAVGCFE GDEEEEEDDE DEEEIEVRSR DISRE                             35

SEQ ID NO: 284         moltype = AA  length = 34
FEATURE                Location/Qualifiers
REGION                 1..34
                       note = Ciz1 b-variant peptide comprising an exon 14b/exon
                        15 junction
source                 1..34
                       mol_type = protein
                       organism = synthetic construct
SEQUENCE: 284
TVDAVGCFEG DEEEEEDDED EEEIEVRSRD ISRE                              34

SEQ ID NO: 285         moltype = AA  length = 33
FEATURE                Location/Qualifiers
REGION                 1..33
                       note = Ciz1 b-variant peptide comprising an exon 14b/exon
                        15 junction
source                 1..33
                       mol_type = protein
                       organism = synthetic construct
SEQUENCE: 285
VDAVGCFEGD EEEEEDDEDE EEIEVRSRDI SRE                               33

SEQ ID NO: 286         moltype = AA  length = 32
FEATURE                Location/Qualifiers
REGION                 1..32
                       note = Ciz1 b-variant peptide comprising an exon 14b/exon
                        15 junction
source                 1..32
                       mol_type = protein
                       organism = synthetic construct
SEQUENCE: 286
DAVGCFEGDE EEEEDDEDEE EIEVRSRDIS RE                                32

SEQ ID NO: 287         moltype = AA  length = 31
FEATURE                Location/Qualifiers
REGION                 1..31
                       note = Ciz1 b-variant peptide comprising an exon 14b/exon
                        15 junction
source                 1..31
                       mol_type = protein
                       organism = synthetic construct
SEQUENCE: 287
AVGCFEGDEE EEEDDEDEEE IEVRSRDISR E                                 31

SEQ ID NO: 288         moltype = AA  length = 30
FEATURE                Location/Qualifiers
REGION                 1..30
                       note = Ciz1 b-variant peptide comprising an exon 14b/exon
                        15 junction
source                 1..30
                       mol_type = protein
                       organism = synthetic construct
SEQUENCE: 288
VGCFEGDEEE EEDDEDEEEI EVRSRDISRE                                   30

SEQ ID NO: 289         moltype = AA  length = 29
FEATURE                Location/Qualifiers
REGION                 1..29
```

```
                        note = Ciz1 b-variant peptide comprising an exon 14b/exon
                         15 junction
source                  1..29
                        mol_type = protein
                        organism = synthetic construct
SEQUENCE: 289
GCFEGDEEEE EDDEDEEEIE VRSRDISRE                                     29

SEQ ID NO: 290          moltype = AA  length = 28
FEATURE                 Location/Qualifiers
REGION                  1..28
                        note = Ciz1 b-variant peptide comprising an exon 14b/exon
                         15 junction
source                  1..28
                        mol_type = protein
                        organism = synthetic construct
SEQUENCE: 290
CFEGDEEEEE DDEDEEEIEV RSRDISRE                                      28

SEQ ID NO: 291          moltype = AA  length = 27
FEATURE                 Location/Qualifiers
REGION                  1..27
                        note = Ciz1 b-variant peptide comprising an exon 14b/exon
                         15 junction
source                  1..27
                        mol_type = protein
                        organism = synthetic construct
SEQUENCE: 291
FEGDEEEEED DEDEEEIEVR SRDISRE                                       27

SEQ ID NO: 292          moltype = AA  length = 26
FEATURE                 Location/Qualifiers
REGION                  1..26
                        note = Ciz1 b-variant peptide comprising an exon 14b/exon
                         15 junction
source                  1..26
                        mol_type = protein
                        organism = synthetic construct
SEQUENCE: 292
EGDEEEEEDD EDEEEIEVRS RDISRE                                        26

SEQ ID NO: 293          moltype = AA  length = 25
FEATURE                 Location/Qualifiers
REGION                  1..25
                        note = Ciz1 b-variant peptide comprising an exon 14b/exon
                         15 junction
source                  1..25
                        mol_type = protein
                        organism = synthetic construct
SEQUENCE: 293
GDEEEEEDDE DEEEIEVRSR DISRE                                         25

SEQ ID NO: 294          moltype = AA  length = 24
FEATURE                 Location/Qualifiers
REGION                  1..24
                        note = Ciz1 b-variant peptide comprising an exon 14b/exon
                         15 junction
source                  1..24
                        mol_type = protein
                        organism = synthetic construct
SEQUENCE: 294
DEEEEEDDED EEEIEVRSRD ISRE                                          24

SEQ ID NO: 295          moltype = AA  length = 23
FEATURE                 Location/Qualifiers
REGION                  1..23
                        note = Ciz1 b-variant peptide comprising an exon 14b/exon
                         15 junction
source                  1..23
                        mol_type = protein
                        organism = synthetic construct
SEQUENCE: 295
EEEEEDDEDE EEIEVRSRDI SRE                                           23

SEQ ID NO: 296          moltype = AA  length = 22
FEATURE                 Location/Qualifiers
REGION                  1..22
                        note = Ciz1 b-variant peptide comprising an exon 14b/exon
                         15 junction
```

```
source                  1..22
                        mol_type = protein
                        organism = synthetic construct
SEQUENCE: 296
EEEEDDEDEE EIEVRSRDIS RE                                          22

SEQ ID NO: 297          moltype = AA  length = 21
FEATURE                 Location/Qualifiers
REGION                  1..21
                        note = Ciz1 b-variant peptide comprising an exon 14b/exon
                         15 junction
source                  1..21
                        mol_type = protein
                        organism = synthetic construct
SEQUENCE: 297
EEEDDEDEEE IEVRSRDISR E                                           21

SEQ ID NO: 298          moltype = AA  length = 20
FEATURE                 Location/Qualifiers
REGION                  1..20
                        note = Ciz1 b-variant peptide comprising an exon 14b/exon
                         15 junction
source                  1..20
                        mol_type = protein
                        organism = synthetic construct
SEQUENCE: 298
EEDDEDEEEI EVRSRDISRE                                             20

SEQ ID NO: 299          moltype = AA  length = 19
FEATURE                 Location/Qualifiers
REGION                  1..19
                        note = Ciz1 b-variant peptide comprising an exon 14b/exon
                         15 junction
source                  1..19
                        mol_type = protein
                        organism = synthetic construct
SEQUENCE: 299
EDDEDEEEIE VRSRDISRE                                              19

SEQ ID NO: 300          moltype = AA  length = 18
FEATURE                 Location/Qualifiers
REGION                  1..18
                        note = Ciz1 b-variant peptide comprising an exon 14b/exon
                         15 junction
source                  1..18
                        mol_type = protein
                        organism = synthetic construct
SEQUENCE: 300
DDEDEEEIEV RSRDISRE                                               18

SEQ ID NO: 301          moltype = AA  length = 17
FEATURE                 Location/Qualifiers
REGION                  1..17
                        note = Ciz1 b-variant peptide comprising an exon 14b/exon
                         15 junction
source                  1..17
                        mol_type = protein
                        organism = synthetic construct
SEQUENCE: 301
DEDEEEIEVR SRDISRE                                                17

SEQ ID NO: 302          moltype = AA  length = 16
FEATURE                 Location/Qualifiers
REGION                  1..16
                        note = Ciz1 b-variant peptide comprising an exon 14b/exon
                         15 junction
source                  1..16
                        mol_type = protein
                        organism = synthetic construct
SEQUENCE: 302
EDEEEIEVRS RDISRE                                                 16

SEQ ID NO: 303          moltype = AA  length = 15
FEATURE                 Location/Qualifiers
REGION                  1..15
                        note = Ciz1 b-variant peptide comprising an exon 14b/exon
                         15 junction
source                  1..15
                        mol_type = protein
```

```
                       organism = synthetic construct
SEQUENCE: 303
DEEEIEVRSR DISRE                                                   15

SEQ ID NO: 304         moltype = AA  length = 14
FEATURE                Location/Qualifiers
REGION                 1..14
                       note = Ciz1 b-variant peptide comprising an exon 14b/exon
                        15 junction
source                 1..14
                       mol_type = protein
                       organism = synthetic construct
SEQUENCE: 304
EEEIEVRSRD ISRE                                                    14

SEQ ID NO: 305         moltype = AA  length = 13
FEATURE                Location/Qualifiers
REGION                 1..13
                       note = Ciz1 b-variant peptide comprising an exon 14b/exon
                        15 junction
source                 1..13
                       mol_type = protein
                       organism = synthetic construct
SEQUENCE: 305
EEIEVRSRDI SRE                                                     13

SEQ ID NO: 306         moltype = AA  length = 12
FEATURE                Location/Qualifiers
REGION                 1..12
                       note = Ciz1 b-variant peptide comprising an exon 14b/exon
                        15 junction
source                 1..12
                       mol_type = protein
                       organism = synthetic construct
SEQUENCE: 306
EIEVRSRDIS RE                                                      12

SEQ ID NO: 307         moltype = AA  length = 11
FEATURE                Location/Qualifiers
REGION                 1..11
                       note = Ciz1 b-variant peptide comprising an exon 14b/exon
                        15 junction
source                 1..11
                       mol_type = protein
                       organism = synthetic construct
SEQUENCE: 307
IEVRSRDISR E                                                       11

SEQ ID NO: 308         moltype = AA  length = 10
FEATURE                Location/Qualifiers
REGION                 1..10
                       note = Ciz1 b-variant peptide comprising an exon 14b/exon
                        15 junction
source                 1..10
                       mol_type = protein
                       organism = synthetic construct
SEQUENCE: 308
EVRSRDISRE                                                         10

SEQ ID NO: 309         moltype = AA  length = 46
FEATURE                Location/Qualifiers
REGION                 1..46
                       note = Ciz1 b-variant peptide comprising an exon 14b/exon
                        15 junction
source                 1..46
                       mol_type = protein
                       organism = synthetic construct
SEQUENCE: 309
EIAGQDEDHF ITVDAVGCFE GDEEEEEDDE DEEEIEVRSR DISREE                 46

SEQ ID NO: 310         moltype = AA  length = 45
FEATURE                Location/Qualifiers
REGION                 1..45
                       note = Ciz1 b-variant peptide comprising an exon 14b/exon
                        15 junction
source                 1..45
                       mol_type = protein
                       organism = synthetic construct
SEQUENCE: 310
```

```
IAGQDEDHFI TVDAVGCFEG DEEEEEDDED EEEIEVRSRD ISREE                    45

SEQ ID NO: 311          moltype = AA  length = 44
FEATURE                 Location/Qualifiers
REGION                  1..44
                        note = Ciz1 b-variant peptide comprising an exon 14b/exon
                         15 junction
source                  1..44
                        mol_type = protein
                        organism = synthetic construct
SEQUENCE: 311
AGQDEDHFIT VDAVGCFEGD EEEEEDDEDE EEIEVRSRDI SREE                     44

SEQ ID NO: 312          moltype = AA  length = 43
FEATURE                 Location/Qualifiers
REGION                  1..43
                        note = Ciz1 b-variant peptide comprising an exon 14b/exon
                         15 junction
source                  1..43
                        mol_type = protein
                        organism = synthetic construct
SEQUENCE: 312
GQDEDHFITV DAVGCFEGDE EEEEDDEDEE EIEVRSRDIS REE                      43

SEQ ID NO: 313          moltype = AA  length = 42
FEATURE                 Location/Qualifiers
REGION                  1..42
                        note = Ciz1 b-variant peptide comprising an exon 14b/exon
                         15 junction
source                  1..42
                        mol_type = protein
                        organism = synthetic construct
SEQUENCE: 313
QDEDHFITVD AVGCFEGDEE EEEDDEDEEE IEVRSRDISR EE                       42

SEQ ID NO: 314          moltype = AA  length = 41
FEATURE                 Location/Qualifiers
REGION                  1..41
                        note = Ciz1 b-variant peptide comprising an exon 14b/exon
                         15 junction
source                  1..41
                        mol_type = protein
                        organism = synthetic construct
SEQUENCE: 314
DEDHFITVDA VGCFEGDEEE EEDDEDEEEI EVRSRDISRE E                        41

SEQ ID NO: 315          moltype = AA  length = 40
FEATURE                 Location/Qualifiers
REGION                  1..40
                        note = Ciz1 b-variant peptide comprising an exon 14b/exon
                         15 junction
source                  1..40
                        mol_type = protein
                        organism = synthetic construct
SEQUENCE: 315
EDHFITVDAV GCFEGDEEEE EDDEDEEEIE VRSRDISREE                          40

SEQ ID NO: 316          moltype = AA  length = 39
FEATURE                 Location/Qualifiers
REGION                  1..39
                        note = Ciz1 b-variant peptide comprising an exon 14b/exon
                         15 junction
source                  1..39
                        mol_type = protein
                        organism = synthetic construct
SEQUENCE: 316
DHFITVDAVG CFEGDEEEEE DDEDEEEIEV RSRDISREE                           39

SEQ ID NO: 317          moltype = AA  length = 38
FEATURE                 Location/Qualifiers
REGION                  1..38
                        note = Ciz1 b-variant peptide comprising an exon 14b/exon
                         15 junction
source                  1..38
                        mol_type = protein
                        organism = synthetic construct
SEQUENCE: 317
HFITVDAVGC FEGDEEEEED DEDEEEIEVR SRDISREE                            38
```

```
SEQ ID NO: 318         moltype = AA  length = 37
FEATURE                Location/Qualifiers
REGION                 1..37
                       note = Ciz1 b-variant peptide comprising an exon 14b/exon
                        15 junction
source                 1..37
                       mol_type = protein
                       organism = synthetic construct
SEQUENCE: 318
FITVDAVGCF EGDEEEEEDD EDEEEIEVRS RDISREE                          37

SEQ ID NO: 319         moltype = AA  length = 36
FEATURE                Location/Qualifiers
REGION                 1..36
                       note = Ciz1 b-variant peptide comprising an exon 14b/exon
                        15 junction
source                 1..36
                       mol_type = protein
                       organism = synthetic construct
SEQUENCE: 319
ITVDAVGCFE GDEEEEEDDE DEEEIEVRSR DISREE                           36

SEQ ID NO: 320         moltype = AA  length = 35
FEATURE                Location/Qualifiers
REGION                 1..35
                       note = Ciz1 b-variant peptide comprising an exon 14b/exon
                        15 junction
source                 1..35
                       mol_type = protein
                       organism = synthetic construct
SEQUENCE: 320
TVDAVGCFEG DEEEEEDDED EEEIEVRSRD ISREE                            35

SEQ ID NO: 321         moltype = AA  length = 34
FEATURE                Location/Qualifiers
REGION                 1..34
                       note = Ciz1 b-variant peptide comprising an exon 14b/exon
                        15 junction
source                 1..34
                       mol_type = protein
                       organism = synthetic construct
SEQUENCE: 321
VDAVGCFEGD EEEEEDDEDE EEIEVRSRDI SREE                             34

SEQ ID NO: 322         moltype = AA  length = 33
FEATURE                Location/Qualifiers
REGION                 1..33
                       note = Ciz1 b-variant peptide comprising an exon 14b/exon
                        15 junction
source                 1..33
                       mol_type = protein
                       organism = synthetic construct
SEQUENCE: 322
DAVGCFEGDE EEEEDDEDEE EIEVRSRDIS REE                              33

SEQ ID NO: 323         moltype = AA  length = 32
FEATURE                Location/Qualifiers
REGION                 1..32
                       note = Ciz1 b-variant peptide comprising an exon 14b/exon
                        15 junction
source                 1..32
                       mol_type = protein
                       organism = synthetic construct
SEQUENCE: 323
AVGCFEGDEE EEEDDEDEEE IEVRSRDISR EE                               32

SEQ ID NO: 324         moltype = AA  length = 31
FEATURE                Location/Qualifiers
REGION                 1..31
                       note = Ciz1 b-variant peptide comprising an exon 14b/exon
                        15 junction
source                 1..31
                       mol_type = protein
                       organism = synthetic construct
SEQUENCE: 324
VGCFEGDEEE EEDDEDEEEI EVRSRDISRE E                                31

SEQ ID NO: 325         moltype = AA  length = 30
FEATURE                Location/Qualifiers
```

```
REGION                  1..30
                        note = Ciz1 b-variant peptide comprising an exon 14b/exon
                         15 junction
source                  1..30
                        mol_type = protein
                        organism = synthetic construct
SEQUENCE: 325
GCFEGDEEEE EDDEDEEEIE VRSRDISREE                                   30

SEQ ID NO: 326          moltype = AA  length = 29
FEATURE                 Location/Qualifiers
REGION                  1..29
                        note = Ciz1 b-variant peptide comprising an exon 14b/exon
                         15 junction
source                  1..29
                        mol_type = protein
                        organism = synthetic construct
SEQUENCE: 326
CFEGDEEEEE DDEDEEEIEV RSRDISREE                                    29

SEQ ID NO: 327          moltype = AA  length = 28
FEATURE                 Location/Qualifiers
REGION                  1..28
                        note = Ciz1 b-variant peptide comprising an exon 14b/exon
                         15 junction
source                  1..28
                        mol_type = protein
                        organism = synthetic construct
SEQUENCE: 327
FEGDEEEEED DEDEEEIEVR SRDISREE                                     28

SEQ ID NO: 328          moltype = AA  length = 27
FEATURE                 Location/Qualifiers
REGION                  1..27
                        note = Ciz1 b-variant peptide comprising an exon 14b/exon
                         15 junction
source                  1..27
                        mol_type = protein
                        organism = synthetic construct
SEQUENCE: 328
EGDEEEEEDD EDEEEIEVRS RDISREE                                      27

SEQ ID NO: 329          moltype = AA  length = 26
FEATURE                 Location/Qualifiers
REGION                  1..26
                        note = Ciz1 b-variant peptide comprising an exon 14b/exon
                         15 junction
source                  1..26
                        mol_type = protein
                        organism = synthetic construct
SEQUENCE: 329
GDEEEEEDDE DEEEIEVRSR DISREE                                       26

SEQ ID NO: 330          moltype = AA  length = 25
FEATURE                 Location/Qualifiers
REGION                  1..25
                        note = Ciz1 b-variant peptide comprising an exon 14b/exon
                         15 junction
source                  1..25
                        mol_type = protein
                        organism = synthetic construct
SEQUENCE: 330
DEEEEEDDED EEEIEVRSRD ISREE                                        25

SEQ ID NO: 331          moltype = AA  length = 24
FEATURE                 Location/Qualifiers
REGION                  1..24
                        note = Ciz1 b-variant peptide comprising an exon 14b/exon
                         15 junction
source                  1..24
                        mol_type = protein
                        organism = synthetic construct
SEQUENCE: 331
EEEEEDDEDE EEIEVRSRDI SREE                                         24

SEQ ID NO: 332          moltype = AA  length = 23
FEATURE                 Location/Qualifiers
REGION                  1..23
                        note = Ciz1 b-variant peptide comprising an exon 14b/exon
```

```
                      15 junction
source                1..23
                      mol_type = protein
                      organism = synthetic construct
SEQUENCE: 332
EEEEDDEDEE EIEVRSRDIS REE                                        23

SEQ ID NO: 333        moltype = AA  length = 22
FEATURE               Location/Qualifiers
REGION                1..22
                      note = Ciz1 b-variant peptide comprising an exon 14b/exon
                       15 junction
source                1..22
                      mol_type = protein
                      organism = synthetic construct
SEQUENCE: 333
EEEDDEDEEE IEVRSRDISR EE                                         22

SEQ ID NO: 334        moltype = AA  length = 21
FEATURE               Location/Qualifiers
REGION                1..21
                      note = Ciz1 b-variant peptide comprising an exon 14b/exon
                       15 junction
source                1..21
                      mol_type = protein
                      organism = synthetic construct
SEQUENCE: 334
EEDDEDEEEI EVRSRDISRE E                                          21

SEQ ID NO: 335        moltype = AA  length = 20
FEATURE               Location/Qualifiers
REGION                1..20
                      note = Ciz1 b-variant peptide comprising an exon 14b/exon
                       15 junction
source                1..20
                      mol_type = protein
                      organism = synthetic construct
SEQUENCE: 335
EDDEDEEEIE VRSRDISREE                                            20

SEQ ID NO: 336        moltype = AA  length = 19
FEATURE               Location/Qualifiers
REGION                1..19
                      note = Ciz1 b-variant peptide comprising an exon 14b/exon
                       15 junction
source                1..19
                      mol_type = protein
                      organism = synthetic construct
SEQUENCE: 336
DDEDEEEIEV RSRDISREE                                             19

SEQ ID NO: 337        moltype = AA  length = 18
FEATURE               Location/Qualifiers
REGION                1..18
                      note = Ciz1 b-variant peptide comprising an exon 14b/exon
                       15 junction
source                1..18
                      mol_type = protein
                      organism = synthetic construct
SEQUENCE: 337
DEDEEEIEVR SRDISREE                                              18

SEQ ID NO: 338        moltype = AA  length = 17
FEATURE               Location/Qualifiers
REGION                1..17
                      note = Ciz1 b-variant peptide comprising an exon 14b/exon
                       15 junction
source                1..17
                      mol_type = protein
                      organism = synthetic construct
SEQUENCE: 338
EDEEEIEVRS RDISREE                                               17

SEQ ID NO: 339        moltype = AA  length = 16
FEATURE               Location/Qualifiers
REGION                1..16
                      note = Ciz1 b-variant peptide comprising an exon 14b/exon
                       15 junction
source                1..16
```

```
                        mol_type = protein
                        organism = synthetic construct
SEQUENCE: 339
DEEEIEVRSR DISREE                                                      16

SEQ ID NO: 340          moltype = AA  length = 15
FEATURE                 Location/Qualifiers
REGION                  1..15
                        note = Ciz1 b-variant peptide comprising an exon 14b/exon
                         15 junction
source                  1..15
                        mol_type = protein
                        organism = synthetic construct
SEQUENCE: 340
EEEIEVRSRD ISREE                                                       15

SEQ ID NO: 341          moltype = AA  length = 14
FEATURE                 Location/Qualifiers
REGION                  1..14
                        note = Ciz1 b-variant peptide comprising an exon 14b/exon
                         15 junction
source                  1..14
                        mol_type = protein
                        organism = synthetic construct
SEQUENCE: 341
EEIEVRSRDI SREE                                                        14

SEQ ID NO: 342          moltype = AA  length = 13
FEATURE                 Location/Qualifiers
REGION                  1..13
                        note = Ciz1 b-variant peptide comprising an exon 14b/exon
                         15 junction
source                  1..13
                        mol_type = protein
                        organism = synthetic construct
SEQUENCE: 342
EIEVRSRDIS REE                                                         13

SEQ ID NO: 343          moltype = AA  length = 12
FEATURE                 Location/Qualifiers
REGION                  1..12
                        note = Ciz1 b-variant peptide comprising an exon 14b/exon
                         15 junction
source                  1..12
                        mol_type = protein
                        organism = synthetic construct
SEQUENCE: 343
IEVRSRDISR EE                                                          12

SEQ ID NO: 344          moltype = AA  length = 11
FEATURE                 Location/Qualifiers
REGION                  1..11
                        note = Ciz1 b-variant peptide comprising an exon 14b/exon
                         15 junction
source                  1..11
                        mol_type = protein
                        organism = synthetic construct
SEQUENCE: 344
EVRSRDISRE E                                                           11

SEQ ID NO: 345          moltype = AA  length = 47
FEATURE                 Location/Qualifiers
REGION                  1..47
                        note = Ciz1 b-variant peptide comprising an exon 14b/exon
                         15 junction
source                  1..47
                        mol_type = protein
                        organism = synthetic construct
SEQUENCE: 345
EIAGQDEDHF ITVDAVGCFE GDEEEEEDDE DEEEIEVRSR DISREEW                    47

SEQ ID NO: 346          moltype = AA  length = 46
FEATURE                 Location/Qualifiers
REGION                  1..46
                        note = Ciz1 b-variant peptide comprising an exon 14b/exon
                         15 junction
source                  1..46
                        mol_type = protein
                        organism = synthetic construct
```

```
SEQUENCE: 346
IAGQDEDHFI TVDAVGCFEG DEEEEEDDED EEEIEVRSRD ISREEW                46

SEQ ID NO: 347         moltype = AA  length = 45
FEATURE                Location/Qualifiers
REGION                 1..45
                       note = Ciz1 b-variant peptide comprising an exon 14b/exon
                        15 junction
source                 1..45
                       mol_type = protein
                       organism = synthetic construct
SEQUENCE: 347
AGQDEDHFIT VDAVGCFEGD EEEEEDDEDE EEIEVRSRDI SREEW                 45

SEQ ID NO: 348         moltype = AA  length = 44
FEATURE                Location/Qualifiers
REGION                 1..44
                       note = Ciz1 b-variant peptide comprising an exon 14b/exon
                        15 junction
source                 1..44
                       mol_type = protein
                       organism = synthetic construct
SEQUENCE: 348
GQDEDHFITV DAVGCFEGDE EEEEDDEDEE EIEVRSRDIS REEW                  44

SEQ ID NO: 349         moltype = AA  length = 43
FEATURE                Location/Qualifiers
REGION                 1..43
                       note = Ciz1 b-variant peptide comprising an exon 14b/exon
                        15 junction
source                 1..43
                       mol_type = protein
                       organism = synthetic construct
SEQUENCE: 349
QDEDHFITVD AVGCFEGDEE EEEDDEDEEE IEVRSRDISR EEW                   43

SEQ ID NO: 350         moltype = AA  length = 42
FEATURE                Location/Qualifiers
REGION                 1..42
                       note = Ciz1 b-variant peptide comprising an exon 14b/exon
                        15 junction
source                 1..42
                       mol_type = protein
                       organism = synthetic construct
SEQUENCE: 350
DEDHFITVDA VGCFEGDEEE EEDDEDEEEI EVRSRDISRE EW                    42

SEQ ID NO: 351         moltype = AA  length = 41
FEATURE                Location/Qualifiers
REGION                 1..41
                       note = Ciz1 b-variant peptide comprising an exon 14b/exon
                        15 junction
source                 1..41
                       mol_type = protein
                       organism = synthetic construct
SEQUENCE: 351
EDHFITVDAV GCFEGDEEEE EDDEDEEEIE VRSRDISREE W                     41

SEQ ID NO: 352         moltype = AA  length = 40
FEATURE                Location/Qualifiers
REGION                 1..40
                       note = Ciz1 b-variant peptide comprising an exon 14b/exon
                        15 junction
source                 1..40
                       mol_type = protein
                       organism = synthetic construct
SEQUENCE: 352
DHFITVDAVG CFEGDEEEEE DDEDEEEIEV RSRDISREEW                       40

SEQ ID NO: 353         moltype = AA  length = 39
FEATURE                Location/Qualifiers
REGION                 1..39
                       note = Ciz1 b-variant peptide comprising an exon 14b/exon
                        15 junction
source                 1..39
                       mol_type = protein
                       organism = synthetic construct
SEQUENCE: 353
HFITVDAVGC FEGDEEEEED DEDEEEIEVR SRDISREEW                        39
```

```
SEQ ID NO: 354          moltype = AA  length = 38
FEATURE                 Location/Qualifiers
REGION                  1..38
                        note = Ciz1 b-variant peptide comprising an exon 14b/exon
                         15 junction
source                  1..38
                        mol_type = protein
                        organism = synthetic construct
SEQUENCE: 354
FITVDAVGCF EGDEEEEEDD EDEEEIEVRS RDISREEW                        38

SEQ ID NO: 355          moltype = AA  length = 37
FEATURE                 Location/Qualifiers
REGION                  1..37
                        note = Ciz1 b-variant peptide comprising an exon 14b/exon
                         15 junction
source                  1..37
                        mol_type = protein
                        organism = synthetic construct
SEQUENCE: 355
ITVDAVGCFE GDEEEEEDDE DEEEIEVRSR DISREEW                         37

SEQ ID NO: 356          moltype = AA  length = 36
FEATURE                 Location/Qualifiers
REGION                  1..36
                        note = Ciz1 b-variant peptide comprising an exon 14b/exon
                         15 junction
source                  1..36
                        mol_type = protein
                        organism = synthetic construct
SEQUENCE: 356
TVDAVGCFEG DEEEEEDDED EEEIEVRSRD ISREEW                          36

SEQ ID NO: 357          moltype = AA  length = 35
FEATURE                 Location/Qualifiers
REGION                  1..35
                        note = Ciz1 b-variant peptide comprising an exon 14b/exon
                         15 junction
source                  1..35
                        mol_type = protein
                        organism = synthetic construct
SEQUENCE: 357
VDAVGCFEGD EEEEEDDEDE EEIEVRSRDI SREEW                           35

SEQ ID NO: 358          moltype = AA  length = 34
FEATURE                 Location/Qualifiers
REGION                  1..34
                        note = Ciz1 b-variant peptide comprising an exon 14b/exon
                         15 junction
source                  1..34
                        mol_type = protein
                        organism = synthetic construct
SEQUENCE: 358
DAVGCFEGDE EEEEDDEDEE EIEVRSRDIS REEW                            34

SEQ ID NO: 359          moltype = AA  length = 33
FEATURE                 Location/Qualifiers
REGION                  1..33
                        note = Ciz1 b-variant peptide comprising an exon 14b/exon
                         15 junction
source                  1..33
                        mol_type = protein
                        organism = synthetic construct
SEQUENCE: 359
AVGCFEGDEE EEEDDEDEEE IEVRSRDISR EEW                             33

SEQ ID NO: 360          moltype = AA  length = 32
FEATURE                 Location/Qualifiers
REGION                  1..32
                        note = Ciz1 b-variant peptide comprising an exon 14b/exon
                         15 junction
source                  1..32
                        mol_type = protein
                        organism = synthetic construct
SEQUENCE: 360
VGCFEGDEEE EEDDEDEEEI EVRSRDISRE EW                              32

SEQ ID NO: 361          moltype = AA  length = 31
```

```
FEATURE                Location/Qualifiers
REGION                 1..31
                       note = Ciz1 b-variant peptide comprising an exon 14b/exon
                        15 junction
source                 1..31
                       mol_type = protein
                       organism = synthetic construct
SEQUENCE: 361
GCFEGDEEEE EDDEDEEEIE VRSRDISREE W                                 31

SEQ ID NO: 362         moltype = AA  length = 30
FEATURE                Location/Qualifiers
REGION                 1..30
                       note = Ciz1 b-variant peptide comprising an exon 14b/exon
                        15 junction
source                 1..30
                       mol_type = protein
                       organism = synthetic construct
SEQUENCE: 362
CFEGDEEEEE DDEDEEEIEV RSRDISREEW                                   30

SEQ ID NO: 363         moltype = AA  length = 29
FEATURE                Location/Qualifiers
REGION                 1..29
                       note = Ciz1 b-variant peptide comprising an exon 14b/exon
                        15 junction
source                 1..29
                       mol_type = protein
                       organism = synthetic construct
SEQUENCE: 363
FEGDEEEEED DEDEEEIEVR SRDISREEW                                    29

SEQ ID NO: 364         moltype = AA  length = 28
FEATURE                Location/Qualifiers
REGION                 1..28
                       note = Ciz1 b-variant peptide comprising an exon 14b/exon
                        15 junction
source                 1..28
                       mol_type = protein
                       organism = synthetic construct
SEQUENCE: 364
EGDEEEEEDD EDEEEIEVRS RDISREEW                                     28

SEQ ID NO: 365         moltype = AA  length = 27
FEATURE                Location/Qualifiers
REGION                 1..27
                       note = Ciz1 b-variant peptide comprising an exon 14b/exon
                        15 junction
source                 1..27
                       mol_type = protein
                       organism = synthetic construct
SEQUENCE: 365
GDEEEEEDDE DEEEIEVRSR DISREEW                                      27

SEQ ID NO: 366         moltype = AA  length = 26
FEATURE                Location/Qualifiers
REGION                 1..26
                       note = Ciz1 b-variant peptide comprising an exon 14b/exon
                        15 junction
source                 1..26
                       mol_type = protein
                       organism = synthetic construct
SEQUENCE: 366
DEEEEEDDED EEEIEVRSRD ISREEW                                       26

SEQ ID NO: 367         moltype = AA  length = 25
FEATURE                Location/Qualifiers
REGION                 1..25
                       note = Ciz1 b-variant peptide comprising an exon 14b/exon
                        15 junction
source                 1..25
                       mol_type = protein
                       organism = synthetic construct
SEQUENCE: 367
EEEEEDDEDE EEIEVRSRDI SREEW                                        25

SEQ ID NO: 368         moltype = AA  length = 24
FEATURE                Location/Qualifiers
REGION                 1..24
```

```
                        note = Ciz1 b-variant peptide comprising an exon 14b/exon
                         15 junction
source                  1..24
                        mol_type = protein
                        organism = synthetic construct
SEQUENCE: 368
EEEEDDEDEE EIEVRSRDIS REEW                                          24

SEQ ID NO: 369          moltype = AA  length = 23
FEATURE                 Location/Qualifiers
REGION                  1..23
                        note = Ciz1 b-variant peptide comprising an exon 14b/exon
                         15 junction
source                  1..23
                        mol_type = protein
                        organism = synthetic construct
SEQUENCE: 369
EEEDDEDEEE IEVRSRDISR EEW                                           23

SEQ ID NO: 370          moltype = AA  length = 22
FEATURE                 Location/Qualifiers
REGION                  1..22
                        note = Ciz1 b-variant peptide comprising an exon 14b/exon
                         15 junction
source                  1..22
                        mol_type = protein
                        organism = synthetic construct
SEQUENCE: 370
EEDDEDEEEI EVRSRDISRE EW                                            22

SEQ ID NO: 371          moltype = AA  length = 21
FEATURE                 Location/Qualifiers
REGION                  1..21
                        note = Ciz1 b-variant peptide comprising an exon 14b/exon
                         15 junction
source                  1..21
                        mol_type = protein
                        organism = synthetic construct
SEQUENCE: 371
EDDEDEEEIE VRSRDISREE W                                             21

SEQ ID NO: 372          moltype = AA  length = 20
FEATURE                 Location/Qualifiers
REGION                  1..20
                        note = Ciz1 b-variant peptide comprising an exon 14b/exon
                         15 junction
source                  1..20
                        mol_type = protein
                        organism = synthetic construct
SEQUENCE: 372
DDEDEEEIEV RSRDISREEW                                               20

SEQ ID NO: 373          moltype = AA  length = 19
FEATURE                 Location/Qualifiers
REGION                  1..19
                        note = Ciz1 b-variant peptide comprising an exon 14b/exon
                         15 junction
source                  1..19
                        mol_type = protein
                        organism = synthetic construct
SEQUENCE: 373
DEDEEEIEVR SRDISREEW                                                19

SEQ ID NO: 374          moltype = AA  length = 18
FEATURE                 Location/Qualifiers
REGION                  1..18
                        note = Ciz1 b-variant peptide comprising an exon 14b/exon
                         15 junction
source                  1..18
                        mol_type = protein
                        organism = synthetic construct
SEQUENCE: 374
EDEEEIEVRS RDISREEW                                                 18

SEQ ID NO: 375          moltype = AA  length = 17
FEATURE                 Location/Qualifiers
REGION                  1..17
                        note = Ciz1 b-variant peptide comprising an exon 14b/exon
                         15 junction
```

```
source                  1..17
                        mol_type = protein
                        organism = synthetic construct
SEQUENCE: 375
DEEEIEVRSR DISREEW                                                        17

SEQ ID NO: 376          moltype = AA  length = 16
FEATURE                 Location/Qualifiers
REGION                  1..16
                        note = Ciz1 b-variant peptide comprising an exon 14b/exon
                         15 junction
source                  1..16
                        mol_type = protein
                        organism = synthetic construct
SEQUENCE: 376
EEEIEVRSRD ISREEW                                                         16

SEQ ID NO: 377          moltype = AA  length = 15
FEATURE                 Location/Qualifiers
REGION                  1..15
                        note = Ciz1 b-variant peptide comprising an exon 14b/exon
                         15 junction
source                  1..15
                        mol_type = protein
                        organism = synthetic construct
SEQUENCE: 377
EEIEVRSRDI SREEW                                                          15

SEQ ID NO: 378          moltype = AA  length = 14
FEATURE                 Location/Qualifiers
REGION                  1..14
                        note = Ciz1 b-variant peptide comprising an exon 14b/exon
                         15 junction
source                  1..14
                        mol_type = protein
                        organism = synthetic construct
SEQUENCE: 378
EIEVRSRDIS REEW                                                           14

SEQ ID NO: 379          moltype = AA  length = 13
FEATURE                 Location/Qualifiers
REGION                  1..13
                        note = Ciz1 b-variant peptide comprising an exon 14b/exon
                         15 junction
source                  1..13
                        mol_type = protein
                        organism = synthetic construct
SEQUENCE: 379
IEVRSRDISR EEW                                                            13

SEQ ID NO: 380          moltype = AA  length = 12
FEATURE                 Location/Qualifiers
REGION                  1..12
                        note = Ciz1 b-variant peptide comprising an exon 14b/exon
                         15 junction
source                  1..12
                        mol_type = protein
                        organism = synthetic construct
SEQUENCE: 380
EVRSRDISRE EW                                                             12

SEQ ID NO: 381          moltype = AA  length = 48
FEATURE                 Location/Qualifiers
REGION                  1..48
                        note = Ciz1 b-variant peptide comprising an exon 14b/exon
                         15 junction
source                  1..48
                        mol_type = protein
                        organism = synthetic construct
SEQUENCE: 381
EIAGQDEDHF ITVDAVGCFE GDEEEEEDDE DEEEIEVRSR DISREEWK                      48

SEQ ID NO: 382          moltype = AA  length = 47
FEATURE                 Location/Qualifiers
REGION                  1..47
                        note = Ciz1 b-variant peptide comprising an exon 14b/exon
                         15 junction
source                  1..47
                        mol_type = protein
```

```
                        organism = synthetic construct
SEQUENCE: 382
IAGQDEDHFI TVDAVGCFEG DEEEEEDDED EEEIEVRSRD ISREEWK                47

SEQ ID NO: 383          moltype = AA  length = 46
FEATURE                 Location/Qualifiers
REGION                  1..46
                        note = Ciz1 b-variant peptide comprising an exon 14b/exon
                         15 junction
source                  1..46
                        mol_type = protein
                        organism = synthetic construct
SEQUENCE: 383
AGQDEDHFIT VDAVGCFEGD EEEEEDDEDE EEIEVRSRDI SREEWK                 46

SEQ ID NO: 384          moltype = AA  length = 45
FEATURE                 Location/Qualifiers
REGION                  1..45
                        note = Ciz1 b-variant peptide comprising an exon 14b/exon
                         15 junction
source                  1..45
                        mol_type = protein
                        organism = synthetic construct
SEQUENCE: 384
GQDEDHFITV DAVGCFEGDE EEEEDDEDEE EIEVRSRDIS REEWK                  45

SEQ ID NO: 385          moltype = AA  length = 44
FEATURE                 Location/Qualifiers
REGION                  1..44
                        note = Ciz1 b-variant peptide comprising an exon 14b/exon
                         15 junction
source                  1..44
                        mol_type = protein
                        organism = synthetic construct
SEQUENCE: 385
QDEDHFITVD AVGCFEGDEE EEEDDEDEEE IEVRSRDISR EEWK                   44

SEQ ID NO: 386          moltype = AA  length = 43
FEATURE                 Location/Qualifiers
REGION                  1..43
                        note = Ciz1 b-variant peptide comprising an exon 14b/exon
                         15 junction
source                  1..43
                        mol_type = protein
                        organism = synthetic construct
SEQUENCE: 386
DEDHFITVDA VGCFEGDEEE EEDDEDEEEI EVRSRDISRE EWK                    43

SEQ ID NO: 387          moltype = AA  length = 42
FEATURE                 Location/Qualifiers
REGION                  1..42
                        note = Ciz1 b-variant peptide comprising an exon 14b/exon
                         15 junction
source                  1..42
                        mol_type = protein
                        organism = synthetic construct
SEQUENCE: 387
EDHFITVDAV GCFEGDEEEE EDDEDEEEIE VRSRDISREE WK                     42

SEQ ID NO: 388          moltype = AA  length = 41
FEATURE                 Location/Qualifiers
REGION                  1..41
                        note = Ciz1 b-variant peptide comprising an exon 14b/exon
                         15 junction
source                  1..41
                        mol_type = protein
                        organism = synthetic construct
SEQUENCE: 388
DHFITVDAVG CFEGDEEEEE DDEDEEEIEV RSRDISREEW K                      41

SEQ ID NO: 389          moltype = AA  length = 40
FEATURE                 Location/Qualifiers
REGION                  1..40
                        note = Ciz1 b-variant peptide comprising an exon 14b/exon
                         15 junction
source                  1..40
                        mol_type = protein
                        organism = synthetic construct
SEQUENCE: 389
```

```
HFITVDAVGC FEGDEEEEED DEDEEEIEVR SRDISREEWK                   40

SEQ ID NO: 390        moltype = AA  length = 39
FEATURE               Location/Qualifiers
REGION                1..39
                      note = Ciz1 b-variant peptide comprising an exon 14b/exon
                       15 junction
source                1..39
                      mol_type = protein
                      organism = synthetic construct
SEQUENCE: 390
FITVDAVGCF EGDEEEEEDD EDEEEIEVRS RDISREEWK                    39

SEQ ID NO: 391        moltype = AA  length = 38
FEATURE               Location/Qualifiers
REGION                1..38
                      note = Ciz1 b-variant peptide comprising an exon 14b/exon
                       15 junction
source                1..38
                      mol_type = protein
                      organism = synthetic construct
SEQUENCE: 391
ITVDAVGCFE GDEEEEEDDE DEEEIEVRSR DISREEWK                     38

SEQ ID NO: 392        moltype = AA  length = 37
FEATURE               Location/Qualifiers
REGION                1..37
                      note = Ciz1 b-variant peptide comprising an exon 14b/exon
                       15 junction
source                1..37
                      mol_type = protein
                      organism = synthetic construct
SEQUENCE: 392
TVDAVGCFEG DEEEEEDDED EEEIEVRSRD ISREEWK                      37

SEQ ID NO: 393        moltype = AA  length = 36
FEATURE               Location/Qualifiers
REGION                1..36
                      note = Ciz1 b-variant peptide comprising an exon 14b/exon
                       15 junction
source                1..36
                      mol_type = protein
                      organism = synthetic construct
SEQUENCE: 393
VDAVGCFEGD EEEEEDDEDE EEIEVRSRDI SREEWK                       36

SEQ ID NO: 394        moltype = AA  length = 35
FEATURE               Location/Qualifiers
REGION                1..35
                      note = Ciz1 b-variant peptide comprising an exon 14b/exon
                       15 junction
source                1..35
                      mol_type = protein
                      organism = synthetic construct
SEQUENCE: 394
DAVGCFEGDE EEEEDDEDEE EIEVRSRDIS REEWK                        35

SEQ ID NO: 395        moltype = AA  length = 34
FEATURE               Location/Qualifiers
REGION                1..34
                      note = Ciz1 b-variant peptide comprising an exon 14b/exon
                       15 junction
source                1..34
                      mol_type = protein
                      organism = synthetic construct
SEQUENCE: 395
AVGCFEGDEE EEEDDEDEEE IEVRSRDISR EEWK                         34

SEQ ID NO: 396        moltype = AA  length = 33
FEATURE               Location/Qualifiers
REGION                1..33
                      note = Ciz1 b-variant peptide comprising an exon 14b/exon
                       15 junction
source                1..33
                      mol_type = protein
                      organism = synthetic construct
SEQUENCE: 396
VGCFEGDEEE EEDDEDEEEI EVRSRDISRE EWK                          33
```

```
SEQ ID NO: 397          moltype = AA  length = 32
FEATURE                 Location/Qualifiers
REGION                  1..32
                        note = Ciz1 b-variant peptide comprising an exon 14b/exon
                         15 junction
source                  1..32
                        mol_type = protein
                        organism = synthetic construct
SEQUENCE: 397
GCFEGDEEEE EDDEDEEEIE VRSRDISREE WK                                 32

SEQ ID NO: 398          moltype = AA  length = 31
FEATURE                 Location/Qualifiers
REGION                  1..31
                        note = Ciz1 b-variant peptide comprising an exon 14b/exon
                         15 junction
source                  1..31
                        mol_type = protein
                        organism = synthetic construct
SEQUENCE: 398
CFEGDEEEEE DDEDEEEIEV RSRDISREEW K                                  31

SEQ ID NO: 399          moltype = AA  length = 30
FEATURE                 Location/Qualifiers
REGION                  1..30
                        note = Ciz1 b-variant peptide comprising an exon 14b/exon
                         15 junction
source                  1..30
                        mol_type = protein
                        organism = synthetic construct
SEQUENCE: 399
FEGDEEEEED DEDEEEIEVR SRDISREEWK                                    30

SEQ ID NO: 400          moltype = AA  length = 29
FEATURE                 Location/Qualifiers
REGION                  1..29
                        note = Ciz1 b-variant peptide comprising an exon 14b/exon
                         15 junction
source                  1..29
                        mol_type = protein
                        organism = synthetic construct
SEQUENCE: 400
EGDEEEEEDD EDEEEIEVRS RDISREEWK                                     29

SEQ ID NO: 401          moltype = AA  length = 28
FEATURE                 Location/Qualifiers
REGION                  1..28
                        note = Ciz1 b-variant peptide comprising an exon 14b/exon
                         15 junction
source                  1..28
                        mol_type = protein
                        organism = synthetic construct
SEQUENCE: 401
GDEEEEEDDE DEEEIEVRSR DISREEWK                                      28

SEQ ID NO: 402          moltype = AA  length = 27
FEATURE                 Location/Qualifiers
REGION                  1..27
                        note = Ciz1 b-variant peptide comprising an exon 14b/exon
                         15 junction
source                  1..27
                        mol_type = protein
                        organism = synthetic construct
SEQUENCE: 402
DEEEEEDDED EEEIEVRSRD ISREEWK                                       27

SEQ ID NO: 403          moltype = AA  length = 26
FEATURE                 Location/Qualifiers
REGION                  1..26
                        note = Ciz1 b-variant peptide comprising an exon 14b/exon
                         15 junction
source                  1..26
                        mol_type = protein
                        organism = synthetic construct
SEQUENCE: 403
EEEEEDDEDE EEIEVRSRDI SREEWK                                        26

SEQ ID NO: 404          moltype = AA  length = 25
FEATURE                 Location/Qualifiers
```

```
REGION                  1..25
                        note = Ciz1 b-variant peptide comprising an exon 14b/exon
                         15 junction
source                  1..25
                        mol_type = protein
                        organism = synthetic construct
SEQUENCE: 404
EEEEDDEDEE EIEVRSRDIS REEWK                                         25

SEQ ID NO: 405          moltype = AA  length = 24
FEATURE                 Location/Qualifiers
REGION                  1..24
                        note = Ciz1 b-variant peptide comprising an exon 14b/exon
                         15 junction
source                  1..24
                        mol_type = protein
                        organism = synthetic construct
SEQUENCE: 405
EEEDDEDEEE IEVRSRDISR EEWK                                          24

SEQ ID NO: 406          moltype = AA  length = 23
FEATURE                 Location/Qualifiers
REGION                  1..23
                        note = Ciz1 b-variant peptide comprising an exon 14b/exon
                         15 junction
source                  1..23
                        mol_type = protein
                        organism = synthetic construct
SEQUENCE: 406
EEDDEDEEEI EVRSRDISRE EWK                                           23

SEQ ID NO: 407          moltype = AA  length = 22
FEATURE                 Location/Qualifiers
REGION                  1..22
                        note = Ciz1 b-variant peptide comprising an exon 14b/exon
                         15 junction
source                  1..22
                        mol_type = protein
                        organism = synthetic construct
SEQUENCE: 407
EDDEDEEEIE VRSRDISREE WK                                            22

SEQ ID NO: 408          moltype = AA  length = 21
FEATURE                 Location/Qualifiers
REGION                  1..21
                        note = Ciz1 b-variant peptide comprising an exon 14b/exon
                         15 junction
source                  1..21
                        mol_type = protein
                        organism = synthetic construct
SEQUENCE: 408
DDEDEEEIEV RSRDISREEW K                                             21

SEQ ID NO: 409          moltype = AA  length = 20
FEATURE                 Location/Qualifiers
REGION                  1..20
                        note = Ciz1 b-variant peptide comprising an exon 14b/exon
                         15 junction
source                  1..20
                        mol_type = protein
                        organism = synthetic construct
SEQUENCE: 409
DEDEEEIEVR SRDISREEWK                                               20

SEQ ID NO: 410          moltype = AA  length = 19
FEATURE                 Location/Qualifiers
REGION                  1..19
                        note = Ciz1 b-variant peptide comprising an exon 14b/exon
                         15 junction
source                  1..19
                        mol_type = protein
                        organism = synthetic construct
SEQUENCE: 410
EDEEEIEVRS RDISREEWK                                                19

SEQ ID NO: 411          moltype = AA  length = 18
FEATURE                 Location/Qualifiers
REGION                  1..18
                        note = Ciz1 b-variant peptide comprising an exon 14b/exon
```

```
                         15 junction
source                  1..18
                        mol_type = protein
                        organism = synthetic construct
SEQUENCE: 411
DEEEIEVRSR DISREEWK                                           18

SEQ ID NO: 412          moltype = AA  length = 17
FEATURE                 Location/Qualifiers
REGION                  1..17
                        note = Ciz1 b-variant peptide comprising an exon 14b/exon
                         15 junction
source                  1..17
                        mol_type = protein
                        organism = synthetic construct
SEQUENCE: 412
EEEIEVRSRD ISREEWK                                            17

SEQ ID NO: 413          moltype = AA  length = 16
FEATURE                 Location/Qualifiers
REGION                  1..16
                        note = Ciz1 b-variant peptide comprising an exon 14b/exon
                         15 junction
source                  1..16
                        mol_type = protein
                        organism = synthetic construct
SEQUENCE: 413
EEIEVRSRDI SREEWK                                             16

SEQ ID NO: 414          moltype = AA  length = 15
FEATURE                 Location/Qualifiers
REGION                  1..15
                        note = Ciz1 b-variant peptide comprising an exon 14b/exon
                         15 junction
source                  1..15
                        mol_type = protein
                        organism = synthetic construct
SEQUENCE: 414
EIEVRSRDIS REEWK                                              15

SEQ ID NO: 415          moltype = AA  length = 14
FEATURE                 Location/Qualifiers
REGION                  1..14
                        note = Ciz1 b-variant peptide comprising an exon 14b/exon
                         15 junction
source                  1..14
                        mol_type = protein
                        organism = synthetic construct
SEQUENCE: 415
IEVRSRDISR EEWK                                               14

SEQ ID NO: 416          moltype = AA  length = 13
FEATURE                 Location/Qualifiers
REGION                  1..13
                        note = Ciz1 b-variant peptide comprising an exon 14b/exon
                         15 junction
source                  1..13
                        mol_type = protein
                        organism = synthetic construct
SEQUENCE: 416
EVRSRDISRE EWK                                                13

SEQ ID NO: 417          moltype = AA  length = 49
FEATURE                 Location/Qualifiers
REGION                  1..49
                        note = Ciz1 b-variant peptide comprising an exon 14b/exon
                         15 junction
source                  1..49
                        mol_type = protein
                        organism = synthetic construct
SEQUENCE: 417
EIAGQDEDHF ITVDAVGCFE GDEEEEEDDE DEEEIEVRSR DISREEWKG         49

SEQ ID NO: 418          moltype = AA  length = 48
FEATURE                 Location/Qualifiers
REGION                  1..48
                        note = Ciz1 b-variant peptide comprising an exon 14b/exon
                         15 junction
source                  1..48
```

```
                        mol_type = protein
                        organism = synthetic construct
SEQUENCE: 418
IAGQDEDHFI TVDAVGCFEG DEEEEEDDED EEEIEVRSRD ISREEWKG               48

SEQ ID NO: 419          moltype = AA  length = 47
FEATURE                 Location/Qualifiers
REGION                  1..47
                        note = Ciz1 b-variant peptide comprising an exon 14b/exon
                         15 junction
source                  1..47
                        mol_type = protein
                        organism = synthetic construct
SEQUENCE: 419
AGQDEDHFIT VDAVGCFEGD EEEEEDDEDE EEIEVRSRDI SREEWKG                47

SEQ ID NO: 420          moltype = AA  length = 46
FEATURE                 Location/Qualifiers
REGION                  1..46
                        note = Ciz1 b-variant peptide comprising an exon 14b/exon
                         15 junction
source                  1..46
                        mol_type = protein
                        organism = synthetic construct
SEQUENCE: 420
GQDEDHFITV DAVGCFEGDE EEEEDDEDEE EIEVRSRDIS REEWKG                 46

SEQ ID NO: 421          moltype = AA  length = 45
FEATURE                 Location/Qualifiers
REGION                  1..45
                        note = Ciz1 b-variant peptide comprising an exon 14b/exon
                         15 junction
source                  1..45
                        mol_type = protein
                        organism = synthetic construct
SEQUENCE: 421
QDEDHFITVD AVGCFEGDEE EEEDDEDEEE IEVRSRDISR EEWKG                  45

SEQ ID NO: 422          moltype = AA  length = 44
FEATURE                 Location/Qualifiers
REGION                  1..44
                        note = Ciz1 b-variant peptide comprising an exon 14b/exon
                         15 junction
source                  1..44
                        mol_type = protein
                        organism = synthetic construct
SEQUENCE: 422
DEDHFITVDA VGCFEGDEEE EEDDEDEEEI EVRSRDISRE EWKG                   44

SEQ ID NO: 423          moltype = AA  length = 43
FEATURE                 Location/Qualifiers
REGION                  1..43
                        note = Ciz1 b-variant peptide comprising an exon 14b/exon
                         15 junction
source                  1..43
                        mol_type = protein
                        organism = synthetic construct
SEQUENCE: 423
EDHFITVDAV GCFEGDEEEE EDDEDEEEIE VRSRDISREE WKG                    43

SEQ ID NO: 424          moltype = AA  length = 42
FEATURE                 Location/Qualifiers
REGION                  1..42
                        note = Ciz1 b-variant peptide comprising an exon 14b/exon
                         15 junction
source                  1..42
                        mol_type = protein
                        organism = synthetic construct
SEQUENCE: 424
DHFITVDAVG CFEGDEEEEE DDEDEEEIEV RSRDISREEW KG                     42

SEQ ID NO: 425          moltype = AA  length = 41
FEATURE                 Location/Qualifiers
REGION                  1..41
                        note = Ciz1 b-variant peptide comprising an exon 14b/exon
                         15 junction
source                  1..41
                        mol_type = protein
                        organism = synthetic construct
```

```
SEQUENCE: 425
HFITVDAVGC FEGDEEEEED DEDEEEIEVR SRDISREEWK G                       41

SEQ ID NO: 426          moltype = AA  length = 40
FEATURE                 Location/Qualifiers
REGION                  1..40
                        note = Ciz1 b-variant peptide comprising an exon 14b/exon
                         15 junction
source                  1..40
                        mol_type = protein
                        organism = synthetic construct
SEQUENCE: 426
FITVDAVGCF EGDEEEEEDD EDEEEIEVRS RDISREEWKG                         40

SEQ ID NO: 427          moltype = AA  length = 39
FEATURE                 Location/Qualifiers
REGION                  1..39
                        note = Ciz1 b-variant peptide comprising an exon 14b/exon
                         15 junction
source                  1..39
                        mol_type = protein
                        organism = synthetic construct
SEQUENCE: 427
ITVDAVGCFE GDEEEEEDDE DEEEIEVRSR DISREEWKG                          39

SEQ ID NO: 428          moltype = AA  length = 38
FEATURE                 Location/Qualifiers
REGION                  1..38
                        note = Ciz1 b-variant peptide comprising an exon 14b/exon
                         15 junction
source                  1..38
                        mol_type = protein
                        organism = synthetic construct
SEQUENCE: 428
TVDAVGCFEG DEEEEEDDED EEEIEVRSRD ISREEWKG                           38

SEQ ID NO: 429          moltype = AA  length = 37
FEATURE                 Location/Qualifiers
REGION                  1..37
                        note = Ciz1 b-variant peptide comprising an exon 14b/exon
                         15 junction
source                  1..37
                        mol_type = protein
                        organism = synthetic construct
SEQUENCE: 429
VDAVGCFEGD EEEEEDDEDE EEIEVRSRDI SREEWKG                            37

SEQ ID NO: 430          moltype = AA  length = 36
FEATURE                 Location/Qualifiers
REGION                  1..36
                        note = Ciz1 b-variant peptide comprising an exon 14b/exon
                         15 junction
source                  1..36
                        mol_type = protein
                        organism = synthetic construct
SEQUENCE: 430
DAVGCFEGDE EEEEDDEDEE EIEVRSRDIS REEWKG                             36

SEQ ID NO: 431          moltype = AA  length = 35
FEATURE                 Location/Qualifiers
REGION                  1..35
                        note = Ciz1 b-variant peptide comprising an exon 14b/exon
                         15 junction
source                  1..35
                        mol_type = protein
                        organism = synthetic construct
SEQUENCE: 431
AVGCFEGDEE EEEDDEDEEE IEVRSRDISR EEWKG                              35

SEQ ID NO: 432          moltype = AA  length = 34
FEATURE                 Location/Qualifiers
REGION                  1..34
                        note = Ciz1 b-variant peptide comprising an exon 14b/exon
                         15 junction
source                  1..34
                        mol_type = protein
                        organism = synthetic construct
SEQUENCE: 432
VGCFEGDEEE EEDDEDEEEI EVRSRDISRE EWKG                               34
```

```
SEQ ID NO: 433          moltype = AA  length = 33
FEATURE                 Location/Qualifiers
REGION                  1..33
                        note = Ciz1 b-variant peptide comprising an exon 14b/exon
                         15 junction
source                  1..33
                        mol_type = protein
                        organism = synthetic construct
SEQUENCE: 433
GCFEGDEEEE EDDEDEEEIE VRSRDISREE WKG                                 33

SEQ ID NO: 434          moltype = AA  length = 32
FEATURE                 Location/Qualifiers
REGION                  1..32
                        note = Ciz1 b-variant peptide comprising an exon 14b/exon
                         15 junction
source                  1..32
                        mol_type = protein
                        organism = synthetic construct
SEQUENCE: 434
CFEGDEEEEE DDEDEEEIEV RSRDISREEW KG                                  32

SEQ ID NO: 435          moltype = AA  length = 31
FEATURE                 Location/Qualifiers
REGION                  1..31
                        note = Ciz1 b-variant peptide comprising an exon 14b/exon
                         15 junction
source                  1..31
                        mol_type = protein
                        organism = synthetic construct
SEQUENCE: 435
FEGDEEEEED DEDEEEIEVR SRDISREEWK G                                   31

SEQ ID NO: 436          moltype = AA  length = 30
FEATURE                 Location/Qualifiers
REGION                  1..30
                        note = Ciz1 b-variant peptide comprising an exon 14b/exon
                         15 junction
source                  1..30
                        mol_type = protein
                        organism = synthetic construct
SEQUENCE: 436
EGDEEEEEDD EDEEEIEVRS RDISREEWKG                                     30

SEQ ID NO: 437          moltype = AA  length = 29
FEATURE                 Location/Qualifiers
REGION                  1..29
                        note = Ciz1 b-variant peptide comprising an exon 14b/exon
                         15 junction
source                  1..29
                        mol_type = protein
                        organism = synthetic construct
SEQUENCE: 437
GDEEEEEDDE DEEEIEVRSR DISREEWKG                                      29

SEQ ID NO: 438          moltype = AA  length = 28
FEATURE                 Location/Qualifiers
REGION                  1..28
                        note = Ciz1 b-variant peptide comprising an exon 14b/exon
                         15 junction
source                  1..28
                        mol_type = protein
                        organism = synthetic construct
SEQUENCE: 438
DEEEEEDDED EEEIEVRSRD ISREEWKG                                       28

SEQ ID NO: 439          moltype = AA  length = 27
FEATURE                 Location/Qualifiers
REGION                  1..27
                        note = Ciz1 b-variant peptide comprising an exon 14b/exon
                         15 junction
source                  1..27
                        mol_type = protein
                        organism = synthetic construct
SEQUENCE: 439
EEEEEDDEDE EEIEVRSRDI SREEWKG                                        27

SEQ ID NO: 440          moltype = AA  length = 26
```

```
FEATURE                Location/Qualifiers
REGION                 1..26
                       note = Ciz1 b-variant peptide comprising an exon 14b/exon
                        15 junction
source                 1..26
                       mol_type = protein
                       organism = synthetic construct
SEQUENCE: 440
EEEEDDEDEE EIEVRSRDIS REEWKG                                        26

SEQ ID NO: 441         moltype = AA  length = 25
FEATURE                Location/Qualifiers
REGION                 1..25
                       note = Ciz1 b-variant peptide comprising an exon 14b/exon
                        15 junction
source                 1..25
                       mol_type = protein
                       organism = synthetic construct
SEQUENCE: 441
EEEDDEDEEE IEVRSRDISR EEWKG                                         25

SEQ ID NO: 442         moltype = AA  length = 24
FEATURE                Location/Qualifiers
REGION                 1..24
                       note = Ciz1 b-variant peptide comprising an exon 14b/exon
                        15 junction
source                 1..24
                       mol_type = protein
                       organism = synthetic construct
SEQUENCE: 442
EEDDEDEEEI EVRSRDISRE EWKG                                          24

SEQ ID NO: 443         moltype = AA  length = 23
FEATURE                Location/Qualifiers
REGION                 1..23
                       note = Ciz1 b-variant peptide comprising an exon 14b/exon
                        15 junction
source                 1..23
                       mol_type = protein
                       organism = synthetic construct
SEQUENCE: 443
EDDEDEEEIE VRSRDISREE WKG                                           23

SEQ ID NO: 444         moltype = AA  length = 22
FEATURE                Location/Qualifiers
REGION                 1..22
                       note = Ciz1 b-variant peptide comprising an exon 14b/exon
                        15 junction
source                 1..22
                       mol_type = protein
                       organism = synthetic construct
SEQUENCE: 444
DDEDEEEIEV RSRDISREEW KG                                            22

SEQ ID NO: 445         moltype = AA  length = 21
FEATURE                Location/Qualifiers
REGION                 1..21
                       note = Ciz1 b-variant peptide comprising an exon 14b/exon
                        15 junction
source                 1..21
                       mol_type = protein
                       organism = synthetic construct
SEQUENCE: 445
DEDEEEIEVR SRDISREEWK G                                             21

SEQ ID NO: 446         moltype = AA  length = 20
FEATURE                Location/Qualifiers
REGION                 1..20
                       note = Ciz1 b-variant peptide comprising an exon 14b/exon
                        15 junction
source                 1..20
                       mol_type = protein
                       organism = synthetic construct
SEQUENCE: 446
EDEEEIEVRS RDISREEWKG                                               20

SEQ ID NO: 447         moltype = AA  length = 19
FEATURE                Location/Qualifiers
REGION                 1..19
```

```
                        note = Ciz1 b-variant peptide comprising an exon 14b/exon
                         15 junction
source                  1..19
                        mol_type = protein
                        organism = synthetic construct
SEQUENCE: 447
DEEEIEVRSR DISREEWKG                                             19

SEQ ID NO: 448          moltype = AA  length = 18
FEATURE                 Location/Qualifiers
REGION                  1..18
                        note = Ciz1 b-variant peptide comprising an exon 14b/exon
                         15 junction
source                  1..18
                        mol_type = protein
                        organism = synthetic construct
SEQUENCE: 448
EEEIEVRSRD ISREEWKG                                              18

SEQ ID NO: 449          moltype = AA  length = 17
FEATURE                 Location/Qualifiers
REGION                  1..17
                        note = Ciz1 b-variant peptide comprising an exon 14b/exon
                         15 junction
source                  1..17
                        mol_type = protein
                        organism = synthetic construct
SEQUENCE: 449
EEIEVRSRDI SREEWKG                                               17

SEQ ID NO: 450          moltype = AA  length = 16
FEATURE                 Location/Qualifiers
REGION                  1..16
                        note = Ciz1 b-variant peptide comprising an exon 14b/exon
                         15 junction
source                  1..16
                        mol_type = protein
                        organism = synthetic construct
SEQUENCE: 450
EIEVRSRDIS REEWKG                                                16

SEQ ID NO: 451          moltype = AA  length = 15
FEATURE                 Location/Qualifiers
REGION                  1..15
                        note = Ciz1 b-variant peptide comprising an exon 14b/exon
                         15 junction
source                  1..15
                        mol_type = protein
                        organism = synthetic construct
SEQUENCE: 451
IEVRSRDISR EEWKG                                                 15

SEQ ID NO: 452          moltype = AA  length = 14
FEATURE                 Location/Qualifiers
REGION                  1..14
                        note = Ciz1 b-variant peptide comprising an exon 14b/exon
                         15 junction
source                  1..14
                        mol_type = protein
                        organism = synthetic construct
SEQUENCE: 452
EVRSRDISRE EWKG                                                  14

SEQ ID NO: 453          moltype = AA  length = 50
FEATURE                 Location/Qualifiers
REGION                  1..50
                        note = Ciz1 b-variant peptide comprising an exon 14b/exon
                         15 junction
source                  1..50
                        mol_type = protein
                        organism = synthetic construct
SEQUENCE: 453
EIAGQDEDHF ITVDAVGCFE GDEEEEEDDE DEEEIEVRSR DISREEWKGS           50

SEQ ID NO: 454          moltype = AA  length = 49
FEATURE                 Location/Qualifiers
REGION                  1..49
                        note = Ciz1 b-variant peptide comprising an exon 14b/exon
                         15 junction
```

```
source                  1..49
                        mol_type = protein
                        organism = synthetic construct
SEQUENCE: 454
IAGQDEDHFI TVDAVGCFEG DEEEEEDDED EEEIEVRSRD ISREEWKGS              49

SEQ ID NO: 455          moltype = AA  length = 48
FEATURE                 Location/Qualifiers
REGION                  1..48
                        note = Ciz1 b-variant peptide comprising an exon 14b/exon
                         15 junction
source                  1..48
                        mol_type = protein
                        organism = synthetic construct
SEQUENCE: 455
AGQDEDHFIT VDAVGCFEGD EEEEEDDEDE EEIEVRSRDI SREEWKGS               48

SEQ ID NO: 456          moltype = AA  length = 47
FEATURE                 Location/Qualifiers
REGION                  1..47
                        note = Ciz1 b-variant peptide comprising an exon 14b/exon
                         15 junction
source                  1..47
                        mol_type = protein
                        organism = synthetic construct
SEQUENCE: 456
GQDEDHFITV DAVGCFEGDE EEEEDDEDEE EIEVRSRDIS REEWKGS                47

SEQ ID NO: 457          moltype = AA  length = 46
FEATURE                 Location/Qualifiers
REGION                  1..46
                        note = Ciz1 b-variant peptide comprising an exon 14b/exon
                         15 junction
source                  1..46
                        mol_type = protein
                        organism = synthetic construct
SEQUENCE: 457
QDEDHFITVD AVGCFEGDEE EEEDDEDEEE IEVRSRDISR EEWKGS                 46

SEQ ID NO: 458          moltype = AA  length = 45
FEATURE                 Location/Qualifiers
REGION                  1..45
                        note = Ciz1 b-variant peptide comprising an exon 14b/exon
                         15 junction
source                  1..45
                        mol_type = protein
                        organism = synthetic construct
SEQUENCE: 458
DEDHFITVDA VGCFEGDEEE EEDDEDEEEI EVRSRDISRE EWKGS                  45

SEQ ID NO: 459          moltype = AA  length = 44
FEATURE                 Location/Qualifiers
REGION                  1..44
                        note = Ciz1 b-variant peptide comprising an exon 14b/exon
                         15 junction
source                  1..44
                        mol_type = protein
                        organism = synthetic construct
SEQUENCE: 459
EDHFITVDAV GCFEGDEEEE EDDEDEEEIE VRSRDISREE WKGS                   44

SEQ ID NO: 460          moltype = AA  length = 43
FEATURE                 Location/Qualifiers
REGION                  1..43
                        note = Ciz1 b-variant peptide comprising an exon 14b/exon
                         15 junction
source                  1..43
                        mol_type = protein
                        organism = synthetic construct
SEQUENCE: 460
DHFITVDAVG CFEGDEEEEE DDEDEEEIEV RSRDISREEW KGS                    43

SEQ ID NO: 461          moltype = AA  length = 42
FEATURE                 Location/Qualifiers
REGION                  1..42
                        note = Ciz1 b-variant peptide comprising an exon 14b/exon
                         15 junction
source                  1..42
                        mol_type = protein
```

```
                         organism = synthetic construct
SEQUENCE: 461
HFITVDAVGC FEGDEEEEED DEDEEEIEVR SRDISREEWK GS                      42

SEQ ID NO: 462           moltype = AA  length = 41
FEATURE                  Location/Qualifiers
REGION                   1..41
                         note = Ciz1 b-variant peptide comprising an exon 14b/exon
                          15 junction
source                   1..41
                         mol_type = protein
                         organism = synthetic construct
SEQUENCE: 462
FITVDAVGCF EGDEEEEEDD EDEEEIEVRS RDISREEWKG S                       41

SEQ ID NO: 463           moltype = AA  length = 40
FEATURE                  Location/Qualifiers
REGION                   1..40
                         note = Ciz1 b-variant peptide comprising an exon 14b/exon
                          15 junction
source                   1..40
                         mol_type = protein
                         organism = synthetic construct
SEQUENCE: 463
ITVDAVGCFE GDEEEEEDDE DEEEIEVRSR DISREEWKGS                         40

SEQ ID NO: 464           moltype = AA  length = 39
FEATURE                  Location/Qualifiers
REGION                   1..39
                         note = Ciz1 b-variant peptide comprising an exon 14b/exon
                          15 junction
source                   1..39
                         mol_type = protein
                         organism = synthetic construct
SEQUENCE: 464
TVDAVGCFEG DEEEEEDDED EEEIEVRSRD ISREEWKGS                          39

SEQ ID NO: 465           moltype = AA  length = 38
FEATURE                  Location/Qualifiers
REGION                   1..38
                         note = Ciz1 b-variant peptide comprising an exon 14b/exon
                          15 junction
source                   1..38
                         mol_type = protein
                         organism = synthetic construct
SEQUENCE: 465
VDAVGCFEGD EEEEEDDEDE EEIEVRSRDI SREEWKGS                           38

SEQ ID NO: 466           moltype = AA  length = 37
FEATURE                  Location/Qualifiers
REGION                   1..37
                         note = Ciz1 b-variant peptide comprising an exon 14b/exon
                          15 junction
source                   1..37
                         mol_type = protein
                         organism = synthetic construct
SEQUENCE: 466
DAVGCFEGDE EEEEDDEDEE EIEVRSRDIS REEWKGS                            37

SEQ ID NO: 467           moltype = AA  length = 36
FEATURE                  Location/Qualifiers
REGION                   1..36
                         note = Ciz1 b-variant peptide comprising an exon 14b/exon
                          15 junction
source                   1..36
                         mol_type = protein
                         organism = synthetic construct
SEQUENCE: 467
AVGCFEGDEE EEEDDEDEEE IEVRSRDISR EEWKGS                             36

SEQ ID NO: 468           moltype = AA  length = 35
FEATURE                  Location/Qualifiers
REGION                   1..35
                         note = Ciz1 b-variant peptide comprising an exon 14b/exon
                          15 junction
source                   1..35
                         mol_type = protein
                         organism = synthetic construct
SEQUENCE: 468
```

```
VGCFEGDEEE EEDDEDEEEI EVRSRDISRE EWKGS                          35

SEQ ID NO: 469         moltype = AA  length = 34
FEATURE                Location/Qualifiers
REGION                 1..34
                       note = Ciz1 b-variant peptide comprising an exon 14b/exon
                        15 junction
source                 1..34
                       mol_type = protein
                       organism = synthetic construct
SEQUENCE: 469
GCFEGDEEEE EDDEDEEEIE VRSRDISREE WKGS                           34

SEQ ID NO: 470         moltype = AA  length = 33
FEATURE                Location/Qualifiers
REGION                 1..33
                       note = Ciz1 b-variant peptide comprising an exon 14b/exon
                        15 junction
source                 1..33
                       mol_type = protein
                       organism = synthetic construct
SEQUENCE: 470
CFEGDEEEEE DDEDEEEIEV RSRDISREEW KGS                            33

SEQ ID NO: 471         moltype = AA  length = 32
FEATURE                Location/Qualifiers
REGION                 1..32
                       note = Ciz1 b-variant peptide comprising an exon 14b/exon
                        15 junction
source                 1..32
                       mol_type = protein
                       organism = synthetic construct
SEQUENCE: 471
FEGDEEEEED DEDEEEIEVR SRDISREEWK GS                             32

SEQ ID NO: 472         moltype = AA  length = 31
FEATURE                Location/Qualifiers
REGION                 1..31
                       note = Ciz1 b-variant peptide comprising an exon 14b/exon
                        15 junction
source                 1..31
                       mol_type = protein
                       organism = synthetic construct
SEQUENCE: 472
EGDEEEEEDD EDEEEIEVRS RDISREEWKG S                              31

SEQ ID NO: 473         moltype = AA  length = 30
FEATURE                Location/Qualifiers
REGION                 1..30
                       note = Ciz1 b-variant peptide comprising an exon 14b/exon
                        15 junction
source                 1..30
                       mol_type = protein
                       organism = synthetic construct
SEQUENCE: 473
GDEEEEEDDE DEEEIEVRSR DISREEWKGS                                30

SEQ ID NO: 474         moltype = AA  length = 29
FEATURE                Location/Qualifiers
REGION                 1..29
                       note = Ciz1 b-variant peptide comprising an exon 14b/exon
                        15 junction
source                 1..29
                       mol_type = protein
                       organism = synthetic construct
SEQUENCE: 474
DEEEEEDDED EEEIEVRSRD ISREEWKGS                                 29

SEQ ID NO: 475         moltype = AA  length = 28
FEATURE                Location/Qualifiers
REGION                 1..28
                       note = Ciz1 b-variant peptide comprising an exon 14b/exon
                        15 junction
source                 1..28
                       mol_type = protein
                       organism = synthetic construct
SEQUENCE: 475
EEEEEDDEDE EEIEVRSRDI SREEWKGS                                  28
```

```
SEQ ID NO: 476         moltype = AA  length = 27
FEATURE                Location/Qualifiers
REGION                 1..27
                       note = Ciz1 b-variant peptide comprising an exon 14b/exon
                        15 junction
source                 1..27
                       mol_type = protein
                       organism = synthetic construct
SEQUENCE: 476
EEEEDDEDEE EIEVRSRDIS REEWKGS                                        27

SEQ ID NO: 477         moltype = AA  length = 26
FEATURE                Location/Qualifiers
REGION                 1..26
                       note = Ciz1 b-variant peptide comprising an exon 14b/exon
                        15 junction
source                 1..26
                       mol_type = protein
                       organism = synthetic construct
SEQUENCE: 477
EEEDDEDEEE IEVRSRDISR EEWKGS                                         26

SEQ ID NO: 478         moltype = AA  length = 25
FEATURE                Location/Qualifiers
REGION                 1..25
                       note = Ciz1 b-variant peptide comprising an exon 14b/exon
                        15 junction
source                 1..25
                       mol_type = protein
                       organism = synthetic construct
SEQUENCE: 478
EEDDEDEEEI EVRSRDISRE EWKGS                                          25

SEQ ID NO: 479         moltype = AA  length = 24
FEATURE                Location/Qualifiers
REGION                 1..24
                       note = Ciz1 b-variant peptide comprising an exon 14b/exon
                        15 junction
source                 1..24
                       mol_type = protein
                       organism = synthetic construct
SEQUENCE: 479
EDDEDEEEIE VRSRDISREE WKGS                                           24

SEQ ID NO: 480         moltype = AA  length = 23
FEATURE                Location/Qualifiers
REGION                 1..23
                       note = Ciz1 b-variant peptide comprising an exon 14b/exon
                        15 junction
source                 1..23
                       mol_type = protein
                       organism = synthetic construct
SEQUENCE: 480
DDEDEEEIEV RSRDISREEW KGS                                            23

SEQ ID NO: 481         moltype = AA  length = 22
FEATURE                Location/Qualifiers
REGION                 1..22
                       note = Ciz1 b-variant peptide comprising an exon 14b/exon
                        15 junction
source                 1..22
                       mol_type = protein
                       organism = synthetic construct
SEQUENCE: 481
DEDEEEIEVR SRDISREEWK GS                                             22

SEQ ID NO: 482         moltype = AA  length = 21
FEATURE                Location/Qualifiers
REGION                 1..21
                       note = Ciz1 b-variant peptide comprising an exon 14b/exon
                        15 junction
source                 1..21
                       mol_type = protein
                       organism = synthetic construct
SEQUENCE: 482
EDEEEIEVRS RDISREEWKG S                                              21

SEQ ID NO: 483         moltype = AA  length = 20
FEATURE                Location/Qualifiers
```

```
REGION                  1..20
                        note = Ciz1 b-variant peptide comprising an exon 14b/exon
                         15 junction
source                  1..20
                        mol_type = protein
                        organism = synthetic construct
SEQUENCE: 483
DEEEIEVRSR DISREEWKGS                                                20

SEQ ID NO: 484          moltype = AA  length = 19
FEATURE                 Location/Qualifiers
REGION                  1..19
                        note = Ciz1 b-variant peptide comprising an exon 14b/exon
                         15 junction
source                  1..19
                        mol_type = protein
                        organism = synthetic construct
SEQUENCE: 484
EEEIEVRSRD ISREEWKGS                                                 19

SEQ ID NO: 485          moltype = AA  length = 18
FEATURE                 Location/Qualifiers
REGION                  1..18
                        note = Ciz1 b-variant peptide comprising an exon 14b/exon
                         15 junction
source                  1..18
                        mol_type = protein
                        organism = synthetic construct
SEQUENCE: 485
EEIEVRSRDI SREEWKGS                                                  18

SEQ ID NO: 486          moltype = AA  length = 17
FEATURE                 Location/Qualifiers
REGION                  1..17
                        note = Ciz1 b-variant peptide comprising an exon 14b/exon
                         15 junction
source                  1..17
                        mol_type = protein
                        organism = synthetic construct
SEQUENCE: 486
EIEVRSRDIS REEWKGS                                                   17

SEQ ID NO: 487          moltype = AA  length = 16
FEATURE                 Location/Qualifiers
REGION                  1..16
                        note = Ciz1 b-variant peptide comprising an exon 14b/exon
                         15 junction
source                  1..16
                        mol_type = protein
                        organism = synthetic construct
SEQUENCE: 487
IEVRSRDISR EEWKGS                                                    16

SEQ ID NO: 488          moltype = AA  length = 15
FEATURE                 Location/Qualifiers
REGION                  1..15
                        note = Ciz1 b-variant peptide comprising an exon 14b/exon
                         15 junction
source                  1..15
                        mol_type = protein
                        organism = synthetic construct
SEQUENCE: 488
EVRSRDISRE EWKGS                                                     15

SEQ ID NO: 489          moltype = AA  length = 51
FEATURE                 Location/Qualifiers
REGION                  1..51
                        note = Ciz1 b-variant peptide comprising an exon 14b/exon
                         15 junction
source                  1..51
                        mol_type = protein
                        organism = synthetic construct
SEQUENCE: 489
EIAGQDEDHF ITVDAVGCFE GDEEEEEDDE DEEEIEVRSR DISREEWKGS E             51

SEQ ID NO: 490          moltype = AA  length = 50
FEATURE                 Location/Qualifiers
REGION                  1..50
                        note = Ciz1 b-variant peptide comprising an exon 14b/exon
```

```
                         15 junction
source                  1..50
                        mol_type = protein
                        organism = synthetic construct
SEQUENCE: 490
IAGQDEDHFI TVDAVGCFEG DEEEEEDDED EEEIEVRSRD ISREEWKGSE             50

SEQ ID NO: 491          moltype = AA  length = 49
FEATURE                 Location/Qualifiers
REGION                  1..49
                        note = Ciz1 b-variant peptide comprising an exon 14b/exon
                         15 junction
source                  1..49
                        mol_type = protein
                        organism = synthetic construct
SEQUENCE: 491
AGQDEDHFIT VDAVGCFEGD EEEEEDDEDE EEIEVRSRDI SREEWKGSE              49

SEQ ID NO: 492          moltype = AA  length = 48
FEATURE                 Location/Qualifiers
REGION                  1..48
                        note = Ciz1 b-variant peptide comprising an exon 14b/exon
                         15 junction
source                  1..48
                        mol_type = protein
                        organism = synthetic construct
SEQUENCE: 492
GQDEDHFITV DAVGCFEGDE EEEEDDEDEE EIEVRSRDIS REEWKGSE               48

SEQ ID NO: 493          moltype = AA  length = 47
FEATURE                 Location/Qualifiers
REGION                  1..47
                        note = Ciz1 b-variant peptide comprising an exon 14b/exon
                         15 junction
source                  1..47
                        mol_type = protein
                        organism = synthetic construct
SEQUENCE: 493
QDEDHFITVD AVGCFEGDEE EEEDDEDEEE IEVRSRDISR EEWKGSE                47

SEQ ID NO: 494          moltype = AA  length = 46
FEATURE                 Location/Qualifiers
REGION                  1..46
                        note = Ciz1 b-variant peptide comprising an exon 14b/exon
                         15 junction
source                  1..46
                        mol_type = protein
                        organism = synthetic construct
SEQUENCE: 494
DEDHFITVDA VGCFEGDEEE EEDDEDEEEI EVRSRDISRE EWKGSE                 46

SEQ ID NO: 495          moltype = AA  length = 45
FEATURE                 Location/Qualifiers
REGION                  1..45
                        note = Ciz1 b-variant peptide comprising an exon 14b/exon
                         15 junction
source                  1..45
                        mol_type = protein
                        organism = synthetic construct
SEQUENCE: 495
EDHFITVDAV GCFEGDEEEE EDDEDEEEIE VRSRDISREE WKGSE                  45

SEQ ID NO: 496          moltype = AA  length = 44
FEATURE                 Location/Qualifiers
REGION                  1..44
                        note = Ciz1 b-variant peptide comprising an exon 14b/exon
                         15 junction
source                  1..44
                        mol_type = protein
                        organism = synthetic construct
SEQUENCE: 496
DHFITVDAVG CFEGDEEEEE DDEDEEEIEV RSRDISREEW KGSE                   44

SEQ ID NO: 497          moltype = AA  length = 43
FEATURE                 Location/Qualifiers
REGION                  1..43
                        note = Ciz1 b-variant peptide comprising an exon 14b/exon
                         15 junction
source                  1..43
```

```
                        mol_type = protein
                        organism = synthetic construct
SEQUENCE: 497
HFITVDAVGC FEGDEEEEED DEDEEEIEVR SRDISREEWK GSE                      43

SEQ ID NO: 498          moltype = AA  length = 42
FEATURE                 Location/Qualifiers
REGION                  1..42
                        note = Ciz1 b-variant peptide comprising an exon 14b/exon
                         15 junction
source                  1..42
                        mol_type = protein
                        organism = synthetic construct
SEQUENCE: 498
FITVDAVGCF EGDEEEEEDD EDEEEIEVRS RDISREEWKG SE                       42

SEQ ID NO: 499          moltype = AA  length = 41
FEATURE                 Location/Qualifiers
REGION                  1..41
                        note = Ciz1 b-variant peptide comprising an exon 14b/exon
                         15 junction
source                  1..41
                        mol_type = protein
                        organism = synthetic construct
SEQUENCE: 499
ITVDAVGCFE GDEEEEEDDE DEEEIEVRSR DISREEWKGS E                        41

SEQ ID NO: 500          moltype = AA  length = 40
FEATURE                 Location/Qualifiers
REGION                  1..40
                        note = Ciz1 b-variant peptide comprising an exon 14b/exon
                         15 junction
source                  1..40
                        mol_type = protein
                        organism = synthetic construct
SEQUENCE: 500
TVDAVGCFEG DEEEEEDDED EEEIEVRSRD ISREEWKGSE                          40

SEQ ID NO: 501          moltype = AA  length = 39
FEATURE                 Location/Qualifiers
REGION                  1..39
                        note = Ciz1 b-variant peptide comprising an exon 14b/exon
                         15 junction
source                  1..39
                        mol_type = protein
                        organism = synthetic construct
SEQUENCE: 501
VDAVGCFEGD EEEEEDDEDE EEIEVRSRDI SREEWKGSE                           39

SEQ ID NO: 502          moltype = AA  length = 38
FEATURE                 Location/Qualifiers
REGION                  1..38
                        note = Ciz1 b-variant peptide comprising an exon 14b/exon
                         15 junction
source                  1..38
                        mol_type = protein
                        organism = synthetic construct
SEQUENCE: 502
DAVGCFEGDE EEEEDDEDEE EIEVRSRDIS REEWKGSE                            38

SEQ ID NO: 503          moltype = AA  length = 37
FEATURE                 Location/Qualifiers
REGION                  1..37
                        note = Ciz1 b-variant peptide comprising an exon 14b/exon
                         15 junction
source                  1..37
                        mol_type = protein
                        organism = synthetic construct
SEQUENCE: 503
AVGCFEGDEE EEEDDEDEEE IEVRSRDISR EEWKGSE                             37

SEQ ID NO: 504          moltype = AA  length = 36
FEATURE                 Location/Qualifiers
REGION                  1..36
                        note = Ciz1 b-variant peptide comprising an exon 14b/exon
                         15 junction
source                  1..36
                        mol_type = protein
                        organism = synthetic construct
```

```
SEQUENCE: 504
VGCFEGDEEE EEDDEDEEEI EVRSRDISRE EWKGSE                         36

SEQ ID NO: 505         moltype = AA  length = 35
FEATURE                Location/Qualifiers
REGION                 1..35
                       note = Ciz1 b-variant peptide comprising an exon 14b/exon
                        15 junction
source                 1..35
                       mol_type = protein
                       organism = synthetic construct
SEQUENCE: 505
GCFEGDEEEE EDDEDEEEIE VRSRDISREE WKGSE                          35

SEQ ID NO: 506         moltype = AA  length = 34
FEATURE                Location/Qualifiers
REGION                 1..34
                       note = Ciz1 b-variant peptide comprising an exon 14b/exon
                        15 junction
source                 1..34
                       mol_type = protein
                       organism = synthetic construct
SEQUENCE: 506
CFEGDEEEEE DDEDEEEIEV RSRDISREEW KGSE                           34

SEQ ID NO: 507         moltype = AA  length = 33
FEATURE                Location/Qualifiers
REGION                 1..33
                       note = Ciz1 b-variant peptide comprising an exon 14b/exon
                        15 junction
source                 1..33
                       mol_type = protein
                       organism = synthetic construct
SEQUENCE: 507
FEGDEEEEED DEDEEEIEVR SRDISREEWK GSE                            33

SEQ ID NO: 508         moltype = AA  length = 32
FEATURE                Location/Qualifiers
REGION                 1..32
                       note = Ciz1 b-variant peptide comprising an exon 14b/exon
                        15 junction
source                 1..32
                       mol_type = protein
                       organism = synthetic construct
SEQUENCE: 508
EGDEEEEEDD EDEEEIEVRS RDISREEWKG SE                             32

SEQ ID NO: 509         moltype = AA  length = 31
FEATURE                Location/Qualifiers
REGION                 1..31
                       note = Ciz1 b-variant peptide comprising an exon 14b/exon
                        15 junction
source                 1..31
                       mol_type = protein
                       organism = synthetic construct
SEQUENCE: 509
GDEEEEEDDE DEEEIEVRSR DISREEWKGS E                              31

SEQ ID NO: 510         moltype = AA  length = 30
FEATURE                Location/Qualifiers
REGION                 1..30
                       note = Ciz1 b-variant peptide comprising an exon 14b/exon
                        15 junction
source                 1..30
                       mol_type = protein
                       organism = synthetic construct
SEQUENCE: 510
DEEEEEDDED EEEIEVRSRD ISREEWKGSE                                30

SEQ ID NO: 511         moltype = AA  length = 29
FEATURE                Location/Qualifiers
REGION                 1..29
                       note = Ciz1 b-variant peptide comprising an exon 14b/exon
                        15 junction
source                 1..29
                       mol_type = protein
                       organism = synthetic construct
SEQUENCE: 511
EEEEEDDEDE EEIEVRSRDI SREEWKGSE                                 29
```

```
SEQ ID NO: 512         moltype = AA  length = 28
FEATURE                Location/Qualifiers
REGION                 1..28
                       note = Ciz1 b-variant peptide comprising an exon 14b/exon
                        15 junction
source                 1..28
                       mol_type = protein
                       organism = synthetic construct
SEQUENCE: 512
EEEEDDEDEE EIEVRSRDIS REEWKGSE                                        28

SEQ ID NO: 513         moltype = AA  length = 27
FEATURE                Location/Qualifiers
REGION                 1..27
                       note = Ciz1 b-variant peptide comprising an exon 14b/exon
                        15 junction
source                 1..27
                       mol_type = protein
                       organism = synthetic construct
SEQUENCE: 513
EEEDDEDEEE IEVRSRDISR EEWKGSE                                         27

SEQ ID NO: 514         moltype = AA  length = 26
FEATURE                Location/Qualifiers
REGION                 1..26
                       note = Ciz1 b-variant peptide comprising an exon 14b/exon
                        15 junction
source                 1..26
                       mol_type = protein
                       organism = synthetic construct
SEQUENCE: 514
EEDDEDEEEI EVRSRDISRE EWKGSE                                          26

SEQ ID NO: 515         moltype = AA  length = 25
FEATURE                Location/Qualifiers
REGION                 1..25
                       note = Ciz1 b-variant peptide comprising an exon 14b/exon
                        15 junction
source                 1..25
                       mol_type = protein
                       organism = synthetic construct
SEQUENCE: 515
EDDEDEEEIE VRSRDISREE WKGSE                                           25

SEQ ID NO: 516         moltype = AA  length = 24
FEATURE                Location/Qualifiers
REGION                 1..24
                       note = Ciz1 b-variant peptide comprising an exon 14b/exon
                        15 junction
source                 1..24
                       mol_type = protein
                       organism = synthetic construct
SEQUENCE: 516
DDEDEEEIEV RSRDISREEW KGSE                                            24

SEQ ID NO: 517         moltype = AA  length = 23
FEATURE                Location/Qualifiers
REGION                 1..23
                       note = Ciz1 b-variant peptide comprising an exon 14b/exon
                        15 junction
source                 1..23
                       mol_type = protein
                       organism = synthetic construct
SEQUENCE: 517
DEDEEEIEVR SRDISREEWK GSE                                             23

SEQ ID NO: 518         moltype = AA  length = 22
FEATURE                Location/Qualifiers
REGION                 1..22
                       note = Ciz1 b-variant peptide comprising an exon 14b/exon
                        15 junction
source                 1..22
                       mol_type = protein
                       organism = synthetic construct
SEQUENCE: 518
EDEEEIEVRS RDISREEWKG SE                                              22

SEQ ID NO: 519         moltype = AA  length = 21
```

```
FEATURE                 Location/Qualifiers
REGION                  1..21
                        note = Ciz1 b-variant peptide comprising an exon 14b/exon
                         15 junction
source                  1..21
                        mol_type = protein
                        organism = synthetic construct
SEQUENCE: 519
DEEEIEVRSR DISREEWKGS E                                            21

SEQ ID NO: 520          moltype = AA  length = 20
FEATURE                 Location/Qualifiers
REGION                  1..20
                        note = Ciz1 b-variant peptide comprising an exon 14b/exon
                         15 junction
source                  1..20
                        mol_type = protein
                        organism = synthetic construct
SEQUENCE: 520
EEEIEVRSRD ISREEWKGSE                                              20

SEQ ID NO: 521          moltype = AA  length = 19
FEATURE                 Location/Qualifiers
REGION                  1..19
                        note = Ciz1 b-variant peptide comprising an exon 14b/exon
                         15 junction
source                  1..19
                        mol_type = protein
                        organism = synthetic construct
SEQUENCE: 521
EEIEVRSRDI SREEWKGSE                                               19

SEQ ID NO: 522          moltype = AA  length = 18
FEATURE                 Location/Qualifiers
REGION                  1..18
                        note = Ciz1 b-variant peptide comprising an exon 14b/exon
                         15 junction
source                  1..18
                        mol_type = protein
                        organism = synthetic construct
SEQUENCE: 522
EIEVRSRDIS REEWKGSE                                                18

SEQ ID NO: 523          moltype = AA  length = 17
FEATURE                 Location/Qualifiers
REGION                  1..17
                        note = Ciz1 b-variant peptide comprising an exon 14b/exon
                         15 junction
source                  1..17
                        mol_type = protein
                        organism = synthetic construct
SEQUENCE: 523
IEVRSRDISR EEWKGSE                                                 17

SEQ ID NO: 524          moltype = AA  length = 16
FEATURE                 Location/Qualifiers
REGION                  1..16
                        note = Ciz1 b-variant peptide comprising an exon 14b/exon
                         15 junction
source                  1..16
                        mol_type = protein
                        organism = synthetic construct
SEQUENCE: 524
EVRSRDISRE EWKGSE                                                  16

SEQ ID NO: 525          moltype = AA  length = 52
FEATURE                 Location/Qualifiers
REGION                  1..52
                        note = Ciz1 b-variant peptide comprising an exon 14b/exon
                         15 junction
source                  1..52
                        mol_type = protein
                        organism = synthetic construct
SEQUENCE: 525
EIAGQDEDHF ITVDAVGCFE GDEEEEEDDE DEEEIEVRSR DISREEWKGS ET          52

SEQ ID NO: 526          moltype = AA  length = 51
FEATURE                 Location/Qualifiers
REGION                  1..51
```

```
                        note = Ciz1 b-variant peptide comprising an exon 14b/exon
                         15 junction
source                  1..51
                        mol_type = protein
                        organism = synthetic construct
SEQUENCE: 526
IAGQDEDHFI TVDAVGCFEG DEEEEEDDED EEEIEVRSRD ISREEWKGSE T           51

SEQ ID NO: 527          moltype = AA  length = 50
FEATURE                 Location/Qualifiers
REGION                  1..50
                        note = Ciz1 b-variant peptide comprising an exon 14b/exon
                         15 junction
source                  1..50
                        mol_type = protein
                        organism = synthetic construct
SEQUENCE: 527
AGQDEDHFIT VDAVGCFEGD EEEEEDDEDE EEIEVRSRDI SREEWKGSET             50

SEQ ID NO: 528          moltype = AA  length = 49
FEATURE                 Location/Qualifiers
REGION                  1..49
                        note = Ciz1 b-variant peptide comprising an exon 14b/exon
                         15 junction
source                  1..49
                        mol_type = protein
                        organism = synthetic construct
SEQUENCE: 528
GQDEDHFITV DAVGCFEGDE EEEEDDEDEE EIEVRSRDIS REEWKGSET              49

SEQ ID NO: 529          moltype = AA  length = 48
FEATURE                 Location/Qualifiers
REGION                  1..48
                        note = Ciz1 b-variant peptide comprising an exon 14b/exon
                         15 junction
source                  1..48
                        mol_type = protein
                        organism = synthetic construct
SEQUENCE: 529
QDEDHFITVD AVGCFEGDEE EEEDDEDEEE IEVRSRDISR EEWKGSET               48

SEQ ID NO: 530          moltype = AA  length = 47
FEATURE                 Location/Qualifiers
REGION                  1..47
                        note = Ciz1 b-variant peptide comprising an exon 14b/exon
                         15 junction
source                  1..47
                        mol_type = protein
                        organism = synthetic construct
SEQUENCE: 530
DEDHFITVDA VGCFEGDEEE EEDDEDEEEI EVRSRDISRE EWKGSET                47

SEQ ID NO: 531          moltype = AA  length = 46
FEATURE                 Location/Qualifiers
REGION                  1..46
                        note = Ciz1 b-variant peptide comprising an exon 14b/exon
                         15 junction
source                  1..46
                        mol_type = protein
                        organism = synthetic construct
SEQUENCE: 531
EDHFITVDAV GCFEGDEEEE EDDEDEEEIE VRSRDISREE WKGSET                 46

SEQ ID NO: 532          moltype = AA  length = 45
FEATURE                 Location/Qualifiers
REGION                  1..45
                        note = Ciz1 b-variant peptide comprising an exon 14b/exon
                         15 junction
source                  1..45
                        mol_type = protein
                        organism = synthetic construct
SEQUENCE: 532
DHFITVDAVG CFEGDEEEEE DDEDEEEIEV RSRDISREEW KGSET                  45

SEQ ID NO: 533          moltype = AA  length = 44
FEATURE                 Location/Qualifiers
REGION                  1..44
                        note = Ciz1 b-variant peptide comprising an exon 14b/exon
                         15 junction
```

```
source                  1..44
                        mol_type = protein
                        organism = synthetic construct
SEQUENCE: 533
HFITVDAVGC FEGDEEEEED DEDEEEIEVR SRDISREEWK GSET                    44

SEQ ID NO: 534          moltype = AA  length = 43
FEATURE                 Location/Qualifiers
REGION                  1..43
                        note = Ciz1 b-variant peptide comprising an exon 14b/exon
                         15 junction
source                  1..43
                        mol_type = protein
                        organism = synthetic construct
SEQUENCE: 534
FITVDAVGCF EGDEEEEEDD EDEEEIEVRS RDISREEWKG SET                     43

SEQ ID NO: 535          moltype = AA  length = 42
FEATURE                 Location/Qualifiers
REGION                  1..42
                        note = Ciz1 b-variant peptide comprising an exon 14b/exon
                         15 junction
source                  1..42
                        mol_type = protein
                        organism = synthetic construct
SEQUENCE: 535
ITVDAVGCFE GDEEEEEDDE DEEEIEVRSR DISREEWKGS ET                      42

SEQ ID NO: 536          moltype = AA  length = 41
FEATURE                 Location/Qualifiers
REGION                  1..41
                        note = Ciz1 b-variant peptide comprising an exon 14b/exon
                         15 junction
source                  1..41
                        mol_type = protein
                        organism = synthetic construct
SEQUENCE: 536
TVDAVGCFEG DEEEEEDDED EEEIEVRSRD ISREEWKGSE T                       41

SEQ ID NO: 537          moltype = AA  length = 40
FEATURE                 Location/Qualifiers
REGION                  1..40
                        note = Ciz1 b-variant peptide comprising an exon 14b/exon
                         15 junction
source                  1..40
                        mol_type = protein
                        organism = synthetic construct
SEQUENCE: 537
VDAVGCFEGD EEEEEDDEDE EEIEVRSRDI SREEWKGSET                         40

SEQ ID NO: 538          moltype = AA  length = 39
FEATURE                 Location/Qualifiers
REGION                  1..39
                        note = Ciz1 b-variant peptide comprising an exon 14b/exon
                         15 junction
source                  1..39
                        mol_type = protein
                        organism = synthetic construct
SEQUENCE: 538
DAVGCFEGDE EEEEDDEDEE EIEVRSRDIS REEWKGSET                          39

SEQ ID NO: 539          moltype = AA  length = 38
FEATURE                 Location/Qualifiers
REGION                  1..38
                        note = Ciz1 b-variant peptide comprising an exon 14b/exon
                         15 junction
source                  1..38
                        mol_type = protein
                        organism = synthetic construct
SEQUENCE: 539
AVGCFEGDEE EEEDDEDEEE IEVRSRDISR EEWKGSET                           38

SEQ ID NO: 540          moltype = AA  length = 37
FEATURE                 Location/Qualifiers
REGION                  1..37
                        note = Ciz1 b-variant peptide comprising an exon 14b/exon
                         15 junction
source                  1..37
                        mol_type = protein
```

```
                       organism = synthetic construct
SEQUENCE: 540
VGCFEGDEEE EEDDEDEEEI EVRSRDISRE EWKGSET                           37

SEQ ID NO: 541         moltype = AA  length = 36
FEATURE                Location/Qualifiers
REGION                 1..36
                       note = Ciz1 b-variant peptide comprising an exon 14b/exon
                        15 junction
source                 1..36
                       mol_type = protein
                       organism = synthetic construct
SEQUENCE: 541
GCFEGDEEEE EDDEDEEEIE VRSRDISREE WKGSET                            36

SEQ ID NO: 542         moltype = AA  length = 35
FEATURE                Location/Qualifiers
REGION                 1..35
                       note = Ciz1 b-variant peptide comprising an exon 14b/exon
                        15 junction
source                 1..35
                       mol_type = protein
                       organism = synthetic construct
SEQUENCE: 542
CFEGDEEEEE DDEDEEEIEV RSRDISREEW KGSET                             35

SEQ ID NO: 543         moltype = AA  length = 34
FEATURE                Location/Qualifiers
REGION                 1..34
                       note = Ciz1 b-variant peptide comprising an exon 14b/exon
                        15 junction
source                 1..34
                       mol_type = protein
                       organism = synthetic construct
SEQUENCE: 543
FEGDEEEEED DEDEEEIEVR SRDISREEWK GSET                              34

SEQ ID NO: 544         moltype = AA  length = 33
FEATURE                Location/Qualifiers
REGION                 1..33
                       note = Ciz1 b-variant peptide comprising an exon 14b/exon
                        15 junction
source                 1..33
                       mol_type = protein
                       organism = synthetic construct
SEQUENCE: 544
EGDEEEEEDD EDEEEIEVRS RDISREEWKG SET                               33

SEQ ID NO: 545         moltype = AA  length = 32
FEATURE                Location/Qualifiers
REGION                 1..32
                       note = Ciz1 b-variant peptide comprising an exon 14b/exon
                        15 junction
source                 1..32
                       mol_type = protein
                       organism = synthetic construct
SEQUENCE: 545
GDEEEEEDDE DEEEIEVRSR DISREEWKGS ET                                32

SEQ ID NO: 546         moltype = AA  length = 31
FEATURE                Location/Qualifiers
REGION                 1..31
                       note = Ciz1 b-variant peptide comprising an exon 14b/exon
                        15 junction
source                 1..31
                       mol_type = protein
                       organism = synthetic construct
SEQUENCE: 546
DEEEEEDDED EEEIEVRSRD ISREEWKGSE T                                 31

SEQ ID NO: 547         moltype = AA  length = 30
FEATURE                Location/Qualifiers
REGION                 1..30
                       note = Ciz1 b-variant peptide comprising an exon 14b/exon
                        15 junction
source                 1..30
                       mol_type = protein
                       organism = synthetic construct
SEQUENCE: 547
```

```
EEEEEDDEDE EEIEVRSRDI SREEWKGSET                                    30

SEQ ID NO: 548          moltype = AA  length = 29
FEATURE                 Location/Qualifiers
REGION                  1..29
                        note = Ciz1 b-variant peptide comprising an exon 14b/exon
                         15 junction
source                  1..29
                        mol_type = protein
                        organism = synthetic construct
SEQUENCE: 548
EEEEDDEDEE EIEVRSRDIS REEWKGSET                                     29

SEQ ID NO: 549          moltype = AA  length = 28
FEATURE                 Location/Qualifiers
REGION                  1..28
                        note = Ciz1 b-variant peptide comprising an exon 14b/exon
                         15 junction
source                  1..28
                        mol_type = protein
                        organism = synthetic construct
SEQUENCE: 549
EEEDDEDEEE IEVRSRDISR EEWKGSET                                      28

SEQ ID NO: 550          moltype = AA  length = 27
FEATURE                 Location/Qualifiers
REGION                  1..27
                        note = Ciz1 b-variant peptide comprising an exon 14b/exon
                         15 junction
source                  1..27
                        mol_type = protein
                        organism = synthetic construct
SEQUENCE: 550
EEDDEDEEEI EVRSRDISRE EWKGSET                                       27

SEQ ID NO: 551          moltype = AA  length = 26
FEATURE                 Location/Qualifiers
REGION                  1..26
                        note = Ciz1 b-variant peptide comprising an exon 14b/exon
                         15 junction
source                  1..26
                        mol_type = protein
                        organism = synthetic construct
SEQUENCE: 551
EDDEDEEEIE VRSRDISREE WKGSET                                        26

SEQ ID NO: 552          moltype = AA  length = 25
FEATURE                 Location/Qualifiers
REGION                  1..25
                        note = Ciz1 b-variant peptide comprising an exon 14b/exon
                         15 junction
source                  1..25
                        mol_type = protein
                        organism = synthetic construct
SEQUENCE: 552
DDEDEEEIEV RSRDISREEW KGSET                                         25

SEQ ID NO: 553          moltype = AA  length = 24
FEATURE                 Location/Qualifiers
REGION                  1..24
                        note = Ciz1 b-variant peptide comprising an exon 14b/exon
                         15 junction
source                  1..24
                        mol_type = protein
                        organism = synthetic construct
SEQUENCE: 553
DEDEEEIEVR SRDISREEWK GSET                                          24

SEQ ID NO: 554          moltype = AA  length = 23
FEATURE                 Location/Qualifiers
REGION                  1..23
                        note = Ciz1 b-variant peptide comprising an exon 14b/exon
                         15 junction
source                  1..23
                        mol_type = protein
                        organism = synthetic construct
SEQUENCE: 554
EDEEEIEVRS RDISREEWKG SET                                           23
```

```
SEQ ID NO: 555          moltype = AA  length = 22
FEATURE                 Location/Qualifiers
REGION                  1..22
                        note = Ciz1 b-variant peptide comprising an exon 14b/exon
                         15 junction
source                  1..22
                        mol_type = protein
                        organism = synthetic construct
SEQUENCE: 555
DEEEIEVRSR DISREEWKGS ET                                            22

SEQ ID NO: 556          moltype = AA  length = 21
FEATURE                 Location/Qualifiers
REGION                  1..21
                        note = Ciz1 b-variant peptide comprising an exon 14b/exon
                         15 junction
source                  1..21
                        mol_type = protein
                        organism = synthetic construct
SEQUENCE: 556
EEEIEVRSRD ISREEWKGSE T                                             21

SEQ ID NO: 557          moltype = AA  length = 20
FEATURE                 Location/Qualifiers
REGION                  1..20
                        note = Ciz1 b-variant peptide comprising an exon 14b/exon
                         15 junction
source                  1..20
                        mol_type = protein
                        organism = synthetic construct
SEQUENCE: 557
EEIEVRSRDI SREEWKGSET                                               20

SEQ ID NO: 558          moltype = AA  length = 19
FEATURE                 Location/Qualifiers
REGION                  1..19
                        note = Ciz1 b-variant peptide comprising an exon 14b/exon
                         15 junction
source                  1..19
                        mol_type = protein
                        organism = synthetic construct
SEQUENCE: 558
EIEVRSRDIS REEWKGSET                                                19

SEQ ID NO: 559          moltype = AA  length = 18
FEATURE                 Location/Qualifiers
REGION                  1..18
                        note = Ciz1 b-variant peptide comprising an exon 14b/exon
                         15 junction
source                  1..18
                        mol_type = protein
                        organism = synthetic construct
SEQUENCE: 559
IEVRSRDISR EEWKGSET                                                 18

SEQ ID NO: 560          moltype = AA  length = 17
FEATURE                 Location/Qualifiers
REGION                  1..17
                        note = Ciz1 b-variant peptide comprising an exon 14b/exon
                         15 junction
source                  1..17
                        mol_type = protein
                        organism = synthetic construct
SEQUENCE: 560
EVRSRDISRE EWKGSET                                                  17

SEQ ID NO: 561          moltype = AA  length = 53
FEATURE                 Location/Qualifiers
REGION                  1..53
                        note = Ciz1 b-variant peptide comprising an exon 14b/exon
                         15 junction
source                  1..53
                        mol_type = protein
                        organism = synthetic construct
SEQUENCE: 561
EIAGQDEDHF ITVDAVGCFE GDEEEEEDDE DEEEIEVRSR DISREEWKGS ETY          53

SEQ ID NO: 562          moltype = AA  length = 52
FEATURE                 Location/Qualifiers
```

```
REGION                  1..52
                        note = Ciz1 b-variant peptide comprising an exon 14b/exon
                         15 junction
source                  1..52
                        mol_type = protein
                        organism = synthetic construct
SEQUENCE: 562
IAGQDEDHFI TVDAVGCFEG DEEEEEDDED EEEIEVRSRD ISREEWKGSE TY          52

SEQ ID NO: 563          moltype = AA  length = 51
FEATURE                 Location/Qualifiers
REGION                  1..51
                        note = Ciz1 b-variant peptide comprising an exon 14b/exon
                         15 junction
source                  1..51
                        mol_type = protein
                        organism = synthetic construct
SEQUENCE: 563
AGQDEDHFIT VDAVGCFEGD EEEEEDDEDE EEIEVRSRDI SREEWKGSET Y           51

SEQ ID NO: 564          moltype = AA  length = 50
FEATURE                 Location/Qualifiers
REGION                  1..50
                        note = Ciz1 b-variant peptide comprising an exon 14b/exon
                         15 junction
source                  1..50
                        mol_type = protein
                        organism = synthetic construct
SEQUENCE: 564
GQDEDHFITV DAVGCFEGDE EEEEDDEDEE EIEVRSRDIS REEWKGSETY             50

SEQ ID NO: 565          moltype = AA  length = 49
FEATURE                 Location/Qualifiers
REGION                  1..49
                        note = Ciz1 b-variant peptide comprising an exon 14b/exon
                         15 junction
source                  1..49
                        mol_type = protein
                        organism = synthetic construct
SEQUENCE: 565
QDEDHFITVD AVGCFEGDEE EEEDDEDEEE IEVRSRDISR EEWKGSETY              49

SEQ ID NO: 566          moltype = AA  length = 48
FEATURE                 Location/Qualifiers
REGION                  1..48
                        note = Ciz1 b-variant peptide comprising an exon 14b/exon
                         15 junction
source                  1..48
                        mol_type = protein
                        organism = synthetic construct
SEQUENCE: 566
DEDHFITVDA VGCFEGDEEE EEDDEDEEEI EVRSRDISRE EWKGSETY               48

SEQ ID NO: 567          moltype = AA  length = 47
FEATURE                 Location/Qualifiers
REGION                  1..47
                        note = Ciz1 b-variant peptide comprising an exon 14b/exon
                         15 junction
source                  1..47
                        mol_type = protein
                        organism = synthetic construct
SEQUENCE: 567
EDHFITVDAV GCFEGDEEEE EDDEDEEEIE VRSRDISREE WKGSETY                47

SEQ ID NO: 568          moltype = AA  length = 46
FEATURE                 Location/Qualifiers
REGION                  1..46
                        note = Ciz1 b-variant peptide comprising an exon 14b/exon
                         15 junction
source                  1..46
                        mol_type = protein
                        organism = synthetic construct
SEQUENCE: 568
DHFITVDAVG CFEGDEEEEE DDEDEEEIEV RSRDISREEW KGSETY                 46

SEQ ID NO: 569          moltype = AA  length = 45
FEATURE                 Location/Qualifiers
REGION                  1..45
                        note = Ciz1 b-variant peptide comprising an exon 14b/exon
```

```
                          15 junction
source                   1..45
                         mol_type = protein
                         organism = synthetic construct
SEQUENCE: 569
HFITVDAVGC FEGDEEEEED DEDEEEIEVR SRDISREEWK GSETY                  45

SEQ ID NO: 570           moltype = AA  length = 44
FEATURE                  Location/Qualifiers
REGION                   1..44
                         note = Ciz1 b-variant peptide comprising an exon 14b/exon
                          15 junction
source                   1..44
                         mol_type = protein
                         organism = synthetic construct
SEQUENCE: 570
FITVDAVGCF EGDEEEEEDD EDEEEIEVRS RDISREEWKG SETY                   44

SEQ ID NO: 571           moltype = AA  length = 43
FEATURE                  Location/Qualifiers
REGION                   1..43
                         note = Ciz1 b-variant peptide comprising an exon 14b/exon
                          15 junction
source                   1..43
                         mol_type = protein
                         organism = synthetic construct
SEQUENCE: 571
ITVDAVGCFE GDEEEEEDDE DEEEIEVRSR DISREEWKGS ETY                    43

SEQ ID NO: 572           moltype = AA  length = 42
FEATURE                  Location/Qualifiers
REGION                   1..42
                         note = Ciz1 b-variant peptide comprising an exon 14b/exon
                          15 junction
source                   1..42
                         mol_type = protein
                         organism = synthetic construct
SEQUENCE: 572
TVDAVGCFEG DEEEEEDDED EEEIEVRSRD ISREEWKGSE TY                     42

SEQ ID NO: 573           moltype = AA  length = 41
FEATURE                  Location/Qualifiers
REGION                   1..41
                         note = Ciz1 b-variant peptide comprising an exon 14b/exon
                          15 junction
source                   1..41
                         mol_type = protein
                         organism = synthetic construct
SEQUENCE: 573
VDAVGCFEGD EEEEEDDEDE EEIEVRSRDI SREEWKGSET Y                      41

SEQ ID NO: 574           moltype = AA  length = 40
FEATURE                  Location/Qualifiers
REGION                   1..40
                         note = Ciz1 b-variant peptide comprising an exon 14b/exon
                          15 junction
source                   1..40
                         mol_type = protein
                         organism = synthetic construct
SEQUENCE: 574
DAVGCFEGDE EEEEDDEDEE EIEVRSRDIS REEWKGSETY                        40

SEQ ID NO: 575           moltype = AA  length = 39
FEATURE                  Location/Qualifiers
REGION                   1..39
                         note = Ciz1 b-variant peptide comprising an exon 14b/exon
                          15 junction
source                   1..39
                         mol_type = protein
                         organism = synthetic construct
SEQUENCE: 575
AVGCFEGDEE EEEDDEDEEE IEVRSRDISR EEWKGSETY                         39

SEQ ID NO: 576           moltype = AA  length = 38
FEATURE                  Location/Qualifiers
REGION                   1..38
                         note = Ciz1 b-variant peptide comprising an exon 14b/exon
                          15 junction
source                   1..38
```

```
                        mol_type = protein
                        organism = synthetic construct
SEQUENCE: 576
VGCFEGDEEE EEDDEDEEEI EVRSRDISRE EWKGSETY                          38

SEQ ID NO: 577          moltype = AA  length = 37
FEATURE                 Location/Qualifiers
REGION                  1..37
                        note = Ciz1 b-variant peptide comprising an exon 14b/exon
                         15 junction
source                  1..37
                        mol_type = protein
                        organism = synthetic construct
SEQUENCE: 577
GCFEGDEEEE EDDEDEEEIE VRSRDISREE WKGSETY                           37

SEQ ID NO: 578          moltype = AA  length = 36
FEATURE                 Location/Qualifiers
REGION                  1..36
                        note = Ciz1 b-variant peptide comprising an exon 14b/exon
                         15 junction
source                  1..36
                        mol_type = protein
                        organism = synthetic construct
SEQUENCE: 578
CFEGDEEEEE DDEDEEEIEV RSRDISREEW KGSETY                            36

SEQ ID NO: 579          moltype = AA  length = 35
FEATURE                 Location/Qualifiers
REGION                  1..35
                        note = Ciz1 b-variant peptide comprising an exon 14b/exon
                         15 junction
source                  1..35
                        mol_type = protein
                        organism = synthetic construct
SEQUENCE: 579
FEGDEEEEED DEDEEEIEVR SRDISREEWK GSETY                             35

SEQ ID NO: 580          moltype = AA  length = 34
FEATURE                 Location/Qualifiers
REGION                  1..34
                        note = Ciz1 b-variant peptide comprising an exon 14b/exon
                         15 junction
source                  1..34
                        mol_type = protein
                        organism = synthetic construct
SEQUENCE: 580
EGDEEEEEDD EDEEEIEVRS RDISREEWKG SETY                              34

SEQ ID NO: 581          moltype = AA  length = 33
FEATURE                 Location/Qualifiers
REGION                  1..33
                        note = Ciz1 b-variant peptide comprising an exon 14b/exon
                         15 junction
source                  1..33
                        mol_type = protein
                        organism = synthetic construct
SEQUENCE: 581
GDEEEEEDDE DEEEIEVRSR DISREEWKGS ETY                               33

SEQ ID NO: 582          moltype = AA  length = 32
FEATURE                 Location/Qualifiers
REGION                  1..32
                        note = Ciz1 b-variant peptide comprising an exon 14b/exon
                         15 junction
source                  1..32
                        mol_type = protein
                        organism = synthetic construct
SEQUENCE: 582
DEEEEEDDED EEEIEVRSRD ISREEWKGSE TY                                32

SEQ ID NO: 583          moltype = AA  length = 31
FEATURE                 Location/Qualifiers
REGION                  1..31
                        note = Ciz1 b-variant peptide comprising an exon 14b/exon
                         15 junction
source                  1..31
                        mol_type = protein
                        organism = synthetic construct
```

```
SEQUENCE: 583
EEEEEDDEDE EEIEVRSRDI SREEWKGSET Y                                31

SEQ ID NO: 584          moltype = AA  length = 30
FEATURE                 Location/Qualifiers
REGION                  1..30
                        note = Ciz1 b-variant peptide comprising an exon 14b/exon
                         15 junction
source                  1..30
                        mol_type = protein
                        organism = synthetic construct
SEQUENCE: 584
EEEEDDEDEE EIEVRSRDIS REEWKGSETY                                  30

SEQ ID NO: 585          moltype = AA  length = 29
FEATURE                 Location/Qualifiers
REGION                  1..29
                        note = Ciz1 b-variant peptide comprising an exon 14b/exon
                         15 junction
source                  1..29
                        mol_type = protein
                        organism = synthetic construct
SEQUENCE: 585
EEEDDEDEEE IEVRSRDISR EEWKGSETY                                   29

SEQ ID NO: 586          moltype = AA  length = 28
FEATURE                 Location/Qualifiers
REGION                  1..28
                        note = Ciz1 b-variant peptide comprising an exon 14b/exon
                         15 junction
source                  1..28
                        mol_type = protein
                        organism = synthetic construct
SEQUENCE: 586
EEDDEDEEEI EVRSRDISRE EWKGSETY                                    28

SEQ ID NO: 587          moltype = AA  length = 27
FEATURE                 Location/Qualifiers
REGION                  1..27
                        note = Ciz1 b-variant peptide comprising an exon 14b/exon
                         15 junction
source                  1..27
                        mol_type = protein
                        organism = synthetic construct
SEQUENCE: 587
EDDEDEEEIE VRSRDISREE WKGSETY                                     27

SEQ ID NO: 588          moltype = AA  length = 26
FEATURE                 Location/Qualifiers
REGION                  1..26
                        note = Ciz1 b-variant peptide comprising an exon 14b/exon
                         15 junction
source                  1..26
                        mol_type = protein
                        organism = synthetic construct
SEQUENCE: 588
DDEDEEEIEV RSRDISREEW KGSETY                                      26

SEQ ID NO: 589          moltype = AA  length = 25
FEATURE                 Location/Qualifiers
REGION                  1..25
                        note = Ciz1 b-variant peptide comprising an exon 14b/exon
                         15 junction
source                  1..25
                        mol_type = protein
                        organism = synthetic construct
SEQUENCE: 589
DEDEEEIEVR SRDISREEWK GSETY                                       25

SEQ ID NO: 590          moltype = AA  length = 24
FEATURE                 Location/Qualifiers
REGION                  1..24
                        note = Ciz1 b-variant peptide comprising an exon 14b/exon
                         15 junction
source                  1..24
                        mol_type = protein
                        organism = synthetic construct
SEQUENCE: 590
EDEEEIEVRS RDISREEWKG SETY                                        24
```

```
SEQ ID NO: 591          moltype = AA  length = 23
FEATURE                 Location/Qualifiers
REGION                  1..23
                        note = Ciz1 b-variant peptide comprising an exon 14b/exon
                         15 junction
source                  1..23
                        mol_type = protein
                        organism = synthetic construct
SEQUENCE: 591
DEEEIEVRSR DISREEWKGS ETY                                             23

SEQ ID NO: 592          moltype = AA  length = 22
FEATURE                 Location/Qualifiers
REGION                  1..22
                        note = Ciz1 b-variant peptide comprising an exon 14b/exon
                         15 junction
source                  1..22
                        mol_type = protein
                        organism = synthetic construct
SEQUENCE: 592
EEEIEVRSRD ISREEWKGSE TY                                              22

SEQ ID NO: 593          moltype = AA  length = 21
FEATURE                 Location/Qualifiers
REGION                  1..21
                        note = Ciz1 b-variant peptide comprising an exon 14b/exon
                         15 junction
source                  1..21
                        mol_type = protein
                        organism = synthetic construct
SEQUENCE: 593
EEIEVRSRDI SREEWKGSET Y                                               21

SEQ ID NO: 594          moltype = AA  length = 20
FEATURE                 Location/Qualifiers
REGION                  1..20
                        note = Ciz1 b-variant peptide comprising an exon 14b/exon
                         15 junction
source                  1..20
                        mol_type = protein
                        organism = synthetic construct
SEQUENCE: 594
EIEVRSRDIS REEWKGSETY                                                 20

SEQ ID NO: 595          moltype = AA  length = 19
FEATURE                 Location/Qualifiers
REGION                  1..19
                        note = Ciz1 b-variant peptide comprising an exon 14b/exon
                         15 junction
source                  1..19
                        mol_type = protein
                        organism = synthetic construct
SEQUENCE: 595
IEVRSRDISR EEWKGSETY                                                  19

SEQ ID NO: 596          moltype = AA  length = 18
FEATURE                 Location/Qualifiers
REGION                  1..18
                        note = Ciz1 b-variant peptide comprising an exon 14b/exon
                         15 junction
source                  1..18
                        mol_type = protein
                        organism = synthetic construct
SEQUENCE: 596
EVRSRDISRE EWKGSETY                                                   18

SEQ ID NO: 597          moltype = AA  length = 54
FEATURE                 Location/Qualifiers
REGION                  1..54
                        note = Ciz1 b-variant peptide comprising an exon 14b/exon
                         15 junction
source                  1..54
                        mol_type = protein
                        organism = synthetic construct
SEQUENCE: 597
EIAGQDEDHF ITVDAVGCFE GDEEEEEDDE DEEEIEVRSR DISREEWKGS ETYS           54

SEQ ID NO: 598          moltype = AA  length = 53
```

```
FEATURE                Location/Qualifiers
REGION                 1..53
                       note = Ciz1 b-variant peptide comprising an exon 14b/exon
                        15 junction
source                 1..53
                       mol_type = protein
                       organism = synthetic construct
SEQUENCE: 598
IAGQDEDHFI TVDAVGCFEG DEEEEEDDED EEEIEVRSRD ISREEWKGSE TYS         53

SEQ ID NO: 599         moltype = AA  length = 52
FEATURE                Location/Qualifiers
REGION                 1..52
                       note = Ciz1 b-variant peptide comprising an exon 14b/exon
                        15 junction
source                 1..52
                       mol_type = protein
                       organism = synthetic construct
SEQUENCE: 599
AGQDEDHFIT VDAVGCFEGD EEEEEDDEDE EEIEVRSRDI SREEWKGSET YS          52

SEQ ID NO: 600         moltype = AA  length = 51
FEATURE                Location/Qualifiers
REGION                 1..51
                       note = Ciz1 b-variant peptide comprising an exon 14b/exon
                        15 junction
source                 1..51
                       mol_type = protein
                       organism = synthetic construct
SEQUENCE: 600
GQDEDHFITV DAVGCFEGDE EEEEDDEDEE EIEVRSRDIS REEWKGSETY S           51

SEQ ID NO: 601         moltype = AA  length = 50
FEATURE                Location/Qualifiers
REGION                 1..50
                       note = Ciz1 b-variant peptide comprising an exon 14b/exon
                        15 junction
source                 1..50
                       mol_type = protein
                       organism = synthetic construct
SEQUENCE: 601
QDEDHFITVD AVGCFEGDEE EEEDDEDEEE IEVRSRDISR EEWKGSETYS            50

SEQ ID NO: 602         moltype = AA  length = 49
FEATURE                Location/Qualifiers
REGION                 1..49
                       note = Ciz1 b-variant peptide comprising an exon 14b/exon
                        15 junction
source                 1..49
                       mol_type = protein
                       organism = synthetic construct
SEQUENCE: 602
DEDHFITVDA VGCFEGDEEE EEDDEDEEEI EVRSRDISRE EWKGSETYS             49

SEQ ID NO: 603         moltype = AA  length = 48
FEATURE                Location/Qualifiers
REGION                 1..48
                       note = Ciz1 b-variant peptide comprising an exon 14b/exon
                        15 junction
source                 1..48
                       mol_type = protein
                       organism = synthetic construct
SEQUENCE: 603
EDHFITVDAV GCFEGDEEEE EDDEDEEEIE VRSRDISREE WKGSETYS              48

SEQ ID NO: 604         moltype = AA  length = 47
FEATURE                Location/Qualifiers
REGION                 1..47
                       note = Ciz1 b-variant peptide comprising an exon 14b/exon
                        15 junction
source                 1..47
                       mol_type = protein
                       organism = synthetic construct
SEQUENCE: 604
DHFITVDAVG CFEGDEEEEE DDEDEEEIEV RSRDISREEW KGSETYS               47

SEQ ID NO: 605         moltype = AA  length = 46
FEATURE                Location/Qualifiers
REGION                 1..46
```

```
                         note = Ciz1 b-variant peptide comprising an exon 14b/exon
                          15 junction
source                   1..46
                         mol_type = protein
                         organism = synthetic construct
SEQUENCE: 605
HFITVDAVGC FEGDEEEEED DEDEEEIEVR SRDISREEWK GSETYS                  46

SEQ ID NO: 606           moltype = AA  length = 45
FEATURE                  Location/Qualifiers
REGION                   1..45
                         note = Ciz1 b-variant peptide comprising an exon 14b/exon
                          15 junction
source                   1..45
                         mol_type = protein
                         organism = synthetic construct
SEQUENCE: 606
FITVDAVGCF EGDEEEEEDD EDEEEIEVRS RDISREEWKG SETYS                   45

SEQ ID NO: 607           moltype = AA  length = 44
FEATURE                  Location/Qualifiers
REGION                   1..44
                         note = Ciz1 b-variant peptide comprising an exon 14b/exon
                          15 junction
source                   1..44
                         mol_type = protein
                         organism = synthetic construct
SEQUENCE: 607
ITVDAVGCFE GDEEEEEDDE DEEEIEVRSR DISREEWKGS ETYS                    44

SEQ ID NO: 608           moltype = AA  length = 43
FEATURE                  Location/Qualifiers
REGION                   1..43
                         note = Ciz1 b-variant peptide comprising an exon 14b/exon
                          15 junction
source                   1..43
                         mol_type = protein
                         organism = synthetic construct
SEQUENCE: 608
TVDAVGCFEG DEEEEEDDED EEEIEVRSRD ISREEWKGSE TYS                     43

SEQ ID NO: 609           moltype = AA  length = 42
FEATURE                  Location/Qualifiers
REGION                   1..42
                         note = Ciz1 b-variant peptide comprising an exon 14b/exon
                          15 junction
source                   1..42
                         mol_type = protein
                         organism = synthetic construct
SEQUENCE: 609
VDAVGCFEGD EEEEEDDEDE EEIEVRSRDI SREEWKGSET YS                      42

SEQ ID NO: 610           moltype = AA  length = 41
FEATURE                  Location/Qualifiers
REGION                   1..41
                         note = Ciz1 b-variant peptide comprising an exon 14b/exon
                          15 junction
source                   1..41
                         mol_type = protein
                         organism = synthetic construct
SEQUENCE: 610
DAVGCFEGDE EEEEDDEDEE EIEVRSRDIS REEWKGSETY S                       41

SEQ ID NO: 611           moltype = AA  length = 40
FEATURE                  Location/Qualifiers
REGION                   1..40
                         note = Ciz1 b-variant peptide comprising an exon 14b/exon
                          15 junction
source                   1..40
                         mol_type = protein
                         organism = synthetic construct
SEQUENCE: 611
AVGCFEGDEE EEEDDEDEEE IEVRSRDISR EEWKGSETYS                         40

SEQ ID NO: 612           moltype = AA  length = 39
FEATURE                  Location/Qualifiers
REGION                   1..39
                         note = Ciz1 b-variant peptide comprising an exon 14b/exon
                          15 junction
```

```
source                  1..39
                        mol_type = protein
                        organism = synthetic construct
SEQUENCE: 612
VGCFEGDEEE EEDDEDEEEI EVRSRDISRE EWKGSETYS                         39

SEQ ID NO: 613          moltype = AA  length = 38
FEATURE                 Location/Qualifiers
REGION                  1..38
                        note = Ciz1 b-variant peptide comprising an exon 14b/exon
                         15 junction
source                  1..38
                        mol_type = protein
                        organism = synthetic construct
SEQUENCE: 613
GCFEGDEEEE EDDEDEEEIE VRSRDISREE WKGSETYS                          38

SEQ ID NO: 614          moltype = AA  length = 37
FEATURE                 Location/Qualifiers
REGION                  1..37
                        note = Ciz1 b-variant peptide comprising an exon 14b/exon
                         15 junction
source                  1..37
                        mol_type = protein
                        organism = synthetic construct
SEQUENCE: 614
CFEGDEEEEE DDEDEEEIEV RSRDISREEW KGSETYS                           37

SEQ ID NO: 615          moltype = AA  length = 36
FEATURE                 Location/Qualifiers
REGION                  1..36
                        note = Ciz1 b-variant peptide comprising an exon 14b/exon
                         15 junction
source                  1..36
                        mol_type = protein
                        organism = synthetic construct
SEQUENCE: 615
FEGDEEEEED DEDEEEIEVR SRDISREEWK GSETYS                            36

SEQ ID NO: 616          moltype = AA  length = 35
FEATURE                 Location/Qualifiers
REGION                  1..35
                        note = Ciz1 b-variant peptide comprising an exon 14b/exon
                         15 junction
source                  1..35
                        mol_type = protein
                        organism = synthetic construct
SEQUENCE: 616
EGDEEEEEDD EDEEEIEVRS RDISREEWKG SETYS                             35

SEQ ID NO: 617          moltype = AA  length = 34
FEATURE                 Location/Qualifiers
REGION                  1..34
                        note = Ciz1 b-variant peptide comprising an exon 14b/exon
                         15 junction
source                  1..34
                        mol_type = protein
                        organism = synthetic construct
SEQUENCE: 617
GDEEEEEDDE DEEEIEVRSR DISREEWKGS ETYS                              34

SEQ ID NO: 618          moltype = AA  length = 33
FEATURE                 Location/Qualifiers
REGION                  1..33
                        note = Ciz1 b-variant peptide comprising an exon 14b/exon
                         15 junction
source                  1..33
                        mol_type = protein
                        organism = synthetic construct
SEQUENCE: 618
DEEEEEDDED EEEIEVRSRD ISREEWKGSE TYS                               33

SEQ ID NO: 619          moltype = AA  length = 32
FEATURE                 Location/Qualifiers
REGION                  1..32
                        note = Ciz1 b-variant peptide comprising an exon 14b/exon
                         15 junction
source                  1..32
                        mol_type = protein
```

```
                         organism = synthetic construct
SEQUENCE: 619
EEEEEDDEDE EEIEVRSRDI SREEWKGSET YS                                 32

SEQ ID NO: 620           moltype = AA  length = 31
FEATURE                  Location/Qualifiers
REGION                   1..31
                         note = Ciz1 b-variant peptide comprising an exon 14b/exon
                          15 junction
source                   1..31
                         mol_type = protein
                         organism = synthetic construct
SEQUENCE: 620
EEEEDDEDEE EIEVRSRDIS REEWKGSETY S                                  31

SEQ ID NO: 621           moltype = AA  length = 30
FEATURE                  Location/Qualifiers
REGION                   1..30
                         note = Ciz1 b-variant peptide comprising an exon 14b/exon
                          15 junction
source                   1..30
                         mol_type = protein
                         organism = synthetic construct
SEQUENCE: 621
EEEDDEDEEE IEVRSRDISR EEWKGSETYS                                    30

SEQ ID NO: 622           moltype = AA  length = 29
FEATURE                  Location/Qualifiers
REGION                   1..29
                         note = Ciz1 b-variant peptide comprising an exon 14b/exon
                          15 junction
source                   1..29
                         mol_type = protein
                         organism = synthetic construct
SEQUENCE: 622
EEDDEDEEEI EVRSRDISRE EWKGSETYS                                     29

SEQ ID NO: 623           moltype = AA  length = 28
FEATURE                  Location/Qualifiers
REGION                   1..28
                         note = Ciz1 b-variant peptide comprising an exon 14b/exon
                          15 junction
source                   1..28
                         mol_type = protein
                         organism = synthetic construct
SEQUENCE: 623
EDDEDEEEIE VRSRDISREE WKGSETYS                                      28

SEQ ID NO: 624           moltype = AA  length = 27
FEATURE                  Location/Qualifiers
REGION                   1..27
                         note = Ciz1 b-variant peptide comprising an exon 14b/exon
                          15 junction
source                   1..27
                         mol_type = protein
                         organism = synthetic construct
SEQUENCE: 624
DDEDEEEIEV RSRDISREEW KGSETYS                                       27

SEQ ID NO: 625           moltype = AA  length = 26
FEATURE                  Location/Qualifiers
REGION                   1..26
                         note = Ciz1 b-variant peptide comprising an exon 14b/exon
                          15 junction
source                   1..26
                         mol_type = protein
                         organism = synthetic construct
SEQUENCE: 625
DEDEEEIEVR SRDISREEWK GSETYS                                        26

SEQ ID NO: 626           moltype = AA  length = 25
FEATURE                  Location/Qualifiers
REGION                   1..25
                         note = Ciz1 b-variant peptide comprising an exon 14b/exon
                          15 junction
source                   1..25
                         mol_type = protein
                         organism = synthetic construct
SEQUENCE: 626
```

```
EDEEEIEVRS RDISREEWKG SETYS                                      25

SEQ ID NO: 627          moltype = AA  length = 24
FEATURE                 Location/Qualifiers
REGION                  1..24
                        note = Ciz1 b-variant peptide comprising an exon 14b/exon
                         15 junction
source                  1..24
                        mol_type = protein
                        organism = synthetic construct
SEQUENCE: 627
DEEEIEVRSR DISREEWKGS ETYS                                       24

SEQ ID NO: 628          moltype = AA  length = 23
FEATURE                 Location/Qualifiers
REGION                  1..23
                        note = Ciz1 b-variant peptide comprising an exon 14b/exon
                         15 junction
source                  1..23
                        mol_type = protein
                        organism = synthetic construct
SEQUENCE: 628
EEEIEVRSRD ISREEWKGSE TYS                                        23

SEQ ID NO: 629          moltype = AA  length = 22
FEATURE                 Location/Qualifiers
REGION                  1..22
                        note = Ciz1 b-variant peptide comprising an exon 14b/exon
                         15 junction
source                  1..22
                        mol_type = protein
                        organism = synthetic construct
SEQUENCE: 629
EEIEVRSRDI SREEWKGSET YS                                         22

SEQ ID NO: 630          moltype = AA  length = 21
FEATURE                 Location/Qualifiers
REGION                  1..21
                        note = Ciz1 b-variant peptide comprising an exon 14b/exon
                         15 junction
source                  1..21
                        mol_type = protein
                        organism = synthetic construct
SEQUENCE: 630
EIEVRSRDIS REEWKGSETY S                                          21

SEQ ID NO: 631          moltype = AA  length = 20
FEATURE                 Location/Qualifiers
REGION                  1..20
                        note = Ciz1 b-variant peptide comprising an exon 14b/exon
                         15 junction
source                  1..20
                        mol_type = protein
                        organism = synthetic construct
SEQUENCE: 631
IEVRSRDISR EEWKGSETYS                                            20

SEQ ID NO: 632          moltype = AA  length = 19
FEATURE                 Location/Qualifiers
REGION                  1..19
                        note = Ciz1 b-variant peptide comprising an exon 14b/exon
                         15 junction
source                  1..19
                        mol_type = protein
                        organism = synthetic construct
SEQUENCE: 632
EVRSRDISRE EWKGSETYS                                             19

SEQ ID NO: 633          moltype = AA  length = 55
FEATURE                 Location/Qualifiers
REGION                  1..55
                        note = Ciz1 b-variant peptide comprising an exon 14b/exon
                         15 junction
source                  1..55
                        mol_type = protein
                        organism = synthetic construct
SEQUENCE: 633
EIAGQDEDHF ITVDAVGCFE GDEEEEEDDE DEEEIEVRSR DISREEWKGS ETYSP       55
```

```
SEQ ID NO: 634          moltype = AA  length = 54
FEATURE                 Location/Qualifiers
REGION                  1..54
                        note = Ciz1 b-variant peptide comprising an exon 14b/exon
                         15 junction
source                  1..54
                        mol_type = protein
                        organism = synthetic construct
SEQUENCE: 634
IAGQDEDHFI TVDAVGCFEG DEEEEEDDED EEEIEVRSRD ISREEWKGSE TYSP         54

SEQ ID NO: 635          moltype = AA  length = 53
FEATURE                 Location/Qualifiers
REGION                  1..53
                        note = Ciz1 b-variant peptide comprising an exon 14b/exon
                         15 junction
source                  1..53
                        mol_type = protein
                        organism = synthetic construct
SEQUENCE: 635
AGQDEDHFIT VDAVGCFEGD EEEEEDDEDE EEIEVRSRDI SREEWKGSET YSP          53

SEQ ID NO: 636          moltype = AA  length = 52
FEATURE                 Location/Qualifiers
REGION                  1..52
                        note = Ciz1 b-variant peptide comprising an exon 14b/exon
                         15 junction
source                  1..52
                        mol_type = protein
                        organism = synthetic construct
SEQUENCE: 636
GQDEDHFITV DAVGCFEGDE EEEEDDEDEE EIEVRSRDIS REEWKGSETY SP           52

SEQ ID NO: 637          moltype = AA  length = 51
FEATURE                 Location/Qualifiers
REGION                  1..51
                        note = Ciz1 b-variant peptide comprising an exon 14b/exon
                         15 junction
source                  1..51
                        mol_type = protein
                        organism = synthetic construct
SEQUENCE: 637
QDEDHFITVD AVGCFEGDEE EEEDDEDEEE IEVRSRDISR EEWKGSETYS P            51

SEQ ID NO: 638          moltype = AA  length = 50
FEATURE                 Location/Qualifiers
REGION                  1..50
                        note = Ciz1 b-variant peptide comprising an exon 14b/exon
                         15 junction
source                  1..50
                        mol_type = protein
                        organism = synthetic construct
SEQUENCE: 638
DEDHFITVDA VGCFEGDEEE EEDDEDEEEI EVRSRDISRE EWKGSETYSP              50

SEQ ID NO: 639          moltype = AA  length = 49
FEATURE                 Location/Qualifiers
REGION                  1..49
                        note = Ciz1 b-variant peptide comprising an exon 14b/exon
                         15 junction
source                  1..49
                        mol_type = protein
                        organism = synthetic construct
SEQUENCE: 639
EDHFITVDAV GCFEGDEEEE EDDEDEEEIE VRSRDISREE WKGSETYSP               49

SEQ ID NO: 640          moltype = AA  length = 48
FEATURE                 Location/Qualifiers
REGION                  1..48
                        note = Ciz1 b-variant peptide comprising an exon 14b/exon
                         15 junction
source                  1..48
                        mol_type = protein
                        organism = synthetic construct
SEQUENCE: 640
DHFITVDAVG CFEGDEEEEE DDEDEEEIEV RSRDISREEW KGSETYSP                48

SEQ ID NO: 641          moltype = AA  length = 47
FEATURE                 Location/Qualifiers
```

```
REGION                 1..47
                       note = Ciz1 b-variant peptide comprising an exon 14b/exon
                        15 junction
source                 1..47
                       mol_type = protein
                       organism = synthetic construct
SEQUENCE: 641
HFITVDAVGC FEGDEEEEED DEDEEEIEVR SRDISREEWK GSETYSP                47

SEQ ID NO: 642         moltype = AA  length = 46
FEATURE                Location/Qualifiers
REGION                 1..46
                       note = Ciz1 b-variant peptide comprising an exon 14b/exon
                        15 junction
source                 1..46
                       mol_type = protein
                       organism = synthetic construct
SEQUENCE: 642
FITVDAVGCF EGDEEEEEDD EDEEEIEVRS RDISREEWKG SETYSP                 46

SEQ ID NO: 643         moltype = AA  length = 45
FEATURE                Location/Qualifiers
REGION                 1..45
                       note = Ciz1 b-variant peptide comprising an exon 14b/exon
                        15 junction
source                 1..45
                       mol_type = protein
                       organism = synthetic construct
SEQUENCE: 643
ITVDAVGCFE GDEEEEEDDE DEEEIEVRSR DISREEWKGS ETYSP                  45

SEQ ID NO: 644         moltype = AA  length = 44
FEATURE                Location/Qualifiers
REGION                 1..44
                       note = Ciz1 b-variant peptide comprising an exon 14b/exon
                        15 junction
source                 1..44
                       mol_type = protein
                       organism = synthetic construct
SEQUENCE: 644
TVDAVGCFEG DEEEEEDDED EEEIEVRSRD ISREEWKGSE TYSP                   44

SEQ ID NO: 645         moltype = AA  length = 43
FEATURE                Location/Qualifiers
REGION                 1..43
                       note = Ciz1 b-variant peptide comprising an exon 14b/exon
                        15 junction
source                 1..43
                       mol_type = protein
                       organism = synthetic construct
SEQUENCE: 645
VDAVGCFEGD EEEEEDDEDE EEIEVRSRDI SREEWKGSET YSP                    43

SEQ ID NO: 646         moltype = AA  length = 42
FEATURE                Location/Qualifiers
REGION                 1..42
                       note = Ciz1 b-variant peptide comprising an exon 14b/exon
                        15 junction
source                 1..42
                       mol_type = protein
                       organism = synthetic construct
SEQUENCE: 646
DAVGCFEGDE EEEEDDEDEE EIEVRSRDIS REEWKGSETY SP                     42

SEQ ID NO: 647         moltype = AA  length = 41
FEATURE                Location/Qualifiers
REGION                 1..41
                       note = Ciz1 b-variant peptide comprising an exon 14b/exon
                        15 junction
source                 1..41
                       mol_type = protein
                       organism = synthetic construct
SEQUENCE: 647
AVGCFEGDEE EEEDDEDEEE IEVRSRDISR EEWKGSETYS P                      41

SEQ ID NO: 648         moltype = AA  length = 40
FEATURE                Location/Qualifiers
REGION                 1..40
                       note = Ciz1 b-variant peptide comprising an exon 14b/exon
```

```
                        15 junction
source                 1..40
                       mol_type = protein
                       organism = synthetic construct
SEQUENCE: 648
VGCFEGDEEE EEDDEDEEEI EVRSRDISRE EWKGSETYSP                         40

SEQ ID NO: 649         moltype = AA  length = 39
FEATURE                Location/Qualifiers
REGION                 1..39
                       note = Ciz1 b-variant peptide comprising an exon 14b/exon
                        15 junction
source                 1..39
                       mol_type = protein
                       organism = synthetic construct
SEQUENCE: 649
GCFEGDEEEE EDDEDEEEIE VRSRDISREE WKGSETYSP                          39

SEQ ID NO: 650         moltype = AA  length = 38
FEATURE                Location/Qualifiers
REGION                 1..38
                       note = Ciz1 b-variant peptide comprising an exon 14b/exon
                        15 junction
source                 1..38
                       mol_type = protein
                       organism = synthetic construct
SEQUENCE: 650
CFEGDEEEEE DDEDEEEIEV RSRDISREEW KGSETYSP                           38

SEQ ID NO: 651         moltype = AA  length = 37
FEATURE                Location/Qualifiers
REGION                 1..37
                       note = Ciz1 b-variant peptide comprising an exon 14b/exon
                        15 junction
source                 1..37
                       mol_type = protein
                       organism = synthetic construct
SEQUENCE: 651
FEGDEEEEED DEDEEEIEVR SRDISREEWK GSETYSP                            37

SEQ ID NO: 652         moltype = AA  length = 36
FEATURE                Location/Qualifiers
REGION                 1..36
                       note = Ciz1 b-variant peptide comprising an exon 14b/exon
                        15 junction
source                 1..36
                       mol_type = protein
                       organism = synthetic construct
SEQUENCE: 652
EGDEEEEEDD EDEEEIEVRS RDISREEWKG SETYSP                             36

SEQ ID NO: 653         moltype = AA  length = 35
FEATURE                Location/Qualifiers
REGION                 1..35
                       note = Ciz1 b-variant peptide comprising an exon 14b/exon
                        15 junction
source                 1..35
                       mol_type = protein
                       organism = synthetic construct
SEQUENCE: 653
GDEEEEEDDE DEEEIEVRSR DISREEWKGS ETYSP                              35

SEQ ID NO: 654         moltype = AA  length = 34
FEATURE                Location/Qualifiers
REGION                 1..34
                       note = Ciz1 b-variant peptide comprising an exon 14b/exon
                        15 junction
source                 1..34
                       mol_type = protein
                       organism = synthetic construct
SEQUENCE: 654
DEEEEEDDED EEEIEVRSRD ISREEWKGSE TYSP                               34

SEQ ID NO: 655         moltype = AA  length = 33
FEATURE                Location/Qualifiers
REGION                 1..33
                       note = Ciz1 b-variant peptide comprising an exon 14b/exon
                        15 junction
source                 1..33
```

```
                        mol_type = protein
                        organism = synthetic construct
SEQUENCE: 655
EEEEEDDEDE EEIEVRSRDI SREEWKGSET YSP                                33

SEQ ID NO: 656          moltype = AA  length = 32
FEATURE                 Location/Qualifiers
REGION                  1..32
                        note = Ciz1 b-variant peptide comprising an exon 14b/exon
                         15 junction
source                  1..32
                        mol_type = protein
                        organism = synthetic construct
SEQUENCE: 656
EEEEDDEDEE EIEVRSRDIS REEWKGSETY SP                                 32

SEQ ID NO: 657          moltype = AA  length = 31
FEATURE                 Location/Qualifiers
REGION                  1..31
                        note = Ciz1 b-variant peptide comprising an exon 14b/exon
                         15 junction
source                  1..31
                        mol_type = protein
                        organism = synthetic construct
SEQUENCE: 657
EEEDDEDEEE IEVRSRDISR EEWKGSETYS P                                  31

SEQ ID NO: 658          moltype = AA  length = 30
FEATURE                 Location/Qualifiers
REGION                  1..30
                        note = Ciz1 b-variant peptide comprising an exon 14b/exon
                         15 junction
source                  1..30
                        mol_type = protein
                        organism = synthetic construct
SEQUENCE: 658
EEDDEDEEEI EVRSRDISRE EWKGSETYSP                                    30

SEQ ID NO: 659          moltype = AA  length = 29
FEATURE                 Location/Qualifiers
REGION                  1..29
                        note = Ciz1 b-variant peptide comprising an exon 14b/exon
                         15 junction
source                  1..29
                        mol_type = protein
                        organism = synthetic construct
SEQUENCE: 659
EDDEDEEEIE VRSRDISREE WKGSETYSP                                     29

SEQ ID NO: 660          moltype = AA  length = 28
FEATURE                 Location/Qualifiers
REGION                  1..28
                        note = Ciz1 b-variant peptide comprising an exon 14b/exon
                         15 junction
source                  1..28
                        mol_type = protein
                        organism = synthetic construct
SEQUENCE: 660
DDEDEEEIEV RSRDISREEW KGSETYSP                                      28

SEQ ID NO: 661          moltype = AA  length = 27
FEATURE                 Location/Qualifiers
REGION                  1..27
                        note = Ciz1 b-variant peptide comprising an exon 14b/exon
                         15 junction
source                  1..27
                        mol_type = protein
                        organism = synthetic construct
SEQUENCE: 661
DEDEEEIEVR SRDISREEWK GSETYSP                                       27

SEQ ID NO: 662          moltype = AA  length = 26
FEATURE                 Location/Qualifiers
REGION                  1..26
                        note = Ciz1 b-variant peptide comprising an exon 14b/exon
                         15 junction
source                  1..26
                        mol_type = protein
                        organism = synthetic construct
```

```
SEQUENCE: 662
EDEEEIEVRS RDISREEWKG SETYSP                                    26

SEQ ID NO: 663          moltype = AA  length = 25
FEATURE                 Location/Qualifiers
REGION                  1..25
                        note = Ciz1 b-variant peptide comprising an exon 14b/exon
                         15 junction
source                  1..25
                        mol_type = protein
                        organism = synthetic construct
SEQUENCE: 663
DEEEIEVRSR DISREEWKGS ETYSP                                     25

SEQ ID NO: 664          moltype = AA  length = 24
FEATURE                 Location/Qualifiers
REGION                  1..24
                        note = Ciz1 b-variant peptide comprising an exon 14b/exon
                         15 junction
source                  1..24
                        mol_type = protein
                        organism = synthetic construct
SEQUENCE: 664
EEEIEVRSRD ISREEWKGSE TYSP                                      24

SEQ ID NO: 665          moltype = AA  length = 23
FEATURE                 Location/Qualifiers
REGION                  1..23
                        note = Ciz1 b-variant peptide comprising an exon 14b/exon
                         15 junction
source                  1..23
                        mol_type = protein
                        organism = synthetic construct
SEQUENCE: 665
EEIEVRSRDI SREEWKGSET YSP                                       23

SEQ ID NO: 666          moltype = AA  length = 22
FEATURE                 Location/Qualifiers
REGION                  1..22
                        note = Ciz1 b-variant peptide comprising an exon 14b/exon
                         15 junction
source                  1..22
                        mol_type = protein
                        organism = synthetic construct
SEQUENCE: 666
EIEVRSRDIS REEWKGSETY SP                                        22

SEQ ID NO: 667          moltype = AA  length = 21
FEATURE                 Location/Qualifiers
REGION                  1..21
                        note = Ciz1 b-variant peptide comprising an exon 14b/exon
                         15 junction
source                  1..21
                        mol_type = protein
                        organism = synthetic construct
SEQUENCE: 667
IEVRSRDISR EEWKGSETYS P                                         21

SEQ ID NO: 668          moltype = AA  length = 20
FEATURE                 Location/Qualifiers
REGION                  1..20
                        note = Ciz1 b-variant peptide comprising an exon 14b/exon
                         15 junction
source                  1..20
                        mol_type = protein
                        organism = synthetic construct
SEQUENCE: 668
EVRSRDISRE EWKGSETYSP                                           20

SEQ ID NO: 669          moltype = AA  length = 56
FEATURE                 Location/Qualifiers
REGION                  1..56
                        note = Ciz1 b-variant peptide comprising an exon 14b/exon
                         15 junction
source                  1..56
                        mol_type = protein
                        organism = synthetic construct
SEQUENCE: 669
EIAGQDEDHF ITVDAVGCFE GDEEEEEDDE DEEEIEVRSR DISREEWKGS ETYSPN      56
```

```
SEQ ID NO: 670          moltype = AA  length = 55
FEATURE                 Location/Qualifiers
REGION                  1..55
                        note = Ciz1 b-variant peptide comprising an exon 14b/exon
                         15 junction
source                  1..55
                        mol_type = protein
                        organism = synthetic construct
SEQUENCE: 670
IAGQDEDHFI TVDAVGCFEG DEEEEEDDED EEEIEVRSRD ISREEWKGSE TYSPN       55

SEQ ID NO: 671          moltype = AA  length = 54
FEATURE                 Location/Qualifiers
REGION                  1..54
                        note = Ciz1 b-variant peptide comprising an exon 14b/exon
                         15 junction
source                  1..54
                        mol_type = protein
                        organism = synthetic construct
SEQUENCE: 671
AGQDEDHFIT VDAVGCFEGD EEEEEDDEDE EEIEVRSRDI SREEWKGSET YSPN        54

SEQ ID NO: 672          moltype = AA  length = 53
FEATURE                 Location/Qualifiers
REGION                  1..53
                        note = Ciz1 b-variant peptide comprising an exon 14b/exon
                         15 junction
source                  1..53
                        mol_type = protein
                        organism = synthetic construct
SEQUENCE: 672
GQDEDHFITV DAVGCFEGDE EEEEDDEDEE EIEVRSRDIS REEWKGSETY SPN         53

SEQ ID NO: 673          moltype = AA  length = 52
FEATURE                 Location/Qualifiers
REGION                  1..52
                        note = Ciz1 b-variant peptide comprising an exon 14b/exon
                         15 junction
source                  1..52
                        mol_type = protein
                        organism = synthetic construct
SEQUENCE: 673
QDEDHFITVD AVGCFEGDEE EEEDDEDEEE IEVRSRDISR EEWKGSETYS PN          52

SEQ ID NO: 674          moltype = AA  length = 51
FEATURE                 Location/Qualifiers
REGION                  1..51
                        note = Ciz1 b-variant peptide comprising an exon 14b/exon
                         15 junction
source                  1..51
                        mol_type = protein
                        organism = synthetic construct
SEQUENCE: 674
DEDHFITVDA VGCFEGDEEE EEDDEDEEEI EVRSRDISRE EWKGSETYSP N           51

SEQ ID NO: 675          moltype = AA  length = 50
FEATURE                 Location/Qualifiers
REGION                  1..50
                        note = Ciz1 b-variant peptide comprising an exon 14b/exon
                         15 junction
source                  1..50
                        mol_type = protein
                        organism = synthetic construct
SEQUENCE: 675
EDHFITVDAV GCFEGDEEEE EDDEDEEEIE VRSRDISREE WKGSETYSPN             50

SEQ ID NO: 676          moltype = AA  length = 49
FEATURE                 Location/Qualifiers
REGION                  1..49
                        note = Ciz1 b-variant peptide comprising an exon 14b/exon
                         15 junction
source                  1..49
                        mol_type = protein
                        organism = synthetic construct
SEQUENCE: 676
DHFITVDAVG CFEGDEEEEE DDEDEEEIEV RSRDISREEW KGSETYSPN              49

SEQ ID NO: 677          moltype = AA  length = 48
```

```
FEATURE                Location/Qualifiers
REGION                 1..48
                       note = Ciz1 b-variant peptide comprising an exon 14b/exon
                        15 junction
source                 1..48
                       mol_type = protein
                       organism = synthetic construct
SEQUENCE: 677
HFITVDAVGC FEGDEEEEED DEDEEEIEVR SRDISREEWK GSETYSPN               48

SEQ ID NO: 678         moltype = AA  length = 47
FEATURE                Location/Qualifiers
REGION                 1..47
                       note = Ciz1 b-variant peptide comprising an exon 14b/exon
                        15 junction
source                 1..47
                       mol_type = protein
                       organism = synthetic construct
SEQUENCE: 678
FITVDAVGCF EGDEEEEEDD EDEEEIEVRS RDISREEWKG SETYSPN                47

SEQ ID NO: 679         moltype = AA  length = 46
FEATURE                Location/Qualifiers
REGION                 1..46
                       note = Ciz1 b-variant peptide comprising an exon 14b/exon
                        15 junction
source                 1..46
                       mol_type = protein
                       organism = synthetic construct
SEQUENCE: 679
ITVDAVGCFE GDEEEEEDDE DEEEIEVRSR DISREEWKGS ETYSPN                 46

SEQ ID NO: 680         moltype = AA  length = 45
FEATURE                Location/Qualifiers
REGION                 1..45
                       note = Ciz1 b-variant peptide comprising an exon 14b/exon
                        15 junction
source                 1..45
                       mol_type = protein
                       organism = synthetic construct
SEQUENCE: 680
TVDAVGCFEG DEEEEEDDED EEEIEVRSRD ISREEWKGSE TYSPN                  45

SEQ ID NO: 681         moltype = AA  length = 44
FEATURE                Location/Qualifiers
REGION                 1..44
                       note = Ciz1 b-variant peptide comprising an exon 14b/exon
                        15 junction
source                 1..44
                       mol_type = protein
                       organism = synthetic construct
SEQUENCE: 681
VDAVGCFEGD EEEEEDDEDE EEIEVRSRDI SREEWKGSET YSPN                   44

SEQ ID NO: 682         moltype = AA  length = 43
FEATURE                Location/Qualifiers
REGION                 1..43
                       note = Ciz1 b-variant peptide comprising an exon 14b/exon
                        15 junction
source                 1..43
                       mol_type = protein
                       organism = synthetic construct
SEQUENCE: 682
DAVGCFEGDE EEEEDDEDEE EIEVRSRDIS REEWKGSETY SPN                    43

SEQ ID NO: 683         moltype = AA  length = 42
FEATURE                Location/Qualifiers
REGION                 1..42
                       note = Ciz1 b-variant peptide comprising an exon 14b/exon
                        15 junction
source                 1..42
                       mol_type = protein
                       organism = synthetic construct
SEQUENCE: 683
AVGCFEGDEE EEEDDEDEEE IEVRSRDISR EEWKGSETYS PN                     42

SEQ ID NO: 684         moltype = AA  length = 41
FEATURE                Location/Qualifiers
REGION                 1..41
```

```
                      note = Ciz1 b-variant peptide comprising an exon 14b/exon
                       15 junction
source                1..41
                      mol_type = protein
                      organism = synthetic construct
SEQUENCE: 684
VGCFEGDEEE EEDDEDEEEI EVRSRDISRE EWKGSETYSP N                     41

SEQ ID NO: 685        moltype = AA  length = 40
FEATURE               Location/Qualifiers
REGION                1..40
                      note = Ciz1 b-variant peptide comprising an exon 14b/exon
                       15 junction
source                1..40
                      mol_type = protein
                      organism = synthetic construct
SEQUENCE: 685
GCFEGDEEEE EDDEDEEEIE VRSRDISREE WKGSETYSPN                       40

SEQ ID NO: 686        moltype = AA  length = 39
FEATURE               Location/Qualifiers
REGION                1..39
                      note = Ciz1 b-variant peptide comprising an exon 14b/exon
                       15 junction
source                1..39
                      mol_type = protein
                      organism = synthetic construct
SEQUENCE: 686
CFEGDEEEEE DDEDEEEIEV RSRDISREEW KGSETYSPN                        39

SEQ ID NO: 687        moltype = AA  length = 38
FEATURE               Location/Qualifiers
REGION                1..38
                      note = Ciz1 b-variant peptide comprising an exon 14b/exon
                       15 junction
source                1..38
                      mol_type = protein
                      organism = synthetic construct
SEQUENCE: 687
FEGDEEEEED DEDEEEIEVR SRDISREEWK GSETYSPN                         38

SEQ ID NO: 688        moltype = AA  length = 37
FEATURE               Location/Qualifiers
REGION                1..37
                      note = Ciz1 b-variant peptide comprising an exon 14b/exon
                       15 junction
source                1..37
                      mol_type = protein
                      organism = synthetic construct
SEQUENCE: 688
EGDEEEEEDD EDEEEIEVRS RDISREEWKG SETYSPN                          37

SEQ ID NO: 689        moltype = AA  length = 36
FEATURE               Location/Qualifiers
REGION                1..36
                      note = Ciz1 b-variant peptide comprising an exon 14b/exon
                       15 junction
source                1..36
                      mol_type = protein
                      organism = synthetic construct
SEQUENCE: 689
GDEEEEEDDE DEEEIEVRSR DISREEWKGS ETYSPN                           36

SEQ ID NO: 690        moltype = AA  length = 35
FEATURE               Location/Qualifiers
REGION                1..35
                      note = Ciz1 b-variant peptide comprising an exon 14b/exon
                       15 junction
source                1..35
                      mol_type = protein
                      organism = synthetic construct
SEQUENCE: 690
DEEEEEDDED EEEIEVRSRD ISREEWKGSE TYSPN                            35

SEQ ID NO: 691        moltype = AA  length = 34
FEATURE               Location/Qualifiers
REGION                1..34
                      note = Ciz1 b-variant peptide comprising an exon 14b/exon
                       15 junction
```

```
source                  1..34
                        mol_type = protein
                        organism = synthetic construct
SEQUENCE: 691
EEEEEDDEDE EEIEVRSRDI SREEWKGSET YSPN                                   34

SEQ ID NO: 692          moltype = AA  length = 33
FEATURE                 Location/Qualifiers
REGION                  1..33
                        note = Ciz1 b-variant peptide comprising an exon 14b/exon
                         15 junction
source                  1..33
                        mol_type = protein
                        organism = synthetic construct
SEQUENCE: 692
EEEEDDEDEE EIEVRSRDIS REEWKGSETY SPN                                    33

SEQ ID NO: 693          moltype = AA  length = 32
FEATURE                 Location/Qualifiers
REGION                  1..32
                        note = Ciz1 b-variant peptide comprising an exon 14b/exon
                         15 junction
source                  1..32
                        mol_type = protein
                        organism = synthetic construct
SEQUENCE: 693
EEEDDEDEEE IEVRSRDISR EEWKGSETYS PN                                     32

SEQ ID NO: 694          moltype = AA  length = 31
FEATURE                 Location/Qualifiers
REGION                  1..31
                        note = Ciz1 b-variant peptide comprising an exon 14b/exon
                         15 junction
source                  1..31
                        mol_type = protein
                        organism = synthetic construct
SEQUENCE: 694
EEDDEDEEEI EVRSRDISRE EWKGSETYSP N                                      31

SEQ ID NO: 695          moltype = AA  length = 30
FEATURE                 Location/Qualifiers
REGION                  1..30
                        note = Ciz1 b-variant peptide comprising an exon 14b/exon
                         15 junction
source                  1..30
                        mol_type = protein
                        organism = synthetic construct
SEQUENCE: 695
EDDEDEEEIE VRSRDISREE WKGSETYSPN                                        30

SEQ ID NO: 696          moltype = AA  length = 29
FEATURE                 Location/Qualifiers
REGION                  1..29
                        note = Ciz1 b-variant peptide comprising an exon 14b/exon
                         15 junction
source                  1..29
                        mol_type = protein
                        organism = synthetic construct
SEQUENCE: 696
DDEDEEEIEV RSRDISREEW KGSETYSPN                                         29

SEQ ID NO: 697          moltype = AA  length = 28
FEATURE                 Location/Qualifiers
REGION                  1..28
                        note = Ciz1 b-variant peptide comprising an exon 14b/exon
                         15 junction
source                  1..28
                        mol_type = protein
                        organism = synthetic construct
SEQUENCE: 697
DEDEEEIEVR SRDISREEWK GSETYSPN                                          28

SEQ ID NO: 698          moltype = AA  length = 27
FEATURE                 Location/Qualifiers
REGION                  1..27
                        note = Ciz1 b-variant peptide comprising an exon 14b/exon
                         15 junction
source                  1..27
                        mol_type = protein
```

```
                        organism = synthetic construct
SEQUENCE: 698
EDEEEIEVRS RDISREEWKG SETYSPN                                       27

SEQ ID NO: 699          moltype = AA  length = 26
FEATURE                 Location/Qualifiers
REGION                  1..26
                        note = Ciz1 b-variant peptide comprising an exon 14b/exon
                         15 junction
source                  1..26
                        mol_type = protein
                        organism = synthetic construct
SEQUENCE: 699
DEEEIEVRSR DISREEWKGS ETYSPN                                        26

SEQ ID NO: 700          moltype = AA  length = 25
FEATURE                 Location/Qualifiers
REGION                  1..25
                        note = Ciz1 b-variant peptide comprising an exon 14b/exon
                         15 junction
source                  1..25
                        mol_type = protein
                        organism = synthetic construct
SEQUENCE: 700
EEEIEVRSRD ISREEWKGSE TYSPN                                         25

SEQ ID NO: 701          moltype = AA  length = 24
FEATURE                 Location/Qualifiers
REGION                  1..24
                        note = Ciz1 b-variant peptide comprising an exon 14b/exon
                         15 junction
source                  1..24
                        mol_type = protein
                        organism = synthetic construct
SEQUENCE: 701
EEIEVRSRDI SREEWKGSET YSPN                                          24

SEQ ID NO: 702          moltype = AA  length = 23
FEATURE                 Location/Qualifiers
REGION                  1..23
                        note = Ciz1 b-variant peptide comprising an exon 14b/exon
                         15 junction
source                  1..23
                        mol_type = protein
                        organism = synthetic construct
SEQUENCE: 702
EIEVRSRDIS REEWKGSETY SPN                                           23

SEQ ID NO: 703          moltype = AA  length = 22
FEATURE                 Location/Qualifiers
REGION                  1..22
                        note = Ciz1 b-variant peptide comprising an exon 14b/exon
                         15 junction
source                  1..22
                        mol_type = protein
                        organism = synthetic construct
SEQUENCE: 703
IEVRSRDISR EEWKGSETYS PN                                            22

SEQ ID NO: 704          moltype = AA  length = 21
FEATURE                 Location/Qualifiers
REGION                  1..21
                        note = Ciz1 b-variant peptide comprising an exon 14b/exon
                         15 junction
source                  1..21
                        mol_type = protein
                        organism = synthetic construct
SEQUENCE: 704
EVRSRDISRE EWKGSETYSP N                                             21

SEQ ID NO: 705          moltype = AA  length = 57
FEATURE                 Location/Qualifiers
REGION                  1..57
                        note = Ciz1 b-variant peptide comprising an exon 14b/exon
                         15 junction
source                  1..57
                        mol_type = protein
                        organism = synthetic construct
SEQUENCE: 705
```

```
EIAGQDEDHF ITVDAVGCFE GDEEEEEDDE DEEEIEVRSR DISREEWKGS ETYSPNT     57

SEQ ID NO: 706         moltype = AA  length = 56
FEATURE                Location/Qualifiers
REGION                 1..56
                       note = Ciz1 b-variant peptide comprising an exon 14b/exon
                        15 junction
source                 1..56
                       mol_type = protein
                       organism = synthetic construct
SEQUENCE: 706
IAGQDEDHFI TVDAVGCFEG DEEEEEDDED EEEIEVRSRD ISREEWKGSE TYSPNT      56

SEQ ID NO: 707         moltype = AA  length = 55
FEATURE                Location/Qualifiers
REGION                 1..55
                       note = Ciz1 b-variant peptide comprising an exon 14b/exon
                        15 junction
source                 1..55
                       mol_type = protein
                       organism = synthetic construct
SEQUENCE: 707
AGQDEDHFIT VDAVGCFEGD EEEEEDDEDE EEIEVRSRDI SREEWKGSET YSPNT       55

SEQ ID NO: 708         moltype = AA  length = 54
FEATURE                Location/Qualifiers
REGION                 1..54
                       note = Ciz1 b-variant peptide comprising an exon 14b/exon
                        15 junction
source                 1..54
                       mol_type = protein
                       organism = synthetic construct
SEQUENCE: 708
GQDEDHFITV DAVGCFEGDE EEEEDDEDEE EIEVRSRDIS REEWKGSETY SPNT        54

SEQ ID NO: 709         moltype = AA  length = 53
FEATURE                Location/Qualifiers
REGION                 1..53
                       note = Ciz1 b-variant peptide comprising an exon 14b/exon
                        15 junction
source                 1..53
                       mol_type = protein
                       organism = synthetic construct
SEQUENCE: 709
QDEDHFITVD AVGCFEGDEE EEEDDEDEEE IEVRSRDISR EEWKGSETYS PNT         53

SEQ ID NO: 710         moltype = AA  length = 52
FEATURE                Location/Qualifiers
REGION                 1..52
                       note = Ciz1 b-variant peptide comprising an exon 14b/exon
                        15 junction
source                 1..52
                       mol_type = protein
                       organism = synthetic construct
SEQUENCE: 710
DEDHFITVDA VGCFEGDEEE EEDDEDEEEI EVRSRDISRE EWKGSETYSP NT          52

SEQ ID NO: 711         moltype = AA  length = 51
FEATURE                Location/Qualifiers
REGION                 1..51
                       note = Ciz1 b-variant peptide comprising an exon 14b/exon
                        15 junction
source                 1..51
                       mol_type = protein
                       organism = synthetic construct
SEQUENCE: 711
EDHFITVDAV GCFEGDEEEE EDDEDEEEIE VRSRDISREE WKGSETYSPN T           51

SEQ ID NO: 712         moltype = AA  length = 50
FEATURE                Location/Qualifiers
REGION                 1..50
                       note = Ciz1 b-variant peptide comprising an exon 14b/exon
                        15 junction
source                 1..50
                       mol_type = protein
                       organism = synthetic construct
SEQUENCE: 712
DHFITVDAVG CFEGDEEEEE DDEDEEEIEV RSRDISREEW KGSETYSPNT             50
```

```
SEQ ID NO: 713         moltype = AA  length = 49
FEATURE                Location/Qualifiers
REGION                 1..49
                       note = Ciz1 b-variant peptide comprising an exon 14b/exon
                        15 junction
source                 1..49
                       mol_type = protein
                       organism = synthetic construct
SEQUENCE: 713
HFITVDAVGC FEGDEEEEED DEDEEEIEVR SRDISREEWK GSETYSPNT             49

SEQ ID NO: 714         moltype = AA  length = 48
FEATURE                Location/Qualifiers
REGION                 1..48
                       note = Ciz1 b-variant peptide comprising an exon 14b/exon
                        15 junction
source                 1..48
                       mol_type = protein
                       organism = synthetic construct
SEQUENCE: 714
FITVDAVGCF EGDEEEEEDD EDEEEIEVRS RDISREEWKG SETYSPNT              48

SEQ ID NO: 715         moltype = AA  length = 47
FEATURE                Location/Qualifiers
REGION                 1..47
                       note = Ciz1 b-variant peptide comprising an exon 14b/exon
                        15 junction
source                 1..47
                       mol_type = protein
                       organism = synthetic construct
SEQUENCE: 715
ITVDAVGCFE GDEEEEEDDE DEEEIEVRSR DISREEWKGS ETYSPNT               47

SEQ ID NO: 716         moltype = AA  length = 46
FEATURE                Location/Qualifiers
REGION                 1..46
                       note = Ciz1 b-variant peptide comprising an exon 14b/exon
                        15 junction
source                 1..46
                       mol_type = protein
                       organism = synthetic construct
SEQUENCE: 716
TVDAVGCFEG DEEEEEDDED EEEIEVRSRD ISREEWKGSE TYSPNT                46

SEQ ID NO: 717         moltype = AA  length = 45
FEATURE                Location/Qualifiers
REGION                 1..45
                       note = Ciz1 b-variant peptide comprising an exon 14b/exon
                        15 junction
source                 1..45
                       mol_type = protein
                       organism = synthetic construct
SEQUENCE: 717
VDAVGCFEGD EEEEEDDEDE EEIEVRSRDI SREEWKGSET YSPNT                 45

SEQ ID NO: 718         moltype = AA  length = 44
FEATURE                Location/Qualifiers
REGION                 1..44
                       note = Ciz1 b-variant peptide comprising an exon 14b/exon
                        15 junction
source                 1..44
                       mol_type = protein
                       organism = synthetic construct
SEQUENCE: 718
DAVGCFEGDE EEEEDDEDEE EIEVRSRDIS REEWKGSETY SPNT                  44

SEQ ID NO: 719         moltype = AA  length = 43
FEATURE                Location/Qualifiers
REGION                 1..43
                       note = Ciz1 b-variant peptide comprising an exon 14b/exon
                        15 junction
source                 1..43
                       mol_type = protein
                       organism = synthetic construct
SEQUENCE: 719
AVGCFEGDEE EEEDDEDEEE IEVRSRDISR EEWKGSETYS PNT                   43

SEQ ID NO: 720         moltype = AA  length = 42
FEATURE                Location/Qualifiers
```

```
REGION                  1..42
                        note = Ciz1 b-variant peptide comprising an exon 14b/exon
                         15 junction
source                  1..42
                        mol_type = protein
                        organism = synthetic construct
SEQUENCE: 720
VGCFEGDEEE EEDDEDEEEI EVRSRDISRE EWKGSETYSP NT                    42

SEQ ID NO: 721          moltype = AA  length = 41
FEATURE                 Location/Qualifiers
REGION                  1..41
                        note = Ciz1 b-variant peptide comprising an exon 14b/exon
                         15 junction
source                  1..41
                        mol_type = protein
                        organism = synthetic construct
SEQUENCE: 721
GCFEGDEEEE EDDEDEEEIE VRSRDISREE WKGSETYSPN T                     41

SEQ ID NO: 722          moltype = AA  length = 40
FEATURE                 Location/Qualifiers
REGION                  1..40
                        note = Ciz1 b-variant peptide comprising an exon 14b/exon
                         15 junction
source                  1..40
                        mol_type = protein
                        organism = synthetic construct
SEQUENCE: 722
CFEGDEEEEE DDEDEEEIEV RSRDISREEW KGSETYSPNT                       40

SEQ ID NO: 723          moltype = AA  length = 39
FEATURE                 Location/Qualifiers
REGION                  1..39
                        note = Ciz1 b-variant peptide comprising an exon 14b/exon
                         15 junction
source                  1..39
                        mol_type = protein
                        organism = synthetic construct
SEQUENCE: 723
FEGDEEEEED DEDEEEIEVR SRDISREEWK GSETYSPNT                        39

SEQ ID NO: 724          moltype = AA  length = 38
FEATURE                 Location/Qualifiers
REGION                  1..38
                        note = Ciz1 b-variant peptide comprising an exon 14b/exon
                         15 junction
source                  1..38
                        mol_type = protein
                        organism = synthetic construct
SEQUENCE: 724
EGDEEEEEDD EDEEEIEVRS RDISREEWKG SETYSPNT                         38

SEQ ID NO: 725          moltype = AA  length = 37
FEATURE                 Location/Qualifiers
REGION                  1..37
                        note = Ciz1 b-variant peptide comprising an exon 14b/exon
                         15 junction
source                  1..37
                        mol_type = protein
                        organism = synthetic construct
SEQUENCE: 725
GDEEEEEDDE DEEEIEVRSR DISREEWKGS ETYSPNT                          37

SEQ ID NO: 726          moltype = AA  length = 36
FEATURE                 Location/Qualifiers
REGION                  1..36
                        note = Ciz1 b-variant peptide comprising an exon 14b/exon
                         15 junction
source                  1..36
                        mol_type = protein
                        organism = synthetic construct
SEQUENCE: 726
DEEEEEDDED EEEIEVRSRD ISREEWKGSE TYSPNT                           36

SEQ ID NO: 727          moltype = AA  length = 35
FEATURE                 Location/Qualifiers
REGION                  1..35
                        note = Ciz1 b-variant peptide comprising an exon 14b/exon
```

```
                       15 junction
source                 1..35
                       mol_type = protein
                       organism = synthetic construct
SEQUENCE: 727
EEEEEDDEDE EEIEVRSRDI SREEWKGSET YSPNT                            35

SEQ ID NO: 728         moltype = AA  length = 34
FEATURE                Location/Qualifiers
REGION                 1..34
                       note = Ciz1 b-variant peptide comprising an exon 14b/exon
                        15 junction
source                 1..34
                       mol_type = protein
                       organism = synthetic construct
SEQUENCE: 728
EEEEDDEDEE EIEVRSRDIS REEWKGSETY SPNT                             34

SEQ ID NO: 729         moltype = AA  length = 33
FEATURE                Location/Qualifiers
REGION                 1..33
                       note = Ciz1 b-variant peptide comprising an exon 14b/exon
                        15 junction
source                 1..33
                       mol_type = protein
                       organism = synthetic construct
SEQUENCE: 729
EEEDDEDEEE IEVRSRDISR EEWKGSETYS PNT                              33

SEQ ID NO: 730         moltype = AA  length = 32
FEATURE                Location/Qualifiers
REGION                 1..32
                       note = Ciz1 b-variant peptide comprising an exon 14b/exon
                        15 junction
source                 1..32
                       mol_type = protein
                       organism = synthetic construct
SEQUENCE: 730
EEDDEDEEEI EVRSRDISRE EWKGSETYSP NT                               32

SEQ ID NO: 731         moltype = AA  length = 31
FEATURE                Location/Qualifiers
REGION                 1..31
                       note = Ciz1 b-variant peptide comprising an exon 14b/exon
                        15 junction
source                 1..31
                       mol_type = protein
                       organism = synthetic construct
SEQUENCE: 731
EDDEDEEEIE VRSRDISREE WKGSETYSPN T                                31

SEQ ID NO: 732         moltype = AA  length = 30
FEATURE                Location/Qualifiers
REGION                 1..30
                       note = Ciz1 b-variant peptide comprising an exon 14b/exon
                        15 junction
source                 1..30
                       mol_type = protein
                       organism = synthetic construct
SEQUENCE: 732
DDEDEEEIEV RSRDISREEW KGSETYSPNT                                  30

SEQ ID NO: 733         moltype = AA  length = 29
FEATURE                Location/Qualifiers
REGION                 1..29
                       note = Ciz1 b-variant peptide comprising an exon 14b/exon
                        15 junction
source                 1..29
                       mol_type = protein
                       organism = synthetic construct
SEQUENCE: 733
DEDEEEIEVR SRDISREEWK GSETYSPNT                                   29

SEQ ID NO: 734         moltype = AA  length = 28
FEATURE                Location/Qualifiers
REGION                 1..28
                       note = Ciz1 b-variant peptide comprising an exon 14b/exon
                        15 junction
source                 1..28
```

```
                        mol_type = protein
                        organism = synthetic construct
SEQUENCE: 734
EDEEEIEVRS RDISREEWKG SETYSPNT                                       28

SEQ ID NO: 735          moltype = AA  length = 27
FEATURE                 Location/Qualifiers
REGION                  1..27
                        note = Ciz1 b-variant peptide comprising an exon 14b/exon
                         15 junction
source                  1..27
                        mol_type = protein
                        organism = synthetic construct
SEQUENCE: 735
DEEEIEVRSR DISREEWKGS ETYSPNT                                        27

SEQ ID NO: 736          moltype = AA  length = 26
FEATURE                 Location/Qualifiers
REGION                  1..26
                        note = Ciz1 b-variant peptide comprising an exon 14b/exon
                         15 junction
source                  1..26
                        mol_type = protein
                        organism = synthetic construct
SEQUENCE: 736
EEEIEVRSRD ISREEWKGSE TYSPNT                                         26

SEQ ID NO: 737          moltype = AA  length = 25
FEATURE                 Location/Qualifiers
REGION                  1..25
                        note = Ciz1 b-variant peptide comprising an exon 14b/exon
                         15 junction
source                  1..25
                        mol_type = protein
                        organism = synthetic construct
SEQUENCE: 737
EEIEVRSRDI SREEWKGSET YSPNT                                          25

SEQ ID NO: 738          moltype = AA  length = 24
FEATURE                 Location/Qualifiers
REGION                  1..24
                        note = Ciz1 b-variant peptide comprising an exon 14b/exon
                         15 junction
source                  1..24
                        mol_type = protein
                        organism = synthetic construct
SEQUENCE: 738
EIEVRSRDIS REEWKGSETY SPNT                                           24

SEQ ID NO: 739          moltype = AA  length = 23
FEATURE                 Location/Qualifiers
REGION                  1..23
                        note = Ciz1 b-variant peptide comprising an exon 14b/exon
                         15 junction
source                  1..23
                        mol_type = protein
                        organism = synthetic construct
SEQUENCE: 739
IEVRSRDISR EEWKGSETYS PNT                                            23

SEQ ID NO: 740          moltype = AA  length = 22
FEATURE                 Location/Qualifiers
REGION                  1..22
                        note = Ciz1 b-variant peptide comprising an exon 14b/exon
                         15 junction
source                  1..22
                        mol_type = protein
                        organism = synthetic construct
SEQUENCE: 740
EVRSRDISRE EWKGSETYSP NT                                             22

SEQ ID NO: 741          moltype = AA  length = 58
FEATURE                 Location/Qualifiers
REGION                  1..58
                        note = Ciz1 b-variant peptide comprising an exon 14b/exon
                         15 junction
source                  1..58
                        mol_type = protein
                        organism = synthetic construct
```

```
SEQUENCE: 741
EIAGQDEDHF ITVDAVGCFE GDEEEEEDDE DEEEIEVRSR DISREEWKGS ETYSPNTA    58

SEQ ID NO: 742         moltype = AA  length = 57
FEATURE                Location/Qualifiers
REGION                 1..57
                       note = Ciz1 b-variant peptide comprising an exon 14b/exon
                        15 junction
source                 1..57
                       mol_type = protein
                       organism = synthetic construct
SEQUENCE: 742
IAGQDEDHFI TVDAVGCFEG DEEEEEDDED EEEIEVRSRD ISREEWKGSE TYSPNTA     57

SEQ ID NO: 743         moltype = AA  length = 56
FEATURE                Location/Qualifiers
REGION                 1..56
                       note = Ciz1 b-variant peptide comprising an exon 14b/exon
                        15 junction
source                 1..56
                       mol_type = protein
                       organism = synthetic construct
SEQUENCE: 743
AGQDEDHFIT VDAVGCFEGD EEEEEDDEDE EEIEVRSRDI SREEWKGSET YSPNTA      56

SEQ ID NO: 744         moltype = AA  length = 55
FEATURE                Location/Qualifiers
REGION                 1..55
                       note = Ciz1 b-variant peptide comprising an exon 14b/exon
                        15 junction
source                 1..55
                       mol_type = protein
                       organism = synthetic construct
SEQUENCE: 744
GQDEDHFITV DAVGCFEGDE EEEEDDEDEE EIEVRSRDIS REEWKGSETY SPNTA       55

SEQ ID NO: 745         moltype = AA  length = 54
FEATURE                Location/Qualifiers
REGION                 1..54
                       note = Ciz1 b-variant peptide comprising an exon 14b/exon
                        15 junction
source                 1..54
                       mol_type = protein
                       organism = synthetic construct
SEQUENCE: 745
QDEDHFITVD AVGCFEGDEE EEEDDEDEEE IEVRSRDISR EEWKGSETYS PNTA        54

SEQ ID NO: 746         moltype = AA  length = 53
FEATURE                Location/Qualifiers
REGION                 1..53
                       note = Ciz1 b-variant peptide comprising an exon 14b/exon
                        15 junction
source                 1..53
                       mol_type = protein
                       organism = synthetic construct
SEQUENCE: 746
DEDHFITVDA VGCFEGDEEE EEDDEDEEEI EVRSRDISRE EWKGSETYSP NTA         53

SEQ ID NO: 747         moltype = AA  length = 52
FEATURE                Location/Qualifiers
REGION                 1..52
                       note = Ciz1 b-variant peptide comprising an exon 14b/exon
                        15 junction
source                 1..52
                       mol_type = protein
                       organism = synthetic construct
SEQUENCE: 747
EDHFITVDAV GCFEGDEEEE EDDEDEEEIE VRSRDISREE WKGSETYSPN TA          52

SEQ ID NO: 748         moltype = AA  length = 51
FEATURE                Location/Qualifiers
REGION                 1..51
                       note = Ciz1 b-variant peptide comprising an exon 14b/exon
                        15 junction
source                 1..51
                       mol_type = protein
                       organism = synthetic construct
SEQUENCE: 748
DHFITVDAVG CFEGDEEEEE DDEDEEEIEV RSRDISREEW KGSETYSPNT A           51
```

```
SEQ ID NO: 749          moltype = AA  length = 50
FEATURE                 Location/Qualifiers
REGION                  1..50
                        note = Ciz1 b-variant peptide comprising an exon 14b/exon
                         15 junction
source                  1..50
                        mol_type = protein
                        organism = synthetic construct
SEQUENCE: 749
HFITVDAVGC FEGDEEEEED DEDEEEIEVR SRDISREEWK GSETYSPNTA             50

SEQ ID NO: 750          moltype = AA  length = 49
FEATURE                 Location/Qualifiers
REGION                  1..49
                        note = Ciz1 b-variant peptide comprising an exon 14b/exon
                         15 junction
source                  1..49
                        mol_type = protein
                        organism = synthetic construct
SEQUENCE: 750
FITVDAVGCF EGDEEEEEDD EDEEEIEVRS RDISREEWKG SETYSPNTA              49

SEQ ID NO: 751          moltype = AA  length = 48
FEATURE                 Location/Qualifiers
REGION                  1..48
                        note = Ciz1 b-variant peptide comprising an exon 14b/exon
                         15 junction
source                  1..48
                        mol_type = protein
                        organism = synthetic construct
SEQUENCE: 751
ITVDAVGCFE GDEEEEEDDE DEEEIEVRSR DISREEWKGS ETYSPNTA               48

SEQ ID NO: 752          moltype = AA  length = 47
FEATURE                 Location/Qualifiers
REGION                  1..47
                        note = Ciz1 b-variant peptide comprising an exon 14b/exon
                         15 junction
source                  1..47
                        mol_type = protein
                        organism = synthetic construct
SEQUENCE: 752
TVDAVGCFEG DEEEEEDDED EEEIEVRSRD ISREEWKGSE TYSPNTA                47

SEQ ID NO: 753          moltype = AA  length = 46
FEATURE                 Location/Qualifiers
REGION                  1..46
                        note = Ciz1 b-variant peptide comprising an exon 14b/exon
                         15 junction
source                  1..46
                        mol_type = protein
                        organism = synthetic construct
SEQUENCE: 753
VDAVGCFEGD EEEEEDDEDE EEIEVRSRDI SREEWKGSET YSPNTA                 46

SEQ ID NO: 754          moltype = AA  length = 45
FEATURE                 Location/Qualifiers
REGION                  1..45
                        note = Ciz1 b-variant peptide comprising an exon 14b/exon
                         15 junction
source                  1..45
                        mol_type = protein
                        organism = synthetic construct
SEQUENCE: 754
DAVGCFEGDE EEEEDDEDEE EIEVRSRDIS REEWKGSETY SPNTA                  45

SEQ ID NO: 755          moltype = AA  length = 44
FEATURE                 Location/Qualifiers
REGION                  1..44
                        note = Ciz1 b-variant peptide comprising an exon 14b/exon
                         15 junction
source                  1..44
                        mol_type = protein
                        organism = synthetic construct
SEQUENCE: 755
AVGCFEGDEE EEEDDEDEEE IEVRSRDISR EEWKGSETYS PNTA                   44

SEQ ID NO: 756          moltype = AA  length = 43
```

```
FEATURE                Location/Qualifiers
REGION                 1..43
                       note = Ciz1 b-variant peptide comprising an exon 14b/exon
                        15 junction
source                 1..43
                       mol_type = protein
                       organism = synthetic construct
SEQUENCE: 756
VGCFEGDEEE EEDDEDEEEI EVRSRDISRE EWKGSETYSP NTA                        43

SEQ ID NO: 757         moltype = AA  length = 42
FEATURE                Location/Qualifiers
REGION                 1..42
                       note = Ciz1 b-variant peptide comprising an exon 14b/exon
                        15 junction
source                 1..42
                       mol_type = protein
                       organism = synthetic construct
SEQUENCE: 757
GCFEGDEEEE EDDEDEEEIE VRSRDISREE WKGSETYSPN TA                         42

SEQ ID NO: 758         moltype = AA  length = 41
FEATURE                Location/Qualifiers
REGION                 1..41
                       note = Ciz1 b-variant peptide comprising an exon 14b/exon
                        15 junction
source                 1..41
                       mol_type = protein
                       organism = synthetic construct
SEQUENCE: 758
CFEGDEEEEE DDEDEEEIEV RSRDISREEW KGSETYSPNT A                          41

SEQ ID NO: 759         moltype = AA  length = 40
FEATURE                Location/Qualifiers
REGION                 1..40
                       note = Ciz1 b-variant peptide comprising an exon 14b/exon
                        15 junction
source                 1..40
                       mol_type = protein
                       organism = synthetic construct
SEQUENCE: 759
FEGDEEEEED DEDEEEIEVR SRDISREEWK GSETYSPNTA                            40

SEQ ID NO: 760         moltype = AA  length = 39
FEATURE                Location/Qualifiers
REGION                 1..39
                       note = Ciz1 b-variant peptide comprising an exon 14b/exon
                        15 junction
source                 1..39
                       mol_type = protein
                       organism = synthetic construct
SEQUENCE: 760
EGDEEEEEDD EDEEEIEVRS RDISREEWKG SETYSPNTA                             39

SEQ ID NO: 761         moltype = AA  length = 38
FEATURE                Location/Qualifiers
REGION                 1..38
                       note = Ciz1 b-variant peptide comprising an exon 14b/exon
                        15 junction
source                 1..38
                       mol_type = protein
                       organism = synthetic construct
SEQUENCE: 761
GDEEEEEDDE DEEEIEVRSR DISREEWKGS ETYSPNTA                              38

SEQ ID NO: 762         moltype = AA  length = 37
FEATURE                Location/Qualifiers
REGION                 1..37
                       note = Ciz1 b-variant peptide comprising an exon 14b/exon
                        15 junction
source                 1..37
                       mol_type = protein
                       organism = synthetic construct
SEQUENCE: 762
DEEEEEDDED EEEIEVRSRD ISREEWKGSE TYSPNTA                               37

SEQ ID NO: 763         moltype = AA  length = 36
FEATURE                Location/Qualifiers
REGION                 1..36
```

```
                        note = Ciz1 b-variant peptide comprising an exon 14b/exon
                         15 junction
source                  1..36
                        mol_type = protein
                        organism = synthetic construct
SEQUENCE: 763
EEEEEDDEDE EEIEVRSRDI SREEWKGSET YSPNTA                          36

SEQ ID NO: 764          moltype = AA  length = 35
FEATURE                 Location/Qualifiers
REGION                  1..35
                        note = Ciz1 b-variant peptide comprising an exon 14b/exon
                         15 junction
source                  1..35
                        mol_type = protein
                        organism = synthetic construct
SEQUENCE: 764
EEEEDDEDEE EIEVRSRDIS REEWKGSETY SPNTA                           35

SEQ ID NO: 765          moltype = AA  length = 34
FEATURE                 Location/Qualifiers
REGION                  1..34
                        note = Ciz1 b-variant peptide comprising an exon 14b/exon
                         15 junction
source                  1..34
                        mol_type = protein
                        organism = synthetic construct
SEQUENCE: 765
EEEDDEDEEE IEVRSRDISR EEWKGSETYS PNTA                            34

SEQ ID NO: 766          moltype = AA  length = 33
FEATURE                 Location/Qualifiers
REGION                  1..33
                        note = Ciz1 b-variant peptide comprising an exon 14b/exon
                         15 junction
source                  1..33
                        mol_type = protein
                        organism = synthetic construct
SEQUENCE: 766
EEDDEDEEEI EVRSRDISRE EWKGSETYSP NTA                             33

SEQ ID NO: 767          moltype = AA  length = 32
FEATURE                 Location/Qualifiers
REGION                  1..32
                        note = Ciz1 b-variant peptide comprising an exon 14b/exon
                         15 junction
source                  1..32
                        mol_type = protein
                        organism = synthetic construct
SEQUENCE: 767
EDDEDEEEIE VRSRDISREE WKGSETYSPN TA                              32

SEQ ID NO: 768          moltype = AA  length = 31
FEATURE                 Location/Qualifiers
REGION                  1..31
                        note = Ciz1 b-variant peptide comprising an exon 14b/exon
                         15 junction
source                  1..31
                        mol_type = protein
                        organism = synthetic construct
SEQUENCE: 768
DDEDEEEIEV RSRDISREEW KGSETYSPNT A                               31

SEQ ID NO: 769          moltype = AA  length = 30
FEATURE                 Location/Qualifiers
REGION                  1..30
                        note = Ciz1 b-variant peptide comprising an exon 14b/exon
                         15 junction
source                  1..30
                        mol_type = protein
                        organism = synthetic construct
SEQUENCE: 769
DEDEEEIEVR SRDISREEWK GSETYSPNTA                                 30

SEQ ID NO: 770          moltype = AA  length = 29
FEATURE                 Location/Qualifiers
REGION                  1..29
                        note = Ciz1 b-variant peptide comprising an exon 14b/exon
                         15 junction
```

```
source                  1..29
                        mol_type = protein
                        organism = synthetic construct
SEQUENCE: 770
EDEEEIEVRS RDISREEWKG SETYSPNTA                                    29

SEQ ID NO: 771          moltype = AA  length = 28
FEATURE                 Location/Qualifiers
REGION                  1..28
                        note = Ciz1 b-variant peptide comprising an exon 14b/exon
                         15 junction
source                  1..28
                        mol_type = protein
                        organism = synthetic construct
SEQUENCE: 771
DEEEIEVRSR DISREEWKGS ETYSPNTA                                     28

SEQ ID NO: 772          moltype = AA  length = 27
FEATURE                 Location/Qualifiers
REGION                  1..27
                        note = Ciz1 b-variant peptide comprising an exon 14b/exon
                         15 junction
source                  1..27
                        mol_type = protein
                        organism = synthetic construct
SEQUENCE: 772
EEEIEVRSRD ISREEWKGSE TYSPNTA                                      27

SEQ ID NO: 773          moltype = AA  length = 26
FEATURE                 Location/Qualifiers
REGION                  1..26
                        note = Ciz1 b-variant peptide comprising an exon 14b/exon
                         15 junction
source                  1..26
                        mol_type = protein
                        organism = synthetic construct
SEQUENCE: 773
EEIEVRSRDI SREEWKGSET YSPNTA                                       26

SEQ ID NO: 774          moltype = AA  length = 25
FEATURE                 Location/Qualifiers
REGION                  1..25
                        note = Ciz1 b-variant peptide comprising an exon 14b/exon
                         15 junction
source                  1..25
                        mol_type = protein
                        organism = synthetic construct
SEQUENCE: 774
EIEVRSRDIS REEWKGSETY SPNTA                                        25

SEQ ID NO: 775          moltype = AA  length = 24
FEATURE                 Location/Qualifiers
REGION                  1..24
                        note = Ciz1 b-variant peptide comprising an exon 14b/exon
                         15 junction
source                  1..24
                        mol_type = protein
                        organism = synthetic construct
SEQUENCE: 775
IEVRSRDISR EEWKGSETYS PNTA                                         24

SEQ ID NO: 776          moltype = AA  length = 23
FEATURE                 Location/Qualifiers
REGION                  1..23
                        note = Ciz1 b-variant peptide comprising an exon 14b/exon
                         15 junction
source                  1..23
                        mol_type = protein
                        organism = synthetic construct
SEQUENCE: 776
EVRSRDISRE EWKGSETYSP NTA                                          23

SEQ ID NO: 777          moltype = AA  length = 59
FEATURE                 Location/Qualifiers
REGION                  1..59
                        note = Ciz1 b-variant peptide comprising an exon 14b/exon
                         15 junction
source                  1..59
                        mol_type = protein
```

```
                         organism = synthetic construct
SEQUENCE: 777
EIAGQDEDHF ITVDAVGCFE GDEEEEEDDE DEEEIEVRSR DISREEWKGS ETYSPNTAY   59

SEQ ID NO: 778           moltype = AA  length = 58
FEATURE                  Location/Qualifiers
REGION                   1..58
                         note = Ciz1 b-variant peptide comprising an exon 14b/exon
                          15 junction
source                   1..58
                         mol_type = protein
                         organism = synthetic construct
SEQUENCE: 778
IAGQDEDHFI TVDAVGCFEG DEEEEEDDED EEEIEVRSRD ISREEWKGSE TYSPNTAY    58

SEQ ID NO: 779           moltype = AA  length = 57
FEATURE                  Location/Qualifiers
REGION                   1..57
                         note = Ciz1 b-variant peptide comprising an exon 14b/exon
                          15 junction
source                   1..57
                         mol_type = protein
                         organism = synthetic construct
SEQUENCE: 779
AGQDEDHFIT VDAVGCFEGD EEEEEDDEDE EEIEVRSRDI SREEWKGSET YSPNTAY     57

SEQ ID NO: 780           moltype = AA  length = 56
FEATURE                  Location/Qualifiers
REGION                   1..56
                         note = Ciz1 b-variant peptide comprising an exon 14b/exon
                          15 junction
source                   1..56
                         mol_type = protein
                         organism = synthetic construct
SEQUENCE: 780
GQDEDHFITV DAVGCFEGDE EEEEDDEDEE EIEVRSRDIS REEWKGSETY SPNTAY      56

SEQ ID NO: 781           moltype = AA  length = 55
FEATURE                  Location/Qualifiers
REGION                   1..55
                         note = Ciz1 b-variant peptide comprising an exon 14b/exon
                          15 junction
source                   1..55
                         mol_type = protein
                         organism = synthetic construct
SEQUENCE: 781
QDEDHFITVD AVGCFEGDEE EEEDDEDEEE IEVRSRDISR EEWKGSETYS PNTAY       55

SEQ ID NO: 782           moltype = AA  length = 54
FEATURE                  Location/Qualifiers
REGION                   1..54
                         note = Ciz1 b-variant peptide comprising an exon 14b/exon
                          15 junction
source                   1..54
                         mol_type = protein
                         organism = synthetic construct
SEQUENCE: 782
DEDHFITVDA VGCFEGDEEE EEDDEDEEEI EVRSRDISRE EWKGSETYSP NTAY        54

SEQ ID NO: 783           moltype = AA  length = 53
FEATURE                  Location/Qualifiers
REGION                   1..53
                         note = Ciz1 b-variant peptide comprising an exon 14b/exon
                          15 junction
source                   1..53
                         mol_type = protein
                         organism = synthetic construct
SEQUENCE: 783
EDHFITVDAV GCFEGDEEEE EDDEDEEEIE VRSRDISREE WKGSETYSPN TAY         53

SEQ ID NO: 784           moltype = AA  length = 52
FEATURE                  Location/Qualifiers
REGION                   1..52
                         note = Ciz1 b-variant peptide comprising an exon 14b/exon
                          15 junction
source                   1..52
                         mol_type = protein
                         organism = synthetic construct
SEQUENCE: 784
```

DHFITVDAVG CFEGDEEEEE DDEDEEEIEV RSRDISREEW KGSETYSPNT AY 52

SEQ ID NO: 785 moltype = AA length = 51
FEATURE Location/Qualifiers
REGION 1..51
note = Ciz1 b-variant peptide comprising an exon 14b/exon 15 junction
source 1..51
mol_type = protein
organism = synthetic construct
SEQUENCE: 785
HFITVDAVGC FEGDEEEEED DEDEEEIEVR SRDISREEWK GSETYSPNTA Y 51

SEQ ID NO: 786 moltype = AA length = 50
FEATURE Location/Qualifiers
REGION 1..50
note = Ciz1 b-variant peptide comprising an exon 14b/exon 15 junction
source 1..50
mol_type = protein
organism = synthetic construct
SEQUENCE: 786
FITVDAVGCF EGDEEEEEDD EDEEEIEVRS RDISREEWKG SETYSPNTAY 50

SEQ ID NO: 787 moltype = AA length = 49
FEATURE Location/Qualifiers
REGION 1..49
note = Ciz1 b-variant peptide comprising an exon 14b/exon 15 junction
source 1..49
mol_type = protein
organism = synthetic construct
SEQUENCE: 787
ITVDAVGCFE GDEEEEEDDE DEEEIEVRSR DISREEWKGS ETYSPNTAY 49

SEQ ID NO: 788 moltype = AA length = 48
FEATURE Location/Qualifiers
REGION 1..48
note = Ciz1 b-variant peptide comprising an exon 14b/exon 15 junction
source 1..48
mol_type = protein
organism = synthetic construct
SEQUENCE: 788
TVDAVGCFEG DEEEEEDDED EEEIEVRSRD ISREEWKGSE TYSPNTAY 48

SEQ ID NO: 789 moltype = AA length = 47
FEATURE Location/Qualifiers
REGION 1..47
note = Ciz1 b-variant peptide comprising an exon 14b/exon 15 junction
source 1..47
mol_type = protein
organism = synthetic construct
SEQUENCE: 789
VDAVGCFEGD EEEEEDDEDE EEIEVRSRDI SREEWKGSET YSPNTAY 47

SEQ ID NO: 790 moltype = AA length = 46
FEATURE Location/Qualifiers
REGION 1..46
note = Ciz1 b-variant peptide comprising an exon 14b/exon 15 junction
source 1..46
mol_type = protein
organism = synthetic construct
SEQUENCE: 790
DAVGCFEGDE EEEEDDEDEE EIEVRSRDIS REEWKGSETY SPNTAY 46

SEQ ID NO: 791 moltype = AA length = 45
FEATURE Location/Qualifiers
REGION 1..45
note = Ciz1 b-variant peptide comprising an exon 14b/exon 15 junction
source 1..45
mol_type = protein
organism = synthetic construct
SEQUENCE: 791
AVGCFEGDEE EEEDDEDEEE IEVRSRDISR EEWKGSETYS PNTAY 45

```
SEQ ID NO: 792          moltype = AA  length = 44
FEATURE                 Location/Qualifiers
REGION                  1..44
                        note = Ciz1 b-variant peptide comprising an exon 14b/exon
                         15 junction
source                  1..44
                        mol_type = protein
                        organism = synthetic construct
SEQUENCE: 792
VGCFEGDEEE EEDDEDEEEI EVRSRDISRE EWKGSETYSP NTAY                   44

SEQ ID NO: 793          moltype = AA  length = 43
FEATURE                 Location/Qualifiers
REGION                  1..43
                        note = Ciz1 b-variant peptide comprising an exon 14b/exon
                         15 junction
source                  1..43
                        mol_type = protein
                        organism = synthetic construct
SEQUENCE: 793
GCFEGDEEEE EDDEDEEEIE VRSRDISREE WKGSETYSPN TAY                    43

SEQ ID NO: 794          moltype = AA  length = 42
FEATURE                 Location/Qualifiers
REGION                  1..42
                        note = Ciz1 b-variant peptide comprising an exon 14b/exon
                         15 junction
source                  1..42
                        mol_type = protein
                        organism = synthetic construct
SEQUENCE: 794
CFEGDEEEEE DDEDEEEIEV RSRDISREEW KGSETYSPNT AY                     42

SEQ ID NO: 795          moltype = AA  length = 41
FEATURE                 Location/Qualifiers
REGION                  1..41
                        note = Ciz1 b-variant peptide comprising an exon 14b/exon
                         15 junction
source                  1..41
                        mol_type = protein
                        organism = synthetic construct
SEQUENCE: 795
FEGDEEEEED DEDEEEIEVR SRDISREEWK GSETYSPNTA Y                      41

SEQ ID NO: 796          moltype = AA  length = 40
FEATURE                 Location/Qualifiers
REGION                  1..40
                        note = Ciz1 b-variant peptide comprising an exon 14b/exon
                         15 junction
source                  1..40
                        mol_type = protein
                        organism = synthetic construct
SEQUENCE: 796
EGDEEEEEDD EDEEEIEVRS RDISREEWKG SETYSPNTAY                        40

SEQ ID NO: 797          moltype = AA  length = 39
FEATURE                 Location/Qualifiers
REGION                  1..39
                        note = Ciz1 b-variant peptide comprising an exon 14b/exon
                         15 junction
source                  1..39
                        mol_type = protein
                        organism = synthetic construct
SEQUENCE: 797
GDEEEEEDDE DEEEIEVRSR DISREEWKGS ETYSPNTAY                         39

SEQ ID NO: 798          moltype = AA  length = 38
FEATURE                 Location/Qualifiers
REGION                  1..38
                        note = Ciz1 b-variant peptide comprising an exon 14b/exon
                         15 junction
source                  1..38
                        mol_type = protein
                        organism = synthetic construct
SEQUENCE: 798
DEEEEEDDED EEEIEVRSRD ISREEWKGSE TYSPNTAY                          38

SEQ ID NO: 799          moltype = AA  length = 37
FEATURE                 Location/Qualifiers
```

```
REGION                  1..37
                        note = Ciz1 b-variant peptide comprising an exon 14b/exon
                         15 junction
source                  1..37
                        mol_type = protein
                        organism = synthetic construct
SEQUENCE: 799
EEEEEDDEDE EEIEVRSRDI SREEWKGSET YSPNTAY                          37

SEQ ID NO: 800          moltype = AA  length = 36
FEATURE                 Location/Qualifiers
REGION                  1..36
                        note = Ciz1 b-variant peptide comprising an exon 14b/exon
                         15 junction
source                  1..36
                        mol_type = protein
                        organism = synthetic construct
SEQUENCE: 800
EEEEDDEDEE EIEVRSRDIS REEWKGSETY SPNTAY                           36

SEQ ID NO: 801          moltype = AA  length = 35
FEATURE                 Location/Qualifiers
REGION                  1..35
                        note = Ciz1 b-variant peptide comprising an exon 14b/exon
                         15 junction
source                  1..35
                        mol_type = protein
                        organism = synthetic construct
SEQUENCE: 801
EEEDDEDEEE IEVRSRDISR EEWKGSETYS PNTAY                            35

SEQ ID NO: 802          moltype = AA  length = 34
FEATURE                 Location/Qualifiers
REGION                  1..34
                        note = Ciz1 b-variant peptide comprising an exon 14b/exon
                         15 junction
source                  1..34
                        mol_type = protein
                        organism = synthetic construct
SEQUENCE: 802
EEDDEDEEEI EVRSRDISRE EWKGSETYSP NTAY                             34

SEQ ID NO: 803          moltype = AA  length = 33
FEATURE                 Location/Qualifiers
REGION                  1..33
                        note = Ciz1 b-variant peptide comprising an exon 14b/exon
                         15 junction
source                  1..33
                        mol_type = protein
                        organism = synthetic construct
SEQUENCE: 803
EDDEDEEEIE VRSRDISREE WKGSETYSPN TAY                              33

SEQ ID NO: 804          moltype = AA  length = 32
FEATURE                 Location/Qualifiers
REGION                  1..32
                        note = Ciz1 b-variant peptide comprising an exon 14b/exon
                         15 junction
source                  1..32
                        mol_type = protein
                        organism = synthetic construct
SEQUENCE: 804
DDEDEEEIEV RSRDISREEW KGSETYSPNT AY                               32

SEQ ID NO: 805          moltype = AA  length = 31
FEATURE                 Location/Qualifiers
REGION                  1..31
                        note = Ciz1 b-variant peptide comprising an exon 14b/exon
                         15 junction
source                  1..31
                        mol_type = protein
                        organism = synthetic construct
SEQUENCE: 805
DEDEEEIEVR SRDISREEWK GSETYSPNTA Y                                31

SEQ ID NO: 806          moltype = AA  length = 30
FEATURE                 Location/Qualifiers
REGION                  1..30
                        note = Ciz1 b-variant peptide comprising an exon 14b/exon
```

```
                          15 junction
source                   1..30
                         mol_type = protein
                         organism = synthetic construct
SEQUENCE: 806
EDEEEIEVRS RDISREEWKG SETYSPNTAY                                    30

SEQ ID NO: 807           moltype = AA  length = 29
FEATURE                  Location/Qualifiers
REGION                   1..29
                         note = Ciz1 b-variant peptide comprising an exon 14b/exon
                          15 junction
source                   1..29
                         mol_type = protein
                         organism = synthetic construct
SEQUENCE: 807
DEEEIEVRSR DISREEWKGS ETYSPNTAY                                     29

SEQ ID NO: 808           moltype = AA  length = 28
FEATURE                  Location/Qualifiers
REGION                   1..28
                         note = Ciz1 b-variant peptide comprising an exon 14b/exon
                          15 junction
source                   1..28
                         mol_type = protein
                         organism = synthetic construct
SEQUENCE: 808
EEEIEVRSRD ISREEWKGSE TYSPNTAY                                      28

SEQ ID NO: 809           moltype = AA  length = 27
FEATURE                  Location/Qualifiers
REGION                   1..27
                         note = Ciz1 b-variant peptide comprising an exon 14b/exon
                          15 junction
source                   1..27
                         mol_type = protein
                         organism = synthetic construct
SEQUENCE: 809
EEIEVRSRDI SREEWKGSET YSPNTAY                                       27

SEQ ID NO: 810           moltype = AA  length = 26
FEATURE                  Location/Qualifiers
REGION                   1..26
                         note = Ciz1 b-variant peptide comprising an exon 14b/exon
                          15 junction
source                   1..26
                         mol_type = protein
                         organism = synthetic construct
SEQUENCE: 810
EIEVRSRDIS REEWKGSETY SPNTAY                                        26

SEQ ID NO: 811           moltype = AA  length = 25
FEATURE                  Location/Qualifiers
REGION                   1..25
                         note = Ciz1 b-variant peptide comprising an exon 14b/exon
                          15 junction
source                   1..25
                         mol_type = protein
                         organism = synthetic construct
SEQUENCE: 811
IEVRSRDISR EEWKGSETYS PNTAY                                         25

SEQ ID NO: 812           moltype = AA  length = 24
FEATURE                  Location/Qualifiers
REGION                   1..24
                         note = Ciz1 b-variant peptide comprising an exon 14b/exon
                          15 junction
source                   1..24
                         mol_type = protein
                         organism = synthetic construct
SEQUENCE: 812
EVRSRDISRE EWKGSETYSP NTAY                                          24

SEQ ID NO: 813           moltype = AA  length = 60
FEATURE                  Location/Qualifiers
REGION                   1..60
                         note = Ciz1 b-variant peptide comprising an exon 14b/exon
                          15 junction
source                   1..60
```

```
                        mol_type = protein
                        organism = synthetic construct
SEQUENCE: 813
EIAGQDEDHF ITVDAVGCFE GDEEEEEDDE DEEEIEVRSR DISREEWKGS ETYSPNTAYG  60

SEQ ID NO: 814          moltype = AA  length = 59
FEATURE                 Location/Qualifiers
REGION                  1..59
                        note = Ciz1 b-variant peptide comprising an exon 14b/exon
                         15 junction
source                  1..59
                        mol_type = protein
                        organism = synthetic construct
SEQUENCE: 814
IAGQDEDHFI TVDAVGCFEG DEEEEEDDED EEEIEVRSRD ISREEWKGSE TYSPNTAYG   59

SEQ ID NO: 815          moltype = AA  length = 58
FEATURE                 Location/Qualifiers
REGION                  1..58
                        note = Ciz1 b-variant peptide comprising an exon 14b/exon
                         15 junction
source                  1..58
                        mol_type = protein
                        organism = synthetic construct
SEQUENCE: 815
AGQDEDHFIT VDAVGCFEGD EEEEEDDEDE EEIEVRSRDI SREEWKGSET YSPNTAYG    58

SEQ ID NO: 816          moltype = AA  length = 57
FEATURE                 Location/Qualifiers
REGION                  1..57
                        note = Ciz1 b-variant peptide comprising an exon 14b/exon
                         15 junction
source                  1..57
                        mol_type = protein
                        organism = synthetic construct
SEQUENCE: 816
GQDEDHFITV DAVGCFEGDE EEEEDDEDEE EIEVRSRDIS REEWKGSETY SPNTAYG     57

SEQ ID NO: 817          moltype = AA  length = 56
FEATURE                 Location/Qualifiers
REGION                  1..56
                        note = Ciz1 b-variant peptide comprising an exon 14b/exon
                         15 junction
source                  1..56
                        mol_type = protein
                        organism = synthetic construct
SEQUENCE: 817
QDEDHFITVD AVGCFEGDEE EEEDDEDEEE IEVRSRDISR EEWKGSETYS PNTAYG      56

SEQ ID NO: 818          moltype = AA  length = 55
FEATURE                 Location/Qualifiers
REGION                  1..55
                        note = Ciz1 b-variant peptide comprising an exon 14b/exon
                         15 junction
source                  1..55
                        mol_type = protein
                        organism = synthetic construct
SEQUENCE: 818
DEDHFITVDA VGCFEGDEEE EEDDEDEEEI EVRSRDISRE EWKGSETYSP NTAYG       55

SEQ ID NO: 819          moltype = AA  length = 54
FEATURE                 Location/Qualifiers
REGION                  1..54
                        note = Ciz1 b-variant peptide comprising an exon 14b/exon
                         15 junction
source                  1..54
                        mol_type = protein
                        organism = synthetic construct
SEQUENCE: 819
EDHFITVDAV GCFEGDEEEE EDDEDEEEIE VRSRDISREE WKGSETYSPN TAYG        54

SEQ ID NO: 820          moltype = AA  length = 53
FEATURE                 Location/Qualifiers
REGION                  1..53
                        note = Ciz1 b-variant peptide comprising an exon 14b/exon
                         15 junction
source                  1..53
                        mol_type = protein
                        organism = synthetic construct
```

```
SEQUENCE: 820
DHFITVDAVG CFEGDEEEEE DDEDEEEIEV RSRDISREEW KGSETYSPNT AYG          53

SEQ ID NO: 821          moltype = AA  length = 52
FEATURE                 Location/Qualifiers
REGION                  1..52
                        note = Ciz1 b-variant peptide comprising an exon 14b/exon
                         15 junction
source                  1..52
                        mol_type = protein
                        organism = synthetic construct
SEQUENCE: 821
HFITVDAVGC FEGDEEEEED DEDEEEIEVR SRDISREEWK GSETYSPNTA YG           52

SEQ ID NO: 822          moltype = AA  length = 51
FEATURE                 Location/Qualifiers
REGION                  1..51
                        note = Ciz1 b-variant peptide comprising an exon 14b/exon
                         15 junction
source                  1..51
                        mol_type = protein
                        organism = synthetic construct
SEQUENCE: 822
FITVDAVGCF EGDEEEEEDD EDEEEIEVRS RDISREEWKG SETYSPNTAY G            51

SEQ ID NO: 823          moltype = AA  length = 50
FEATURE                 Location/Qualifiers
REGION                  1..50
                        note = Ciz1 b-variant peptide comprising an exon 14b/exon
                         15 junction
source                  1..50
                        mol_type = protein
                        organism = synthetic construct
SEQUENCE: 823
ITVDAVGCFE GDEEEEEDDE DEEEIEVRSR DISREEWKGS ETYSPNTAYG              50

SEQ ID NO: 824          moltype = AA  length = 49
FEATURE                 Location/Qualifiers
REGION                  1..49
                        note = Ciz1 b-variant peptide comprising an exon 14b/exon
                         15 junction
source                  1..49
                        mol_type = protein
                        organism = synthetic construct
SEQUENCE: 824
TVDAVGCFEG DEEEEEDDED EEEIEVRSRD ISREEWKGSE TYSPNTAYG               49

SEQ ID NO: 825          moltype = AA  length = 48
FEATURE                 Location/Qualifiers
REGION                  1..48
                        note = Ciz1 b-variant peptide comprising an exon 14b/exon
                         15 junction
source                  1..48
                        mol_type = protein
                        organism = synthetic construct
SEQUENCE: 825
VDAVGCFEGD EEEEEDDEDE EEIEVRSRDI SREEWKGSET YSPNTAYG                48

SEQ ID NO: 826          moltype = AA  length = 47
FEATURE                 Location/Qualifiers
REGION                  1..47
                        note = Ciz1 b-variant peptide comprising an exon 14b/exon
                         15 junction
source                  1..47
                        mol_type = protein
                        organism = synthetic construct
SEQUENCE: 826
DAVGCFEGDE EEEEDDEDEE EIEVRSRDIS REEWKGSETY SPNTAYG                 47

SEQ ID NO: 827          moltype = AA  length = 46
FEATURE                 Location/Qualifiers
REGION                  1..46
                        note = Ciz1 b-variant peptide comprising an exon 14b/exon
                         15 junction
source                  1..46
                        mol_type = protein
                        organism = synthetic construct
SEQUENCE: 827
AVGCFEGDEE EEEDDEDEEE IEVRSRDISR EEWKGSETYS PNTAYG                  46
```

```
SEQ ID NO: 828          moltype = AA  length = 45
FEATURE                 Location/Qualifiers
REGION                  1..45
                        note = Ciz1 b-variant peptide comprising an exon 14b/exon
                         15 junction
source                  1..45
                        mol_type = protein
                        organism = synthetic construct
SEQUENCE: 828
VGCFEGDEEE EEDDEDEEEI EVRSRDISRE EWKGSETYSP NTAYG                  45

SEQ ID NO: 829          moltype = AA  length = 44
FEATURE                 Location/Qualifiers
REGION                  1..44
                        note = Ciz1 b-variant peptide comprising an exon 14b/exon
                         15 junction
source                  1..44
                        mol_type = protein
                        organism = synthetic construct
SEQUENCE: 829
GCFEGDEEEE EDDEDEEEIE VRSRDISREE WKGSETYSPN TAYG                   44

SEQ ID NO: 830          moltype = AA  length = 43
FEATURE                 Location/Qualifiers
REGION                  1..43
                        note = Ciz1 b-variant peptide comprising an exon 14b/exon
                         15 junction
source                  1..43
                        mol_type = protein
                        organism = synthetic construct
SEQUENCE: 830
CFEGDEEEEE DDEDEEEIEV RSRDISREEW KGSETYSPNT AYG                    43

SEQ ID NO: 831          moltype = AA  length = 42
FEATURE                 Location/Qualifiers
REGION                  1..42
                        note = Ciz1 b-variant peptide comprising an exon 14b/exon
                         15 junction
source                  1..42
                        mol_type = protein
                        organism = synthetic construct
SEQUENCE: 831
FEGDEEEEED DEDEEEIEVR SRDISREEWK GSETYSPNTA YG                     42

SEQ ID NO: 832          moltype = AA  length = 41
FEATURE                 Location/Qualifiers
REGION                  1..41
                        note = Ciz1 b-variant peptide comprising an exon 14b/exon
                         15 junction
source                  1..41
                        mol_type = protein
                        organism = synthetic construct
SEQUENCE: 832
EGDEEEEEDD EDEEEIEVRS RDISREEWKG SETYSPNTAY G                      41

SEQ ID NO: 833          moltype = AA  length = 40
FEATURE                 Location/Qualifiers
REGION                  1..40
                        note = Ciz1 b-variant peptide comprising an exon 14b/exon
                         15 junction
source                  1..40
                        mol_type = protein
                        organism = synthetic construct
SEQUENCE: 833
GDEEEEEDDE DEEEIEVRSR DISREEWKGS ETYSPNTAYG                        40

SEQ ID NO: 834          moltype = AA  length = 39
FEATURE                 Location/Qualifiers
REGION                  1..39
                        note = Ciz1 b-variant peptide comprising an exon 14b/exon
                         15 junction
source                  1..39
                        mol_type = protein
                        organism = synthetic construct
SEQUENCE: 834
DEEEEEDDED EEEIEVRSRD ISREEWKGSE TYSPNTAYG                         39

SEQ ID NO: 835          moltype = AA  length = 38
```

```
FEATURE                Location/Qualifiers
REGION                 1..38
                       note = Ciz1 b-variant peptide comprising an exon 14b/exon
                        15 junction
source                 1..38
                       mol_type = protein
                       organism = synthetic construct
SEQUENCE: 835
EEEEEDDEDE EEIEVRSRDI SREEWKGSET YSPNTAYG                          38

SEQ ID NO: 836         moltype = AA  length = 37
FEATURE                Location/Qualifiers
REGION                 1..37
                       note = Ciz1 b-variant peptide comprising an exon 14b/exon
                        15 junction
source                 1..37
                       mol_type = protein
                       organism = synthetic construct
SEQUENCE: 836
EEEEDDEDEE EIEVRSRDIS REEWKGSETY SPNTAYG                           37

SEQ ID NO: 837         moltype = AA  length = 36
FEATURE                Location/Qualifiers
REGION                 1..36
                       note = Ciz1 b-variant peptide comprising an exon 14b/exon
                        15 junction
source                 1..36
                       mol_type = protein
                       organism = synthetic construct
SEQUENCE: 837
EEEDDEDEEE IEVRSRDISR EEWKGSETYS PNTAYG                            36

SEQ ID NO: 838         moltype = AA  length = 35
FEATURE                Location/Qualifiers
REGION                 1..35
                       note = Ciz1 b-variant peptide comprising an exon 14b/exon
                        15 junction
source                 1..35
                       mol_type = protein
                       organism = synthetic construct
SEQUENCE: 838
EEDDEDEEEI EVRSRDISRE EWKGSETYSP NTAYG                             35

SEQ ID NO: 839         moltype = AA  length = 34
FEATURE                Location/Qualifiers
REGION                 1..34
                       note = Ciz1 b-variant peptide comprising an exon 14b/exon
                        15 junction
source                 1..34
                       mol_type = protein
                       organism = synthetic construct
SEQUENCE: 839
EDDEDEEEIE VRSRDISREE WKGSETYSPN TAYG                              34

SEQ ID NO: 840         moltype = AA  length = 33
FEATURE                Location/Qualifiers
REGION                 1..33
                       note = Ciz1 b-variant peptide comprising an exon 14b/exon
                        15 junction
source                 1..33
                       mol_type = protein
                       organism = synthetic construct
SEQUENCE: 840
DDEDEEEIEV RSRDISREEW KGSETYSPNT AYG                               33

SEQ ID NO: 841         moltype = AA  length = 32
FEATURE                Location/Qualifiers
REGION                 1..32
                       note = Ciz1 b-variant peptide comprising an exon 14b/exon
                        15 junction
source                 1..32
                       mol_type = protein
                       organism = synthetic construct
SEQUENCE: 841
DEDEEEIEVR SRDISREEWK GSETYSPNTA YG                                32

SEQ ID NO: 842         moltype = AA  length = 31
FEATURE                Location/Qualifiers
REGION                 1..31
```

```
                        note = Ciz1 b-variant peptide comprising an exon 14b/exon
                         15 junction
source                  1..31
                        mol_type = protein
                        organism = synthetic construct
SEQUENCE: 842
EDEEEIEVRS RDISREEWKG SETYSPNTAY G                                  31

SEQ ID NO: 843          moltype = AA  length = 30
FEATURE                 Location/Qualifiers
REGION                  1..30
                        note = Ciz1 b-variant peptide comprising an exon 14b/exon
                         15 junction
source                  1..30
                        mol_type = protein
                        organism = synthetic construct
SEQUENCE: 843
DEEEIEVRSR DISREEWKGS ETYSPNTAYG                                    30

SEQ ID NO: 844          moltype = AA  length = 29
FEATURE                 Location/Qualifiers
REGION                  1..29
                        note = Ciz1 b-variant peptide comprising an exon 14b/exon
                         15 junction
source                  1..29
                        mol_type = protein
                        organism = synthetic construct
SEQUENCE: 844
EEEIEVRSRD ISREEWKGSE TYSPNTAYG                                     29

SEQ ID NO: 845          moltype = AA  length = 28
FEATURE                 Location/Qualifiers
REGION                  1..28
                        note = Ciz1 b-variant peptide comprising an exon 14b/exon
                         15 junction
source                  1..28
                        mol_type = protein
                        organism = synthetic construct
SEQUENCE: 845
EEIEVRSRDI SREEWKGSET YSPNTAYG                                      28

SEQ ID NO: 846          moltype = AA  length = 27
FEATURE                 Location/Qualifiers
REGION                  1..27
                        note = Ciz1 b-variant peptide comprising an exon 14b/exon
                         15 junction
source                  1..27
                        mol_type = protein
                        organism = synthetic construct
SEQUENCE: 846
EIEVRSRDIS REEWKGSETY SPNTAYG                                       27

SEQ ID NO: 847          moltype = AA  length = 26
FEATURE                 Location/Qualifiers
REGION                  1..26
                        note = Ciz1 b-variant peptide comprising an exon 14b/exon
                         15 junction
source                  1..26
                        mol_type = protein
                        organism = synthetic construct
SEQUENCE: 847
IEVRSRDISR EEWKGSETYS PNTAYG                                        26

SEQ ID NO: 848          moltype = AA  length = 25
FEATURE                 Location/Qualifiers
REGION                  1..25
                        note = Ciz1 b-variant peptide comprising an exon 14b/exon
                         15 junction
source                  1..25
                        mol_type = protein
                        organism = synthetic construct
SEQUENCE: 848
EVRSRDISRE EWKGSETYSP NTAYG                                         25

SEQ ID NO: 849          moltype = AA  length = 61
FEATURE                 Location/Qualifiers
REGION                  1..61
                        note = Ciz1 b-variant peptide comprising an exon 14b/exon
                         15 junction
```

```
source                  1..61
                        mol_type = protein
                        organism = synthetic construct
SEQUENCE: 849
EIAGQDEDHF ITVDAVGCFE GDEEEEEDDE DEEEIEVRSR DISREEWKGS ETYSPNTAYG  60
V                                                                  61

SEQ ID NO: 850          moltype = AA  length = 60
FEATURE                 Location/Qualifiers
REGION                  1..60
                        note = Ciz1 b-variant peptide comprising an exon 14b/exon
                         15 junction
source                  1..60
                        mol_type = protein
                        organism = synthetic construct
SEQUENCE: 850
IAGQDEDHFI TVDAVGCFEG DEEEEEDDED EEEIEVRSRD ISREEWKGSE TYSPNTAYGV  60

SEQ ID NO: 851          moltype = AA  length = 59
FEATURE                 Location/Qualifiers
REGION                  1..59
                        note = Ciz1 b-variant peptide comprising an exon 14b/exon
                         15 junction
source                  1..59
                        mol_type = protein
                        organism = synthetic construct
SEQUENCE: 851
AGQDEDHFIT VDAVGCFEGD EEEEEDDEDE EEIEVRSRDI SREEWKGSET YSPNTAYGV   59

SEQ ID NO: 852          moltype = AA  length = 58
FEATURE                 Location/Qualifiers
REGION                  1..58
                        note = Ciz1 b-variant peptide comprising an exon 14b/exon
                         15 junction
source                  1..58
                        mol_type = protein
                        organism = synthetic construct
SEQUENCE: 852
GQDEDHFITV DAVGCFEGDE EEEEDDEDEE EIEVRSRDIS REEWKGSETY SPNTAYGV    58

SEQ ID NO: 853          moltype = AA  length = 57
FEATURE                 Location/Qualifiers
REGION                  1..57
                        note = Ciz1 b-variant peptide comprising an exon 14b/exon
                         15 junction
source                  1..57
                        mol_type = protein
                        organism = synthetic construct
SEQUENCE: 853
QDEDHFITVD AVGCFEGDEE EEEDDEDEEE IEVRSRDISR EEWKGSETYS PNTAYGV     57

SEQ ID NO: 854          moltype = AA  length = 56
FEATURE                 Location/Qualifiers
REGION                  1..56
                        note = Ciz1 b-variant peptide comprising an exon 14b/exon
                         15 junction
source                  1..56
                        mol_type = protein
                        organism = synthetic construct
SEQUENCE: 854
DEDHFITVDA VGCFEGDEEE EEDDEDEEEI EVRSRDISRE EWKGSETYSP NTAYGV      56

SEQ ID NO: 855          moltype = AA  length = 55
FEATURE                 Location/Qualifiers
REGION                  1..55
                        note = Ciz1 b-variant peptide comprising an exon 14b/exon
                         15 junction
source                  1..55
                        mol_type = protein
                        organism = synthetic construct
SEQUENCE: 855
EDHFITVDAV GCFEGDEEEE EDDEDEEEIE VRSRDISREE WKGSETYSPN TAYGV       55

SEQ ID NO: 856          moltype = AA  length = 54
FEATURE                 Location/Qualifiers
REGION                  1..54
                        note = Ciz1 b-variant peptide comprising an exon 14b/exon
                         15 junction
source                  1..54
```

```
                         mol_type = protein
                         organism = synthetic construct
SEQUENCE: 856
DHFITVDAVG CFEGDEEEEE DDEDEEEIEV RSRDISREEW KGSETYSPNT AYGV        54

SEQ ID NO: 857           moltype = AA  length = 53
FEATURE                  Location/Qualifiers
REGION                   1..53
                         note = Ciz1 b-variant peptide comprising an exon 14b/exon
                          15 junction
source                   1..53
                         mol_type = protein
                         organism = synthetic construct
SEQUENCE: 857
HFITVDAVGC FEGDEEEEED DEDEEEIEVR SRDISREEWK GSETYSPNTA YGV         53

SEQ ID NO: 858           moltype = AA  length = 52
FEATURE                  Location/Qualifiers
REGION                   1..52
                         note = Ciz1 b-variant peptide comprising an exon 14b/exon
                          15 junction
source                   1..52
                         mol_type = protein
                         organism = synthetic construct
SEQUENCE: 858
FITVDAVGCF EGDEEEEEDD EDEEEIEVRS RDISREEWKG SETYSPNTAY GV          52

SEQ ID NO: 859           moltype = AA  length = 51
FEATURE                  Location/Qualifiers
REGION                   1..51
                         note = Ciz1 b-variant peptide comprising an exon 14b/exon
                          15 junction
source                   1..51
                         mol_type = protein
                         organism = synthetic construct
SEQUENCE: 859
ITVDAVGCFE GDEEEEEDDE DEEEIEVRSR DISREEWKGS ETYSPNTAYG V           51

SEQ ID NO: 860           moltype = AA  length = 50
FEATURE                  Location/Qualifiers
REGION                   1..50
                         note = Ciz1 b-variant peptide comprising an exon 14b/exon
                          15 junction
source                   1..50
                         mol_type = protein
                         organism = synthetic construct
SEQUENCE: 860
TVDAVGCFEG DEEEEEDDED EEEIEVRSRD ISREEWKGSE TYSPNTAYGV             50

SEQ ID NO: 861           moltype = AA  length = 49
FEATURE                  Location/Qualifiers
REGION                   1..49
                         note = Ciz1 b-variant peptide comprising an exon 14b/exon
                          15 junction
source                   1..49
                         mol_type = protein
                         organism = synthetic construct
SEQUENCE: 861
VDAVGCFEGD EEEEEDDEDE EEIEVRSRDI SREEWKGSET YSPNTAYGV              49

SEQ ID NO: 862           moltype = AA  length = 48
FEATURE                  Location/Qualifiers
REGION                   1..48
                         note = Ciz1 b-variant peptide comprising an exon 14b/exon
                          15 junction
source                   1..48
                         mol_type = protein
                         organism = synthetic construct
SEQUENCE: 862
DAVGCFEGDE EEEEDDEDEE EIEVRSRDIS REEWKGSETY SPNTAYGV               48

SEQ ID NO: 863           moltype = AA  length = 47
FEATURE                  Location/Qualifiers
REGION                   1..47
                         note = Ciz1 b-variant peptide comprising an exon 14b/exon
                          15 junction
source                   1..47
                         mol_type = protein
                         organism = synthetic construct
```

```
SEQUENCE: 863
AVGCFEGDEE EEEDDEDEEE IEVRSRDISR EEWKGSETYS PNTAYGV                47

SEQ ID NO: 864         moltype = AA  length = 46
FEATURE                Location/Qualifiers
REGION                 1..46
                       note = Ciz1 b-variant peptide comprising an exon 14b/exon
                        15 junction
source                 1..46
                       mol_type = protein
                       organism = synthetic construct
SEQUENCE: 864
VGCFEGDEEE EEDDEDEEEI EVRSRDISRE EWKGSETYSP NTAYGV                 46

SEQ ID NO: 865         moltype = AA  length = 45
FEATURE                Location/Qualifiers
REGION                 1..45
                       note = Ciz1 b-variant peptide comprising an exon 14b/exon
                        15 junction
source                 1..45
                       mol_type = protein
                       organism = synthetic construct
SEQUENCE: 865
GCFEGDEEEE EDDEDEEEIE VRSRDISREE WKGSETYSPN TAYGV                  45

SEQ ID NO: 866         moltype = AA  length = 44
FEATURE                Location/Qualifiers
REGION                 1..44
                       note = Ciz1 b-variant peptide comprising an exon 14b/exon
                        15 junction
source                 1..44
                       mol_type = protein
                       organism = synthetic construct
SEQUENCE: 866
CFEGDEEEEE DDEDEEEIEV RSRDISREEW KGSETYSPNT AYGV                   44

SEQ ID NO: 867         moltype = AA  length = 43
FEATURE                Location/Qualifiers
REGION                 1..43
                       note = Ciz1 b-variant peptide comprising an exon 14b/exon
                        15 junction
source                 1..43
                       mol_type = protein
                       organism = synthetic construct
SEQUENCE: 867
FEGDEEEEED DEDEEEIEVR SRDISREEWK GSETYSPNTA YGV                    43

SEQ ID NO: 868         moltype = AA  length = 42
FEATURE                Location/Qualifiers
REGION                 1..42
                       note = Ciz1 b-variant peptide comprising an exon 14b/exon
                        15 junction
source                 1..42
                       mol_type = protein
                       organism = synthetic construct
SEQUENCE: 868
EGDEEEEEDD EDEEEIEVRS RDISREEWKG SETYSPNTAY GV                     42

SEQ ID NO: 869         moltype = AA  length = 41
FEATURE                Location/Qualifiers
REGION                 1..41
                       note = Ciz1 b-variant peptide comprising an exon 14b/exon
                        15 junction
source                 1..41
                       mol_type = protein
                       organism = synthetic construct
SEQUENCE: 869
GDEEEEEDDE DEEEIEVRSR DISREEWKGS ETYSPNTAYG V                      41

SEQ ID NO: 870         moltype = AA  length = 40
FEATURE                Location/Qualifiers
REGION                 1..40
                       note = Ciz1 b-variant peptide comprising an exon 14b/exon
                        15 junction
source                 1..40
                       mol_type = protein
                       organism = synthetic construct
SEQUENCE: 870
DEEEEEDDED EEEIEVRSRD ISREEWKGSE TYSPNTAYGV                        40
```

```
SEQ ID NO: 871         moltype = AA  length = 39
FEATURE                Location/Qualifiers
REGION                 1..39
                       note = Ciz1 b-variant peptide comprising an exon 14b/exon
                        15 junction
source                 1..39
                       mol_type = protein
                       organism = synthetic construct
SEQUENCE: 871
EEEEEDDEDE EEIEVRSRDI SREEWKGSET YSPNTAYGV                          39

SEQ ID NO: 872         moltype = AA  length = 38
FEATURE                Location/Qualifiers
REGION                 1..38
                       note = Ciz1 b-variant peptide comprising an exon 14b/exon
                        15 junction
source                 1..38
                       mol_type = protein
                       organism = synthetic construct
SEQUENCE: 872
EEEEDDEDEE EIEVRSRDIS REEWKGSETY SPNTAYGV                           38

SEQ ID NO: 873         moltype = AA  length = 37
FEATURE                Location/Qualifiers
REGION                 1..37
                       note = Ciz1 b-variant peptide comprising an exon 14b/exon
                        15 junction
source                 1..37
                       mol_type = protein
                       organism = synthetic construct
SEQUENCE: 873
EEEDDEDEEE IEVRSRDISR EEWKGSETYS PNTAYGV                            37

SEQ ID NO: 874         moltype = AA  length = 36
FEATURE                Location/Qualifiers
REGION                 1..36
                       note = Ciz1 b-variant peptide comprising an exon 14b/exon
                        15 junction
source                 1..36
                       mol_type = protein
                       organism = synthetic construct
SEQUENCE: 874
EEDDEDEEEI EVRSRDISRE EWKGSETYSP NTAYGV                             36

SEQ ID NO: 875         moltype = AA  length = 35
FEATURE                Location/Qualifiers
REGION                 1..35
                       note = Ciz1 b-variant peptide comprising an exon 14b/exon
                        15 junction
source                 1..35
                       mol_type = protein
                       organism = synthetic construct
SEQUENCE: 875
EDDEDEEEIE VRSRDISREE WKGSETYSPN TAYGV                              35

SEQ ID NO: 876         moltype = AA  length = 34
FEATURE                Location/Qualifiers
REGION                 1..34
                       note = Ciz1 b-variant peptide comprising an exon 14b/exon
                        15 junction
source                 1..34
                       mol_type = protein
                       organism = synthetic construct
SEQUENCE: 876
DDEDEEEIEV RSRDISREEW KGSETYSPNT AYGV                               34

SEQ ID NO: 877         moltype = AA  length = 33
FEATURE                Location/Qualifiers
REGION                 1..33
                       note = Ciz1 b-variant peptide comprising an exon 14b/exon
                        15 junction
source                 1..33
                       mol_type = protein
                       organism = synthetic construct
SEQUENCE: 877
DEDEEEIEVR SRDISREEWK GSETYSPNTA YGV                                33

SEQ ID NO: 878         moltype = AA  length = 32
```

```
FEATURE                 Location/Qualifiers
REGION                  1..32
                        note = Ciz1 b-variant peptide comprising an exon 14b/exon
                         15 junction
source                  1..32
                        mol_type = protein
                        organism = synthetic construct
SEQUENCE: 878
EDEEEIEVRS RDISREEWKG SETYSPNTAY GV                                 32

SEQ ID NO: 879          moltype = AA  length = 31
FEATURE                 Location/Qualifiers
REGION                  1..31
                        note = Ciz1 b-variant peptide comprising an exon 14b/exon
                         15 junction
source                  1..31
                        mol_type = protein
                        organism = synthetic construct
SEQUENCE: 879
DEEEIEVRSR DISREEWKGS ETYSPNTAYG V                                  31

SEQ ID NO: 880          moltype = AA  length = 30
FEATURE                 Location/Qualifiers
REGION                  1..30
                        note = Ciz1 b-variant peptide comprising an exon 14b/exon
                         15 junction
source                  1..30
                        mol_type = protein
                        organism = synthetic construct
SEQUENCE: 880
EEEIEVRSRD ISREEWKGSE TYSPNTAYGV                                    30

SEQ ID NO: 881          moltype = AA  length = 29
FEATURE                 Location/Qualifiers
REGION                  1..29
                        note = Ciz1 b-variant peptide comprising an exon 14b/exon
                         15 junction
source                  1..29
                        mol_type = protein
                        organism = synthetic construct
SEQUENCE: 881
EEIEVRSRDI SREEWKGSET YSPNTAYGV                                     29

SEQ ID NO: 882          moltype = AA  length = 28
FEATURE                 Location/Qualifiers
REGION                  1..28
                        note = Ciz1 b-variant peptide comprising an exon 14b/exon
                         15 junction
source                  1..28
                        mol_type = protein
                        organism = synthetic construct
SEQUENCE: 882
EIEVRSRDIS REEWKGSETY SPNTAYGV                                      28

SEQ ID NO: 883          moltype = AA  length = 27
FEATURE                 Location/Qualifiers
REGION                  1..27
                        note = Ciz1 b-variant peptide comprising an exon 14b/exon
                         15 junction
source                  1..27
                        mol_type = protein
                        organism = synthetic construct
SEQUENCE: 883
IEVRSRDISR EEWKGSETYS PNTAYGV                                       27

SEQ ID NO: 884          moltype = AA  length = 26
FEATURE                 Location/Qualifiers
REGION                  1..26
                        note = Ciz1 b-variant peptide comprising an exon 14b/exon
                         15 junction
source                  1..26
                        mol_type = protein
                        organism = synthetic construct
SEQUENCE: 884
EVRSRDISRE EWKGSETYSP NTAYGV                                        26

SEQ ID NO: 885          moltype = AA  length = 62
FEATURE                 Location/Qualifiers
REGION                  1..62
```

```
                        note = Ciz1 b-variant peptide comprising an exon 14b/exon
                         15 junction
source                  1..62
                        mol_type = protein
                        organism = synthetic construct
SEQUENCE: 885
EIAGQDEDHF ITVDAVGCFE GDEEEEEDDE DEEEIEVRSR DISREEWKGS ETYSPNTAYG  60
VD                                                                62

SEQ ID NO: 886          moltype = AA  length = 61
FEATURE                 Location/Qualifiers
REGION                  1..61
                        note = Ciz1 b-variant peptide comprising an exon 14b/exon
                         15 junction
source                  1..61
                        mol_type = protein
                        organism = synthetic construct
SEQUENCE: 886
IAGQDEDHFI TVDAVGCFEG DEEEEEDDED EEEIEVRSRD ISREEWKGSE TYSPNTAYGV  60
D                                                                 61

SEQ ID NO: 887          moltype = AA  length = 60
FEATURE                 Location/Qualifiers
REGION                  1..60
                        note = Ciz1 b-variant peptide comprising an exon 14b/exon
                         15 junction
source                  1..60
                        mol_type = protein
                        organism = synthetic construct
SEQUENCE: 887
AGQDEDHFIT VDAVGCFEGD EEEEEDDEDE EEIEVRSRDI SREEWKGSET YSPNTAYGVD  60

SEQ ID NO: 888          moltype = AA  length = 59
FEATURE                 Location/Qualifiers
REGION                  1..59
                        note = Ciz1 b-variant peptide comprising an exon 14b/exon
                         15 junction
source                  1..59
                        mol_type = protein
                        organism = synthetic construct
SEQUENCE: 888
GQDEDHFITV DAVGCFEGDE EEEEDDEDEE EIEVRSRDIS REEWKGSETY SPNTAYGVD   59

SEQ ID NO: 889          moltype = AA  length = 58
FEATURE                 Location/Qualifiers
REGION                  1..58
                        note = Ciz1 b-variant peptide comprising an exon 14b/exon
                         15 junction
source                  1..58
                        mol_type = protein
                        organism = synthetic construct
SEQUENCE: 889
QDEDHFITVD AVGCFEGDEE EEEDDEDEEE IEVRSRDISR EEWKGSETYS PNTAYGVD    58

SEQ ID NO: 890          moltype = AA  length = 57
FEATURE                 Location/Qualifiers
REGION                  1..57
                        note = Ciz1 b-variant peptide comprising an exon 14b/exon
                         15 junction
source                  1..57
                        mol_type = protein
                        organism = synthetic construct
SEQUENCE: 890
DEDHFITVDA VGCFEGDEEE EEDDEDEEEI EVRSRDISRE EWKGSETYSP NTAYGVD     57

SEQ ID NO: 891          moltype = AA  length = 56
FEATURE                 Location/Qualifiers
REGION                  1..56
                        note = Ciz1 b-variant peptide comprising an exon 14b/exon
                         15 junction
source                  1..56
                        mol_type = protein
                        organism = synthetic construct
SEQUENCE: 891
EDHFITVDAV GCFEGDEEEE EDDEDEEEIE VRSRDISREE WKGSETYSPN TAYGVD      56

SEQ ID NO: 892          moltype = AA  length = 55
FEATURE                 Location/Qualifiers
REGION                  1..55
```

```
                        note = Ciz1 b-variant peptide comprising an exon 14b/exon
                         15 junction
source                  1..55
                        mol_type = protein
                        organism = synthetic construct
SEQUENCE: 892
DHFITVDAVG CFEGDEEEEE DDEDEEEIEV RSRDISREEW KGSETYSPNT AYGVD       55

SEQ ID NO: 893          moltype = AA  length = 54
FEATURE                 Location/Qualifiers
REGION                  1..54
                        note = Ciz1 b-variant peptide comprising an exon 14b/exon
                         15 junction
source                  1..54
                        mol_type = protein
                        organism = synthetic construct
SEQUENCE: 893
HFITVDAVGC FEGDEEEEED DEDEEEIEVR SRDISREEWK GSETYSPNTA YGVD        54

SEQ ID NO: 894          moltype = AA  length = 53
FEATURE                 Location/Qualifiers
REGION                  1..53
                        note = Ciz1 b-variant peptide comprising an exon 14b/exon
                         15 junction
source                  1..53
                        mol_type = protein
                        organism = synthetic construct
SEQUENCE: 894
FITVDAVGCF EGDEEEEEDD EDEEEIEVRS RDISREEWKG SETYSPNTAY GVD         53

SEQ ID NO: 895          moltype = AA  length = 52
FEATURE                 Location/Qualifiers
REGION                  1..52
                        note = Ciz1 b-variant peptide comprising an exon 14b/exon
                         15 junction
source                  1..52
                        mol_type = protein
                        organism = synthetic construct
SEQUENCE: 895
ITVDAVGCFE GDEEEEEDDE DEEEIEVRSR DISREEWKGS ETYSPNTAYG VD          52

SEQ ID NO: 896          moltype = AA  length = 51
FEATURE                 Location/Qualifiers
REGION                  1..51
                        note = Ciz1 b-variant peptide comprising an exon 14b/exon
                         15 junction
source                  1..51
                        mol_type = protein
                        organism = synthetic construct
SEQUENCE: 896
TVDAVGCFEG DEEEEEDDED EEEIEVRSRD ISREEWKGSE TYSPNTAYGV D           51

SEQ ID NO: 897          moltype = AA  length = 50
FEATURE                 Location/Qualifiers
REGION                  1..50
                        note = Ciz1 b-variant peptide comprising an exon 14b/exon
                         15 junction
source                  1..50
                        mol_type = protein
                        organism = synthetic construct
SEQUENCE: 897
VDAVGCFEGD EEEEEDDEDE EEIEVRSRDI SREEWKGSET YSPNTAYGVD             50

SEQ ID NO: 898          moltype = AA  length = 49
FEATURE                 Location/Qualifiers
REGION                  1..49
                        note = Ciz1 b-variant peptide comprising an exon 14b/exon
                         15 junction
source                  1..49
                        mol_type = protein
                        organism = synthetic construct
SEQUENCE: 898
DAVGCFEGDE EEEEDDEDEE EIEVRSRDIS REEWKGSETY SPNTAYGVD              49

SEQ ID NO: 899          moltype = AA  length = 48
FEATURE                 Location/Qualifiers
REGION                  1..48
                        note = Ciz1 b-variant peptide comprising an exon 14b/exon
                         15 junction
```

```
source                  1..48
                        mol_type = protein
                        organism = synthetic construct
SEQUENCE: 899
AVGCFEGDEE EEEDDEDEEE IEVRSRDISR EEWKGSETYS PNTAYGVD               48

SEQ ID NO: 900          moltype = AA  length = 47
FEATURE                 Location/Qualifiers
REGION                  1..47
                        note = Ciz1 b-variant peptide comprising an exon 14b/exon
                         15 junction
source                  1..47
                        mol_type = protein
                        organism = synthetic construct
SEQUENCE: 900
VGCFEGDEEE EEDDEDEEEI EVRSRDISRE EWKGSETYSP NTAYGVD                47

SEQ ID NO: 901          moltype = AA  length = 46
FEATURE                 Location/Qualifiers
REGION                  1..46
                        note = Ciz1 b-variant peptide comprising an exon 14b/exon
                         15 junction
source                  1..46
                        mol_type = protein
                        organism = synthetic construct
SEQUENCE: 901
GCFEGDEEEE EDDEDEEEIE VRSRDISREE WKGSETYSPN TAYGVD                 46

SEQ ID NO: 902          moltype = AA  length = 45
FEATURE                 Location/Qualifiers
REGION                  1..45
                        note = Ciz1 b-variant peptide comprising an exon 14b/exon
                         15 junction
source                  1..45
                        mol_type = protein
                        organism = synthetic construct
SEQUENCE: 902
CFEGDEEEEE DDEDEEEIEV RSRDISREEW KGSETYSPNT AYGVD                  45

SEQ ID NO: 903          moltype = AA  length = 44
FEATURE                 Location/Qualifiers
REGION                  1..44
                        note = Ciz1 b-variant peptide comprising an exon 14b/exon
                         15 junction
source                  1..44
                        mol_type = protein
                        organism = synthetic construct
SEQUENCE: 903
FEGDEEEEED DEDEEEIEVR SRDISREEWK GSETYSPNTA YGVD                   44

SEQ ID NO: 904          moltype = AA  length = 43
FEATURE                 Location/Qualifiers
REGION                  1..43
                        note = Ciz1 b-variant peptide comprising an exon 14b/exon
                         15 junction
source                  1..43
                        mol_type = protein
                        organism = synthetic construct
SEQUENCE: 904
EGDEEEEEDD EDEEEIEVRS RDISREEWKG SETYSPNTAY GVD                    43

SEQ ID NO: 905          moltype = AA  length = 42
FEATURE                 Location/Qualifiers
REGION                  1..42
                        note = Ciz1 b-variant peptide comprising an exon 14b/exon
                         15 junction
source                  1..42
                        mol_type = protein
                        organism = synthetic construct
SEQUENCE: 905
GDEEEEEDDE DEEEIEVRSR DISREEWKGS ETYSPNTAYG VD                     42

SEQ ID NO: 906          moltype = AA  length = 41
FEATURE                 Location/Qualifiers
REGION                  1..41
                        note = Ciz1 b-variant peptide comprising an exon 14b/exon
                         15 junction
source                  1..41
                        mol_type = protein
```

```
                         organism = synthetic construct
SEQUENCE: 906
DEEEEEDDED EEEIEVRSRD ISREEWKGSE TYSPNTAYGV D                       41

SEQ ID NO: 907           moltype = AA  length = 40
FEATURE                  Location/Qualifiers
REGION                   1..40
                         note = Ciz1 b-variant peptide comprising an exon 14b/exon
                          15 junction
source                   1..40
                         mol_type = protein
                         organism = synthetic construct
SEQUENCE: 907
EEEEEDDEDE EEIEVRSRDI SREEWKGSET YSPNTAYGVD                         40

SEQ ID NO: 908           moltype = AA  length = 39
FEATURE                  Location/Qualifiers
REGION                   1..39
                         note = Ciz1 b-variant peptide comprising an exon 14b/exon
                          15 junction
source                   1..39
                         mol_type = protein
                         organism = synthetic construct
SEQUENCE: 908
EEEEDDEDEE EIEVRSRDIS REEWKGSETY SPNTAYGVD                          39

SEQ ID NO: 909           moltype = AA  length = 38
FEATURE                  Location/Qualifiers
REGION                   1..38
                         note = Ciz1 b-variant peptide comprising an exon 14b/exon
                          15 junction
source                   1..38
                         mol_type = protein
                         organism = synthetic construct
SEQUENCE: 909
EEEDDEDEEE IEVRSRDISR EEWKGSETYS PNTAYGVD                           38

SEQ ID NO: 910           moltype = AA  length = 37
FEATURE                  Location/Qualifiers
REGION                   1..37
                         note = Ciz1 b-variant peptide comprising an exon 14b/exon
                          15 junction
source                   1..37
                         mol_type = protein
                         organism = synthetic construct
SEQUENCE: 910
EEDDEDEEEI EVRSRDISRE EWKGSETYSP NTAYGVD                            37

SEQ ID NO: 911           moltype = AA  length = 36
FEATURE                  Location/Qualifiers
REGION                   1..36
                         note = Ciz1 b-variant peptide comprising an exon 14b/exon
                          15 junction
source                   1..36
                         mol_type = protein
                         organism = synthetic construct
SEQUENCE: 911
EDDEDEEEIE VRSRDISREE WKGSETYSPN TAYGVD                             36

SEQ ID NO: 912           moltype = AA  length = 35
FEATURE                  Location/Qualifiers
REGION                   1..35
                         note = Ciz1 b-variant peptide comprising an exon 14b/exon
                          15 junction
source                   1..35
                         mol_type = protein
                         organism = synthetic construct
SEQUENCE: 912
DDEDEEEIEV RSRDISREEW KGSETYSPNT AYGVD                              35

SEQ ID NO: 913           moltype = AA  length = 34
FEATURE                  Location/Qualifiers
REGION                   1..34
                         note = Ciz1 b-variant peptide comprising an exon 14b/exon
                          15 junction
source                   1..34
                         mol_type = protein
                         organism = synthetic construct
SEQUENCE: 913
```

```
DEDEEEIEVR SRDISREEWK GSETYSPNTA YGVD                              34

SEQ ID NO: 914          moltype = AA  length = 33
FEATURE                 Location/Qualifiers
REGION                  1..33
                        note = Ciz1 b-variant peptide comprising an exon 14b/exon
                         15 junction
source                  1..33
                        mol_type = protein
                        organism = synthetic construct
SEQUENCE: 914
EDEEEIEVRS RDISREEWKG SETYSPNTAY GVD                               33

SEQ ID NO: 915          moltype = AA  length = 32
FEATURE                 Location/Qualifiers
REGION                  1..32
                        note = Ciz1 b-variant peptide comprising an exon 14b/exon
                         15 junction
source                  1..32
                        mol_type = protein
                        organism = synthetic construct
SEQUENCE: 915
DEEEIEVRSR DISREEWKGS ETYSPNTAYG VD                                32

SEQ ID NO: 916          moltype = AA  length = 31
FEATURE                 Location/Qualifiers
REGION                  1..31
                        note = Ciz1 b-variant peptide comprising an exon 14b/exon
                         15 junction
source                  1..31
                        mol_type = protein
                        organism = synthetic construct
SEQUENCE: 916
EEEIEVRSRD ISREEWKGSE TYSPNTAYGV D                                 31

SEQ ID NO: 917          moltype = AA  length = 30
FEATURE                 Location/Qualifiers
REGION                  1..30
                        note = Ciz1 b-variant peptide comprising an exon 14b/exon
                         15 junction
source                  1..30
                        mol_type = protein
                        organism = synthetic construct
SEQUENCE: 917
EEIEVRSRDI SREEWKGSET YSPNTAYGVD                                   30

SEQ ID NO: 918          moltype = AA  length = 29
FEATURE                 Location/Qualifiers
REGION                  1..29
                        note = Ciz1 b-variant peptide comprising an exon 14b/exon
                         15 junction
source                  1..29
                        mol_type = protein
                        organism = synthetic construct
SEQUENCE: 918
EIEVRSRDIS REEWKGSETY SPNTAYGVD                                    29

SEQ ID NO: 919          moltype = AA  length = 28
FEATURE                 Location/Qualifiers
REGION                  1..28
                        note = Ciz1 b-variant peptide comprising an exon 14b/exon
                         15 junction
source                  1..28
                        mol_type = protein
                        organism = synthetic construct
SEQUENCE: 919
IEVRSRDISR EEWKGSETYS PNTAYGVD                                     28

SEQ ID NO: 920          moltype = AA  length = 27
FEATURE                 Location/Qualifiers
REGION                  1..27
                        note = Ciz1 b-variant peptide comprising an exon 14b/exon
                         15 junction
source                  1..27
                        mol_type = protein
                        organism = synthetic construct
SEQUENCE: 920
EVRSRDISRE EWKGSETYSP NTAYGVD                                      27
```

```
SEQ ID NO: 921          moltype = AA  length = 63
FEATURE                 Location/Qualifiers
REGION                  1..63
                        note = Ciz1 b-variant peptide comprising an exon 14b/exon
                         15 junction
source                  1..63
                        mol_type = protein
                        organism = synthetic construct
SEQUENCE: 921
EIAGQDEDHF ITVDAVGCFE GDEEEEEDDE DEEEIEVRSR DISREEWKGS ETYSPNTAYG  60
VDF                                                                63

SEQ ID NO: 922          moltype = AA  length = 62
FEATURE                 Location/Qualifiers
REGION                  1..62
                        note = Ciz1 b-variant peptide comprising an exon 14b/exon
                         15 junction
source                  1..62
                        mol_type = protein
                        organism = synthetic construct
SEQUENCE: 922
IAGQDEDHFI TVDAVGCFEG DEEEEEDDED EEEIEVRSRD ISREEWKGSE TYSPNTAYGV  60
DF                                                                 62

SEQ ID NO: 923          moltype = AA  length = 61
FEATURE                 Location/Qualifiers
REGION                  1..61
                        note = Ciz1 b-variant peptide comprising an exon 14b/exon
                         15 junction
source                  1..61
                        mol_type = protein
                        organism = synthetic construct
SEQUENCE: 923
AGQDEDHFIT VDAVGCFEGD EEEEEDDEDE EEIEVRSRDI SREEWKGSET YSPNTAYGVD  60
F                                                                  61

SEQ ID NO: 924          moltype = AA  length = 60
FEATURE                 Location/Qualifiers
REGION                  1..60
                        note = Ciz1 b-variant peptide comprising an exon 14b/exon
                         15 junction
source                  1..60
                        mol_type = protein
                        organism = synthetic construct
SEQUENCE: 924
GQDEDHFITV DAVGCFEGDE EEEEDDEDEE EIEVRSRDIS REEWKGSETY SPNTAYGVDF  60

SEQ ID NO: 925          moltype = AA  length = 59
FEATURE                 Location/Qualifiers
REGION                  1..59
                        note = Ciz1 b-variant peptide comprising an exon 14b/exon
                         15 junction
source                  1..59
                        mol_type = protein
                        organism = synthetic construct
SEQUENCE: 925
QDEDHFITVD AVGCFEGDEE EEEDDEDEEE IEVRSRDISR EEWKGSETYS PNTAYGVDF   59

SEQ ID NO: 926          moltype = AA  length = 58
FEATURE                 Location/Qualifiers
REGION                  1..58
                        note = Ciz1 b-variant peptide comprising an exon 14b/exon
                         15 junction
source                  1..58
                        mol_type = protein
                        organism = synthetic construct
SEQUENCE: 926
DEDHFITVDA VGCFEGDEEE EEDDEDEEEI EVRSRDISRE EWKGSETYSP NTAYGVDF    58

SEQ ID NO: 927          moltype = AA  length = 57
FEATURE                 Location/Qualifiers
REGION                  1..57
                        note = Ciz1 b-variant peptide comprising an exon 14b/exon
                         15 junction
source                  1..57
                        mol_type = protein
                        organism = synthetic construct
SEQUENCE: 927
EDHFITVDAV GCFEGDEEEE EDDEDEEEIE VRSRDISREE WKGSETYSPN TAYGVDF     57
```

```
SEQ ID NO: 928          moltype = AA  length = 56
FEATURE                 Location/Qualifiers
REGION                  1..56
                        note = Ciz1 b-variant peptide comprising an exon 14b/exon
                         15 junction
source                  1..56
                        mol_type = protein
                        organism = synthetic construct
SEQUENCE: 928
DHFITVDAVG CFEGDEEEEE DDEDEEEIEV RSRDISREEW KGSETYSPNT AYGVDF      56

SEQ ID NO: 929          moltype = AA  length = 55
FEATURE                 Location/Qualifiers
REGION                  1..55
                        note = Ciz1 b-variant peptide comprising an exon 14b/exon
                         15 junction
source                  1..55
                        mol_type = protein
                        organism = synthetic construct
SEQUENCE: 929
HFITVDAVGC FEGDEEEEED DEDEEEIEVR SRDISREEWK GSETYSPNTA YGVDF       55

SEQ ID NO: 930          moltype = AA  length = 54
FEATURE                 Location/Qualifiers
REGION                  1..54
                        note = Ciz1 b-variant peptide comprising an exon 14b/exon
                         15 junction
source                  1..54
                        mol_type = protein
                        organism = synthetic construct
SEQUENCE: 930
FITVDAVGCF EGDEEEEEDD EDEEEIEVRS RDISREEWKG SETYSPNTAY GVDF        54

SEQ ID NO: 931          moltype = AA  length = 53
FEATURE                 Location/Qualifiers
REGION                  1..53
                        note = Ciz1 b-variant peptide comprising an exon 14b/exon
                         15 junction
source                  1..53
                        mol_type = protein
                        organism = synthetic construct
SEQUENCE: 931
ITVDAVGCFE GDEEEEEDDE DEEEIEVRSR DISREEWKGS ETYSPNTAYG VDF         53

SEQ ID NO: 932          moltype = AA  length = 52
FEATURE                 Location/Qualifiers
REGION                  1..52
                        note = Ciz1 b-variant peptide comprising an exon 14b/exon
                         15 junction
source                  1..52
                        mol_type = protein
                        organism = synthetic construct
SEQUENCE: 932
TVDAVGCFEG DEEEEEDDED EEEIEVRSRD ISREEWKGSE TYSPNTAYGV DF          52

SEQ ID NO: 933          moltype = AA  length = 51
FEATURE                 Location/Qualifiers
REGION                  1..51
                        note = Ciz1 b-variant peptide comprising an exon 14b/exon
                         15 junction
source                  1..51
                        mol_type = protein
                        organism = synthetic construct
SEQUENCE: 933
VDAVGCFEGD EEEEEDDEDE EEIEVRSRDI SREEWKGSET YSPNTAYGVD F           51

SEQ ID NO: 934          moltype = AA  length = 50
FEATURE                 Location/Qualifiers
REGION                  1..50
                        note = Ciz1 b-variant peptide comprising an exon 14b/exon
                         15 junction
source                  1..50
                        mol_type = protein
                        organism = synthetic construct
SEQUENCE: 934
DAVGCFEGDE EEEEDDEDEE EIEVRSRDIS REEWKGSETY SPNTAYGVDF             50

SEQ ID NO: 935          moltype = AA  length = 49
```

```
FEATURE                Location/Qualifiers
REGION                 1..49
                       note = Ciz1 b-variant peptide comprising an exon 14b/exon
                        15 junction
source                 1..49
                       mol_type = protein
                       organism = synthetic construct
SEQUENCE: 935
AVGCFEGDEE EEEDDEDEEE IEVRSRDISR EEWKGSETYS PNTAYGVDF              49

SEQ ID NO: 936         moltype = AA  length = 48
FEATURE                Location/Qualifiers
REGION                 1..48
                       note = Ciz1 b-variant peptide comprising an exon 14b/exon
                        15 junction
source                 1..48
                       mol_type = protein
                       organism = synthetic construct
SEQUENCE: 936
VGCFEGDEEE EEDDEDEEEI EVRSRDISRE EWKGSETYSP NTAYGVDF               48

SEQ ID NO: 937         moltype = AA  length = 47
FEATURE                Location/Qualifiers
REGION                 1..47
                       note = Ciz1 b-variant peptide comprising an exon 14b/exon
                        15 junction
source                 1..47
                       mol_type = protein
                       organism = synthetic construct
SEQUENCE: 937
GCFEGDEEEE EDDEDEEEIE VRSRDISREE WKGSETYSPN TAYGVDF                47

SEQ ID NO: 938         moltype = AA  length = 46
FEATURE                Location/Qualifiers
REGION                 1..46
                       note = Ciz1 b-variant peptide comprising an exon 14b/exon
                        15 junction
source                 1..46
                       mol_type = protein
                       organism = synthetic construct
SEQUENCE: 938
CFEGDEEEEE DDEDEEEIEV RSRDISREEW KGSETYSPNT AYGVDF                 46

SEQ ID NO: 939         moltype = AA  length = 45
FEATURE                Location/Qualifiers
REGION                 1..45
                       note = Ciz1 b-variant peptide comprising an exon 14b/exon
                        15 junction
source                 1..45
                       mol_type = protein
                       organism = synthetic construct
SEQUENCE: 939
FEGDEEEEED DEDEEEIEVR SRDISREEWK GSETYSPNTA YGVDF                  45

SEQ ID NO: 940         moltype = AA  length = 44
FEATURE                Location/Qualifiers
REGION                 1..44
                       note = Ciz1 b-variant peptide comprising an exon 14b/exon
                        15 junction
source                 1..44
                       mol_type = protein
                       organism = synthetic construct
SEQUENCE: 940
EGDEEEEEDD EDEEEIEVRS RDISREEWKG SETYSPNTAY GVDF                   44

SEQ ID NO: 941         moltype = AA  length = 43
FEATURE                Location/Qualifiers
REGION                 1..43
                       note = Ciz1 b-variant peptide comprising an exon 14b/exon
                        15 junction
source                 1..43
                       mol_type = protein
                       organism = synthetic construct
SEQUENCE: 941
GDEEEEEDDE DEEEIEVRSR DISREEWKGS ETYSPNTAYG VDF                    43

SEQ ID NO: 942         moltype = AA  length = 42
FEATURE                Location/Qualifiers
REGION                 1..42
```

```
                       note = Ciz1 b-variant peptide comprising an exon 14b/exon
                        15 junction
source                 1..42
                       mol_type = protein
                       organism = synthetic construct
SEQUENCE: 942
DEEEEEDDED EEEIEVRSRD ISREEWKGSE TYSPNTAYGV DF                        42

SEQ ID NO: 943         moltype = AA  length = 41
FEATURE                Location/Qualifiers
REGION                 1..41
                       note = Ciz1 b-variant peptide comprising an exon 14b/exon
                        15 junction
source                 1..41
                       mol_type = protein
                       organism = synthetic construct
SEQUENCE: 943
EEEEEDDEDE EEIEVRSRDI SREEWKGSET YSPNTAYGVD F                         41

SEQ ID NO: 944         moltype = AA  length = 40
FEATURE                Location/Qualifiers
REGION                 1..40
                       note = Ciz1 b-variant peptide comprising an exon 14b/exon
                        15 junction
source                 1..40
                       mol_type = protein
                       organism = synthetic construct
SEQUENCE: 944
EEEEDDEDEE EIEVRSRDIS REEWKGSETY SPNTAYGVDF                           40

SEQ ID NO: 945         moltype = AA  length = 39
FEATURE                Location/Qualifiers
REGION                 1..39
                       note = Ciz1 b-variant peptide comprising an exon 14b/exon
                        15 junction
source                 1..39
                       mol_type = protein
                       organism = synthetic construct
SEQUENCE: 945
EEEDDEDEEE IEVRSRDISR EEWKGSETYS PNTAYGVDF                            39

SEQ ID NO: 946         moltype = AA  length = 38
FEATURE                Location/Qualifiers
REGION                 1..38
                       note = Ciz1 b-variant peptide comprising an exon 14b/exon
                        15 junction
source                 1..38
                       mol_type = protein
                       organism = synthetic construct
SEQUENCE: 946
EEDDEDEEEI EVRSRDISRE EWKGSETYSP NTAYGVDF                             38

SEQ ID NO: 947         moltype = AA  length = 37
FEATURE                Location/Qualifiers
REGION                 1..37
                       note = Ciz1 b-variant peptide comprising an exon 14b/exon
                        15 junction
source                 1..37
                       mol_type = protein
                       organism = synthetic construct
SEQUENCE: 947
EDDEDEEEIE VRSRDISREE WKGSETYSPN TAYGVDF                              37

SEQ ID NO: 948         moltype = AA  length = 36
FEATURE                Location/Qualifiers
REGION                 1..36
                       note = Ciz1 b-variant peptide comprising an exon 14b/exon
                        15 junction
source                 1..36
                       mol_type = protein
                       organism = synthetic construct
SEQUENCE: 948
DDEDEEEIEV RSRDISREEW KGSETYSPNT AYGVDF                               36

SEQ ID NO: 949         moltype = AA  length = 35
FEATURE                Location/Qualifiers
REGION                 1..35
                       note = Ciz1 b-variant peptide comprising an exon 14b/exon
                        15 junction
```

```
source                  1..35
                        mol_type = protein
                        organism = synthetic construct
SEQUENCE: 949
DEDEEEIEVR SRDISREEWK GSETYSPNTA YGVDF                         35

SEQ ID NO: 950          moltype = AA  length = 34
FEATURE                 Location/Qualifiers
REGION                  1..34
                        note = Ciz1 b-variant peptide comprising an exon 14b/exon
                         15 junction
source                  1..34
                        mol_type = protein
                        organism = synthetic construct
SEQUENCE: 950
EDEEEIEVRS RDISREEWKG SETYSPNTAY GVDF                          34

SEQ ID NO: 951          moltype = AA  length = 33
FEATURE                 Location/Qualifiers
REGION                  1..33
                        note = Ciz1 b-variant peptide comprising an exon 14b/exon
                         15 junction
source                  1..33
                        mol_type = protein
                        organism = synthetic construct
SEQUENCE: 951
DEEEIEVRSR DISREEWKGS ETYSPNTAYG VDF                           33

SEQ ID NO: 952          moltype = AA  length = 32
FEATURE                 Location/Qualifiers
REGION                  1..32
                        note = Ciz1 b-variant peptide comprising an exon 14b/exon
                         15 junction
source                  1..32
                        mol_type = protein
                        organism = synthetic construct
SEQUENCE: 952
EEEIEVRSRD ISREEWKGSE TYSPNTAYGV DF                            32

SEQ ID NO: 953          moltype = AA  length = 31
FEATURE                 Location/Qualifiers
REGION                  1..31
                        note = Ciz1 b-variant peptide comprising an exon 14b/exon
                         15 junction
source                  1..31
                        mol_type = protein
                        organism = synthetic construct
SEQUENCE: 953
EEIEVRSRDI SREEWKGSET YSPNTAYGVD F                             31

SEQ ID NO: 954          moltype = AA  length = 30
FEATURE                 Location/Qualifiers
REGION                  1..30
                        note = Ciz1 b-variant peptide comprising an exon 14b/exon
                         15 junction
source                  1..30
                        mol_type = protein
                        organism = synthetic construct
SEQUENCE: 954
EIEVRSRDIS REEWKGSETY SPNTAYGVDF                               30

SEQ ID NO: 955          moltype = AA  length = 29
FEATURE                 Location/Qualifiers
REGION                  1..29
                        note = Ciz1 b-variant peptide comprising an exon 14b/exon
                         15 junction
source                  1..29
                        mol_type = protein
                        organism = synthetic construct
SEQUENCE: 955
IEVRSRDISR EEWKGSETYS PNTAYGVDF                                29

SEQ ID NO: 956          moltype = AA  length = 28
FEATURE                 Location/Qualifiers
REGION                  1..28
                        note = Ciz1 b-variant peptide comprising an exon 14b/exon
                         15 junction
source                  1..28
                        mol_type = protein
```

```
                         organism = synthetic construct
SEQUENCE: 956
EVRSRDISRE EWKGSETYSP NTAYGVDF                                        28

SEQ ID NO: 957           moltype = AA  length = 64
FEATURE                  Location/Qualifiers
REGION                   1..64
                         note = Ciz1 b-variant peptide comprising an exon 14b/exon
                          15 junction
source                   1..64
                         mol_type = protein
                         organism = synthetic construct
SEQUENCE: 957
EIAGQDEDHF ITVDAVGCFE GDEEEEEDDE DEEEIEVRSR DISREEWKGS ETYSPNTAYG  60
VDFL                                                                  64

SEQ ID NO: 958           moltype = AA  length = 63
FEATURE                  Location/Qualifiers
REGION                   1..63
                         note = Ciz1 b-variant peptide comprising an exon 14b/exon
                          15 junction
source                   1..63
                         mol_type = protein
                         organism = synthetic construct
SEQUENCE: 958
IAGQDEDHFI TVDAVGCFEG DEEEEEDDED EEEIEVRSRD ISREEWKGSE TYSPNTAYGV  60
DFL                                                                   63

SEQ ID NO: 959           moltype = AA  length = 62
FEATURE                  Location/Qualifiers
REGION                   1..62
                         note = Ciz1 b-variant peptide comprising an exon 14b/exon
                          15 junction
source                   1..62
                         mol_type = protein
                         organism = synthetic construct
SEQUENCE: 959
AGQDEDHFIT VDAVGCFEGD EEEEEDDEDE EEIEVRSRDI SREEWKGSET YSPNTAYGVD  60
FL                                                                    62

SEQ ID NO: 960           moltype = AA  length = 61
FEATURE                  Location/Qualifiers
REGION                   1..61
                         note = Ciz1 b-variant peptide comprising an exon 14b/exon
                          15 junction
source                   1..61
                         mol_type = protein
                         organism = synthetic construct
SEQUENCE: 960
GQDEDHFITV DAVGCFEGDE EEEEDDEDEE EIEVRSRDIS REEWKGSETY SPNTAYGVDF  60
L                                                                     61

SEQ ID NO: 961           moltype = AA  length = 60
FEATURE                  Location/Qualifiers
REGION                   1..60
                         note = Ciz1 b-variant peptide comprising an exon 14b/exon
                          15 junction
source                   1..60
                         mol_type = protein
                         organism = synthetic construct
SEQUENCE: 961
QDEDHFITVD AVGCFEGDEE EEEDDEDEEE IEVRSRDISR EEWKGSETYS PNTAYGVDFL  60

SEQ ID NO: 962           moltype = AA  length = 59
FEATURE                  Location/Qualifiers
REGION                   1..59
                         note = Ciz1 b-variant peptide comprising an exon 14b/exon
                          15 junction
source                   1..59
                         mol_type = protein
                         organism = synthetic construct
SEQUENCE: 962
DEDHFITVDA VGCFEGDEEE EEDDEDEEEI EVRSRDISRE EWKGSETYSP NTAYGVDFL   59

SEQ ID NO: 963           moltype = AA  length = 58
FEATURE                  Location/Qualifiers
REGION                   1..58
                         note = Ciz1 b-variant peptide comprising an exon 14b/exon
                          15 junction
```

```
source                  1..58
                        mol_type = protein
                        organism = synthetic construct
SEQUENCE: 963
EDHFITVDAV GCFEGDEEEE EDDEDEEEIE VRSRDISREE WKGSETYSPN TAYGVDFL    58

SEQ ID NO: 964          moltype = AA  length = 57
FEATURE                 Location/Qualifiers
REGION                  1..57
                        note = Ciz1 b-variant peptide comprising an exon 14b/exon
                         15 junction
source                  1..57
                        mol_type = protein
                        organism = synthetic construct
SEQUENCE: 964
DHFITVDAVG CFEGDEEEEE DDEDEEEIEV RSRDISREEW KGSETYSPNT AYGVDFL     57

SEQ ID NO: 965          moltype = AA  length = 56
FEATURE                 Location/Qualifiers
REGION                  1..56
                        note = Ciz1 b-variant peptide comprising an exon 14b/exon
                         15 junction
source                  1..56
                        mol_type = protein
                        organism = synthetic construct
SEQUENCE: 965
HFITVDAVGC FEGDEEEEED DEDEEEIEVR SRDISREEWK GSETYSPNTA YGVDFL      56

SEQ ID NO: 966          moltype = AA  length = 55
FEATURE                 Location/Qualifiers
REGION                  1..55
                        note = Ciz1 b-variant peptide comprising an exon 14b/exon
                         15 junction
source                  1..55
                        mol_type = protein
                        organism = synthetic construct
SEQUENCE: 966
FITVDAVGCF EGDEEEEEDD EDEEEIEVRS RDISREEWKG SETYSPNTAY GVDFL       55

SEQ ID NO: 967          moltype = AA  length = 54
FEATURE                 Location/Qualifiers
REGION                  1..54
                        note = Ciz1 b-variant peptide comprising an exon 14b/exon
                         15 junction
source                  1..54
                        mol_type = protein
                        organism = synthetic construct
SEQUENCE: 967
ITVDAVGCFE GDEEEEEDDE DEEEIEVRSR DISREEWKGS ETYSPNTAYG VDFL        54

SEQ ID NO: 968          moltype = AA  length = 53
FEATURE                 Location/Qualifiers
REGION                  1..53
                        note = Ciz1 b-variant peptide comprising an exon 14b/exon
                         15 junction
source                  1..53
                        mol_type = protein
                        organism = synthetic construct
SEQUENCE: 968
TVDAVGCFEG DEEEEEDDED EEEIEVRSRD ISREEWKGSE TYSPNTAYGV DFL         53

SEQ ID NO: 969          moltype = AA  length = 52
FEATURE                 Location/Qualifiers
REGION                  1..52
                        note = Ciz1 b-variant peptide comprising an exon 14b/exon
                         15 junction
source                  1..52
                        mol_type = protein
                        organism = synthetic construct
SEQUENCE: 969
VDAVGCFEGD EEEEEDDEDE EEIEVRSRDI SREEWKGSET YSPNTAYGVD FL          52

SEQ ID NO: 970          moltype = AA  length = 51
FEATURE                 Location/Qualifiers
REGION                  1..51
                        note = Ciz1 b-variant peptide comprising an exon 14b/exon
                         15 junction
source                  1..51
                        mol_type = protein
```

```
                        organism = synthetic construct
SEQUENCE: 970
DAVGCFEGDE EEEEDDEDEE EIEVRSRDIS REEWKGSETY SPNTAYGVDF L           51

SEQ ID NO: 971          moltype = AA  length = 50
FEATURE                 Location/Qualifiers
REGION                  1..50
                        note = Ciz1 b-variant peptide comprising an exon 14b/exon
                         15 junction
source                  1..50
                        mol_type = protein
                        organism = synthetic construct
SEQUENCE: 971
AVGCFEGDEE EEEDDEDEEE IEVRSRDISR EEWKGSETYS PNTAYGVDFL             50

SEQ ID NO: 972          moltype = AA  length = 49
FEATURE                 Location/Qualifiers
REGION                  1..49
                        note = Ciz1 b-variant peptide comprising an exon 14b/exon
                         15 junction
source                  1..49
                        mol_type = protein
                        organism = synthetic construct
SEQUENCE: 972
VGCFEGDEEE EEDDEDEEEI EVRSRDISRE EWKGSETYSP NTAYGVDFL              49

SEQ ID NO: 973          moltype = AA  length = 48
FEATURE                 Location/Qualifiers
REGION                  1..48
                        note = Ciz1 b-variant peptide comprising an exon 14b/exon
                         15 junction
source                  1..48
                        mol_type = protein
                        organism = synthetic construct
SEQUENCE: 973
GCFEGDEEEE EDDEDEEEIE VRSRDISREE WKGSETYSPN TAYGVDFL               48

SEQ ID NO: 974          moltype = AA  length = 47
FEATURE                 Location/Qualifiers
REGION                  1..47
                        note = Ciz1 b-variant peptide comprising an exon 14b/exon
                         15 junction
source                  1..47
                        mol_type = protein
                        organism = synthetic construct
SEQUENCE: 974
CFEGDEEEEE DDEDEEEIEV RSRDISREEW KGSETYSPNT AYGVDFL                47

SEQ ID NO: 975          moltype = AA  length = 46
FEATURE                 Location/Qualifiers
REGION                  1..46
                        note = Ciz1 b-variant peptide comprising an exon 14b/exon
                         15 junction
source                  1..46
                        mol_type = protein
                        organism = synthetic construct
SEQUENCE: 975
FEGDEEEEED DEDEEEIEVR SRDISREEWK GSETYSPNTA YGVDFL                 46

SEQ ID NO: 976          moltype = AA  length = 45
FEATURE                 Location/Qualifiers
REGION                  1..45
                        note = Ciz1 b-variant peptide comprising an exon 14b/exon
                         15 junction
source                  1..45
                        mol_type = protein
                        organism = synthetic construct
SEQUENCE: 976
EGDEEEEEDD EDEEEIEVRS RDISREEWKG SETYSPNTAY GVDFL                  45

SEQ ID NO: 977          moltype = AA  length = 44
FEATURE                 Location/Qualifiers
REGION                  1..44
                        note = Ciz1 b-variant peptide comprising an exon 14b/exon
                         15 junction
source                  1..44
                        mol_type = protein
                        organism = synthetic construct
SEQUENCE: 977
```

```
GDEEEEEDDE DEEEIEVRSR DISREEWKGS ETYSPNTAYG VDFL                  44

SEQ ID NO: 978          moltype = AA  length = 43
FEATURE                 Location/Qualifiers
REGION                  1..43
                        note = Ciz1 b-variant peptide comprising an exon 14b/exon
                         15 junction
source                  1..43
                        mol_type = protein
                        organism = synthetic construct
SEQUENCE: 978
DEEEEEDDED EEEIEVRSRD ISREEWKGSE TYSPNTAYGV DFL                   43

SEQ ID NO: 979          moltype = AA  length = 42
FEATURE                 Location/Qualifiers
REGION                  1..42
                        note = Ciz1 b-variant peptide comprising an exon 14b/exon
                         15 junction
source                  1..42
                        mol_type = protein
                        organism = synthetic construct
SEQUENCE: 979
EEEEEDDEDE EEIEVRSRDI SREEWKGSET YSPNTAYGVD FL                    42

SEQ ID NO: 980          moltype = AA  length = 41
FEATURE                 Location/Qualifiers
REGION                  1..41
                        note = Ciz1 b-variant peptide comprising an exon 14b/exon
                         15 junction
source                  1..41
                        mol_type = protein
                        organism = synthetic construct
SEQUENCE: 980
EEEEDDEDEE EIEVRSRDIS REEWKGSETY SPNTAYGVDF L                     41

SEQ ID NO: 981          moltype = AA  length = 40
FEATURE                 Location/Qualifiers
REGION                  1..40
                        note = Ciz1 b-variant peptide comprising an exon 14b/exon
                         15 junction
source                  1..40
                        mol_type = protein
                        organism = synthetic construct
SEQUENCE: 981
EEEDDEDEEE IEVRSRDISR EEWKGSETYS PNTAYGVDFL                       40

SEQ ID NO: 982          moltype = AA  length = 39
FEATURE                 Location/Qualifiers
REGION                  1..39
                        note = Ciz1 b-variant peptide comprising an exon 14b/exon
                         15 junction
source                  1..39
                        mol_type = protein
                        organism = synthetic construct
SEQUENCE: 982
EEDDEDEEEI EVRSRDISRE EWKGSETYSP NTAYGVDFL                        39

SEQ ID NO: 983          moltype = AA  length = 38
FEATURE                 Location/Qualifiers
REGION                  1..38
                        note = Ciz1 b-variant peptide comprising an exon 14b/exon
                         15 junction
source                  1..38
                        mol_type = protein
                        organism = synthetic construct
SEQUENCE: 983
EDDEDEEEIE VRSRDISREE WKGSETYSPN TAYGVDFL                         38

SEQ ID NO: 984          moltype = AA  length = 37
FEATURE                 Location/Qualifiers
REGION                  1..37
                        note = Ciz1 b-variant peptide comprising an exon 14b/exon
                         15 junction
source                  1..37
                        mol_type = protein
                        organism = synthetic construct
SEQUENCE: 984
DDEDEEEIEV RSRDISREEW KGSETYSPNT AYGVDFL                          37
```

```
SEQ ID NO: 985          moltype = AA  length = 36
FEATURE                 Location/Qualifiers
REGION                  1..36
                        note = Ciz1 b-variant peptide comprising an exon 14b/exon
                         15 junction
source                  1..36
                        mol_type = protein
                        organism = synthetic construct
SEQUENCE: 985
DEDEEEIEVR SRDISREEWK GSETYSPNTA YGVDFL                            36

SEQ ID NO: 986          moltype = AA  length = 35
FEATURE                 Location/Qualifiers
REGION                  1..35
                        note = Ciz1 b-variant peptide comprising an exon 14b/exon
                         15 junction
source                  1..35
                        mol_type = protein
                        organism = synthetic construct
SEQUENCE: 986
EDEEEIEVRS RDISREEWKG SETYSPNTAY GVDFL                             35

SEQ ID NO: 987          moltype = AA  length = 34
FEATURE                 Location/Qualifiers
REGION                  1..34
                        note = Ciz1 b-variant peptide comprising an exon 14b/exon
                         15 junction
source                  1..34
                        mol_type = protein
                        organism = synthetic construct
SEQUENCE: 987
DEEEIEVRSR DISREEWKGS ETYSPNTAYG VDFL                              34

SEQ ID NO: 988          moltype = AA  length = 33
FEATURE                 Location/Qualifiers
REGION                  1..33
                        note = Ciz1 b-variant peptide comprising an exon 14b/exon
                         15 junction
source                  1..33
                        mol_type = protein
                        organism = synthetic construct
SEQUENCE: 988
EEEIEVRSRD ISREEWKGSE TYSPNTAYGV DFL                               33

SEQ ID NO: 989          moltype = AA  length = 32
FEATURE                 Location/Qualifiers
REGION                  1..32
                        note = Ciz1 b-variant peptide comprising an exon 14b/exon
                         15 junction
source                  1..32
                        mol_type = protein
                        organism = synthetic construct
SEQUENCE: 989
EEIEVRSRDI SREEWKGSET YSPNTAYGVD FL                                32

SEQ ID NO: 990          moltype = AA  length = 31
FEATURE                 Location/Qualifiers
REGION                  1..31
                        note = Ciz1 b-variant peptide comprising an exon 14b/exon
                         15 junction
source                  1..31
                        mol_type = protein
                        organism = synthetic construct
SEQUENCE: 990
EIEVRSRDIS REEWKGSETY SPNTAYGVDF L                                 31

SEQ ID NO: 991          moltype = AA  length = 30
FEATURE                 Location/Qualifiers
REGION                  1..30
                        note = Ciz1 b-variant peptide comprising an exon 14b/exon
                         15 junction
source                  1..30
                        mol_type = protein
                        organism = synthetic construct
SEQUENCE: 991
IEVRSRDISR EEWKGSETYS PNTAYGVDFL                                   30

SEQ ID NO: 992          moltype = AA  length = 29
FEATURE                 Location/Qualifiers
```

```
REGION                  1..29
                        note = Ciz1 b-variant peptide comprising an exon 14b/exon
                         15 junction
source                  1..29
                        mol_type = protein
                        organism = synthetic construct
SEQUENCE: 992
EVRSRDISRE EWKGSETYSP NTAYGVDFL                                     29

SEQ ID NO: 993          moltype = AA  length = 65
FEATURE                 Location/Qualifiers
REGION                  1..65
                        note = Ciz1 b-variant peptide comprising an exon 14b/exon
                         15 junction
source                  1..65
                        mol_type = protein
                        organism = synthetic construct
SEQUENCE: 993
EIAGQDEDHF ITVDAVGCFE GDEEEEEDDE DEEEIEVRSR DISREEWKGS ETYSPNTAYG  60
VDFLV                                                               65

SEQ ID NO: 994          moltype = AA  length = 64
FEATURE                 Location/Qualifiers
REGION                  1..64
                        note = Ciz1 b-variant peptide comprising an exon 14b/exon
                         15 junction
source                  1..64
                        mol_type = protein
                        organism = synthetic construct
SEQUENCE: 994
IAGQDEDHFI TVDAVGCFEG DEEEEEDDED EEEIEVRSRD ISREEWKGSE TYSPNTAYGV  60
DFLV                                                                64

SEQ ID NO: 995          moltype = AA  length = 63
FEATURE                 Location/Qualifiers
REGION                  1..63
                        note = Ciz1 b-variant peptide comprising an exon 14b/exon
                         15 junction
source                  1..63
                        mol_type = protein
                        organism = synthetic construct
SEQUENCE: 995
AGQDEDHFIT VDAVGCFEGD EEEEEDDEDE EEIEVRSRDI SREEWKGSET YSPNTAYGVD  60
FLV                                                                 63

SEQ ID NO: 996          moltype = AA  length = 62
FEATURE                 Location/Qualifiers
REGION                  1..62
                        note = Ciz1 b-variant peptide comprising an exon 14b/exon
                         15 junction
source                  1..62
                        mol_type = protein
                        organism = synthetic construct
SEQUENCE: 996
GQDEDHFITV DAVGCFEGDE EEEEDDEDEE EIEVRSRDIS REEWKGSETY SPNTAYGVDF  60
LV                                                                  62

SEQ ID NO: 997          moltype = AA  length = 61
FEATURE                 Location/Qualifiers
REGION                  1..61
                        note = Ciz1 b-variant peptide comprising an exon 14b/exon
                         15 junction
source                  1..61
                        mol_type = protein
                        organism = synthetic construct
SEQUENCE: 997
QDEDHFITVD AVGCFEGDEE EEEDDEDEEE IEVRSRDISR EEWKGSETYS PNTAYGVDFL  60
V                                                                   61

SEQ ID NO: 998          moltype = AA  length = 60
FEATURE                 Location/Qualifiers
REGION                  1..60
                        note = Ciz1 b-variant peptide comprising an exon 14b/exon
                         15 junction
source                  1..60
                        mol_type = protein
                        organism = synthetic construct
SEQUENCE: 998
DEDHFITVDA VGCFEGDEEE EEDDEDEEEI EVRSRDISRE EWKGSETYSP NTAYGVDFLV  60
```

```
SEQ ID NO: 999          moltype = AA  length = 59
FEATURE                 Location/Qualifiers
REGION                  1..59
                        note = Ciz1 b-variant peptide comprising an exon 14b/exon
                         15 junction
source                  1..59
                        mol_type = protein
                        organism = synthetic construct
SEQUENCE: 999
EDHFITVDAV GCFEGDEEEE EDDEDEEEIE VRSRDISREE WKGSETYSPN TAYGVDFLV   59

SEQ ID NO: 1000         moltype = AA  length = 58
FEATURE                 Location/Qualifiers
REGION                  1..58
                        note = Ciz1 b-variant peptide comprising an exon 14b/exon
                         15 junction
source                  1..58
                        mol_type = protein
                        organism = synthetic construct
SEQUENCE: 1000
DHFITVDAVG CFEGDEEEEE DDEDEEEIEV RSRDISREEW KGSETYSPNT AYGVDFLV    58

SEQ ID NO: 1001         moltype = AA  length = 57
FEATURE                 Location/Qualifiers
REGION                  1..57
                        note = Ciz1 b-variant peptide comprising an exon 14b/exon
                         15 junction
source                  1..57
                        mol_type = protein
                        organism = synthetic construct
SEQUENCE: 1001
HFITVDAVGC FEGDEEEEED DEDEEEIEVR SRDISREEWK GSETYSPNTA YGVDFLV     57

SEQ ID NO: 1002         moltype = AA  length = 56
FEATURE                 Location/Qualifiers
REGION                  1..56
                        note = Ciz1 b-variant peptide comprising an exon 14b/exon
                         15 junction
source                  1..56
                        mol_type = protein
                        organism = synthetic construct
SEQUENCE: 1002
FITVDAVGCF EGDEEEEEDD EDEEEIEVRS RDISREEWKG SETYSPNTAY GVDFLV      56

SEQ ID NO: 1003         moltype = AA  length = 55
FEATURE                 Location/Qualifiers
REGION                  1..55
                        note = Ciz1 b-variant peptide comprising an exon 14b/exon
                         15 junction
source                  1..55
                        mol_type = protein
                        organism = synthetic construct
SEQUENCE: 1003
ITVDAVGCFE GDEEEEEDDE DEEEIEVRSR DISREEWKGS ETYSPNTAYG VDFLV       55

SEQ ID NO: 1004         moltype = AA  length = 54
FEATURE                 Location/Qualifiers
REGION                  1..54
                        note = Ciz1 b-variant peptide comprising an exon 14b/exon
                         15 junction
source                  1..54
                        mol_type = protein
                        organism = synthetic construct
SEQUENCE: 1004
TVDAVGCFEG DEEEEEDDED EEEIEVRSRD ISREEWKGSE TYSPNTAYGV DFLV        54

SEQ ID NO: 1005         moltype = AA  length = 53
FEATURE                 Location/Qualifiers
REGION                  1..53
                        note = Ciz1 b-variant peptide comprising an exon 14b/exon
                         15 junction
source                  1..53
                        mol_type = protein
                        organism = synthetic construct
SEQUENCE: 1005
VDAVGCFEGD EEEEEDDEDE EEIEVRSRDI SREEWKGSET YSPNTAYGVD FLV         53

SEQ ID NO: 1006         moltype = AA  length = 52
```

```
FEATURE                 Location/Qualifiers
REGION                  1..52
                        note = Ciz1 b-variant peptide comprising an exon 14b/exon
                         15 junction
source                  1..52
                        mol_type = protein
                        organism = synthetic construct
SEQUENCE: 1006
DAVGCFEGDE EEEEDDEDEE EIEVRSRDIS REEWKGSETY SPNTAYGVDF LV          52

SEQ ID NO: 1007         moltype = AA  length = 51
FEATURE                 Location/Qualifiers
REGION                  1..51
                        note = Ciz1 b-variant peptide comprising an exon 14b/exon
                         15 junction
source                  1..51
                        mol_type = protein
                        organism = synthetic construct
SEQUENCE: 1007
AVGCFEGDEE EEEDDEDEEE IEVRSRDISR EEWKGSETYS PNTAYGVDFL V           51

SEQ ID NO: 1008         moltype = AA  length = 50
FEATURE                 Location/Qualifiers
REGION                  1..50
                        note = Ciz1 b-variant peptide comprising an exon 14b/exon
                         15 junction
source                  1..50
                        mol_type = protein
                        organism = synthetic construct
SEQUENCE: 1008
VGCFEGDEEE EEDDEDEEEI EVRSRDISRE EWKGSETYSP NTAYGVDFLV             50

SEQ ID NO: 1009         moltype = AA  length = 49
FEATURE                 Location/Qualifiers
REGION                  1..49
                        note = Ciz1 b-variant peptide comprising an exon 14b/exon
                         15 junction
source                  1..49
                        mol_type = protein
                        organism = synthetic construct
SEQUENCE: 1009
GCFEGDEEEE EDDEDEEEIE VRSRDISREE WKGSETYSPN TAYGVDFLV              49

SEQ ID NO: 1010         moltype = AA  length = 48
FEATURE                 Location/Qualifiers
REGION                  1..48
                        note = Ciz1 b-variant peptide comprising an exon 14b/exon
                         15 junction
source                  1..48
                        mol_type = protein
                        organism = synthetic construct
SEQUENCE: 1010
CFEGDEEEEE DDEDEEEIEV RSRDISREEW KGSETYSPNT AYGVDFLV               48

SEQ ID NO: 1011         moltype = AA  length = 47
FEATURE                 Location/Qualifiers
REGION                  1..47
                        note = Ciz1 b-variant peptide comprising an exon 14b/exon
                         15 junction
source                  1..47
                        mol_type = protein
                        organism = synthetic construct
SEQUENCE: 1011
FEGDEEEEED DEDEEEIEVR SRDISREEWK GSETYSPNTA YGVDFLV                47

SEQ ID NO: 1012         moltype = AA  length = 46
FEATURE                 Location/Qualifiers
REGION                  1..46
                        note = Ciz1 b-variant peptide comprising an exon 14b/exon
                         15 junction
source                  1..46
                        mol_type = protein
                        organism = synthetic construct
SEQUENCE: 1012
EGDEEEEEDD EDEEEIEVRS RDISREEWKG SETYSPNTAY GVDFLV                 46

SEQ ID NO: 1013         moltype = AA  length = 45
FEATURE                 Location/Qualifiers
REGION                  1..45
```

```
                        note = Ciz1 b-variant peptide comprising an exon 14b/exon
                         15 junction
source                  1..45
                        mol_type = protein
                        organism = synthetic construct
SEQUENCE: 1013
GDEEEEEDDE DEEEIEVRSR DISREEWKGS ETYSPNTAYG VDFLV                    45

SEQ ID NO: 1014         moltype = AA  length = 44
FEATURE                 Location/Qualifiers
REGION                  1..44
                        note = Ciz1 b-variant peptide comprising an exon 14b/exon
                         15 junction
source                  1..44
                        mol_type = protein
                        organism = synthetic construct
SEQUENCE: 1014
DEEEEEDDED EEEIEVRSRD ISREEWKGSE TYSPNTAYGV DFLV                     44

SEQ ID NO: 1015         moltype = AA  length = 43
FEATURE                 Location/Qualifiers
REGION                  1..43
                        note = Ciz1 b-variant peptide comprising an exon 14b/exon
                         15 junction
source                  1..43
                        mol_type = protein
                        organism = synthetic construct
SEQUENCE: 1015
EEEEEDDEDE EEIEVRSRDI SREEWKGSET YSPNTAYGVD FLV                      43

SEQ ID NO: 1016         moltype = AA  length = 42
FEATURE                 Location/Qualifiers
REGION                  1..42
                        note = Ciz1 b-variant peptide comprising an exon 14b/exon
                         15 junction
source                  1..42
                        mol_type = protein
                        organism = synthetic construct
SEQUENCE: 1016
EEEEDDEDEE EIEVRSRDIS REEWKGSETY SPNTAYGVDF LV                       42

SEQ ID NO: 1017         moltype = AA  length = 41
FEATURE                 Location/Qualifiers
REGION                  1..41
                        note = Ciz1 b-variant peptide comprising an exon 14b/exon
                         15 junction
source                  1..41
                        mol_type = protein
                        organism = synthetic construct
SEQUENCE: 1017
EEEDDEDEEE IEVRSRDISR EEWKGSETYS PNTAYGVDFL V                        41

SEQ ID NO: 1018         moltype = AA  length = 40
FEATURE                 Location/Qualifiers
REGION                  1..40
                        note = Ciz1 b-variant peptide comprising an exon 14b/exon
                         15 junction
source                  1..40
                        mol_type = protein
                        organism = synthetic construct
SEQUENCE: 1018
EEDDEDEEEI EVRSRDISRE EWKGSETYSP NTAYGVDFLV                          40

SEQ ID NO: 1019         moltype = AA  length = 39
FEATURE                 Location/Qualifiers
REGION                  1..39
                        note = Ciz1 b-variant peptide comprising an exon 14b/exon
                         15 junction
source                  1..39
                        mol_type = protein
                        organism = synthetic construct
SEQUENCE: 1019
EDDEDEEEIE VRSRDISREE WKGSETYSPN TAYGVDFLV                           39

SEQ ID NO: 1020         moltype = AA  length = 38
FEATURE                 Location/Qualifiers
REGION                  1..38
                        note = Ciz1 b-variant peptide comprising an exon 14b/exon
                         15 junction
```

```
source                  1..38
                        mol_type = protein
                        organism = synthetic construct
SEQUENCE: 1020
DDEDEEEIEV RSRDISREEW KGSETYSPNT AYGVDFLV                          38

SEQ ID NO: 1021         moltype = AA  length = 37
FEATURE                 Location/Qualifiers
REGION                  1..37
                        note = Ciz1 b-variant peptide comprising an exon 14b/exon
                         15 junction
source                  1..37
                        mol_type = protein
                        organism = synthetic construct
SEQUENCE: 1021
DEDEEEIEVR SRDISREEWK GSETYSPNTA YGVDFLV                           37

SEQ ID NO: 1022         moltype = AA  length = 36
FEATURE                 Location/Qualifiers
REGION                  1..36
                        note = Ciz1 b-variant peptide comprising an exon 14b/exon
                         15 junction
source                  1..36
                        mol_type = protein
                        organism = synthetic construct
SEQUENCE: 1022
EDEEEIEVRS RDISREEWKG SETYSPNTAY GVDFLV                            36

SEQ ID NO: 1023         moltype = AA  length = 35
FEATURE                 Location/Qualifiers
REGION                  1..35
                        note = Ciz1 b-variant peptide comprising an exon 14b/exon
                         15 junction
source                  1..35
                        mol_type = protein
                        organism = synthetic construct
SEQUENCE: 1023
DEEEIEVRSR DISREEWKGS ETYSPNTAYG VDFLV                             35

SEQ ID NO: 1024         moltype = AA  length = 34
FEATURE                 Location/Qualifiers
REGION                  1..34
                        note = Ciz1 b-variant peptide comprising an exon 14b/exon
                         15 junction
source                  1..34
                        mol_type = protein
                        organism = synthetic construct
SEQUENCE: 1024
EEEIEVRSRD ISREEWKGSE TYSPNTAYGV DFLV                              34

SEQ ID NO: 1025         moltype = AA  length = 33
FEATURE                 Location/Qualifiers
REGION                  1..33
                        note = Ciz1 b-variant peptide comprising an exon 14b/exon
                         15 junction
source                  1..33
                        mol_type = protein
                        organism = synthetic construct
SEQUENCE: 1025
EEIEVRSRDI SREEWKGSET YSPNTAYGVD FLV                               33

SEQ ID NO: 1026         moltype = AA  length = 32
FEATURE                 Location/Qualifiers
REGION                  1..32
                        note = Ciz1 b-variant peptide comprising an exon 14b/exon
                         15 junction
source                  1..32
                        mol_type = protein
                        organism = synthetic construct
SEQUENCE: 1026
EIEVRSRDIS REEWKGSETY SPNTAYGVDF LV                                32

SEQ ID NO: 1027         moltype = AA  length = 31
FEATURE                 Location/Qualifiers
REGION                  1..31
                        note = Ciz1 b-variant peptide comprising an exon 14b/exon
                         15 junction
source                  1..31
                        mol_type = protein
```

```
                      organism = synthetic construct
SEQUENCE: 1027
IEVRSRDISR EEWKGSETYS PNTAYGVDFL V                                31

SEQ ID NO: 1028       moltype = AA  length = 30
FEATURE               Location/Qualifiers
REGION                1..30
                      note = Ciz1 b-variant peptide comprising an exon 14b/exon
                       15 junction
source                1..30
                      mol_type = protein
                      organism = synthetic construct
SEQUENCE: 1028
EVRSRDISRE EWKGSETYSP NTAYGVDFLV                                  30

SEQ ID NO: 1029       moltype = AA  length = 65
FEATURE               Location/Qualifiers
REGION                1..65
                      note = Ciz1 b-variant peptide comprising an exon 14b/exon
                       15 junction
source                1..65
                      mol_type = protein
                      organism = synthetic construct
SEQUENCE: 1029
IAGQDEDHFI TVDAVGCFEG DEEEEEDDED EEEIEVRSRD ISREEWKGSE TYSPNTAYGV  60
DFLVP                                                             65

SEQ ID NO: 1030       moltype = AA  length = 64
FEATURE               Location/Qualifiers
REGION                1..64
                      note = Ciz1 b-variant peptide comprising an exon 14b/exon
                       15 junction
source                1..64
                      mol_type = protein
                      organism = synthetic construct
SEQUENCE: 1030
AGQDEDHFIT VDAVGCFEGD EEEEEDDEDE EEIEVRSRDI SREEWKGSET YSPNTAYGVD  60
FLVP                                                              64

SEQ ID NO: 1031       moltype = AA  length = 63
FEATURE               Location/Qualifiers
REGION                1..63
                      note = Ciz1 b-variant peptide comprising an exon 14b/exon
                       15 junction
source                1..63
                      mol_type = protein
                      organism = synthetic construct
SEQUENCE: 1031
GQDEDHFITV DAVGCFEGDE EEEEDDEDEE EIEVRSRDIS REEWKGSETY SPNTAYGVDF  60
LVP                                                               63

SEQ ID NO: 1032       moltype = AA  length = 62
FEATURE               Location/Qualifiers
REGION                1..62
                      note = Ciz1 b-variant peptide comprising an exon 14b/exon
                       15 junction
source                1..62
                      mol_type = protein
                      organism = synthetic construct
SEQUENCE: 1032
QDEDHFITVD AVGCFEGDEE EEEDDEDEEE IEVRSRDISR EEWKGSETYS PNTAYGVDFL  60
VP                                                                62

SEQ ID NO: 1033       moltype = AA  length = 61
FEATURE               Location/Qualifiers
REGION                1..61
                      note = Ciz1 b-variant peptide comprising an exon 14b/exon
                       15 junction
source                1..61
                      mol_type = protein
                      organism = synthetic construct
SEQUENCE: 1033
DEDHFITVDA VGCFEGDEEE EEDDEDEEEI EVRSRDISRE EWKGSETYSP NTAYGVDFLV  60
P                                                                 61

SEQ ID NO: 1034       moltype = AA  length = 60
FEATURE               Location/Qualifiers
REGION                1..60
                      note = Ciz1 b-variant peptide comprising an exon 14b/exon
```

```
                          15 junction
source                   1..60
                         mol_type = protein
                         organism = synthetic construct
SEQUENCE: 1034
EDHFITVDAV GCFEGDEEEE EDDEDEEEIE VRSRDISREE WKGSETYSPN TAYGVDFLVP  60

SEQ ID NO: 1035          moltype = AA  length = 59
FEATURE                  Location/Qualifiers
REGION                   1..59
                         note = Ciz1 b-variant peptide comprising an exon 14b/exon
                          15 junction
source                   1..59
                         mol_type = protein
                         organism = synthetic construct
SEQUENCE: 1035
DHFITVDAVG CFEGDEEEEE DDEDEEEIEV RSRDISREEW KGSETYSPNT AYGVDFLVP   59

SEQ ID NO: 1036          moltype = AA  length = 58
FEATURE                  Location/Qualifiers
REGION                   1..58
                         note = Ciz1 b-variant peptide comprising an exon 14b/exon
                          15 junction
source                   1..58
                         mol_type = protein
                         organism = synthetic construct
SEQUENCE: 1036
HFITVDAVGC FEGDEEEEED DEDEEEIEVR SRDISREEWK GSETYSPNTA YGVDFLVP    58

SEQ ID NO: 1037          moltype = AA  length = 57
FEATURE                  Location/Qualifiers
REGION                   1..57
                         note = Ciz1 b-variant peptide comprising an exon 14b/exon
                          15 junction
source                   1..57
                         mol_type = protein
                         organism = synthetic construct
SEQUENCE: 1037
FITVDAVGCF EGDEEEEEDD EDEEEIEVRS RDISREEWKG SETYSPNTAY GVDFLVP     57

SEQ ID NO: 1038          moltype = AA  length = 56
FEATURE                  Location/Qualifiers
REGION                   1..56
                         note = Ciz1 b-variant peptide comprising an exon 14b/exon
                          15 junction
source                   1..56
                         mol_type = protein
                         organism = synthetic construct
SEQUENCE: 1038
ITVDAVGCFE GDEEEEEDDE DEEEIEVRSR DISREEWKGS ETYSPNTAYG VDFLVP      56

SEQ ID NO: 1039          moltype = AA  length = 55
FEATURE                  Location/Qualifiers
REGION                   1..55
                         note = Ciz1 b-variant peptide comprising an exon 14b/exon
                          15 junction
source                   1..55
                         mol_type = protein
                         organism = synthetic construct
SEQUENCE: 1039
TVDAVGCFEG DEEEEEDDED EEEIEVRSRD ISREEWKGSE TYSPNTAYGV DFLVP       55

SEQ ID NO: 1040          moltype = AA  length = 54
FEATURE                  Location/Qualifiers
REGION                   1..54
                         note = Ciz1 b-variant peptide comprising an exon 14b/exon
                          15 junction
source                   1..54
                         mol_type = protein
                         organism = synthetic construct
SEQUENCE: 1040
VDAVGCFEGD EEEEEDDEDE EEIEVRSRDI SREEWKGSET YSPNTAYGVD FLVP        54

SEQ ID NO: 1041          moltype = AA  length = 53
FEATURE                  Location/Qualifiers
REGION                   1..53
                         note = Ciz1 b-variant peptide comprising an exon 14b/exon
                          15 junction
source                   1..53
```

```
                         mol_type = protein
                         organism = synthetic construct
SEQUENCE: 1041
DAVGCFEGDE EEEEDDEDEE EIEVRSRDIS REEWKGSETY SPNTAYGVDF LVP        53

SEQ ID NO: 1042          moltype = AA  length = 52
FEATURE                  Location/Qualifiers
REGION                   1..52
                         note = Ciz1 b-variant peptide comprising an exon 14b/exon
                          15 junction
source                   1..52
                         mol_type = protein
                         organism = synthetic construct
SEQUENCE: 1042
AVGCFEGDEE EEEDDEDEEE IEVRSRDISR EEWKGSETYS PNTAYGVDFL VP         52

SEQ ID NO: 1043          moltype = AA  length = 51
FEATURE                  Location/Qualifiers
REGION                   1..51
                         note = Ciz1 b-variant peptide comprising an exon 14b/exon
                          15 junction
source                   1..51
                         mol_type = protein
                         organism = synthetic construct
SEQUENCE: 1043
VGCFEGDEEE EEDDEDEEEI EVRSRDISRE EWKGSETYSP NTAYGVDFLV P          51

SEQ ID NO: 1044          moltype = AA  length = 50
FEATURE                  Location/Qualifiers
REGION                   1..50
                         note = Ciz1 b-variant peptide comprising an exon 14b/exon
                          15 junction
source                   1..50
                         mol_type = protein
                         organism = synthetic construct
SEQUENCE: 1044
GCFEGDEEEE EDDEDEEEIE VRSRDISREE WKGSETYSPN TAYGVDFLVP            50

SEQ ID NO: 1045          moltype = AA  length = 49
FEATURE                  Location/Qualifiers
REGION                   1..49
                         note = Ciz1 b-variant peptide comprising an exon 14b/exon
                          15 junction
source                   1..49
                         mol_type = protein
                         organism = synthetic construct
SEQUENCE: 1045
CFEGDEEEEE DDEDEEEIEV RSRDISREEW KGSETYSPNT AYGVDFLVP             49

SEQ ID NO: 1046          moltype = AA  length = 48
FEATURE                  Location/Qualifiers
REGION                   1..48
                         note = Ciz1 b-variant peptide comprising an exon 14b/exon
                          15 junction
source                   1..48
                         mol_type = protein
                         organism = synthetic construct
SEQUENCE: 1046
FEGDEEEEED DEDEEEIEVR SRDISREEWK GSETYSPNTA YGVDFLVP              48

SEQ ID NO: 1047          moltype = AA  length = 47
FEATURE                  Location/Qualifiers
REGION                   1..47
                         note = Ciz1 b-variant peptide comprising an exon 14b/exon
                          15 junction
source                   1..47
                         mol_type = protein
                         organism = synthetic construct
SEQUENCE: 1047
EGDEEEEEDD EDEEEIEVRS RDISREEWKG SETYSPNTAY GVDFLVP               47

SEQ ID NO: 1048          moltype = AA  length = 46
FEATURE                  Location/Qualifiers
REGION                   1..46
                         note = Ciz1 b-variant peptide comprising an exon 14b/exon
                          15 junction
source                   1..46
                         mol_type = protein
                         organism = synthetic construct
```

```
SEQUENCE: 1048
GDEEEEEDDE DEEEIEVRSR DISREEWKGS ETYSPNTAYG VDFLVP                 46

SEQ ID NO: 1049        moltype = AA  length = 45
FEATURE                Location/Qualifiers
REGION                 1..45
                       note = Ciz1 b-variant peptide comprising an exon 14b/exon
                        15 junction
source                 1..45
                       mol_type = protein
                       organism = synthetic construct
SEQUENCE: 1049
DEEEEEDDED EEEIEVRSRD ISREEWKGSE TYSPNTAYGV DFLVP                  45

SEQ ID NO: 1050        moltype = AA  length = 44
FEATURE                Location/Qualifiers
REGION                 1..44
                       note = Ciz1 b-variant peptide comprising an exon 14b/exon
                        15 junction
source                 1..44
                       mol_type = protein
                       organism = synthetic construct
SEQUENCE: 1050
EEEEEDDEDE EEIEVRSRDI SREEWKGSET YSPNTAYGVD FLVP                   44

SEQ ID NO: 1051        moltype = AA  length = 43
FEATURE                Location/Qualifiers
REGION                 1..43
                       note = Ciz1 b-variant peptide comprising an exon 14b/exon
                        15 junction
source                 1..43
                       mol_type = protein
                       organism = synthetic construct
SEQUENCE: 1051
EEEEDDEDEE EIEVRSRDIS REEWKGSETY SPNTAYGVDF LVP                    43

SEQ ID NO: 1052        moltype = AA  length = 42
FEATURE                Location/Qualifiers
REGION                 1..42
                       note = Ciz1 b-variant peptide comprising an exon 14b/exon
                        15 junction
source                 1..42
                       mol_type = protein
                       organism = synthetic construct
SEQUENCE: 1052
EEEDDEDEEE IEVRSRDISR EEWKGSETYS PNTAYGVDFL VP                     42

SEQ ID NO: 1053        moltype = AA  length = 41
FEATURE                Location/Qualifiers
REGION                 1..41
                       note = Ciz1 b-variant peptide comprising an exon 14b/exon
                        15 junction
source                 1..41
                       mol_type = protein
                       organism = synthetic construct
SEQUENCE: 1053
EEDDEDEEEI EVRSRDISRE EWKGSETYSP NTAYGVDFLV P                      41

SEQ ID NO: 1054        moltype = AA  length = 40
FEATURE                Location/Qualifiers
REGION                 1..40
                       note = Ciz1 b-variant peptide comprising an exon 14b/exon
                        15 junction
source                 1..40
                       mol_type = protein
                       organism = synthetic construct
SEQUENCE: 1054
EDDEDEEEIE VRSRDISREE WKGSETYSPN TAYGVDFLVP                        40

SEQ ID NO: 1055        moltype = AA  length = 39
FEATURE                Location/Qualifiers
REGION                 1..39
                       note = Ciz1 b-variant peptide comprising an exon 14b/exon
                        15 junction
source                 1..39
                       mol_type = protein
                       organism = synthetic construct
SEQUENCE: 1055
DDEDEEEIEV RSRDISREEW KGSETYSPNT AYGVDFLVP                         39
```

```
SEQ ID NO: 1056        moltype = AA  length = 38
FEATURE                Location/Qualifiers
REGION                 1..38
                       note = Ciz1 b-variant peptide comprising an exon 14b/exon
                        15 junction
source                 1..38
                       mol_type = protein
                       organism = synthetic construct
SEQUENCE: 1056
DEDEEEIEVR SRDISREEWK GSETYSPNTA YGVDFLVP                          38

SEQ ID NO: 1057        moltype = AA  length = 37
FEATURE                Location/Qualifiers
REGION                 1..37
                       note = Ciz1 b-variant peptide comprising an exon 14b/exon
                        15 junction
source                 1..37
                       mol_type = protein
                       organism = synthetic construct
SEQUENCE: 1057
EDEEEIEVRS RDISREEWKG SETYSPNTAY GVDFLVP                           37

SEQ ID NO: 1058        moltype = AA  length = 36
FEATURE                Location/Qualifiers
REGION                 1..36
                       note = Ciz1 b-variant peptide comprising an exon 14b/exon
                        15 junction
source                 1..36
                       mol_type = protein
                       organism = synthetic construct
SEQUENCE: 1058
DEEEIEVRSR DISREEWKGS ETYSPNTAYG VDFLVP                            36

SEQ ID NO: 1059        moltype = AA  length = 35
FEATURE                Location/Qualifiers
REGION                 1..35
                       note = Ciz1 b-variant peptide comprising an exon 14b/exon
                        15 junction
source                 1..35
                       mol_type = protein
                       organism = synthetic construct
SEQUENCE: 1059
EEEIEVRSRD ISREEWKGSE TYSPNTAYGV DFLVP                             35

SEQ ID NO: 1060        moltype = AA  length = 34
FEATURE                Location/Qualifiers
REGION                 1..34
                       note = Ciz1 b-variant peptide comprising an exon 14b/exon
                        15 junction
source                 1..34
                       mol_type = protein
                       organism = synthetic construct
SEQUENCE: 1060
EEIEVRSRDI SREEWKGSET YSPNTAYGVD FLVP                              34

SEQ ID NO: 1061        moltype = AA  length = 33
FEATURE                Location/Qualifiers
REGION                 1..33
                       note = Ciz1 b-variant peptide comprising an exon 14b/exon
                        15 junction
source                 1..33
                       mol_type = protein
                       organism = synthetic construct
SEQUENCE: 1061
EIEVRSRDIS REEWKGSETY SPNTAYGVDF LVP                               33

SEQ ID NO: 1062        moltype = AA  length = 32
FEATURE                Location/Qualifiers
REGION                 1..32
                       note = Ciz1 b-variant peptide comprising an exon 14b/exon
                        15 junction
source                 1..32
                       mol_type = protein
                       organism = synthetic construct
SEQUENCE: 1062
IEVRSRDISR EEWKGSETYS PNTAYGVDFL VP                                32

SEQ ID NO: 1063        moltype = AA  length = 31
```

-continued

```
FEATURE                 Location/Qualifiers
REGION                  1..31
                        note = Ciz1 b-variant peptide comprising an exon 14b/exon
                         15 junction
source                  1..31
                        mol_type = protein
                        organism = synthetic construct
SEQUENCE: 1063
EVRSRDISRE EWKGSETYSP NTAYGVDFLV P                                31

SEQ ID NO: 1064         moltype = AA  length = 15
FEATURE                 Location/Qualifiers
source                  1..15
                        mol_type = protein
                        organism = Homo sapiens
SEQUENCE: 1064
KGLIDEVNQD FTNRI                                                  15

SEQ ID NO: 1065         moltype = AA  length = 17
FEATURE                 Location/Qualifiers
source                  1..17
                        mol_type = protein
                        organism = Homo sapiens
SEQUENCE: 1065
KESSSHHPGI AEFPSRG                                                17
```